US012643837B2

(12) United States Patent
Temme et al.

(10) Patent No.: US 12,643,837 B2
(45) Date of Patent: Jun. 2, 2026

(54) MODIFIED BACTERIAL STRAINS FOR IMPROVED FIXATION OF NITROGEN

(71) Applicant: Pivot Bio, Inc., Minnetonka, MN (US)

(72) Inventors: Karsten Temme, Berkeley, CA (US); Neal Shah, Berkeley, CA (US); Bilge Ozaydin Eskiyenenturk, Berkeley, CA (US); Sarah Bloch, Berkeley, CA (US); Alvin Tamsir, Berkeley, CA (US)

(73) Assignee: Pivot Bio, Inc., Minnetonka, MN (US)

( * ) Notice: Subject to any disclaimer, the term of this patent is extended or adjusted under 35 U.S.C. 154(b) by 770 days.

(21) Appl. No.: 17/922,712

(22) PCT Filed: Apr. 29, 2021

(86) PCT No.: PCT/US2021/029895
§ 371 (c)(1),
(2) Date: Nov. 1, 2022

(87) PCT Pub. No.: WO2021/222567
PCT Pub. Date: Nov. 4, 2021

(65) Prior Publication Data
US 2023/0257317 A1 Aug. 17, 2023

Related U.S. Application Data

(60) Provisional application No. 63/019,247, filed on May 1, 2020.

(30) Foreign Application Priority Data

May 1, 2020 (WO) ................ PCT/US2020/031201
Jan. 12, 2021 (WO) ................ PCT/US2021/113120

(51) Int. Cl.
*C05F 11/08* (2006.01)
*C12N 1/205* (2026.01)
(Continued)

(52) U.S. Cl.
CPC .............. *C05F 11/08* (2013.01); *C12N 1/205* (2021.05); *C12N 15/52* (2013.01); *C12N 15/74* (2013.01);
(Continued)

(58) Field of Classification Search
CPC ......... C05F 11/08; C12N 1/205; C12N 15/74; C12N 15/52
See application file for complete search history.

(56) References Cited

U.S. PATENT DOCUMENTS 1,520,545 A 12/1924 Murphy
4,782,022 A 11/1988 Puhler et al.
(Continued)

FOREIGN PATENT DOCUMENTS

AU 636565 5/1993
CA 2051071 3/1993
(Continued)

OTHER PUBLICATIONS

Bürgmann et al., "Effects of model root exudates on structure and activity of a soil diazotroph community," Environmental Microbiology, Nov. 2005, 7(11):1711-1124.
(Continued)

*Primary Examiner* — Wayne A Langel
(74) *Attorney, Agent, or Firm* — Fish & Richardson P.C.

(57) ABSTRACT

Methods and systems are provided for generating and utilizing a genetically engineered bacterium comprising a modification in a gene regulating nitrogen fixation or assimilation, wherein the modification in the gene regulating nitrogen fixation or assimilation results in one or more of: constitutive expression of a nifA gene in nitrogen limiting and non-nitrogen limiting conditions, activity of nifA in non-nitrogen limiting conditions, decreased uridylyl-trans-
(Continued)

Technical Roadmap to Full Fertilizer Replacement

Current Strain (201712002)

ferase activity of GlnD, decreased adenylyl-removing activity of GlnE, and increased ammonium excretion.

14 Claims, 47 Drawing Sheets

Specification includes a Sequence Listing.

(51) Int. Cl.
| | |
|---|---|
| *C12N 15/52* | (2006.01) |
| *C12N 15/74* | (2006.01) |
| *C12R 1/22* | (2006.01) |

(52) U.S. Cl.
CPC .... *C12N 2800/101* (2013.01); *C12R 2001/22* (2021.05)

(56) References Cited

U.S. PATENT DOCUMENTS

| | | | |
|---|---|---|---|
| 4,832,728 A | 5/1989 | Allan et al. | |
| 4,970,147 A | 11/1990 | Huala et al. | |
| 5,071,743 A | 12/1991 | Slilaty et al. | |
| 5,116,506 A | 5/1992 | Williamson et al. | |
| 5,188,960 A | 2/1993 | Payne et al. | |
| 5,229,291 A | 7/1993 | Nielsen et al. | |
| 5,354,670 A | 10/1994 | Nickoloff et al. | |
| 5,427,785 A | 6/1995 | Ronson et al. | |
| 5,610,044 A | 3/1997 | Lam et al. | |
| 5,780,270 A | 7/1998 | Lesley | |
| 5,789,166 A | 8/1998 | Bauer et al. | |
| 5,877,012 A | 3/1999 | Estruch et al. | |
| 5,880,275 A | 3/1999 | Fischhoff et al. | |
| 5,916,029 A | 6/1999 | Smith et al. | |
| 6,033,861 A | 3/2000 | Schaffer et al. | |
| 6,033,874 A | 3/2000 | Baum et al. | |
| 6,083,499 A | 7/2000 | Narva et al. | |
| 6,107,279 A | 8/2000 | Estruch et al. | |
| 6,114,148 A | 9/2000 | Seed et al. | |
| 6,127,180 A | 10/2000 | Narva et al. | |
| 6,137,033 A | 10/2000 | Estruch et al. | |
| 6,218,188 B1 | 4/2001 | Cardineau et al. | |
| 6,248,535 B1 | 6/2001 | Danenberg et al. | |
| 6,326,351 B1 | 12/2001 | Donovan et al. | |
| 6,340,593 B1 | 1/2002 | Cardineau et al. | |
| 6,391,548 B1 | 5/2002 | Bauer et al. | |
| 6,399,330 B1 | 6/2002 | Donovan et al. | |
| 6,548,289 B1 | 4/2003 | Beynon et al. | |
| 6,548,291 B1 | 4/2003 | Narva et al. | |
| 6,596,509 B1 | 7/2003 | Bauer et al. | |
| 6,624,145 B1 | 9/2003 | Narva et al. | |
| 6,673,610 B2 | 1/2004 | Miyawaki et al. | |
| 6,713,063 B1 | 3/2004 | Malvar et al. | |
| 6,713,285 B2 | 3/2004 | Bauer et al. | |
| 6,773,900 B2 | 8/2004 | Short et al. | |
| 6,841,358 B1 | 1/2005 | Locht et al. | |
| 6,949,626 B2 | 9/2005 | Donovan et al. | |
| 6,962,705 B2 | 11/2005 | Malvar et al. | |
| 7,064,249 B2 | 6/2006 | Corbin et al. | |
| 7,070,982 B2 | 7/2006 | Malvar et al. | |
| 7,084,331 B2 | 8/2006 | Isawa et al. | |
| 7,105,332 B2 | 9/2006 | Abad et al. | |
| 7,132,265 B2 | 11/2006 | Bauer et al. | |
| 7,244,820 B2 | 7/2007 | Miles et al. | |
| 7,329,736 B2 | 2/2008 | Abad et al. | |
| 7,378,499 B2 | 5/2008 | Abad et al. | |
| 7,385,107 B2 | 6/2008 | Donovan et al. | |
| 7,449,552 B2 | 11/2008 | Abad et al. | |
| 7,462,760 B2 | 12/2008 | Abad et al. | |
| 7,470,427 B2 | 12/2008 | Cocking | |
| 7,476,781 B2 | 1/2009 | Abad et al. | |
| 7,485,451 B2 | 2/2009 | Vandergheynst et al. | |
| 7,491,698 B2 | 2/2009 | Hey et al. | |
| 7,491,869 B2 | 2/2009 | Abad et al. | |
| 7,504,229 B2 | 3/2009 | Donovan et al. | |
| 7,615,686 B2 | 11/2009 | Miles et al. | |
| 7,803,943 B2 | 9/2010 | Mao et al. | |
| 7,858,849 B2 | 12/2010 | Cerf et al. | |
| 7,888,552 B2 | 2/2011 | Ye et al. | |
| 7,923,602 B2 | 4/2011 | Carozzi et al. | |
| 8,076,142 B2 | 12/2011 | Huang et al. | |
| 8,084,416 B2 | 12/2011 | Sampson et al. | |
| 8,084,418 B2 | 12/2011 | Hey et al. | |
| 8,137,665 B2 | 3/2012 | Cocking | |
| 8,236,757 B2 | 8/2012 | Carozzi et al. | |
| 8,237,020 B2 | 8/2012 | Miles et al. | |
| 8,268,584 B1 | 9/2012 | Hardwood et al. | |
| 8,304,604 B2 | 11/2012 | Lira et al. | |
| 8,304,605 B2 | 11/2012 | Lira et al. | |
| 8,319,019 B2 | 11/2012 | Abad et al. | |
| 8,334,366 B1 | 12/2012 | Hughes et al. | |
| 8,334,431 B2 | 12/2012 | Sampson et al. | |
| 8,377,671 B2 | 2/2013 | Cournac et al. | |
| 8,481,026 B1 | 7/2013 | Woodruff et al. | |
| 8,513,494 B2 | 8/2013 | Wu et al. | |
| 8,530,411 B2 | 9/2013 | Cerf et al. | |
| 8,575,433 B2 | 11/2013 | Cerf et al. | |
| 8,686,233 B2 | 4/2014 | Cerf et al. | |
| 8,759,619 B2 | 6/2014 | Sampson et al. | |
| 8,795,965 B2 | 8/2014 | Zjang | |
| 8,802,933 B2 | 8/2014 | Abad et al. | |
| 8,802,934 B2 | 8/2014 | Abad et al. | |
| 9,150,851 B2 | 10/2015 | Wigley et al. | |
| 9,321,697 B2 | 4/2016 | Das et al. | |
| 9,487,451 B2 | 11/2016 | Doty et al. | |
| 9,512,431 B2 | 12/2016 | Mirsky et al. | |
| 9,657,298 B2 | 5/2017 | Soto et al. | |
| 9,796,957 B2 | 10/2017 | Barney et al. | |
| 9,957,509 B2 | 5/2018 | Mirsky et al. | |
| 9,975,817 B2 | 5/2018 | Temme et al. | |
| 9,994,557 B2 | 6/2018 | Davidson et al. | |
| 10,384,983 B2 | 8/2019 | Temme et al. | |
| 10,525,318 B2 | 1/2020 | Dougherty | |
| 10,556,839 B2 | 2/2020 | Temme et al. | |
| 10,602,744 B2 | 3/2020 | Wigley et al. | |
| 10,662,432 B2 | 5/2020 | Mirsky et al. | |
| 10,919,814 B2 | 2/2021 | Temme et al. | |
| 10,934,226 B2 | 3/2021 | Temme et al. | |
| 10,968,446 B2 | 4/2021 | Zhao et al. | |
| 11,479,516 B2 | 10/2022 | Voigt et al. | |
| 11,565,979 B2 | 1/2023 | Temme et al. | |
| 11,678,667 B2 | 6/2023 | Reisinger et al. | |
| 11,678,668 B2 | 6/2023 | Reisinger et al. | |
| 11,739,032 B2 | 8/2023 | Temme et al. | |
| 11,946,162 B2 | 4/2024 | Zhao et al. | |
| 11,963,530 B2 | 4/2024 | Reisinger et al. | |
| 12,151,988 B2 | 11/2024 | Tamsir et al. | |
| 12,421,519 B2 * | 9/2025 | Higgins ............... C12N 1/205 |
| 2002/0061579 A1 | 5/2002 | Farrand et al. | |
| 2004/0197916 A1 | 10/2004 | Carozzi et al. | |
| 2004/0197917 A1 | 10/2004 | Carozzi et al. | |
| 2004/0210964 A1 | 10/2004 | Carozzi et al. | |
| 2004/0210965 A1 | 10/2004 | Carozzi et al. | |
| 2004/0216186 A1 | 10/2004 | Carozzi et al. | |
| 2004/0235663 A1 | 11/2004 | Cocking | |
| 2004/0241847 A1 | 12/2004 | Okuyama et al. | |
| 2004/0250311 A1 | 12/2004 | Carozzi et al. | |
| 2005/0081262 A1 | 4/2005 | Cook et al. | |
| 2005/0266541 A1 | 12/2005 | Dillon | |
| 2006/0033867 A1 | 2/2006 | Krisko et al. | |
| 2006/0096918 A1 | 5/2006 | Semmens | |
| 2006/0112447 A1 | 5/2006 | Bogdanova et al. | |
| 2006/0127988 A1 | 6/2006 | Wood et al. | |
| 2006/0191034 A1 | 8/2006 | Baum | |
| 2006/0243011 A1 | 11/2006 | Someus | |
| 2007/0249018 A1 | 10/2007 | Vemuri et al. | |
| 2008/0295207 A1 | 11/2008 | Baum et al. | |
| 2008/0311632 A1 | 12/2008 | Figge et al. | |
| 2009/0105076 A1 | 4/2009 | Stewart et al. | |
| 2009/0137390 A1 | 5/2009 | Triplett | |
| 2009/0144852 A1 | 6/2009 | Tomso et al. | |
| 2009/0152195 A1 | 6/2009 | Rodgers et al. | |
| 2009/0162477 A1 | 6/2009 | Nadel | |
| 2009/0221049 A1 | 9/2009 | Shaw et al. | |

(56)  References Cited

U.S. PATENT DOCUMENTS

| 2009/0258404 A1 | 10/2009 | Mikkelsen et al. |
| 2009/0308121 A1 | 12/2009 | Reddy et al. |
| 2010/0005543 A1 | 1/2010 | Sampson et al. |
| 2010/0017914 A1 | 1/2010 | Hart et al. |
| 2010/0028870 A1 | 2/2010 | Welch et al. |
| 2010/0184038 A1 | 7/2010 | Boddy et al. |
| 2010/0197592 A1 | 8/2010 | Heinrichs |
| 2010/0267147 A1 | 10/2010 | Qiao |
| 2010/0298211 A1 | 11/2010 | Carozzi et al. |
| 2011/0023184 A1 | 1/2011 | Desai et al. |
| 2011/0064710 A1 | 3/2011 | Benson et al. |
| 2011/0104690 A1 | 5/2011 | Yu et al. |
| 2011/0263488 A1 | 10/2011 | Carozzi et al. |
| 2012/0015409 A1 | 1/2012 | Tabata et al. |
| 2012/0015806 A1 | 1/2012 | Paikray et al. |
| 2012/0107889 A1 | 5/2012 | Doty et al. |
| 2012/0192605 A1 | 8/2012 | McSpadden Gardener et al. |
| 2012/0220006 A1 | 8/2012 | Hardwood et al. |
| 2012/0266332 A1 | 10/2012 | Kuykendall |
| 2012/0278954 A1 | 11/2012 | Bowen et al. |
| 2012/0284813 A1 | 11/2012 | Oliver et al. |
| 2012/0311745 A1 | 12/2012 | Meade et al. |
| 2012/0311746 A1 | 12/2012 | Meade et al. |
| 2012/0317681 A1 | 12/2012 | Meade et al. |
| 2012/0317682 A1 | 12/2012 | Meade et al. |
| 2012/0324605 A1 | 12/2012 | Meade et al. |
| 2012/0324606 A1 | 12/2012 | Meade et al. |
| 2012/0331589 A1 | 12/2012 | Meade et al. |
| 2012/0331590 A1 | 12/2012 | Meade et al. |
| 2013/0116170 A1 | 5/2013 | Graser et al. |
| 2013/0126428 A1 | 5/2013 | Jones et al. |
| 2013/0167268 A1 | 6/2013 | Narva et al. |
| 2013/0167269 A1 | 6/2013 | Narva et al. |
| 2014/0011261 A1 | 1/2014 | Wang et al. |
| 2014/0155283 A1 | 6/2014 | Venkateswaran et al. |
| 2014/0182018 A1 | 6/2014 | Lang et al. |
| 2014/0196178 A1 | 7/2014 | Zaltsman |
| 2014/0223598 A1 | 8/2014 | Sampson et al. |
| 2014/0223599 A1 | 8/2014 | Sampson et al. |
| 2014/0230504 A1 | 8/2014 | Finlayson et al. |
| 2014/0273226 A1 | 9/2014 | Wu |
| 2014/0283569 A1 | 9/2014 | Doty et al. |
| 2014/0301990 A1 | 10/2014 | Gregory et al. |
| 2014/0329326 A1 | 11/2014 | Mirsky et al. |
| 2014/0336050 A1 | 11/2014 | Soto et al. |
| 2015/0080261 A1 | 3/2015 | Wigley et al. |
| 2015/0101373 A1 | 4/2015 | Munusamy et al. |
| 2015/0128670 A1 | 5/2015 | Das |
| 2015/0237807 A1 | 8/2015 | Valiquette |
| 2015/0239789 A1 | 8/2015 | Kang et al. |
| 2015/0315570 A1 | 11/2015 | Zhao et al. |
| 2016/0174570 A1 | 6/2016 | Vukanovic et al. |
| 2016/0264929 A1 | 9/2016 | Barney et al. |
| 2016/0292355 A1 | 10/2016 | Lou et al. |
| 2016/0295868 A1 | 10/2016 | Jones et al. |
| 2016/0304842 A1 | 10/2016 | Donovan et al. |
| 2017/0035900 A1 | 2/2017 | Kowarik et al. |
| 2017/0086402 A1 | 3/2017 | Meadows-Smith et al. |
| 2017/0107160 A1 | 4/2017 | Newman et al. |
| 2017/0119690 A1 | 5/2017 | Hansen et al. |
| 2017/0152519 A1 | 6/2017 | Mirsky et al. |
| 2017/0267997 A1 | 9/2017 | Nicol et al. |
| 2017/0367349 A1 | 12/2017 | Gruver et al. |
| 2018/0002243 A1 | 1/2018 | Temme et al. |
| 2018/0020671 A1 | 1/2018 | Bioconsortia |
| 2018/0065896 A1 | 3/2018 | Ibema et al. |
| 2018/0073028 A1 | 3/2018 | Mirsky et al. |
| 2018/0273437 A1 | 9/2018 | Temme et al. |
| 2018/0290942 A1 | 10/2018 | Voigt et al. |
| 2018/0297905 A1 | 10/2018 | Temme et al. |
| 2018/0297906 A1 | 10/2018 | Temme et al. |
| 2019/0039964 A1* | 2/2019 | Temme ................. C12N 1/205 |
| 2019/0144352 A1 | 5/2019 | Temme et al. |
| 2020/0087221 A1 | 3/2020 | Temme et al. |
| 2020/0115715 A1 | 4/2020 | Mirsky et al. |
| 2020/0299637 A1 | 9/2020 | Voigt et al. |
| 2020/0308594 A1 | 10/2020 | Tamsir et al. |
| 2020/0331820 A1 | 10/2020 | Tamsir et al. |
| 2021/0009483 A1 | 1/2021 | Temme et al. |
| 2021/0163374 A1 | 6/2021 | Bioch et al. |
| 2021/0214282 A1 | 7/2021 | Temme et al. |
| 2021/0284995 A1 | 9/2021 | Zhao et al. |
| 2021/0315212 A1 | 10/2021 | Rezaei et al. |
| 2022/0017911 A1 | 1/2022 | Temme et al. |
| 2022/0079163 A1 | 3/2022 | Reisinger et al. |
| 2022/0106238 A1* | 4/2022 | Rezaei .................. A01N 25/00 |
| 2022/0127627 A1 | 4/2022 | Bloch et al. |
| 2022/0211048 A1 | 7/2022 | Temme et al. |
| 2022/0282340 A1 | 9/2022 | Ryu et al. |
| 2022/0411344 A1 | 12/2022 | Voigt et al. |
| 2023/0295559 A1 | 9/2023 | Eskiyenenturk et al. |
| 2024/0010576 A1 | 1/2024 | Temme et al. |
| 2024/0294953 A1 | 9/2024 | Eskiyenenturk et al. |
| 2024/0327851 A1 | 10/2024 | Tamsir et al. |
| 2024/0360465 A1* | 10/2024 | Wood .................. C12N 9/0095 |
| 2025/0115529 A1 | 4/2025 | Tamsir et al. |

FOREIGN PATENT DOCUMENTS

| CA | 2991776 | 1/2017 |
| CA | 3072466 A1 * | 2/2019 | ............. C05F 11/08 |
| CN | 1289852 | 4/2001 |
| CN | 1355293 | 6/2002 |
| CN | 1355294 | 6/2002 |
| CN | 1421527 | 6/2003 |
| CN | 1500801 | 6/2004 |
| CN | 1552846 | 12/2004 |
| CN | 1746304 | 3/2006 |
| CN | 101328477 | 12/2008 |
| CN | 101880676 | 11/2010 |
| CN | 101899430 | 12/2010 |
| CN | 102041241 | 5/2011 |
| CN | 102417882 | 4/2012 |
| CN | 102690808 | 9/2012 |
| CN | 103451130 | 12/2013 |
| CN | 103917657 | 7/2014 |
| CN | 104136599 | 11/2014 |
| CN | 104204211 | 12/2014 |
| CN | 106086042 | 11/2016 |
| EA | 002757 | 8/2002 |
| EP | 0256889 | 2/1988 |
| EP | 0292984 | 11/1988 |
| EP | 0339830 | 11/1989 |
| EP | 1535913 | 6/2005 |
| EP | 2186890 | 5/2010 |
| EP | 3231874 | 10/2017 |
| EP | 3322679 | 5/2018 |
| FR | 2494297 A1 | 5/1982 |
| FR | 2910230 | 6/2008 |
| JP | H01-225483 | 9/1989 |
| JP | H02-131581 | 5/1990 |
| JP | 2009-232721 | 10/2009 |
| JP | 2014-096996 | 5/2014 |
| JP | 2015-037385 | 2/2015 |
| JP | 2015-042633 | 3/2015 |
| JP | 2015-113274 | 6/2015 |
| JP | 2015-518023 | 6/2015 |
| JP | 2015-519352 | 7/2015 |
| JP | 2015-173652 | 10/2015 |
| JP | 2017-513480 | 6/2017 |
| RU | 94045882 | 9/1996 |
| WO | WO 1987/004182 | 7/1987 |
| WO | WO 1993/005154 | 3/1993 |
| WO | WO 1998/010088 | 3/1998 |
| WO | WO 1999/009834 | 3/1999 |
| WO | WO 2000/057183 | 9/2000 |
| WO | WO 2001/007567 | 2/2001 |
| WO | WO 2003/089640 A2 | 10/2003 |
| WO | WO 2004/074462 | 9/2004 |
| WO | WO 2005/021585 | 3/2005 |
| WO | WO 2005/038032 | 4/2005 |
| WO | WO 2006/005100 | 1/2006 |
| WO | WO 2006/083891 | 8/2006 |
| WO | WO 2006/098225 | 9/2006 |

(56) References Cited

FOREIGN PATENT DOCUMENTS

| WO | WO 2006/119457 | 11/2006 |
| WO | WO 2007/027776 | 3/2007 |
| WO | WO 2009/060012 | 5/2009 |
| WO | WO 2009/091557 | 7/2009 |
| WO | WO 2010/080184 | 7/2010 |
| WO | WO 2010/105226 A2 | 9/2010 |
| WO | WO 2011/099019 | 8/2011 |
| WO | WO 2011/099024 | 8/2011 |
| WO | WO 2011/103247 | 8/2011 |
| WO | WO 2011/103248 | 8/2011 |
| WO | WO 2011/154960 | 12/2011 |
| WO | WO 2012/139004 | 10/2012 |
| WO | WO 2012/154651 | 11/2012 |
| WO | WO 2012/174271 | 12/2012 |
| WO | WO 2012/174646 | 12/2012 |
| WO | WO 2013/076687 | 5/2013 |
| WO | WO 2013/132518 | 9/2013 |
| WO | WO 2014/042517 | 3/2014 |
| WO | WO 2014/071182 | 5/2014 |
| WO | WO 2014/201044 | 12/2014 |
| WO | WO 2016/016629 | 2/2016 |
| WO | WO 2016/016630 | 2/2016 |
| WO | WO 2016/048587 | 3/2016 |
| WO | WO 2016/100727 | 6/2016 |
| WO | WO 2016/146955 | 9/2016 |
| WO | WO 2016/172655 | 10/2016 |
| WO | WO 2016/178580 | 11/2016 |
| WO | WO 2016/179046 | 11/2016 |
| WO | WO 2016/181228 | 11/2016 |
| WO | WO 2016/191828 | 12/2016 |
| WO | WO 2017/011602 | 1/2017 |
| WO | WO 2017/042833 | 3/2017 |
| WO | WO 2017/062412 | 4/2017 |
| WO | WO 2017/069717 | 4/2017 |
| WO | WO 2017/112827 | 6/2017 |
| WO | WO 2017/085235 | 11/2017 |
| WO | WO 2017/203440 | 11/2017 |
| WO | WO 2018/081543 | 5/2018 |
| WO | WO 2018/132774 | 7/2018 |
| WO | WO 2018/133774 | 7/2018 |
| WO | WO 2019/032926 | 2/2019 |
| WO | WO 2019/084059 | 5/2019 |
| WO | WO 2019/084342 | 5/2019 |
| WO | WO 2019/140125 | 7/2019 |
| WO | WO 2020/006064 | 1/2020 |
| WO | WO 2020/006246 | 1/2020 |
| WO | WO 2020/014498 | 1/2020 |
| WO | WO 2020/023630 | 1/2020 |
| WO | WO 2020/061363 | 3/2020 |
| WO | WO 2020/092940 | 5/2020 |
| WO | WO 2020/118111 | 6/2020 |
| WO | WO 2020/146372 | 7/2020 |
| WO | WO 2020/163251 | 8/2020 |
| WO | WO 2020/190363 | 9/2020 |
| WO | WO 2020/191201 | 9/2020 |
| WO | WO 2020/219893 | 10/2020 |
| WO | WO 2020/219932 | 10/2020 |
| WO | WO 2021/113352 | 6/2021 |
| WO | WO 2021/146209 | 7/2021 |

OTHER PUBLICATIONS

Eberhart et al., "A methodology for markerless genetic modifications in *Azotobacter vinelandii*," Journal of Applied Microbiology, Jun. 2016, 120(6):1595-1604.

Galvão et al., "Adaptation of the Yeast URA3 Selection System to Gram-Negative Bacteria and Generation of a ΔbetCDE *Pseudomonas putida* Strain," Applied and Environmental Microbiology, Feb. 2005, 71(2): 883-892.

Martinez et al., "Symbiotic Autoregulation of nifA Expression in *Rhizobium leguminosarum* bv. *viciae*," J. Bacteriol., Oct. 2004, 186(19):6586-6594.

Parsons, "Physiological regulation of nitrogen fixation in soybean root nodules," Thesis for the degree of Doctor of Philosophy, Australian National University, Sep. 1989, pp. 3-4.

Priyanka et al., "Diversity Study of Nitrate Reducing Bacteria from Soil Samples—A Metagenomics Approach," Journal of Computer Science and Systems Biology, Jul. 2015, 8(4): 191-198.

Gruber et al., "Versatile plasmid-based expression systems for Gram-negative bacteria-General essentials exemplified with the bacterium *Ralstonia eutropha* H16," New Biotechnology, Dec. 25, 2015, 32(6):552-558.

Montañez et al., "Biological nitrogen fixation in maize (*Zea mays* L.) by $^{15}$N isotope-dilution and identification of associated culturable diazotrophs," Biology and Fertility of Soils, Feb. 2009, 45:253-263.

Riggs et al., "Enhanced maize productivity by inoculation with diazotrophic bacteria," Australian Journal of Plant Physiology, Sep. 3, 2001, 28(9):829-836 (Abstract only).

"New Plant Breeding Techniques," Science Council of Japan, retrieved from URL <http://www.scj.go.jp/ja/info/kohyo/pdf/kohyo-22-h140826.pdf>, Aug. 26, 2014, 88 pages (partial English translation).

"T7 RNA Polymerase Expression System for *Bacillus megaterium*," T7 RNAP Expression System Handbook, Jan. 2010, © MoBiTec GmbH, 18 pages.

40 CFR 725.3 U.S. Government Publishing Office (Jul. 1, 2010) https://www.gpo.gov/fdsys/pkg/CFR-2010-title40-vol30/pdf/CFR-2010-title40-vol30-sec725-3.pdf (Year: 2010), 3 pages.

Abd-Elhafeez et al., "Isolation and characterization of *Enterobacter* strains causing potato soft rot disease in Egypt," Minia Science Bulletin, 2018, 29(1):1-13.

Aita, T., Husimi, Y. "Adaptive walks by the fittest among finite random mutants on a Mt. Fugi-type fitness landscape," J. Theor. Biol. 193:383-405 (1998).

Alper et al., "Tuning genetic control through promoter engineering," Proc Natl Acad Sci U SA, 2005, 102(36):12678-12683.

Altschul et al. "Basic local alignment search tool," J Mol Biol., 1990, 215(3):403-441.

Altschul et al., "Gapped BLAST and PSI-BLAST: a new generation of protein database search programs," Nucleic Acids Res., 1997, 25:3389-3402.

Amalraj et al., "Effect of Polymeric Additives, Adjuvants, Surfactants on Survival, Stability and Plant Growth Promoting Ability of Liquid Bioinoculants," J. Plant Physiol Pathol, 2013, 1:2, 6 pages.

Ambrosio et al., "Metabolic engineering of a diazotrophic bacterium improves ammonium release and biofertilization of plants and microalgae," Metab Eng., Mar. 2017, 40:59-68.

An et al., "Constitutive expression of the nifA gene activates associative nitrogen fixation of *Enterobacter gergoviae* 57-7, an opportunistic endophytic diazotroph," Journal of Applied Microbiology, 2007, 103(3):613-620.

Andersen et al., "Energetics of biological nitrogen fixation: determination of the ratio of formation of $H_2$ to $NH_4^+$ catalysed by nitrogenase of *Klebsiella pneumoniae* in vivo," J Gen Microbial., Nov. 1977, 103(1):107-22.

Andersen et al., "Herpesvirus-mediated gene delivery into the rat brain: specificity and efficiency of the neuron-specific enolase promoter," Cell. Mol. Neurobiol., 1993, 13:503-515.

Anderson et al., "BglBricks: A flexible standard for biological part assembly," Journal of Biological Engineering, 2010, 4:1, 12 pages.

Andrews et al., "Use of Nitrogen Fixing Bacteria Inoculants as a Substitute for Nitrogen Fertiliser for Dryland Graminaceous Crops: Progress Made, Mechanisms of Action and Future Potential," Symbiosis, 2003, 34:21 pages.

Andrianantoandro et al., "Synthetic biology: new engineering rules for an emerging discipline," Mol. Syst. Biol., 2006, 2:2006.0028, 14 pages.

Aquino et al., "Effect of point mutations on *Herbaspirillum seropedicae* NifA activity," Brazilian Journal of Medical and Biological Research, Aug. 2015, 48(8):683-690.

Arbuthnot et al., "In vitro and in vivo hepatoma cell-specific expression of a gene transferred with an adenoviral vector," Hum Gene Ther., 1996, 7(13):1503-1514.

(56)         References Cited

OTHER PUBLICATIONS

Arnold et al., "Nucleotide sequence of a 24,206-base-pair DNA fragment carrying the entire nitrogen fixation gene cluster of *Klebsiella pneumoniae*," J. Mol. Biol., 1988, 203(3):715-738.

Arriel-Elias et al., "Shelf life enhancement of plant growth promoting rhizobacteria using a simple formulation screening method," African Journal of Microbiology Research, Feb. 2018, 12(5):115-126.

Arsene et al., "Modulation of NifA activity by PII in *Azospirillum brasilense*: Evidence for a Regulatory role of the NifA N-Terminal Domain," Journal of Bacteriology, Aug. 1996, 178(16):4830-4838.

Associative and Endophytic Nitrogen-fixing Bacteria and Cyanobacterial Association, C. Elmerich and W. E. Newton (eds.), 2007, Chapter 3, 31 pages.

Austin et al. "Characterisation of the *Klebsiella pneumoniae* nitrogen-fixation regulatory proteins NIFA and NIFL in vitro," Eur J Biochem., 1990, 187(2):353-360.

Ausubel et al., "Glutamine Synthetase Mutations Which Affect Expression of Nitrogen Fixation Genes in *Klebsiella pneumoniae*," J Bacteriol, Nov. 1979, 140(2):597-606.

Bageshwar et al., "An Environmentally Friendly Engineered *Azotobacter* Strain That Replaces a Substantial Amount of Urea Fertilizer while Sustaining the Same Wheat Yield," Appl Environ Microbial., Aug. 2017, 83(15):e00590-17.

Bali et al., "Excretion of Ammonium by a nifL Mutant of *Azotobacter vinelandii* Fixing Nitrogen," Applied and Environmental Microbiology, May 1992, 58(5):1711-1718.

Barney et al., "Gene deletions resulting in increased nitrogen release by *Azotobacter vinelandii*: application of a novel nitrogen biosensor," Appl. Environ. Microbial., Jul. 2015, 81(13):4316-4328.

Barney et al., "Transcriptional analysis of an ammonium-excreting stain of *Azotobacter vinelandii* deregulated for nitrogen fixation," Appl. Environ. Microbial. Jul. 2017, 83(20):1-22.

Barrangou et al., "Exploiting CRISPR-Cas immune systems for genome editing in bacteria," Curr. Opin. Biotechnol., Nov. 2016, 37:61-68.

Bashor, "Understanding biological regulation through synthetic biology," Annu. Rev. Biophys., May 2018, 47:399-423, 52 pages.

Batista et al. "Manipulating nitrogen regulation in diazotrophic bacteria for agronomic benefit," Biochem Soc Trans., 2019, 47(2):603-614.

Batzer et al., "Enhanced evolutionary PCR using oligonucleotides with inosine at the 3'-termins," Nucleic Acid Res., 1991, 19:5081, 1 page.

Baum et al., "Control of coleopteran insect pests through RNA interference," Nature Biotechnology, Nov. 2007, 25(11):1322-1326.

Bayer et al., "Synthesis of Methyl Halides from Biomass Using Engineered Microbes," J. Am. Chem. Soc., 2009, 131(18):6508-6515.

Becker et al., "Comparative Genomics Reveal a Flagellar System, a Type VI Secretion System and Plant Growth-Promoting Gene Clusters Unique to the Endophytic Bacterium *Kosakonia radicincitans*," Front Microbiol., Aug. 2018, 9(1997):1-22.

Bender et al., "Regulatory mutations in the *Klebsiella aerogenes* structural gene for glutamine synthetase," J Bacteriol., Oct. 1977, 132(1):100-105.

Berge et al., "*Rahnella aquatilis*, a nitrogen-fixing enteric bacterium associated with the rhizosphere of wheat and maize," Canadian Journal of Microbiology, 1991, 37(3):195-203.

Berger et al., "Successful Formulation and Application of Plant Growth-Promoting *Kosakonia radicincitans* in Maize Cultivation," Biomed Res. Int., Mar. 2018, 8 pages.

Berger et al., "The plant growth-promoting bacterium *Kosakonia radicincitans* improves fruit yield and quality of *Solanum lycopersicum*," J. Sci. Food Agric., Apr. 2017, 97(14):4865-4871.

Beringer et al., "Genetic engineering and nitrogen fixation," Biotech. Gen. Eng. Rev., Feb. 1984, 1(1):65-88.

Berninger et al., "Maintenance and assessment of cell viability in formulation of non-sporulating bacterial inoculants," Microb. Biotechnol., Mar. 2018, 11(2):277-301 (2018); doi: 10.1111/1751-7915.12880.

Beynon et al., "The nif promoters of *Klebsiella pneumoniae* have a characteristic primary structure," Cell, 1983, 34(2):665-671.

Bhattacharjee et al., "Use of nitrogen-fixing bacteria as biofertiliser for non-legumes: prospects and challenges," Applied Microbiology and Biotechnology, Jul. 2008, 80:199-209.

Biggins et al., "Metabolites from the induced expression of cryptic single operons found in the genome of *Burkolderia pseudomallei*," JACS, 2011, 133:1638-1641.

Bikard et al., "The synthetic integron: an in vivo genetic shuffling device," Nucleic Acids Res., 2010, 38(15):e153, 7 pages.

Bilitchenko et al., "Eugene—a domain specific language for specifying and constraining synthetic biological parts, devices, and systems," PLoS One, Apr. 2011, 6(4):e18882, 12 pages.

Bittner et al., "RpoS and RpoN are involved in the growth-dependent regulation of rfaH transcription and O antigen expression in *Salmonella enterica* serovar *typhi*," Microbial Pathogenesis, Jan. 2004, 36(1):19-24.

Blanco et al., "Sequence and molecular analysis of the nifL gene of *Azotobacter vinelandii*." Mol Microbial. Aug. 1993, 9(4):869-79.

Blast.ncbi.nlm.nih.gov, [online], "BLAST. Basic local alignment search tool," 2021, retrieved on Apr. 8, 2021, retrieved from URL<https://blast.ncbi.nlm.nih.gov/Blast.cgi>, 3 pages.

Bloch et al., "Biological nitrogen fixation in maize: optimizing nitrogenase expression in a root-associated diazotroph," Journal of Experimental Botany, Jul. 2020, 71(15):4591-4603.

Bonde et al., "MODEST: a web-based design tool for oligonucleotide-mediated genome engineering and recombineering," Nucleic Acids Res., 2014, 42(W1):W408-W415.

Boshart et al. "A very strong enhancer is located upstream of an immediate early gene of human cytomegalovirus," Cell, 1985, 41(2):521-30.

Bosmans et al., "Sea anemone venom as a source of insecticidal peptides acting on voltage-gated Na+ channels," Toxicon, Mar. 2007, 49(4):550-560.

Bosworth et al., "Alfalfa yield response to inoculation with recombinant strains of *Rhizobium meliloti* with an extra copy of dctABD and/or modified nifA expression," Appl Environ Microbial. Oct. 1994, 60(10):3815-32.

Boyle et al., "Tools for genome-wide strain design and construction," Curr Opin Biotechnol., 2012, 23(5):666-671.

Brady et al., "Taxonomic evaluation of the genus *Enterobacter* based on multilocus sequence analysis (MLSA): Proposal to reclassify *E. nimipressuralis* and *E. amnigenus* into *Lelliottia* gen. nov. as *Lelliottia nimipressuralis* comb. nov. and *Lelliottia amnigena* comb. nov., respectively, *E. gergoviae* and *E. pyrinus* into *Pluralibacter* gen. nov. as *Pluralibacter gergoviae* comb. nov. and *Pluralibacter pyrinus* comb. nov., respectively, *E. cowanii*, *E. radicincitans*, *E. oryzae* and *E. arachidis* into *Kosakonia* gen. nov. as *Kosakonia cowanii* comb. nov., *Kosakonia radicincitans* comb. nov., *Kosakonia oryzae* comb. nov. and *Kosakonia arachidis* comb. nov., respectively, and *E. turicensis*, *E. helveticus* and *E. pulveris* into *Cronobacter* as *Cronobacter zurichensis* nom. nov., *Cronobacter helveticus* comb. nov. and *Cronobacter pulveris* comb. nov., respectively, and emended description of the genera *Enterobacter* and *Cronobacter*," Syst. Appl. Microbiol., Jul. 2013, 36(5):309-319.

Brandl et al., "*Salmonella* interactions with plants and their associated microbiota," Phytopathology, 2013, 103:316-325.

Brewin et al., "The Basis of Ammonium release in nifL Mutants of *Azotobacter vinelandii*," Journal of Bacteriology, Dec. 1999, 181(23):7356-7362.

Buchanan-Wollaston et al., "Role of the nifA gene product in the regulation of nif expression in *Klebsiella pneumoniae*," Nature., Dec. 1981, 294(5843):776-8.

Buck et al., "Frameshifts close to the *Klebsiella pneumoniae* nifH promoter prevent multicopy inhibition by hybrid nifH plasmids," Mol. Gen. Genet., 1987, 207(2-3):492-498.

Buckley Lab NifH database, retrieved via WayBack Machine from URL <http://www.css.cornell.edu/faculty/buckley/nifh.htm>, available on or before Jan. 10, 2018, 2 pages.

(56)        References Cited

OTHER PUBLICATIONS

Buddrus-Schiemann et al., "Root colonization by *Pseudomonas* sp. DSMZ 13134 and impact on the indigenous rhizosphere bacterial community of barley." Microb Ecol. Aug. 2010, 60(2):381-393.

Burris et al., "Nitrogenases," J. Biol. Chem., 1991, 266(15):9339-9342.

Cardinale et al., "Contextualizing context for synthetic biology identifying causes of failure of synthetic biological systems," Biotechnol. J., 2012, 7:856-866.

Carr et al., "Enhanced multiplex genome engineering through co-operative oligonucleotide coselection," Nucleic Acids Res., 2012, 40(17):e132, 11 pages.

cera-gmc.org [online], "GM Crop Database," Center for Environmental Risk Assessment (CERA), 2010, retrieved from URL <http://ucbiotech.org/biotech_info/PDFs/Center_for_Environmental_Risk_Assessment_CERA_2011_GM_Crop_Database.pdf>, 1 page.

cerestrust.org [online]. "Year-end Final Report" Young et al., Ceres Trust, retrieved from URL <https://cerestrust.org/wpcontent/uploads/NitrogenFixingBacteriaCorn.pdf>, 2012, 9 pages.

Chakroun et al., "Bacterial Vegetative Insecticidal Proteins (Vip) from Entomopathogenic Bacteria," Microbiol Mol Biol Rev., Mar. 2016, 80(2):329-50.

Chan et al., "Refactoring bacteriophage T7," Molecular Systems Biology, 2005, 1(1):E1-E10.

Chen et al., "Characterization of 582 natural and synthetic terminators and quantification of their design constraints," Nat. Methods, 2013, 10:659-664.

Chen et al., "Complete genome sequence of *Kosakonia sacchari* type strain SP1 T," Stand Genomic Sci., Jun. 15, 2014, 9(3):1311-1318.

Chen et al., "Expression of rat bone sialoprotein promoter in transgenic mice," J Bone Miner Res., May 1996, 11(5):654-64.

Chiang et al., "Mutagenic Oligonucleotide-directed PCR Amplification (Mod-PCR): An Efficient Method for Generating Random Base Substitution Mutations in a DNA sequence element," PCR methods and applications, 1993, 2:210-217.

Chin, "Programming and engineering biological networks," Curr. Opin. Struct. Biol., 2006, 16:551-556.

Choi et al., "A Tn7-based broad-range bacterial cloning and expression system," Nat Methods, Jun. 2005, 2(6):443-8.

Choudhary et al., "Interactions of *Bacillus* spp. and Plants—With Special Reference to Induced Systemic Resistance (ISR)," Microbiological Research, 2009, 164(5):493-513.

Clancy et al., "The domains carrying the opposing activities in adenylyltransferase are separated by a central regulatory domain," FEBS Journal, 2007, 274(11):2865-2877.

Cobb et al., "Directed evolution: an evolving and enabling synthetic biology tool," Curr Opin Chem Biol., Aug. 2012, 16(3-4):285-91.

Cohen, "In vitro Tomato Fruit Cultures Demonstrate a Role for Indole-3-acetic Acid in Regulating Fruit Ripening," J. Amer. Soc. Hort. Sci., 1996, 121(3):520-524.

Colby, "Calculating Synergistic and Antagonistic Responses of Herbicide Combinations," Weeds, Jan. 1967, 15(1):20-22, 4 pages.

Colebatch et al., "Symbiotic nitrogen fixation research in the postgenomics era," New Phytologist., 2002, 153(1):37-42.

Colnaghi et al., "Lethality of glnD null mutations in *Azotobacter vinelandii* is suppressible by prevention of glutamine synthetase adenylylation," Microbiology, May 2001, 147(Pt 5):1267-76.

Colnaghi et al., "Strategies for increased ammonium production in free-living or plant associated nitrogen fixing bacteria," Plant and Soil, Nov. 1997, 194:145-154.

Compant et al., "A review on the plant microbiome: Ecology, functions, and emerging trends in microbial application," Journal of Advanced Research, Sep. 2019, 19:29-37.

Conniff, "Microbes Help Grow Better Crops," (Sep. 1, 2013) Scientific American. Retrieved from URL <https://www.scientificamerican.com/article/microbes-helpgrow-better-crops/>, (Year: 2013), 7 pages.

Contreras et al., "The product of the nitrogen fixation regulatory gene nfrX of *Azotobacter vinelandii* is functionally and structurally homologous to the uridylyltransferase encoded by glnD in enteric bacteria." J Bacterial. Dec. 1991, 173(24):7741-7749.

Cornelis et al., "The type III secretion injectisome," Nature Reviews Microbiology, 2006, 4(11):811-825.

Costerton et al., "Microbial Biofilms," Annu. Rev. Microbial., Oct. 1995, 49:711-745.

Crameri et al., "Molecular evolution of an arsenate detoxification pathway by DNA shuffling," Nat. Biotechnol., 1997, 15:436-438.

Crickmore et al., "Revision of the Nomenclature for the *Bacillus thuringiensis* Pesticidal Crystal Proteins," Microbiol Mol Biol Rev., Sep. 1998, 62(3):807-813.

Crook et al., "Re-engineering multicloning sites for function and convenience," Nucl. Acids Res., 2011, 39:e92, 10 pages.

Curatti et al., "Genes required for rapid expression of nitrogenase activity in *Azotobacter vinelandii*," PNAS, May 2005, 102(18):6291-6296.

Czar et al., "Gene synthesis demystified," Trends Biotechnol, 2009, 27(2):63-72.

Da Silva et al., "Survival of endophytic bacteria in polymer-based inoculants and efficiency of their application to sugarcane," Plant Soil, May 2012, 356:231-243.

Dandekar et al., "Conservation of gene order: a fingerprint of proteins that physically interact," Trends Biochem. Sci., 1998, 23:324-328.

Das et al., "Microbial assay of $N_2$ fixation rate, a simple alternate for acetylene reduction assay," MethodsX, 2018, 5:909-914.

Datsenko et al., "One-step inactivation of chromosomal genes in *Escherichia coli* K-12 using PCR products," PNAS, Jun. 2000, 97(12):6640-6645.

Davin-Regli et al., "*Enterobacter aerogenes* and *Enterobacter cloacae*; versatile bacterial pathogens confronting antibiotic treatment," Front. Microbiol., 2015, 6:392, 10 pages.

De Bruijn et al., "The Cloning and characterization of the glnF (ntrA) Gene of *Klebsiella pneumoniae*: Role of glnF (ntrA) in the Regulation of Nitrogen Fixation (nif) and other Nitrogen assimilation genes," Mol. Genet., Aug. 1983, 192:342-353.

De Freitas, "Yield and N assimilation of winter wheat (*Triticum aestivum* L., var. *Norstar*) inoculated with rhizobacteria," Pedobiologia, Jan. 2000, 44(2):97-104.

De Raad et al., "A solid-phase platform for combinatorial and scarless multipart gene assembly," ACS Synth. Biol., 2013, 2:316-326.

Delaux et al., "Tracing the evolutionary path to nitrogen-fixing crops." Curr. Opin. Plant Biol., Jun. 2015, 26:95-99.

Dent et al., "Establishing symbiotic nitrogen fixation in cereals and other non-legume crops: The greener nitrogen revolution," Agric & Food Secur, Dec. 2017, 6(7):1-9.

Desnoues et al., "Nitrogen fixation genetics and regulation in a *Pseudomonas stutzeri* strain associated with rice," Microbiology, May 2003, 149:2251-2262.

Dessaux et al., "Engineering the Rhizosphere," Trends in Plant Science, Mar. 2016, 21(3):266-278.

Dixon et al., "Genetic regulation of biological nitrogen fixation," Nature Reviews, Aug. 2004, 2:621-631.

Dixon et al., "Genetic transfer of nitrogen fixation from *Klebsiella pneumoniae* to *Escherichia coli*," Nature, 1972, 237(5350):102-103.

Dong et al., "Kinetics and Strain Specificity of Rhizosphere and Endophytic Colonization by Enteric Bacteria on Seedlings of *Medicago sativa* and *Medicago truncatula*," Appl Environ Microbial., Mar. 2003, 69(3):1783-1790.

Doroshchuk et al., "Regulation of nitrogen metabolism in gram-positive bacteria," Molecular Biology, 2006, 40(5):829-836.

Dos Santos et al., "Distribution of nitrogen fixation and nitrogenase-like sequences amongst microbial genomes," BMC Genomics, Dec. 2012, 13(1):162, 12 pages.

Drummond et al., "Expression from the nifB promoter of *Azotobacter vinelandii* Can Be Activated by NifA, VnfA, or AnfA Transcriptional Activators," Journal of Bacteriology, Feb. 1996, 178(3):788-792.

Du et al., "Customized optimization of metabolic pathways by combinatorial transcriptional engineering," Nucleic Acids Res., Oct. 2012, 40(18):e142, 10 pages.

(56) References Cited

OTHER PUBLICATIONS

Duca et al., "Indole-3-acetic acid in plant-microbe interactions," Antonie van Leeuwenhoek, Jan. 2014, 106(1):85-125, 41 pages.

Dunican et al., "Genetic transfer of nitrogen fixation from *Rhizobium trifolii* to *Klebsiella aerogenes*," Biochemical and Biophysical Research Communications, Mar. 1974, 57(1):62-72.

Dykxhoorn et al., "A set of compatible tac promoter expression vectors," Gene, 1996, 177(1-2):133-136.

Easter et al., "Role of the parCBA Operon of the Broad-Host-Range Plasmid RK2 in Stable Plasmid Maintenance," Journal Of Bacteriology, 1998, 180(22):6023-6030.

Egener et al., "Identification of NifL-like protein in a diazotroph of the b-subgroup of the Proteobacteria, *Azoarcus* sp. strain BH72," Microbiology, Oct. 2002, 148(10):3203-3212.

Emboss. Emboss Needle: Pairwise Sequence Alignment (Nucleotide). Available at URL<http://www.ebi.ac.uk/Tools/psa/emboss_needle/nucleotide.html>, Accessed on Oct. 10, 2016, 1 page.

Emboss. Emboss Water: Pairwise Sequence Alignment (Nucleotide). Available at URL<http://www.ebi.ac.uk/Tools/psa/emboss_water/nucleotide.html>, Accessed on Oct. 10, 2016, 1 page.

Endy et al., "Foundations for engineering biology," Nature, 2005, 438:449-453.

Engler et al., "A one pot, one step, precision cloning method with high throughput capability, " PLoS One, 2008, 3(11):e3647, 7 pages.

Engler et al., "Golden gate shuffling: a one-pot DNA shuffling method based on type lls restriction enzymes," PLoS One, 2009, 4(5):e5553, 9 pages.

Enkh-Amgalan et al., "Molecular evolution of the nif gene cluster carrying nifI1 and nifI2 genes in the Gram-positive phototrophic bacterium *Heliobacterium chlorum*," International Journal of Systematic and Evolutionary Microbiology, 2006, 56:65-74.

Estrem et al., "Identification of an UP element consensus sequence for bacterial promoters," PNAS, 1998, 95(11):9761-9766.

European Partial Supplementary Search Report Appln. No. 16825147.8 dated Mar. 4, 2019, 21 pages.

European Partial Supplementary Search Report Appln. No. 19826654.6 dated Mar. 17, 2022, 11 pages.

European Partial Supplementary Search Report in European Appln. No. 18843845.1, dated Apr. 12, 2021, 17 pages.

European Partial Supplementary Search Report in European Appln. No. 18870036.3, dated Aug. 19, 2021, 19 pages.

European Supplementary Partial Search Report in International Appln. No. 18739050.5, dated Oct. 27, 2020, 18 pages.

Extended European Search Report in European Appln. No. 12800054.4, mailed Dec. 19, 2014, 8 pages.

Extended European Search Report in European Appln. No. 16825147.8, dated Jun. 6, 2019, 19 pages.

Extended European Search Report in European Appln. No. 16854192.8, dated Feb. 20, 2019, 11 pages.

Extended European Search Report in European Appln. No. 18739050.5, dated Feb. 1, 2021, 22 pages.

Extended European Search Report in European Appln. No. 18843845.1, dated Jul. 22, 2021, 20 pages.

Extended European Search Report in European Appln. No. 18870036.3, dated Dec. 14, 2021, 28 pages.

Extended European Search Report in European Appln. No. 18870346.6, dated Jul. 22, 2021, 5 pages.

Extended European Search Report in European Appln. No. 19186353.9, dated Nov. 13, 2019, 9 pages.

Extended European Search Report in European Appln. No. 19826654.6, dated Jul. 4, 2022, 16 pages.

Extended European Search Report in European Appln. No. 19833252.0, dated Mar. 14, 2022, 7 pages.

Eyraud et al., "Expression and Biological Activity of the Cystine Knot Bioinsecticide PA1b (Pea Albumin 1 Subunit b)," PLOS One, Dec. 2013, 8(12):e81619, 9 pages.

Fani et al., "Molecular evolution of nitrogen fixation: the evolutionary history of the nifD, nifK, nifE, and nifN gene," J. Mol. Evol., 2000, 51(1):1-11.

Feher et al. "In the fast lane: large-scale bacterial genome engineering," J Biotechnol., Jul. 2012, 160(1-2):72-9.

Fernandes et al., "Glutamine synthetase stabilizes the binding of GlnR to nitrogen fixation gene operators," The FEBS Journal, Feb. 2017, 284(6):903-918.

Ferrières et al., "The yjbEFGH locus in *Escherichia coli* K-12 is an operon encoding proteins involved in exopolysaccharide production," Microbiology, Apr. 2007, 153(Pt 4):1070-80.

Fischbach et al., "Prokaryotic gene clusters: A rich toolbox for synthetic biology," Biotechnology Journal, 2010, 15(12):1277-1296.

Fischbach et al., "The evolution of gene collectives: how natural selection drives chemical innovation," Proc. Natl. Acad. Sci. USA, 2008, 105:4601-4608.

Fisher et al., "Mutations in the *Bacillus subtilis* glnRA Operon that Cause Nitrogen Source-Dependent Defects in Regulation of TnrA Activity," Journal of Bacteriology, Aug. 2002, 184(16):4636-4639.

Fisher et al., "Novel trans-Acting *Bacillus subtilis* glnA Mutations that Derepress glnRA Expression," Journal of Bacteriology, Apr. 2009, 191(8):2485-2492.

Flores-Núñez et al., "Functional Signatures of the Epiphytic Prokaryotic Microbiome of Agaves and Cacti," Front Microbiol., Jan. 2020, 10(3044):1-13.

Fontana et al., "RNA folding and combinatory landscapes," Phys. Rev. E., 1993, 47:2083-2099.

Forner et al., "Treatment of hepatocellular carcinoma," Crit Rev Oncol Hematol., Nov. 2006, 60(2):89-98.

Fox et al., "Major cereal crops benefit from biological nitrogen fixation when inoculated with the nitrogen-fixing bacterium *Pseudomonas protegens* Pf-5 X940." Environmental Microbiology, 2016, 18(10):3522-3534.

Frasch et al., "Design-based re-engineering of biosynthetic gene clusters: plug-and-play in practice," Curr Opin Biotechnol., Dec. 2013, 24(6):1144-50.

Gaby et al., "A comprehensive aligned nifHI gene database: a multipurpose tool for studies of nitrogen-fixing bacteria," Database, 2014, 2014:bau001, 8 pages.

Gamer et al., "A T7 RNA polymerase-dependent gene expression system for *Bacillus megaterium*," Appl Micro Biol Biotechnol., Apr. 2009, 82(6):1195-203.

Gao et al., "Groundwater nitrogen pollution and assessment of its health risks: a case study of a typical village in rural-urban continuum, China," PLoS One, Apr. 2012, 7(4):e33982, 8 pages.

Gebeyehu et al., "Novel biotinylated nucleotide-analogs for labeling and colorimetric detection of DNA," Nucl. Acids Res., 1987, 15:4513, 22 pages.

Geddes et al., "Use of plant colonizing bacteria as chassis for transfer of N$_2$-fixation to cereals." Curr. Opin. Biotechnol. 2015, 32:216-222.

GenBank Accession No. CP007215.3, "*Kosakonia sacchari* SP1 chromosome, complete genome," Sep. 19, 2017, 729 pages.

GenBank Accession No. CP016337.1 "*Kosakonia sacchari* strain BO-1 chromosome, complete genome," Jul. 11, 2016, 1119 pages.

Georg et al., "cis-antisense RNA, another level of gene regulation in bacteria," Microbiol. Mol. Biol. Rev., 2011, 75(2):286-300.

Gibson et al., "Chemical synthesis of the mouse mitochondrial genome," Nat. Methods, 2010, 7:901-903.

Gibson et al., "Enzymatic assembly of DNA molecules up to several hundred kilobases," Nat Methods, 2009, 6(5):343-345.

Gibson, "Physical Environment and Symbiotic Nitrogen Fixation," Australian Journal of Biological Sciences, 1963, 16(1):28-42.

Giri, "The First Report of Indigenous Free-Living Diazotroph *Kosakonia sacchari* Isolated from Himalayan Alder-Based Shifting Cultivation System in Nagaland, India," Journal of Soil Science and Plant Nutrition, Apr. 2019, 19:574-579.

Gosink et al., "The product of the *Klebsiella pneumoniae* nifX gene is a negative regulator of the nitrogen fixation (nif) regulon," J Bacteriology, 1990, 172(3):1441-1447.

Gossen et al., "Tight control of gene expression in mammalian cells by tetracycline-responsive promoters," PNAS USA, 1992, 89(12):5547-5551.

Gossen et al., "Transcriptional activation by tetracyclines in mammalian cells," Science, 1995, 268(5218):1766-1769.

(56) References Cited

OTHER PUBLICATIONS

Gottelt et al., "Deletion of a regulatory gene within the cpk gene cluster reveals novel antibacterial activity in *Streptomyces coelicolor* A3(2)," Microbiology, 2010, 156:2343-2353.

Govantes et al., "Mechanism of coordinated synthesis of the antagonistic regulatory proteins NifL and NifA of *Klebsiella pneumoniae*," J Bacterial. Dec. 1996, 178(23):6817-6823.

Gu et al., "*Enterobacter xiangfangensis* sp. nov., isolated from Chinese traditional sourdough, and reclassification of *Enterobacter sacchari* Zhu et al. 2013 as *Kosakonia sacchari* comb. nov.," Int. J. Syst. Evo. Micro., Aug. 2014, 64(Pt8):2650-2656.

Guell et al., "Bacterial transcriptomics: what is beyond the RNA horiz-ome?," Nature Reviews Microbiology, 2011, 9(9):658-669.

Guell et al., "Transcriptome complexity in a genome-reduced bacterium," Science, 2009, 326:1268-1271.

Guo et al., "Discovery of Reactive Microbiota-Derived Metabolites that Inhibit Host Proteases," Cell, Jan. 2017, 168(3):517-526, e18.

Haapalainen et al., "Soluble plant cell signals induce the expression of the type Ill secretion system of *Pseudomonas syringae* and upregulate the production of pilus protein HrpA," Mol. Plant Microbe Interact., 2009, 22:282-290.

Hale et al., "An efficient stress-free strategy to displace stable bacterial plasmids," BioTechniques, Mar. 2010, 48:223-228.

Hansal et al., "Cutting Edge: Induction of antigen-specific hyporesponsiveness by transplantation of hemopoietic cells containing an MHC class I transgene regulated by a lymphocyte-specific promoter," J Immunol., Aug. 1998, 161(3):1063-8.

Harvey et al., "Inducible control of gene expression: prospects for gene therapy," Curr Opin Chem Biol., Aug. 1998, 2(4):512-8.

Herlache et al., "Characterization of the Agrobacterium vitis pehA gene and comparison of the encoded polygalacturonase with the homologous enzymes from Erwinia carotovora and Ralstonia solanacearum," Appl Environ Microbial., Jan. 1997, 63(1):338-346.

Hernandez et al., "Biochemical analysis of the recombinant Fur (ferric uptake regulator) protein from *Anabaena* PCC 7119: factors affecting its oligomerization state," Biochem. J., 2002, 366:315-322.

Hett, "Bacterial Growth and Cell Division: a Mycobacterial Perspective," Microbiology and Molecular Biology Reviews, Mar. 2008, 72(1):126-156.

Hidaka et al., "Promotion of the Growth of Rice by Inoculation of Nitrogen-Fixing- Activity-Enhanced Bacteria to the Rhizosphere," Nitrogen Fixation: From Molecules to Crop Productivity (Part of the Current Plant Science and Biotechnology in Agriculture book series (PSBA, vol. 38)), 2002, p. 445.

Higdon et al., "Genomic characterization of a diazotrophic microbiota associated with maize aerial root mucilage," PLoS ONE, Sep. 2020, 26 pages.

Hoeschle-Zeledon et al., "Regulatory challenges for biological control, " The CGIAR Systemwide Program on Integrated Pest Management, Jan. 2013, SP-IPM Secretariat, International Institute of Tropical Agriculture (IITA), Ibadan, Nigeria, 53 pages.

Holden et al., "Colonization outwith the colon: plants as an alternative environmental reservoir for human pathogenic enterobacteria," FEMS Microbiol. Rev., 2009, 33:689-703.

Hosseini-Abari et al., "LC/MS detection of oligogalacturonic acids obtained from tragacanth degradation by pectinase producing bacteria," J Basic Microbiol., Dec. 2018, 59(3):249-255.

Hu et al., "Application of bryophyte rhizoid-associated bacteria increases silicon accumulation and growth in maize (*Zea mays* L.) seedlings," App. Ecol. Env. Res., Oct. 2019, 17(6):13423-13433.

Hu et al., "Assembly of nitrogenase MoFe protein," Biochemistry, 2008, 47(13):3973-3981.

Hunter, "'Genetically Modified Lite' placates public but not activists," EMBO Reports, Jan. 2014, 15(2):138-141.

Huynen et al., "Smoothness within ruggedness: the role of neutrality in adaptation," Proc. Natl. Acad. Sci. USA, 1996, 93:397-401.

Iber, "A quantitative study of the benefits of co-regulation using the spoIIA operon as an example," Mol. Sys. Biol., 2006, 2:1-6.

Idalia et al., "*Escherichia coli* as a model organism and its application in biotechnology," Recent Advances on Physiology, Pathogenesis, and Biotechnological Applications, Chapter 13, 2017, pp. 253-274.

Iniguez et al., "Nitrogen Fixation in Wheat Provided by *Klebsiella pneumoniae* 342," MPMI, 2004, 17(10):1078-1085.

Iniguez et al., "Regulation of Enteric Endophytic Bacterial Colonization by Plant Defense," MPMI, 2005, 18(2):169-178.

Intechopen.com, [online], "*Escherichia coli* as a Model Organism and Its Application in Biotechnology, IntechOpen," 2020, retrieved on Mar. 31, 2020, retrieved from URL<https://www.intechopen.com/books/-i-escherichia-coli-i-recent-advances-on-physiology-pathogenesis-and-biotechnological-applications/-i-escherichi%E2%80%A6>, 15 pages.

International Preliminary Report on Patentability in International Application No. PCT/US2020/031201, mailed on Nov. 10, 2022, 17 pages.

International Preliminary Report on Patentability in International Application No. PCT/US2021/029895, mailed on Nov. 10, 2022, 14 pages.

International Preliminary Report on Patentability in International Application No. PCT/US2021/031808, mailed on Nov. 24, 2022, 17 pages.

International Preliminary Report on Patentability in International Appln. No. PCT/US2012/042502, dated Dec. 17, 2013, 8 pages.

International Preliminary Report on Patentability in International Appln. No. PCT/US2013/068055, dated May 14, 2015, 10 pages.

International Preliminary Report on Patentability in International Appln. No. PCT/US2016/042170, dated Jan. 16, 2018, 19 pages.

International Preliminary Report on Patentability in International Appln. No. PCT/US2016/055429, dated Apr. 10, 2018, 12 pages.

International Preliminary Report on Patentability in International Appln. No. PCT/US2018/013671, dated Jul. 16, 2019, 6 pages.

International Preliminary Report on Patentability in International Appln. No. PCT/US2018/046148, dated Feb. 11, 2020, 10 pages.

International Preliminary Report on Patentability in International Appln. No. PCT/US2018/057174, dated Apr. 28, 2020, 4 pages.

International Preliminary Report on Patentability in International Appln. No. PCT/US2018/057613, dated Apr. 28, 2020, 7 pages.

International Preliminary Report on Patentability in International Appln. No. PCT/US2019/039528, mailed Jan. 7, 2021, 15 pages.

International Preliminary Report on Patentability in International Appln. No. PCT/US2019/041429, dated Jan. 12, 2021, 11 pages.

International Preliminary Report on Patentability in International Appln. No. PCT/US2019/068152, mailed Jul. 1, 2021, 12 pages.

International Preliminary Report on Patentability in International Appln. No. PCT/US2020/029831, mailed Nov. 4, 2021, 8 pages.

International Preliminary Report on Patentability in International Appln. No. PCT/US2020/029894, dated Nov. 4, 2021, 13 pages.

International Search Report and Written Opinion in International Application No. PCT/US2021/031808, mailed on Mar. 9, 2022 , 29 pages.

International Search Report and Written Opinion in International Application No. PCT/US2022/035873, mailed on Dec. 21, 2022, 31 pages.

International Search Report and Written Opinion in International Appln. No. PCT/2020/29831, dated Nov. 3, 2020, 19 pages.

International Search Report and Written Opinion in International Appln. No. PCT/US2012/042502, dated Jan. 31, 2013, 11 pages.

International Search Report and Written Opinion in International Appln. No. PCT/US2013/068055, dated Feb. 18, 2014, 15 pages.

International Search Report and Written Opinion in International Appln. No. PCT/US2016/042170, dated Dec. 2, 2016, 22 pages.

International Search Report and Written Opinion in International Appln. No. PCT/US2016/055429, dated Dec. 30, 2016, 16 pages.

International Search Report and Written Opinion in International Appln. No. PCT/US2018/0013671, dated Mar. 22, 2018, 8 pages.

International Search Report and Written Opinion in International Appln. No. PCT/US2018/046148, dated Dec. 3, 2018, 6 pages.

International Search Report and Written Opinion in International Appln. No. PCT/US2018/057613, dated Mar. 5, 2019, 11 pages.

International Search Report and Written Opinion in International Appln. No. PCT/US2019/039528, dated Nov. 6, 2019, 19 pages.

(56)        References Cited

OTHER PUBLICATIONS

International Search Report and Written Opinion in International Appln. No. PCT/US2019/041429, dated Dec. 3, 2019, 18 pages.

International Search Report and Written Opinion in International Appln. No. PCT/US2019/059450, dated Mar. 10, 2020, 20 pages.

International Search Report and Written Opinion in International Appln. No. PCT/US2019/064782, mailed Apr. 16, 2020, 14 pages.

International Search Report and Written Opinion in International Appln. No. PCT/US2019/068152, dated Jun. 25, 2020, 21 pages.

International Search Report and Written Opinion in International Appln. No. PCT/US2019/39217, dated Nov. 19, 2019, 13 pages.

International Search Report and Written Opinion in International Appln. No. PCT/US2020/014083, mailed Jul. 20, 2020, 24 pages.

International Search Report and Written Opinion in International Appln. No. PCT/US2020/029894, mailed Aug. 31, 2020, 19 pages.

International Search Report and Written Opinion in International Appln. No. PCT/US2020/031201, dated Mar. 9, 2021, 28 pages.

International Search Report and Written Opinion in International Appln. No. PCT/US2021/029993, mailed Sep. 15, 2021, 12 pages.

International Search Report and Written Opinion in International Appln. No. PCT/US2021/055858, dated Mar. 25, 2022, 12 pages.

Invitation to Pay Additional Fees in International Appln. No. PCT/US2020/014083, mailed May 28, 2020, 20 pages.

Invitation to Pay Additional Fees in International Appln. No. PCT/US2022/035873, mailed Sep. 30, 2022, 19 pages.

Ishihama, "Prokaryotic genome regulation: multifactor promoters, multitarget regulators and hierarchic networks," FEMS Microbial Rev., 2010, 34(5):628-645.

Ivanova et al., "Artificial Regulation of Genes, Of the coding proteins of the nitrogenase complex Rhizobial bacteria," Natural Sciences, 2014, 13(174):36-39 (Machine Translation).

Izquierdo et al., "Distribution of Extensive nifH Gene Diversity Across Physical Soil Microenvironments," Microbial Ecology, 2006, 51(4):441-452.

Jacob et al., "Solid-state NMR studies of *Klebsiella pneumoniae* grown under nitrogen-fixing conditions," J. Biol. Chem., 1987, 262(1):254-259.

Jacoby et al., "The Role of Soil Microorganisms in Plant Mineral Nutrition—Current Knowledge and Future Directions," Frontiers in Plant Science, 2017, 8(19):1-19.

Jahn et al., "Extraction of Extracellular Polymeric Substances (EPS) from Biofilms Using a Cation Exchange Resin," Wat. Sci. Tech., 1995, 32(8):157-164.

Janczarek et al., "Multiple copies of rosR and pssA genes enhance exopolysaccharide production, symbiotic competitiveness and clover nodulation in *Rhizobium leguminosarum* bv. *trifolii*," Antonie Van Leeuwenhoek, Nov. 2009, 96(4):471-86.

Jashke et al., "A fully decompressed synthetic bacteriophage 0X174 genome assembled and archived in yeast," Virology, 2012, 434:278-284.

Jensen, "The *Escherichia coli* K-12 "wild types" W3110 and MG1655 have an rph frameshift mutation that leads to pyrimidine starvation due to low pyre expression levels," J. Bacteriol., 1993, 175:3401-3407.

Johnson et al., "Properties of overlapping genes are conserved across microbial genomes," Genome Res., 2004, 14(11):2268-2272.

Joseph et al., "Recent developments of the synthetic biology toolkit for *Clostridum*," Frontiers in Microbiology, 2018, 9(154):1-13.

Kabaluk et al., "The use and regulation of microbial pesticides in representative jurisdictions worldwide," IOBC Global, 2010, 99 pages.

Kalir et al., "Ordering genes in a flagella pathway by analysis of expression kinetics from living bacteria," Science, 2001, 292(5524):2080-2083.

Kaneko et al., "Complete genomic structure of the cultivated rice endophyte *Azospirillum* sp. B510," DNA Res., 2010, 17:37-50.

Kant et al., "Understanding plant response to nitrogen limitation for the improvement of crop nitrogen use efficiency," Journal of Experimental Botany, 2011, 62(4):1499-1509.

Karlin et al., "Applications and statistics for multiple high-scoring segments in molecular sequences," Proc Natl Acad Sci USA, Jun. 1993, 90(12):5873-7.

Karlin et al., "Methods for assessing the statistical significance of molecular sequence features by using general scoring schemes," Proc Natl Acad Sci USA, Mar. 1990, 87(6):2264-8.

Katsnelson, "Engineered bacteria could boost corn yields: Gene-edited microbe offer continuous nitrogen fixation," Chemical & Engineering News, Dec. 28, 2021, retrieved from URL <https://cen.acs.org/food/agriculture/Engineered-bacteria-boost-corn-yields/99/web/2021/12>, 3 pages.

Kececiglu et al., "Of mice and men: Algorithms for evolutionary distances between genomes with translocation," SODA: Proceedings of the sixth annual ACM-SIAM symposium on Discrete algorithms, 1995, 10 pages.

Kelly et al., "Measuring the activity of BioBrick promoters using an in vivo reference standard," J. Biol. Eng., 2009, 3:4, 13 pages.

Kent et al., "A Transposable Partitioning Locus Used To Stabilize Plasmid-Borne Hydrogen Oxidation and Trifolitoxin Production Genes in a *Sinorhizobium* Strain," Appl. Environ. Microbiol., 1998, 64(5):1657-1662.

Kerby et al., "Photoproduction of ammonium by immobilized mutant strains of *Anabaena variabilis*," Applied Microbiology and Biotechnology, Apr. 1986, 24(1):42-46.

Kim et al., "A 20 nucleotide upstream element is essential for the nopaline synthase (nos) promoter activity," Plant Mol Biol., Jan. 1994, 24(1):105-17.

Kim et al., "Constitutive expression of nitrogenase system in *Klebsiella oxytoca* by gene targeting mutation to the chromosomal nifLA operon," Journal of Biotechnology, Jun. 1989, 10(3-4):293-301.

King et al., "Spider-Venom Peptides: Structure, Pharmacology, and Potential for Control of Insect Pests," Annu. Rev. Entomol., 2013, 58:475-96.

Kingsford et al., "Rapid, accurate, computational discovery of Rho-independent transcription terminators illuminates their relationship to DNA uptake," Genome Bio. 2007, 8(2):R22, 12 pages.

Kitano, "Systems biology: a brief overview," Science, 2002, 295(5560):1662-1664.

Klose et al., "Glutamate at the site of phosphorylation of nitrogen-regulatory protein NTRC mimics aspartyl-phosphate and activates the protein," J Mol Biol., Jul. 1993, 232(1):67-78.

Knight, "Idempotent Vector Design for Standard Assembly of Biobricks," MIT Artificial Intelligence Laboratory, The TTL Data Book for Design Engineers, 2003, 11 pages.

Kou et al., "Identification of bacterial communities in sediments of Poyang Lake, the largest freshwater lake in China," Springerplus, Apr. 2016, 5(401):1-9.

Kovacs et al., "Stochasticity in protein levels drives colinearity of gene order in metabolic operons of *Escherichia coli*," PLoS Biol., 2009, 7(5):e1000115, 9 pages.

Kranz et al., "Ammonia-constitutive nitrogen fixation mutants of *Rhodobacter capsulatus*," Gene, Nov. 1988, 71(1):65-74.

Kumar et al., "Metabolic regulation of *Escherichia coli* and its gdhA, glnL, gltB, D mutants under different carbon and nitrogen limitations in the continuous culture," Microbial Cell Factories, Jan. 2010, 9(8):1-17.

Kurzweil, "Plant Bacteria breakthrough enables crops worldwide to take nitrogen from the air," Plant Bacteria Breakthrough Enables Crops Worldwide Take Nitrogen From Air. Aug. 1, 2013. http://www.kurzweilai.neUplant-bacteria-breakthrough-enables-cropsworldwide-to-take-nitrogen-from- the-air, 4 pages.

Kutter et al., "Colonization of barley (*Hordeum vulgare*) with *Salmonella enterica* and *Listeria* spp," FEMS Microbial. Ecol., 2006, 56, 262-271.

Lauber et al., "Pyrosequencing-based assessment of soil pH as a predictor of soil bacterial community structure at the continental scale," Appl. Environ. Microbiol., Aug. 2009, 75(15):5111-5120.

Lauritsen et al., "A versatile one-step CRISPR-Cas9 based approach to plasmid-curing." Microb Cell Fact, 2017, 16(135):1-10.

Leang et al., "Genome-wide analysis of the RpoN regulon in *Geobacter sulfurreducens*," BMC Genomics, Jul. 2009, 10:331, 19 pages.

(56) References Cited

OTHER PUBLICATIONS

Lee et al., "The class IId bacteriocin thuricin-17 increases plant growth," Planta, 2009, 229:747-755.

Leigh et al., "Nitrogen Regulation in Bacteria and Archaea," Annual Review of Microbiology, 2007, 61(10):349-377.

Lenski et al., "Effects of Segregation and Selection on Instability of Plasmid pACYC184 in Escherichia coli B," Journal of Bacteriology, Nov. 1987, 169(11):5314-5316.

Levican et al., "Comparative genomic analysis of carbon and nitrogen assimilation mechanisms in three indigenous bioleaching bacteria: predictions and validations," BMC Genomics, 2008, 9:581, 19 pages.

Levin-Karp et al., "Quantifying translational coupling in E. coli synthetic operons using RBS modulation and fluorescent reporters," ACS Synth. Biol., 2013, 2:327-336.

Li et al., "Human Enhancers Are Fragile and Prone to Deactivating Mutations," Mol Biol Evol., Aug. 2015, 32(8):2161-80.

Liang et al., "Minimal effect of gene clustering on expression in Escherichia coli," Genetics, Feb. 2013, 193(2):453-65.

Lifesci.sussex.ac.uk, [online], "Bacillus thuringiensis Toxin Nomenclature," 2016, retrieved on Mar. 25, 2021, retrieved from URL<www.lifesci.sussex.ac.uk/home/Neil_Crickmore/Bt/> 1 page.

Lim et al., "Fundamental relationship between operon organization and gene expression," Proc Natl Acad Sci USA, Jun. 2011, 108(26):10626-31.

Lin et al., "PC, a Novel Oral Insecticidal Toxin from Bacillus bombysepticus Involved in Host Lethality via APN and BtR-175," Scientific Reports, Jun. 2015, 5:11101, 14 pages.

Lindstrom et al., "Distribution of typical freshwater bacterial groups is associated with pH, temperature, and lake water retention time," Appl. Environ. Microbiol., Dec. 2005, 71(12):8201-8206.

Lindstrom, "Investigating Influential Factors on Bacterioplankton Community Composition: Results from a Field Study of Five Mesotrophic Lakes," Microbial Eco., Nov. 2001, 42(4):598-605.

Liu et al., "Phenazine-1-carboxylic acid biosynthesis in Pseudomonas chlororaphis GP72 is positively regulated by the sigma factor RpoN," World Journal of Microbiology and Biotechnology, Jan. 2008, 24(9):1961-1966.

Liu et al., "Whole genome analysis of halotolerant and alkalotolerant plant growth-promoting rhizobacterium Klebsiella p. D5A," Sci Rep., May 2016, 6:1-10.

Lombo et al., "The mithramycin gene cluster of Streptomyces argillaceus contains a positive regulatory gene and two repeated DNA sequences that are located at both ends of the cluster," J. Bacterial., 1999, 181:642-647.

Lowman et al., "Strategies for enhancement of switchgrass (Panicum virgatum L.) performance under limited nitrogen supply based on utilization of N-fixing bacterial endophytes," Plant and Soil, Aug. 2016, 405(1):47-63, 17 pages.

Lucks et al., "Toward scalable parts families for predictable design of biological circuits," Curr. Opin. Microbiol., 2008, 11:567-573.

Lugtenberg et al., "Molecular Determinants of Rhizosphere Colonization by Pseudomonas," Annu. Rev. Phytopathol., Sep. 2001, 39(1):461-490, 31 pages.

Ma et al., "Effect of nicotine from tobacco root exudates on chemotaxis, growth, biocontrol efficiency, and colonization by Pseudomonas aeruginosa NXHG29," Antonie van Leeuwenhoek, 2018, 111(7):1237-1257.

Mabrouk et al., "Chapter 6: Potential of Rhizobia in Improving Nitrogen Fixation and Yields of Legumes," Symbiosis, May 30, 2018, IntechOpen, pp. 1-16, retrieved on Jan. 12, 2021, retrieved from URL<https://www.intechopen.com/books/symbiosis/potential-of-rhizobia-in-improving- B351nitrogen-fixation-and-yields-of-legumes> 2 pages, Abstract.

Machado et al., "Excretion of ammonium by Azospirillum brasilense mutants resistant to ethylenediamine," Can. J. Microbiol., Jul. 1991, 37(7): 549-553, 2 pages (Abstract Only).

MacNeil et al., "Fine-structure mapping and complementation analysis of nif (nitrogen fixation) genes in Klebsiella pneumoniae," J Bacterial. Oct. 1978, 136(1):253-266.

MacNeil et al., "Mutations in nif genes that cause Klebsiella pneumoniae to be derepressed for nitrogenase synthesis in the presence of ammonium," J Bacterial, Nov. 1980, 144(2):744-751.

Maduro, "Random DNA Generator," retrieved from URL <http://www.faculty.ucr.edu/~mmaduro/random.htm>, 2011, 1 page.

Magari et al., "Pharmacologic control of a humanized gene therapy system implanted into nude mice," J Clin Invest., Dec. 1997, 100(11):2865-2872.

Magasanik, "Genetic control of nitrogen assimilation in bacteria," Ann. Rev. Genet, 1982, 16:135-68.

Mandal et al., "Gene regulation by riboswitches," Nat. Rev. Mol. Cell Biol., 2004, 5(6):451-463.

Mao et al., "Silencing a cotton bollworm P450 monooxygenase gene by plant-mediated RNAi impairs larval tolerance of gossypol," Nature Biotechnology, Nov. 2007, 25(11): 1307-1313.

Marroqui et al., "Enhanced Symbiotic Performance by Rhizobium tropici Glycogen Synthase 17, 18 Mutants," Journal of Bacteriology, Feb. 2001, 183(3):854-864.

Martiez-Noel et al., "NifB and NifEN protein levels are regulated by ClpX2 under nitrogen fixation conditions in Azotobacter vinelandii," Mol Microbiol., Mar. 2011, 79(5):1182-93.

Martinelli et al., "Structure-function studies on jaburetox, a recombinant insecticidal peptide derived from jack bean (Canavalia ensiformis) urease," Biochimica et Biophysica Acta, Mar. 2014, 1840(3):935-44.

Marx et al., "Broad-host-range ere-lox system for antibiotic marker recycling in gram-negative bacteria," Biotechniques, Nov. 2002, 33(5):1062-7.

Masepohl et al., "Organization and regulation of genes encoding the molybdenum nitrogenase and the alternative nitrogenase in Rhodobacter capsulatus," Arch. Microbial., Sep. 1996, 165:80-90.

Mason et al., "Cryptic Growth in Klebsiella-Pneumoniae," Appl. Microbiol. Biot., 1987, 25(6):577-584.

Matsubayashi et al., "Peptide hormones in plants," Annu. Rev Plant Biol., 2006, 57:649-74.

Medema et al., "Computational tools for the synthetic design of biochemical pathways," Nat Rev Microbiol., Jan. 2012, 10(3):191-202.

Medema et al., "Exploiting plug-and-play synthetic biology for drug discovery and production in microorganisms," Nat. Rev. Microbiol., 2011, 9:131-137.

Medema et al., "Synthetic biology in Streptomyces bacteria," Methods Enzymol., 2011, 497:485-502.

Meng et al., "Draft Genome Sequence of Rice Endophyte-Associated Isolate Kosakonia oryzae KO348," Genome Announc., Jun. 2015, 3(3):e00594-15, 1 page.

Mengel, "Roots, growth and nutrient uptake." Dept. of Agronomy publication #AGRY-95-08 (Rev. May 1995), 8 pages.

Merriam-webster.com, [online], "Merriam-Webster Originate," 2020, Retrieved on Jun. 7, 2020, retrieved from URL<https://www.merriam-webster.com/dictionary/originate?utm_campaign=sd&utm_medium=serp&utm_source=jsonld>, 13 pages.

Mirsky, "Refactoring the Salmonella Type III Secretion System," Doctoral Dissertation, Apr. 12, 2012, 60 pages.

Mirzahoseini et al., "Heterologous Proteins Production in Escherichia coli: An Investigation on the Effect of Codon Usage and Expression Host Optimization," Cell Journal (Yakhteh), Dec. 2011, 12(4):453, 7 pages.

Mitra, "Regulation of nifLA operon in Azotobacter vinelandii," Thesis submitted to the Jawaharlal Nehru University, New Delhi, for the degree of doctor of philosophy, 2000, 153 pages.

Miyazaki, "Creating random mutagenesis libraries by megaprimer PCR of whole plasmid (Mega Whop)," Methods Mol. Biol., 2003, 231:23-28.

Moon et al., "Genetic programs constructed from layered logic gates in single cells," Nature, Nov. 2012, 491(7423):249-53.

Mosquito et al. "In Planta Colonization and Role of T6SS in Two Rice Kosakonia Endophytes," Molecular Plant-Microbe Interactions, Feb. 2020, 33(2):349-363.

Mueller et al., "Closing yield gaps through nutrient and water management," Nature, 2012, 490:254-257.

(56) References Cited

OTHER PUBLICATIONS

Mus et al., "Diazotrophic Growth Allows *Azotobacter vinelandii* To Overcome the Deleterious Effects of a glnE Deletion," Appl Environ Microbiol., Jun. 2017, 83(13):e00808-17.

Mus et al., "Symbiotic Nitrogen Fixation and the Challenges to Its Extension to Nonlegumes," Appl Environ Microbial., Jul. 2016, 82(13):3698-3710.

Muse et al., "The nac (Nitrogen Assimilation Control) Gene from *Escherichia coli*," Journal of Bacteriology, Mar. 1998, 180(5):1166-1173.

Mutalik et al., "Quantitative estimation of activity and quality for collections of functional genetic elements," Nat. Methods, 2013, 10:347-353.

Nagy et al., "Nanofibrous solid dosage form of living bacteria prepared by electrospinning," eXPRESS Polymer Letters, 2014, 8(5):352-361.

Naimov et al., "Solubilization, Activation, and Insecticidal Activity of *Bacillus thuringiensis* serovar *thompsoni* HD542 Crystal Proteins," Applied and Environmental Microbiology, Dec. 2008, 74(23):7145-7151.

Nassar et al., "Promotion of plant growth by an auxin-producing isolate of the yeast *Williopsis saturnus* endophytic in maize (*Zea mays* L.) roots," Biology and Fertility of Soils, 2005, 42:97-108.

Nature.com, [online], "Transcription Unit," 2005, retrieved on Apr. 15, 2021, retrieved from URL<https://www.nature.com/scitable/definition/transcription-unit-260>, 2 pages.

Nelissen et al., "Translational research: from pot to plot," Plant Biotechnology Journal, Jan. 2014, 12:277-285.

Nestmann, "Mutagenesis by nitrosoguanidine, ethyl methanesulfonate, and mutator gene mutH in continuous cultures of *Escherichia coli*," Science Direct, Jun. 1975, 28(3):323-330.

Newton et al., "A Guide to the Natural History of Freshwater Lake Bacteria," Microbiol Mol. Biol. Rev., Mar. 2011, 75(1):14-49.

Nichkawade, "Studies on upstream regulatory sequence of the nifLA promoter of *Klebsiella pnuemoniae*," Thesis submitted to the Jawaharlal Nehru University, New Delhi, for the degree of doctor of philosophy, 1996, 166 pages.

Nielsen et al., "Conceptual model for production and composition of exopolymers in biofilms," Wat. Sci. Tech., 1997, 36(1): 11-19.

Nielsen et al., "Extraction of EPS," Wingender et al. (eds.), Microbial Extracellular Polymeric Substances, 1999, 24 pages.

Nielsen, "Transgenic organisms—time for conceptual diversification?," Nature Biotechnology, 2003, 21:227-228.

No et al., "Ecdysone-inducible gene expression in mammalian cells and transgenic mice," Proc. Natl. Acad. Sci. USA, Apr. 1996, 93(8):3346-3351.

Noindorf et al., "Role of PII proteins in nitrogen fixation control of *Herbaspirillum seropedicae* strain SmR1," BMC Microbiology, Jan. 2011, 11(1), 8 pages.

Noskov et al., "Assembly of large, high G+C bacterial DNA fragments in yeast," ACS Synth. Biol., 2012, 1:267-273.

O'Brien et al., "Soil Salinity and pH Drive Soil Bacterial Community Composition and Diversity Along a Lateritic Slope in the Avon River Critical Zone Observatory, Western Australia," Front. Microbiol., Jul. 2019, 10(1486):1-20.

Oh et al., "Organization of nif gene cluster in *Frankia* sp. EuIK1 strain, a symbiont of *Elaeagnus umbellata*," Arch. Microbiol., 2012, 194:29-34.

Ohta et al., "Associative N₂-fixation of Rice with Soil and Microorganisms," 1985, 27:17-27 (Abstract Only).

Ohtsuka et al., "An alternative approach to deoxyoligonucleotides as hybridization probes by insertion of deoxyinosine at ambiguous codon positions," J. Biol. Chem., 1985, 260:2605-2608.

Okubo et al., "Effects of Elevated Carbon Dioxide, Elevated Temperature, and Rice Growth Stage on the Community Structure of Rice Root-Associated Bacteria," Microbes Environ., Jun. 2014, 29(2):184-190.

Orme-Johnson, "Molecular basis of biological nitrogen fixation," Annu. Rev. Biophys. Biophys. Chem., 1985, 14:419-459.

Ortiz-Marquez et al., "Association with an Ammonium-excreting bacterium allows diazotrophic culture of oil-rich Eukaryotic microalgae," Appl. Microbial., 2012, 78(7):2345-2352.

Pakula et al., "Genetic analysis of protein stability and function," Annu Rev Genet, 1989, 23:289-310.

Pankievicz et al., "Robust biological nitrogen fixation in a model grass-bacterial association," The Plant Journal, 81(6), Mar. 2015, 907-919.

Parker et al., "Pore-forming protein toxins: from structure to function," Progress in Biophysics & Molecular Biology, 2005, 88:91-142.

Paschen et al., "*Rhodobacter capsulatus* nifA mutants mediating nif gene expression in the presence of ammonium," FEMS Microbiology Letters, Jan. 2001, 207-213.

Patil et al., "Liquid formulations of *Acetobacter diazotrophicus* L1 and *Herbaspirillum seropedicae* J24 and their field trials on wheat," International Journal of Environmental Science, 2012, 3(3):1116-1129, 4 pages (Abstract Only).

Pfleger et al., "Combinatorial engineering of intergenic regions in operons tunes expression of multiple genes," Nature Biotechnology, 2006, 24(8):1027-1031.

Philippe et al., "Improvement of pCVD442, a suicide plasmid for gene allele exchange in bacteria," Plasmid, 2004, 51(3):246-255.

Piccioli et al. "Neuroantibodies: ectopic expression of a recombinant anti-substance P antibody in the central nervous system of transgenic mice," Neuron., Aug. 1995, 15(2):373-84.

Piccioli et al., "Neuroantibodies: molecular cloning of a monoclonal antibody against substance P for expression in the central nervous system," Proc Natl Acad Sci USA, Jul. 1991, 88(13):5611-5615.

Pickens et al., "Metabolic engineering for the production of natural products," Annu. Rev. Chem. Biomol. Eng., 2011, 2:211-236.

Plotnikova et al., "Pathogenesis of the human opportunistic pathogen *Pseudomonas aeruginosa* PA14 in *Arabidopsis*," Plant Physiol., 2000, 124:1766-1774.

Poliner et al., "Nontransgenic Marker-Free Gene Disruption by an Episomal CRISPR System in the Oleaginous Microalga, *Nannochloropsis oceanica* CCMP1779," ACS Synth. Biol., 2018, 7(4):962-968.

PreNewsWire.com [online], "Global Agricultural Inoculants Market Research Report—Industry Analysis, Size, Share, Growth, Trends and Forecast 2015-2022," Dec. 2016, retrieved on Mar. 24, 2023, retrieved from URL <https://www.prnewswire.com/news-releases/global-agricultural-inoculants-market-research-report---industry-analysis-size-share-growth-trends-and-forecast-2015---2022-300375864.html>, 4 pages.

Price et al., "Operon formation is driven by coregulation and not by horizontal gene transfer," Genome Res., 2005, 15:809-819.

Price et al., "The life-cycle of operons," PLoS Genet., 2006, 2:e96, 15 pages.

Purcell et al., "Cholesterol oxidase: a potent insecticidal protein active against boll weevil larvae," Biochem Biophys Res Commun, Nov. 1993, 196(3):1406-13.

Purnick et al., "The second wave of synthetic biology: from modules to systems," Nat. Rev. Mol. Cell Biol., 2009, 10(6):410-422.

Pyne et al., "Coupling the CRISPR/Cas9 System with Lambda Red Recombineering Enables Simplified Chromosomal Gene Replacement in *Escherichia coli*," Applied and Environmental Microbiology, Aug. 2015, 81(15):5103-5144.

Qaim et al., "Yield Effects of Genetically Modified Crops in Developing Countries," Science, Feb. 2003, 299(5608):900-2.

Qiu et al., "Construction of genetically engineered strains of *Enterobacter cloacae* (nifL~(−)A~(c))," Acta Phytophysiologica Sinica, Jan. 1999, 25(3):269-273.

Rakhee et al., "Extracellular polymeric substances of the marine fouling diatom *Amphora rostrata* Wm.Sm," Biofouling, 2001, 17(2):117-127, 12 pages.

Ramirez et al., "*Burkholderia* and *Paraburkholderia* are Predominant Soybean Rhizobial Genera in Venezuelan Soils in Different Climatic and Topographical Regions," Microbes and Environments, Mar. 2019, 34(1):43-58.

(56) References Cited

OTHER PUBLICATIONS

Ramon et al., "Single-step linker-based combinatorial assembly of promoter and gene cassettes for pathway engineering," Biotechnol. Lett., 2011, 33:549-555.

Ran et al., "Genome erosion in a nitrogen-fixing vertically transmitted endosymbiotic multicellular cyanobacterium," PLoS One, Jul. 2010, 5(7):e11486, 11 pages.

Resendis-Antonio et al., "Systems biology of bacterial nitrogen fixation: High-throughput technology and its integrative description with constraint-based modeling," BMC Syst Biol., 2011, 5:120, 15 pages.

Rey et al., "Redirection of Metabolism for Biological Hydrogen Production," Applied and Environmental Microbiology, Mar. 2007, 73(5):1665-1671.

Riedel et al., "Nitrogen fixation by Klebsiella pneumoniae is inhibited by certain multicopy hybrid nif plasmids," J. Bacterial., 1983, 153(1):45-56.

Rivarez et al., "Defense Biopriming and Antimicrobial Activity of Endophytic Bacteria and Associated Bacillus Species Contribute to Bacterial Crown Rot Tolerance in Papaya," bioRxiv, Dec. 2019, 24 pages.

Roberts et al., "Regulation and characterization of protein products coded by the nif (nitrogen fixation) genes of Klebsiella pneumoniae," J Bacterial., Oct. 1978, 136(1): 267-279.

Robledo et al., "Rhizobium cellulase CelC2 is essential for primary symbiotic infection of legume host roots," Proc Natl Acad Sci USA, May 2008, 105(19):7064-9.

Robledo et al., "Role of Rhizobium endoglucanase CelC2 in cellulose biosynthesis and biofilm formation on plant roots and abiotic surfaces," Microb Cell Fact., Sep. 2012, 11:125, 12 pages.

Robson et al., "Azotobacter Genomes: The Genome of Azotobacter chroococcum NCIMB 8003 (ATCC 4412)," PLOS ONE, Jun. 2015, 35 pages.

Rogers et al., "Synthetic biology approaches to engineering the nitrogen symbiosis in cereals," Journal of Experimental Botany, 2014, 65(8):1939-1946.

Rojas-Tapias et al., "Preservation of Azotobacter chroococcum vegetative cells in dry polymers," Univ. Sci., 2015, 20(2):201-207.

Rommens et al., "Intergeneric transfer and functional expression of the tomato disease resistance gene Pto," Plant Cell, Oct. 1995, 7(10):1537-1544.

Roncato-Maccari et al., "Endophytic Herbaspirillum seropedicae expresses nif genes in gramineous plants," FEMS Microbiology Ecology, 2003, 45:39-47.

Rong et al., "Promoter specificity determinants of T7 RNA polymerase," Proc. Natl. Acad. Sci. USA, 1998, 95(2):515-519.

Rosenblueth et al., "Bacterial endophytes and their interactions with hosts," Mol Plant Microbe Interact., Aug. 2006, 19(8):827-37.

Rosenblueth et al., "Nitrogen Fixation in Cereals," Frontiers in Microbiology, Aug. 2018, 9(1794):13 pages.

Rossolini et al., "Use of Deoxyinosine-Containing Primers vs Degenerate Primers for Polymerase Chain Reaction Based on Ambiguous Sequence Information," Mol. Cell. Probes, 1994, 8:91-98.

Rubio et al., "Maturation of Nitrogenase: a Biochemical Puzzle," J. Bacteriology, 2005, 187(2):405-414.

Ryu et al., "Control of nitrogen fixation in bacteria that associate with cereals," Nat. Microbiol., Feb. 2020, 5(2):314-330, 31 pages.

Saikia et al., "Biological nitrogen fixation with non-legumes: An achievable target or a dogma?," Curr. Sci., Feb. 2007, 92(3): 317-322.

Saleh et al., "Involvement of gacS and rpoS in enhancement of the plant growth-promoting capabilities of Enterobacter cloacae CAL2 and UW4," Canadian Journal of Microbiology, Aug. 2001, 47(8):698-705.

Salis et al., "Automated design of synthetic ribosome binding sites to control protein expression," Nat. Biotechnol., 2009, 27(10):946-950.

Sanahuja et al., "Bacillus thuringiensis: a century of research, development and commercial applications," Plant Biotechnology Journal, Apr. 2011, 9(3):283-300.

Sandoval et al., "Strategy for directing combinatorial genome engineering in Escherichia coli," Proc Natl Acad Sci USA, Jun. 2012, 109(26):10540-5.

Sanjuan et al., "Multicopy plasmids carrying the Klebsiella pneumoniae nifA gene enhance Rhizobium meliloti nodulation competitiveness on alfalfa," Molecular Plant-Microbe Interactions, 1991, 4(4):365-369.

Santi et al., "Biological nitrogen fixation in non-legume plants," Annals of Botany, Jan. 2013, 111:743-767.

Sanyal et al., "The etiology of hepatocellular carcinoma and consequences for treatment," Oncologist, 2010, 15(Suppl 4):14-22.

Schluter et al., "Global mapping of transcription start sites and promoter motifs in the symbiotic α-proteobacterium Sinorhizobium meliloti," BMC Genomics, Mar. 2013, 14(1):156, 21 pages.

Schmidt-Dannert et al., "Molecular breeding of carotenoid biosynthetic pathways," Nat. Biotechnol., 2000, 18:750-753.

Schmitz et al., "Iron is required to relieve inhibitory effects on NifL on transcriptional activation by NifA in Klebsiella pneumoniae," J Bacterial, Aug. 1996, 178(15):4679-4687.

Schouten et al., "Do cisgenic plants warrant less stringent oversight? ," Nature Biotechnology, Jul. 2006, 24(7):753.

Schreier et al., "Bacillus subtilis glnR mutants defective in regulation," Gene., Aug. 1995, 161(1):51-56.

Schuler et al., "Insect-resistant transgenic plants," Trends in Biotechnology, Apr. 1998, 16(4):168-175.

Schuler et al., "Potential side effects of insect-resistant transgenic plants on arthropod natural enemies," Trends Biotechnol., May 1999, 17(5):210-216.

Search Report in AP Appln. No. AP/P/2020/012401, dated Feb. 8, 2022, 4 pages.

Search Report in AP Appln. No. AP/P/2020/012402, dated Feb. 15, 2022, 5 pages.

Search Report in Russian Appln. No. 2020116764, dated Apr. 28, 2022, 15 pages (with English translation).

Service, "Genetically engineered microbes make their own fertilizer, could feed the world's poorest," Science, Apr. 2017, 2 pages.

Setten et al., "Engineering Pseudomonas protegens Pf-5 for Nitrogen Fixation and its Application to Improve Plant Growth Under Nitrogen-Deficient Conditions," PLOS One, 2013, 8(5):1-14.

Shahid et al., "Colonization of Vigna radiata by a halotolerant bacterium Kosakonia sacchari improves the ionic balance, stressor metabolites, antioxidant status and yield under NaCl stress, " Appl. Soil Ecol., Feb. 2021, 158:1-14.

Shamseldin, "The role of different genes involved in symbiotic nitrogen fixation—review," Global Journal of Biotechnology & Biochemistry, 2013, 8(4):84-94.

Shetty et al., "Engineering BioBrick vectors from BioBrick parts," J. Biol. Eng., 2008, 2:5, 12 pages.

Shinjo et al., "Complete Genome Sequence of Kosakonia sacchari Strain BO-1, an Endophytic Diazotroph Isolated from a Sweet Potato," Genome Announcements, ASM., Sep. 2016, 4(5):e00868-16, 2 pages.

Sibold et al., "A nif mutant of Klebsiella pneumoniae fixing nitrogen in the presence of ammonia," FEMS Microbiology Letters, Jan. 1981, 10(1):37-41.

Sibold et al., "Constitutive expression of nitrogen fixation (nif) genes of Klebsiella pneumoniae due to a DNA duplication," EMBO J., 1982, 1(12):1551-8.

Siddavattam et al., "Regulation of nif Gene expression in Enterobacter agglomerans: Nucleotide sequence of the nifLA operon and influence of temperature and ammonium on its transcription," Molecular and general genetics, Dec. 1995, 249(6):629-636.

Simon et al., "Perturbation of niff expression in Klebsiella pneumoniae has limited effect on nitrogen fixation," J. Bacteriol., 1996, 178(10):2975-2977.

Singer et al., "Genes and Genomes," Moscow: Mir, 1998, 1:33, 4 pages (with machine translation).

Singh et al., "An L-methionine-D,L-sulfoximine-resistant mutant of the cyanobacterium Nostoc muscorum showing inhibitor-resistant

(56) References Cited

OTHER PUBLICATIONS y-glutamyl-transferase, defective glutamine synthetase and producing extracellular ammonia during $N_2$ fixation," FESS Letters, Apr. 1983, 154(1):10-14.

Sivaraman et al., "Codon choice in genes depends on flanking sequence information—implications for theoretical reverse translation," Nucleic Acids Res., 2008, 36(3):e16, 8 pages.

Sleight et al., "Designing and engineering evolutionary robust genetic circuits," J Biol Engin., 2010, 4(12):1-20.

Sleight et al., "Randomized BioBrick assembly: a novel DNA assembly method for randomizing and optimizing genetic circuits and metabolic pathways," ACS Synth. Biol., 2013, 2(9):506-518.

Smanski et al., "Engineered *Streptomyces platensis* strains that overproduce antibiotics platensimycin and platencin," Antimicrob. Agents Chemother., 2009, 53:1299-12304.

Smanski et al., "Functional optimization of gene clusters by combinatorial design and assembly," Nat Biotechnol., 2014, 32(12):1241-1249.

Smanski et al., "Synthetic biology to access and expand nature's chemical diversity," Nat Rev Microbiol., Mar. 2016, 14(3):135-49.

Sorek et al., "Prokaryotic transcriptomics: a new view on regulation, physiology, and pathogenicity," Nat. Rev. Genet., 2010, 11:9-16.

Souza et al., "The N-Terminus of the NIFA protein of *Herbaspirillum seropedicae* is probably involved in sensing of ammonia," In Tikhonovich et al. (Eds.) Proceedings of the 10th International Congress on Nitrogen Fixation, St. Petersburg, Russia, May 28-Jun. 3, 1995 (p. 260) Dordrecht: Kluwer.

Spiller et al., "Isolation and characterization of nitrogenase-derepressed mutant strains of cyanobacterium *Anabaena variabilis*," J Bacteriol. Feb. 1986, 165(2):412-419.

Staron et al., "The Third Pillar of Bacterial Signal Transduction: Classification of the Extracytoplasmic Function (ECF) Sigma Factor Protein Family," Mol. Microbiol., 2009, 14(3): 557-81.

Steenhoudt et al., "*Azospirillum*, a free-living nitrogen-fixing bacterium closely associated with grasses: genetic, biochemical and ecological aspects," FEMS Microbial. Rev., 2000, 24:487-506.

Stein et al., "The osteocalcin gene: a model for multiple parameters of skeletal-specific transcriptional control," Mol Biol Rep., Aug. 1997, 24(3):185-96.

Stemmer, "DNA shuffling by random fragmentation and reassembly: In vitro recombination for molecular evolution," Proc. Natl. Acad. Sci. USA, Oct. 1994, 91:10747-10751.

Stemple, "Tilling—a high-throughput harvest for functional genomics," Nature Reviews Genetics, Feb. 2004, 5:1-7.

Stephanopoulos, "Challenges in engineering microbes for biofuels production," Science, Feb. 2007, 315(5813):801-4.

Stewart et al., "In situ studies on nitrogen fixation with the acetylene reduction technique," Science, 1967, 158(3800):536.

Stucken et al., "The smallest known genomes of multicellular and toxic cyanobacteria: comparison, minimal gene sets for linked traits and the evolutionary implications," PLoS ONE, 2010, 5:e9235, 15 pages.

Subtil et al., "Secretion of Predicted Inc Proteins of *Chlamydia pneumoniae* by a Heterologous Type Ill Machinery," Molecular Microbiology, Feb. 2001, 39(3):792-800.

Suh et al., "Functional expression of the FeMo-cofactor-specific biosynthetic genes nifEN as a NifE-N fusion protein synthesizing unit in *Azotobacter vinelandii*," Biochem. Biophys. Res. Comm., 2002, 299:233-240.

Suzuki et al., "Immune-mediated motor polyneuropathy after hematopoietic stem cell transplantation," Bone Marrow Transplant., Aug. 2007, 40(3):289-91.

Swain et al., "Nitrogen fixation and its improvement through genetic engineering," J. Global Biosciences, 2013, 2(5): 98-112.

Tamsir et al., "Robust multicellular computing using genetically encoded NOR gates and chemical 'wires'," Nature, 2011, 469(7329):212-215.

Tan, "A synthetic biology challenge: making cells compute," Mol. Biosyst., 2007, 3:343-353.

Temme et al., "Designing and Engineering Complex Behavior in Living Machines," Doctoral Dissertation, Oct. 2011, Retrieved from URL <escholarship.org/uc/item/1r41x99s>, 75 pages.

Temme et al., "Induction and relaxation dynamics of the regulatory network controlling the type III secretion system encoded within *Salmonella* pathogenicity island 1," J. Mol. Biol., 2008, 377(1):47-61.

Temme et al., "Modular control of multiple pathways using engineered orthogonal T7 polymerases," Nucleic Acids Res, Sep. 2012, 40(17):8773-81.

Temme et al., "Refactoring the nitrogen fixation gene cluster from *Klebsiella oxytoca*," Proc. Natl. Acad. Sci. USA, 2012, 109(18):7085-7090.

Terpolilli et al., "What Determines the Efficiency of $N_2$-Fixing *Rhizobium*-Legume Symbioses?," Advances in Microbial Physiology, 2012, 60:325-389.

Thiel et al., "Characterization of genes for a second Mo-dependent nitrogenase in the cyanobacterium *Anabaena variabilis*," J. Bact., 1997, 179:5222-5225.

Thomas et al., "Ammonium Excretion by an I-Methionine-D,L-Sulfoximine-Resistant Mutant of the Rice Field Cyanobacterium *Anabaena siamensis*," Appl Environ Microbiol., Nov. 1990, 56(11):3499-3504.

Tian et al., "Six New Families of Aerobic Arsenate Reducing Bacteria: *Leclercia, Raoultella, Kosakonia, Lelliottia, Yokenella*, and *Kluyvera*," Geomicrobiology Journal, Feb. 2019, 36(4):339-347.

Tijssen, "Laboratory Techniques In Biochemistry And Molecular Biology," Elsevier, 1993, 24:65 pages.

Tilman et al., "Global food demand and the sustainable intensification of agriculture," PNAS, 2011, 108:20260-20264.

Travis et al., "Molecular dissection of the glutamine synthetase-GlnR nitrogen regulatory circuitry in Gram-positive bacteria," Nature Communications, Jul. 2022, 13(3793), 15 pages.

Triplett, "Diazotrophic endophytes: progress and prospects for nitrogen fixation in monocots," Plant and Soil, 1996, 186:29-38.

Tritt et al., "An Integrated Pipeline for de Novo Assembly of Microbial Genomes," PLoS One, Sep. 2012, 7(9):e42304, 9 pages.

Troisfontaines et al., "Type III Secretion: More Systems Than You Think," Physiology, Oct. 2005, 20:326-339.

Tyler et al., "Plants as a Habitat for Beneficial and/or Human Pathogenic Bacteria," Annu. Rev. Phytopathol., 2008, 46:53-73.

Ueda et al., "Remarkable $N_2$-Fixing Bacterial Diversity Detected in Rice Roots by Molecular Evolutionary Analysis of nifH Gene Sequences," Journal of Bacteriology, Mar. 1995, 177:1414-1417.

Uozumi et al., "Cloning and Expression of the nif A Gene of *Klebsiella oxytoca* in *K. pneumoniae* and *Azospirillum lipoferum*," Agricultural and Biological Chemistry, 1986, 50(6):1539-1544.

Van Dongen, "Performance criteria for graph clustering and Markov cluster experiments," CWI, 2000, 36 pages.

Van Heeswijk et al., "Nitrogen Assimilation in *Escherichia coli*: Putting Molecular Data into a Systems Perspective," Microbiology and Molecular Biology Reviews, Dec. 2013, 77(4):628-695.

Venkateshwaran, "Exploring the Feasibility of Transferring Nitrogen Fixation to Cereal Crops," Principles of Plant-microbe Interactions, 2015, 403-410.

Vernon et al., "Analysis of 16S rRNA gene sequences and circulating cell-free DNA from plasma of chronic fatigue syndrome and non-fatigued subjects," BMC Microbiology, 2002, 2:39, 6 pages.

Villa et al., "*Azotobacter vinelandii* siderophore can provide nitrogen to support the culture of the green algae *Neochloris oleoabundans* and *scenedesmus*," FEMS Microbial. Lett., 2014, 351(1):70-77.

Villalobos et al., "Gene Designer: a synthetic biology tool for constructing artificial ONA segments," BMC Bioinformatics, 2006, 7:285, 8 pages.

Voight, "Genetic parts to program bacteria," Current Opinion in Biotechnology, 2006, 17(5):548-557.

Voigt, "Gaining Access: Rebuilding Genetics from the Ground Up," Institute of Medicine Board on Global Health Forum on Microbial Threats, Mar. 14, 2011. Retrieved from URL<iom.edu//media/Files/ActivityFiles/PublicHealth/MicrobialThreats/2011-MAR- 14Noigt.pdf, 82 pages.

(56) References Cited

OTHER PUBLICATIONS

Wang et al., "A minimal nitrogen fixation gene cluster from *Paenibacillus* sp. WLY78 enables expression of active nitrogenase in *Escheichia coli*," Plos Genetics, 2013, 9(10):1-11.

Wang et al., "Biofilm formation enables free-living nitrogen-fixing rhizobacteria to fix nitrogen under aerobic conditions," The ISME Journal, Jul. 2017, 11:1602-1613.

Wang et al., "Emergence of a novel mobile colistin resistance gene, mcr-8, in NDM-producing *Klebsiella pneumoniae*," Emerging Microbes & Infections, Jul. 2018, 7(1):1-9.

Wang et al., "High throughput sequencing analysis of bacterial communities in soils of a typical Poyang Lake wetland," Acta Ecologica Sinica, 2017, 37(5), 9 pages, English Abstract.

Wang et al., "*Kosakonia quasisacchari* sp. nov. recovered from human wound secretion in China," Int. J. Syst. Evol. Microbio., Oct. 2019, 69(10):3155-3160.

Wang et al., "Ligand-inducible and liver-specific target gene expression in transgenic mice," Nat Biotechnol., Mar. 1997, 15(3):239-43.

Wang et al., "Positive and negative regulation of gene expression in eukaryotic cells with an inducible transcriptional regulator," Gene Ther., May 1997, 4(5):432-441.

Wang et al., "Positive and negative regulation of transferred nif genes mediated by indigenous GlnR in Gram-positive *Paenibacillus polymyxa*," PLOS Genetics, Sep. 2018, 14(9):e1007629.

Wang et al., "Programming cells by multiplex genome engineering and accelerated evolution," Nature, Aug. 2009, 460(7257):894-8.

Wang et al., "Roles of poly-3-hydroxybutyrate (PHB) and glycogen in symbiosis of *Sinorhizobium meliloti* with *Medicago* sp.," Microbiology, Feb. 2007, 153(2):388-398.

Wang et al., Screening, Identification and Growth Promotion Ability of Phosphate Solubilizing Bacteria from Soybean Rhizosphere under Maize-Soybean Intercropping Systems., bioRxiv, Dec. 2020, 25 pages.

Wang et al., "Using Synthetic biology to distinguish and overcome regulatory and functional barriers related to nitrogen fixation," PLoS One, 2013, 8(7):e68677, 11 pages.

Watanabe et al., "Chapter 15. Plasmid-borne gene cluster assemblage and heterologous biosynthesis of nonribosomal peptides in *Escherichia coli*," Methods Enzymol., 2009, 458:379-99.

Watanabe et al., "Total biosynthesis of antitumor nonribosomal peptides in *Escherichia coli*," Nature Chemical Biology, 2006, 2:423-428.

Weber et al., "A modular cloning system for standardized assembly of multigene constructs," PLoS One, Feb. 2011, 6(2):e16765, 11 pages.

Wei et al., "Endophytic nitrogen-fixing *Klebsiella variicola* strain DX120E promotes sugarcane growth," Biology and fertility of soils, 2014, 50:657-666.

Welch et al., "Design Parameters to Control Synthetic Gene Expression in *Escherichia coli*," PLoS One, 2009, 4(9):e7002, 10 pages.

Wells, "Additivity of mutational effects in proteins," Biochemistry, 1990, 29:8509-8517.

Wen et al., "Enabling Biological Nitrogen Fixation for Cereal Crops in Fertilized Fields," ACS Synth. Biol., Dec. 2021, 10(12):3264-3277.

Wenzel et al., "Recent developments towards the heterologous expression of complex bacterial natural product biosynthetic pathways," Curr. Opin. Biotechnol., 2005, 16(6):594-606.

Werner et al., "Fast track assembly of multigene constructs using Golden Gate cloning and the MoClo system," Bioeng Bugs. Jan. 2012, 3(1):38-43.

Widmaier et al., "Engineering the *Salmonella* type Ill secretion system to export spider silk monomers," Mol. Syst. Biol., 2009, 5:309, 9 pages.

Wimpenny et al., "Community structure and co-operation in biofilms," 59th Symposium of the Society for General Microbiology, Allison et al. (eds.), Sep. 2000, 23 pages.

Witkowski et al., "Conversion of a β-Ketoacyl synthase to a malonyl decarboxylase by replacement of the active-site cysteine with glutamine," Biochemistry, Sep. 1999, 38(36):11643-50.

Woolbright et al., "Novel insight into mechanisms of cholestatic liver injury," World J Gastroenterol., Sep. 2012, 18(36):4985-93.

Wootton et al., "Statistics of local complexity in amino acid sequences and sequence databases," Computers & Chemistry, Jun. 1993, 17(2):149-163.

Written Opinion in International Appln. No. PCT/US2018/057174, dated Jan. 4, 2019, 3 pages.

Wu et al., "Effects of biofertilizer containing N-fixer, P and K solubilizers and AM fungi on maize growth: a greenhouse trial," Geodernna, Mar. 2005, 125(1-2):155-166.

Wu et al., "Effects of different amendments on contents of phenolic acids and specific microbes in rhizosphere of *Pseudostellaria heterophylla*," Ying Yong Sheng Tai Xue Bao, Nov. 2016, 18(27):3623-3630, English Abstract.

Wu et al., "Insights into the Mechanism of Proliferation on the Special Microbes Mediated by Phenolic Acids in the *Radix pseudostellariae* Rhizosphere under Continuous Monoculture Regimes," Front. Plant. Sci., May 2017, 8(659):1-15.

Wu et al., "Mixed Phenolic Acids Mediated Proliferation of Pathogens *Talaromyces helices* and *Kosakonia sacchari* in Continuously Monocultured *Radix pseudostellariae* Rhizosphere Soil," Frontiers in Microbiology, Mar. 2016, 7(335):1-14.

Wu et al., "Multivariate modular metabolic engineering of *Escherichia coli* to produce resveratrol from L-tyrosine," J. Biotechnol., 2013, 167:404-411.

Wu et al., "Root exudates from two tobacco cultivars affect colonization of *Ralstonia solanacearum* and the disease index," European Journal of Plant Pathology, 2014, 141(4):667-677.

Wu et al., "The role of organic acids on microbial deterioration in the *Radix pseudostellariae* rhizosphere under continuous monoculture regimes," Sci. Rep., Jun. 2017, 7(1):1-13.

Xie et al., "Interaction between NifL and NifA in the nitrogen-fixing *Pseudomonas stutzeri* A1501," Microbiology (Reading), Dec. 2006, 152(Pt 12):3535-3542.

Xu et al., "ePathBrick: a synthetic biology platform for engineering metabolic pathways in *E. coli*," ACS Synth. Biol., 2012, 1:256-266.

Yan et al., "Global transcriptional analysis of nitrogen fixation and ammonium repression in root-associated *Pseudomonas stutzeri* A1501," BMC Genomics, Jan. 2010, 11(11):1-13.

Yan et al., "Influence of salinity and water content on soil microorganisms," Int. Soil Water Conserv. Res., 2015, 3:316-323.

Yao et al., "Complementation analysis of heterologous nifA genes to nifA mutants of *Sinorhizobium pallida*," Chinese Science Bulletin, Oct. 2006, 51(19):2258-2264, 2 pages (English abstract only).

Yarza et al., "Uniting the classification of cultured and uncultured bacteria and archaea using 16S rRNA gene sequences," Nature Rev. Micro., 2014, 12:635-345.

Ye et al., "Primer-BLAST: a tool to design target-specific primers for polymerase chain reaction," BMC Bioinformatics., Jun. 2012, 13(134):1-11.

Yokobayashi et al., "Directed evolution of a genetic circuit," Proc. Natl. Acad. Sci. USA, 2002, 99(26):16587-16591.

Yoshida et al., "Atmospheric dinitrogen fixation in the flooded rice rhizosphere as determined by the N-15 isotope technique," Soil Science and Plant Nutrition, Dec. 1980, 26(4):551-559.

Yu et al., "Recombineering *Pseudomonas protegens* CHA0: An innovative approach that improves nitrogen fixation with impressive bactericidal potency," Microbiological Research, Jan. 2019, 218:58-65.

Yurgel et al., "A Mutant GlnD Nitrogen Sensor Protein Leads to a Nitrogen-fixing but Ineffective *Sinorhizobium meliloti* Symbiosis with Alfalfa," PNAS, Dec. 2008, 105(48):18958-18963.

Zaller, "Editorial: Non-target Effects of Pesticides on Organisms Inhabiting Agroecosystems," Enviorn. Sci., May 2019, 7(75):1-3.

Zaslaver et al., "Optimal gene partition into operons correlates with gene functional order," Phys. Biol., 2006, 3(3):183-189.

Zazopoulos et al., "A genomics-guided approach for discovering and expressing cryptic metabolic pathways," Nat. Biotechnol., 2003, 21(2):187-190.

Zehr et al., "New Nitrogen-Fixing Microorganisms Detected in Oligotrophic Oceans by Amplification of Nitrogenase (nifH) Genes," Appl Environ Microbiol., Sep. 1998, 64(9):3444-3450.

(56) References Cited

OTHER PUBLICATIONS

Zehr Lab NifH database, retrieved from URL <https://wwwzehr.pmc.ucsc.edu/nifH_Database_Public/>, Apr. 4, 2014, 1 page.

Zhang et al., "Expression of the N₂ fixation gene operon of *Paenibacillus* sp. WLY78 under the control of the T7 promoter in *Escherichia coli* BL21," Biotechnol. Lett., Oct. 2015, 37(10):1999-2004.

Zhang et al., "GlnD Is Essential for NifA Activation, NtrB/NtrC-Regulated Gene Expression, and Posttranslational Regulation of Nitrogenase Activity in the Photosynthetic, Nitrogen-Fixing Bacterium *Rhodospirillum rubrum*," J. Bacteriol., Feb. 2005, 187(4):1254-1265.

Zhang et al., "Influence of different factors on the nitrogenase activity of the engineered *Escherichia coli* 78-7," World J Microbiol Biotechnol., Jun. 2015, 31(6):921-7.

Zhang et al., "Involvement of the ammonium transporter AmtB in nitrogenase regulation and ammonium excretion in *Pseudomonas stutzeri* A 1501," Res. Microbial, Jun. 2012, 163(5):332-339.

Zhang et al., "Mutagenesis and functional characterization of the four domains of GlnD, a bifunctional nitrogen sensor protein," Journal of Bacteriology, Jun. 2010, 192(11):2711-2721.

Zhang et al., "Mutagenesis and Functional Characterization of the glnB, glnA, and nifA Genes from the Photosynthetic Bacterium *Rhodospirillum rubrum*," Journal of Bacteriology, Feb. 2000, 182(4):983-992.

Zhao et al., "Evidence for nifU and nifS participation in the biosynthesis of the iron-molybdenum cofactor of nitrogenase," J. Biol. Chem., 2007, 282(51):37016-37025.

Zhao et al., "Soil bacterial community composition in rice-fish integrated farming systems with different planting years," Sci. Rep., 2021, 11(1):10855, 10 pages.

Zhu et al., "Genome sequence of *Enterobacter* sp. strain SP1, an endophytic nitrogen-fixing bacterium isolated from sugarcane," J. Bacteriol., Dec. 2012, 194(24):6963-6964.

Zhu et al., "*Enterobacter sacchari* sp. nov., a nitrogen-fixing bacterium associated with sugar cane (*Saccharum officinarum* L.)," International Journal of Systematic and Evolutionary Microbiology, 2013, 63(Pt7):2577-2582.

Zomer, "PPP: Perform Promoter Prediction," retrieved from URL <http://bioinformatics.biol.rug.nl/websoftware/ppp/ppp_start.php>, 2011, 2 pages.

Zou et al., "Identification and functional characterization of NifA variants that are independent of GlnB activation in the photosynthetic bacterium *Rhodospirillum rubrum*," Microbiology, Sep. 2008, 154(9):2689-2699.

Bennett, "Engineering Nitrogenases for Synthetic Nitrogen Fixation: From Pathway Engineering to Directed Evolution," BioDesign Research, Feb. 7, 2023, 5(0005):1-12.

Bush et al., "The role of bacterial enhancer binding proteins as specialized activators of σ⁵⁴-dependent transcription," Microbiology and Molecular Biology Reviews, Sep. 2012, 76(3):497-529.

Chen et al., "Engagement of Arginine Finger to ATP Triggers Large Conformational Changes in NtrC1 AAA+ ATPase for Remodeling Bacterial RNA Polymerase," Structure, Nov. 10, 2010, 18(11):1420-1430.

Chen et al., "Functional analysis of the GAF domain of NifA in *Azospirillum brasilense*: effects of Tyr→Phe mutations on NifA and its interaction with GlnB," Mol Genet Genomics, Jun. 2005, 5:415-422.

Chen et al., "Plant Physiology and Molecular Biology," Editor-in-Chief, Higher Education Publishing House, Jun. 30, 2007, 3rd edition, pp. 261-269, 18 pages (with Machine Translation).

De Castro et al., "ScanProsite: detection of PROSITE signature matches and ProRule-associated functional and structural residues in proteins," Nucleic Acids Res., Jul. 2006, 34:W362-365.

Iltis et al., "*Zea diploperennis* (Gramineae): A New Teosinte from Mexico," Science, Jan. 1979, 203(4376):186-188.

Inaba et al., "Mutational analysis of GlnB residues critical for NifA activation in *Azospirillum brasilense*," Microbiological Research, Feb. 2015, 171:65-72.

International Preliminary Report on Patentability in International Application No. PCT/US2022/035873, mailed on Jan. 11, 2024, 18 pages.

Jumper et al., "Highly accurate protein structure prediction with AlphaFold," Nature, Aug. 2021, 596(7873):583-589.

Letunic et al., "20 years of the Smart protein domain annotation resource," Nucleic Acids Res., Jan. 4, 2018, 46(D1):D493-496.

Lim et al., "Methionine in Proteins: It's Not Just for Protein Initiation Anymore," Neurochemical Research, Jan. 15, 2019, 44(1):247-257.

McKinlay et al., "Carbon dioxide fixation as a central redox cofactor recycling mechanism in bacteria," Proceedings of the National Academy of Sciences, Jun. 29, 2010, 107(26):11669-11675.

Monteiro et al., "In-trans regulation of the N-truncated-NIFA protein of *Herbaspirillum seropedicae* by the N-terminal domain," FEMS Microbiol Lett., 1999, 180(2):157-161.

Monteiro et al., "Expression and functional analysis of an N-truncated NifA protein of *Herbaspirillum seropedicae*," FEBS Lett., 1999, 447(2-3):283-286.

Nagy et al., "Structural Characterization of Arginine Fingers: Identification of an Arginine Finger for the Pyrophosphatase dUTPases," J Am Chem Soc., Nov. 16, 2016, 138(45):15035-15045.

Oliveira et al., "Interaction of GlnK with the GAF domain of *Herbaspirillum seropedicae* NifA mediates NH₄⁺-regulation," Biochimie, 2012, 94(4):1041-1047.

Oliveira et al., "Role of conserved cysteine residues in *Herbaspirillum seropedicae* NifA activity," Res Microbiol., Jul. 2009, 160:389-395.

Sotomaior et al., "Effect of ATP and 2-oxoglutarate on the in vitro interaction between the NifA GAF domain and the GlnB protein of *Azospirillum brasilense*," Braz J Med Biol Res., Dec. 2012, 45(12):1135-40.

Souza et al., "Expression of the nifA gene of *Herbaspirillum seropedicae*: role of the NtrC and NifA binding sites and of the-24/-12 promoter element," Microbiology, 2000, 146:1407-1418.

Yousuf et al., "The AAA+ superfamily: a review of the structural and mechanistic principles of these molecular machines," Crit. Rev. Biochem. Mol. Biol., Apr. 2022, 57(2):156-187.

Berrada et al., "Taxonomy of the Rhizobia: Current Perspectives," British Microbiology Research Journal, Jan. 2014, 4(6):616-639.

Merrick et al., "Repressor properties of the nifL gene product in *Klebsiella pneumoniae*," Mol. Gen. Genet., Mar. 1982, 185:75-81.

European Search Report in European Application No. EP 20795673.1, dated May 22, 2023, 9 pages.

Merrick et al., "Nitrogen control of the nif regulon in *Klebsiella pneumoniae*: involvement of the ntrA gene and analogies between ntrC and nifA," The EMBO Journal, Jan. 1, 1983, 2:39-44.

Schreier et al., "Altered Regulation of the glnA Gene in Glutamine Synthetase Mutants of *Bacillus subtilis*," Jul. 1, 1986, 167(1):35-43.

Streicher et al., "Genetic Control of Glutamine Synthetase in *Klebsiella aerogens*," Journal of Bacteriology, Jan. 1, 1975, 121(1):320-331.

Willardson et al., "Development and Testing of a Bacterial Biosensor for Toluene-Based Environmental Contaminants," Applied and Environmental Microbiology, Mar. 1, 1998, 64(3):1006-1012.

Xiao et al., "Developing a Genetically Encoded, Cross-Species Biosensor for Detecting Ammonium and Regulating Biosynthesis of Cyanophycin," ACS Synthetic Biology, Jul. 13, 2017, 6(10):1807-1815.

AddGene.org [online], "Plasmids 101: Inducible Promoters," Jan. 2018, retrieved on Oct. 23, 2023, retrieved from URL<https://blog.addgene.org/plasmids-101-inducible-promoters>, 8 pages.

Genbank Accession No. AGN85586.1, "cellulose synthase [*Enterobacter* sp. R4-368]," Jun. 29, 2015, 2 pages.

GenBank Accession No. AHJ75701.1, "hypothetical protein C813_13915 [*Kosakonia sacchari* SP1]," Sep. 19, 2017, 2 pages.

GenBank Accession No. AHJ76132.1, "hypothetical protein C813_16530 [*Kosakonia sacchari* SP1]," Sep. 19, 2017, 2 pages.

Steyert et al., "Development of a Novel Genetic System To Create Markerless Deletion Mutants of *Bdellovibrio bacteriovorus*," Appl. Environ. Microbiol., Aug. 2007, 73(15):4717-4724.

(56) References Cited

OTHER PUBLICATIONS

Bageshwar et al., "Studies on Some Nitrogen Fixing Genes of *Azotobacter Vinelandii*," Thesis for the degree of Doctor of Philosophy, Jamia Millia Islamia, Department of Biosciences, Aug. 1994, 255 pages.

Bender et al., "A NAC for regulating metabolism: the nitrogen assimilation control protein (NAC) from *Klebsiella pneumoniae*," Journal of Bacteriology, Jul. 30, 2010, 192(19):4801-11.

Bolay et al., "The distinctive regulation of cyanobacterial glutamine synthetase," Life, Oct. 27, 2018, 8(4):52, 21 pages.

Chaurasia et al., "Improved eco-friendly recombinant *Anabaena* sp. strain PCC7120 with enhanced nitrogen biofertilizer potential," Applied and Environmental Microbiology, Jan. 15, 2011, 77(2):395-9.

Espin et al., "Complementation analysis of gln A-linked mutations which affect nitrogen fixation in *Klebsiella pneumoniae*," Molecular and General Genetics, Dec. 1981, 184:213-7.

Hesketh et al., "The GlnD and GlnK homologues of *Streptomyces coelicolor* A3 (2) are functionally dissimilar to their nitrogen regulatory system counterparts from enteric bacteria," Molecular microbiology, Oct. 2002, 46(2):319-30.

Kim et al., "Cloning and expression of pyrroloquinoline quinone (PQQ) genes from a phosphate-solubilizing bacterium *Enterobacter intermedium*," Current Microbiology, Dec. 2003, 47:457-461.

Krishnan et al., "Citrate synthase mutants of *Sinorhizobium fredii* USDA257 form ineffective nodules with aberrant ultrastructure," Applied and environmental microbiology, Jun. 2003, 69(6):3561-8.

Lee et al., "The class IId bacteriocin thuricin-17 increases plant growth," Planta, Mar. 2009, 229:747-55.

Pan et al., "Phosphate-solubilizing bacteria: advances in their physiology, molecular mechanisms and microbial community effects," Microorganisms, Dec. 2023, 11(12):2904, 22 pages.

Peralta et al., "Engineering the nifH promoter region and abolishing poly-β-hydroxybutyrate accumulation in *Rhizobium etli* enhance nitrogen fixation in symbiosis with *Phaseolus vulgaris*," Applied and Environmental Microbiology, Jun. 2004, 70(6):3272-81.

Sia et al., "Different relative importances of the par operons and the effect of conjugal transfer on the maintenance of intact promiscuous plasmid RK2," Journal of bacteriology, May 1995, 177(10):2789-97.

Simon et al., "Importance of cis determinants and nitrogenase activity in regulated stability of the *Klebsiella pneumoniae* nitrogenase structural gene mRNA," Journal of Bacteriology, Jun. 15, 1999, 181(12):3751-60.

Biswas et al., "Rhizobia Inoculation Improves Nutrient Uptake and Growth of Lowland Rice," Soil Science Society of America Journal, Sep. 2000, 64(5):1644-1650.

Biswas et al., "Rhizobial Inoculation Influences Seedling Vigor and Yield of Rice," Agronomy Journal, Sep. 2000, 92(5):880-886.

Brophy et al., "Engineered integrative and conjugative elements for efficient and inducible DNA transfer to undomesticated bacteria.," Nat. Microbio., Sep. 2018, 3(9):1043-1053.

Burén et al., "Formation of Nitrogenase NifDK Tetramers in the Mitochondria of *Saccharomyces cerevisiae*," ACS Synthetic Biology, Jun. 16, 2017, 6(6):1043-1055.

Cannon et al., "Chromosomal Integration of Klebsiella Nitrogen Fixation Genes in *Escherichia coli*," Journal of General Microbiology, Jan. 1974, 80(1):227-239.

Cannon et al., "Plasmids Formed in Nitrogen-fixing *Escherichia coli-Klebsiella pneumoniae* Hybrids," Journal of General Microbiology, Jan. 1974, 80(1):241-25.

Delmotte et al., "An integrated proteomics and transcriptomics reference data set provides new insights into the *Bradyrhizobium japonicum* bacteroid metabolism in soybean root nodules," Proteomics, Apr. 8, 2010, 10(7):1391-1400.

Edgar, "MUSCLE: multiple sequence alignment with high accuracy and high throughput," Nucleic Acids Res., Mar. 19, 2004, 32(5):1792-1797.

Ferri et al., "Plasmid electroporation of *Sinorhizobium* strains: The role of the restriction gene hsdR in type strain Rm1021," Plasmid, May 2010, 63(3):128-135.

Gorochowski et al., "Genetic circuit characterization and debugging using RNA-seq," Mol Syst Biol., Nov. 9, 2017, 13(11):952, 16 pages.

Gutiérrez-Zamora et al., "Natural endophytic association between *Rhizobium etli* and maize (*Zea mays* L.)," J Biotechnol., Oct. 4, 2001, 91(2-3):117-126.

Haskett et al., "Engineered plant control of associative nitrogen fixation," PNAS, Apr. 19, 2022, 119(16):e2117465119, 9 pages.

Hoover et al., "Homocitrate is a Component of the Iron-Molybdenum Cofactor of Nitrogenase," Biochemistry, Apr. 4, 1989, 28(7):2768-2771.

Igiehon et al., "Rhizosphere Microbiome Modulators: Contributions of Nitrogen Fixing Bacteria towards Sustainable Agriculture," Int J Environ Res Public Health, Mar. 23, 2018, 15(4):574, 25 pages.

Jones et al., "Soil microbial community analysis using two-dimensional polyacrylamide gel electrophoresis of the bacterial ribosomal internal transcribed spacer regions," J Microbiol Methods, May 2007, 69(2):256-267.

Kechris et al., "Quantitative exploration of the occurrence of lateral gene transfer by using nitrogen fixation genes as a case study," Proc Natl Acad Sci U S A., Jun. 20, 2006, 103(25):9584-9589.

Kornberg, "DNA Replication," W. H. Freeman & Co., San Francisco, 1980, Section 2-12:75-77.

Li et al., "The anti-Shine-Dalgarno sequence drives translational pausing and codon choice in bacteria," Nature, Mar. 28, 2012, 484(7395):538-541.

Li et al., "Using synthetic biology to increase nitrogenase activity," Microb Cell Fact., 2016, 15(43):1-11.

Mahmood et al., "Seed biopriming with plant growth promoting rhizobacteria: a review," FEMS Microbiol Ecol., Aug. 2016, 92(8): fiw112, 14 pages.

Malik et al., "Association of nitrogen-fixing, plant-growth-promoting rhizobacteria (PGPR) with kallar grass and rice," Plant and Soil, Oct. 1997, 194:37-44.

Martinez-Argudo et al., "The NifL-NifA System: a Multidomain Transcriptional Regulatory Complex That Integrates Environmental Signals," Journal of Bacteriology, Feb. 9, 2004, 186(3):601-10.

Pascuan et al., "Exploring the Ancestral Mechanisms of Regulation of Horizontally Acquired Nitrogenases," J Mol Evol., Oct. 2015, 81(3-4):84-89.

Perrine-Walker et al., "Infection process and the interaction of rice roots with rhizobia," Journal of Experimental Botany, Sep. 2007, 58(12):3343-3350.

Sandig et al., "HBV-derived promoters direct liver-specific expression of an adenovirally transduced LDL receptor gene," Gene Therapy, Nov. 1996, 3(11):1002-1009.

Shanks et al., "*Saccharomyces cerevisiae*-based molecular tool kit for manipulation of genes from gram-negative bacteria," Applied and Environmental Microbiology, Jul. 2006, 72(7):5027-5036.

Tang et al., "Biology of Nitrogen Fixers" (Chinese), Northeast Forestry University Press, First Edition, Jun. 30, 2009, pp. 172-183 (with English Translation).

Thöny, et al., "Dual Control of the *Bradyrhizobium japonicum* Symbiotic Nitrogen Fixation Regulatory Operon fixR nifA: Analysis of cis- and trans-Acting Elements," J Bacteriol., Aug. 1989, 171(8):4162-4169.

Tsukada et al., "Comparative Genome-Wide Transcriptional Profiling of *Azorhizobium caulinodans* ORS571 Grown under Free-Living and Symbiotic Conditions," Appl Environ Microbiol., Aug. 2009, 75(15):5037-5046.

Woodruff et al., "Registry in a tube: multiplexed pools of retrievable parts for genetic design space exploration," Nucleic Acids Research, Feb. 17, 2017, 45(3):1553-1565.

Xu et al., "Advance of Study on Nitrogenase" (Chinese), Journal of Biology, Aug. 31, 2011, 8(4):61-64 (English Abstract).

Yan et al., "Nitrogen fixation island and rhizosphere competence traits in the genome of root-associated *Pseudomonas stutzeri* A1501," Proc Natl Acad Sci U S A, May 27, 2008, 105(21):7564-7569.

* cited by examiner

Schematic of the glnD gene, showing regions corresponding to the functional domain of the GlnD protein.

| Strain ID | Genotype | glnD modification |
|---|---|---|
| 6-404 | ΔnifL::Prm1, ΔglnE_KO1 | none |
| 6-2552 | ΔnifL::Prm1, ΔglnE-AR_KO1,ΔglnD-ACT12_truncation | C-terminal glutamine sensing ACT1 and ACT2 domains deleted |
| 6-2597 | ΔnifL::Prm1, ΔglnE-AR_KO1, ΔglnD-UT_truncation | N-terminal uridylyl-transferase domain deleted |
| 6-2587 | ΔnifL::Prm1, ΔglnE-AR_KO1,ΔglnD | entire gene deleted |
| 6-2636 | ΔnifL::Prm1, ΔglnE-AR_KO1, ΔglnD_UT_deactivation | N-terminal uridylyl-transferase domain deactivated through site-directed mutagenesis: G90D,G91V,D104A |
| 6-412 | ΔnifL::Prm5, ΔglnE_KO1 | none |
| 6-2090 | ΔnifL::Prm5, ΔglnE-AR_KO1,ΔglnD-ACT12_truncation | C-terminal glutamine sensing ACT1 and ACT2 domains deleted |
| PTA-126743 | ΔnifL::Prm5, ΔglnE-AR_KO1,ΔglnD | entire gene deleted |
| 6-2411 | ΔnifL::Prm5, ΔglnE-AR_KO1, ΔglnD_UT_truncation | N-terminal uridylyl-transferase domain deleted |
| 6-2615 | ΔnifL::Prm5, ΔglnE-AR_KO1, ΔglnD_UT_deactivation | N-terminal uridylyl-transferase domain deactivated through site-directed mutagenesis: G90D,G91V,D104A |
| 6-2627 | ΔnifL::Prm5, ΔglnE-AR_KO1, ΔglnD_UR_deactivation | UR (HD) domain deactivated through site-directed mutagenesis: H515A and D516A |

FIG. 3 (Cont.)

Technical Roadmap to Full Fertilizer Replacement

Current Strain (201712002)

Predicted Performance of PBC137.1 strains

Ethylene (mmol/CFU.hr)

| | PTA-126741 | PTA-126749 | PTA-126740 | 137-2084 | 137-1036 | 137-1034 | 137 |
|---|---|---|---|---|---|---|---|
| No Nitrogen | | | | | | | |
| Count | 2 | 10 | 8 | 53 | 32 | 6 | 64 |
| Avg | 8.60E-013 | 7.50E-013 | 3.91E-013 | 7.98E-013 | 4.16E-013 | 3.71E-013 | 3.13E-013 |
| StdDev | 3.68E-013 | 1.28E-013 | 1.22E-013 | 3.47E-013 | 1.20E-013 | 1.32E-013 | 1.40E-013 |
| 5mM (NH$_4$)$_3$PO$_4$ | | | | | | | |
| Count | 2 | No Data | 8 | 53 | 32 | 6 | 61 |
| Avg | 7.10E-013 | | 3.15E-013 | 5.27E-013 | 2.55E-013 | 9.79E-014 | 1.95E-015 |
| StdDev | 1.32E-013 | | 1.54E-013 | 2.48E-013 | 9.98E-014 | 3.59E-014 | 3.96E-015 |
| 10mM (NH$_4$)$_3$PO$_4$ | | | | | | | |
| Count | No Data | 10 | No Data | 3 | 3 | No Data | 6 |
| Avg | | 5.67E-0.13 | | 4.04E-013 | 9.80E-014 | | 1.73E-016 |
| StdDev | | 1.05E-0.13 | | 2.17E-014 | 1.05E-014 | | 2.09E-016 |

Total Inoculated Wells: 42

Experiment Outline

WT Strains (3 reps each)
- 201708001
- 201701001

Media
- ARA minimal medium

Nitrogen
- No Nitrogen
- 10mM Ammonium Phosphate

3 Runs
- Oxygen: 3%, 1.5%, 0.5%

Time
- 4 days (except for the 3rd run – 3 days)

- 50X dilution or 100X depending on visible growth
- Using the 48-deep well flower biolector plates
- Made a duplicate deep well plate and grew in the hypoxic chamber

FIG. 22C

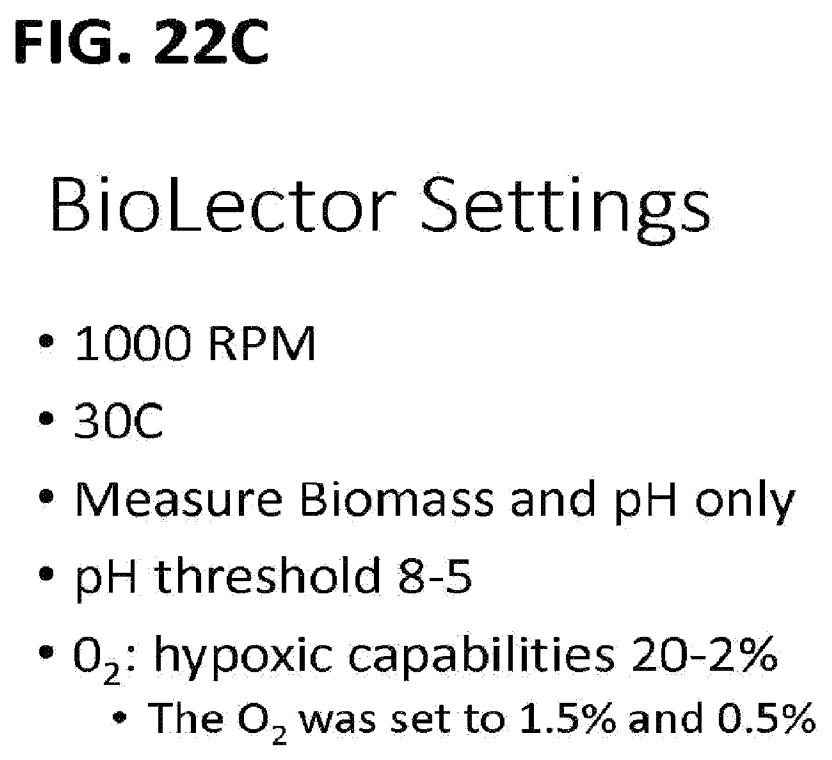

BioLector Settings

- 1000 RPM
- 30C
- Measure Biomass and pH only
- pH threshold 8-5
- $O_2$: hypoxic capabilities 20-2%
  - The $O_2$ was set to 1.5% and 0.5%

Biolector Run 1, 3% - ARA 10mM

*K. sacchari* 201701001

*K. variicola* 201708001 uninoculated control

SEQUENCE LISTING

<160> NUMBER OF SEQ ID NOS: 10

<210> SEQ ID NO 1
<211> LENGTH: 500
<212> TYPE: DNA
<213> ORGANISM: Klebsiella sp.

<400> SEQUENCE: 1
agcgtcaggt accggtcatg attcaccgtg cgattctcgg ttccctggag cgcttcattg       60
gcatcctgac cgaagagttc gctggcttct tcccaacctg gattgcacca gtgcaggtag      120
tggtcatgaa tattaccgat tctcaggctg aatacgttaa cgaattgacg cgtaaactac      180
aaaatgcggg cattcgtgta aaagcagact tgagaaatga gaagattggc tttaaaatcc      240
gcgagcacac tttacgtcgt gtcccgtata tgttggtctg tggcgacaaa gaagtcgaag      300
ccggcaaagt ggccgtgcgc acccgtcgcg ggaaagacct cggcagcatg gacgtaagtg      360
aagtgattga gaagctgcaa caagagattc gcagccgcag tcttcaacaa ctggaggaat      420
aaggtattaa aggcggaaaa cgagttcaaa cggcacgtcc gaatcgtatc aatggcgaga      480
ttcgcgccct ggaagttcgc                                                  500

<210> SEQ ID NO 2
<211> LENGTH: 400
<212> TYPE: DNA
<213> ORGANISM: Klebsiella sp.

<400> SEQUENCE: 2
gcccgctgac cgaccagaac ttccaccttg gactcggcta tacccttggc gtgacggcgc       60
gcgataactg ggactacatc cccattccgg tgatcttacc attggcgtca ataggttacg      120
gtccggcgac tttccagatg acctatattc ccggcaccta caataacggt aacgtttact      180
tcgcctgggc tcgtatacag ttttaattcg ctaagtctta gcaataaatg agataagcgg      240
tgtgtcttgt ggaaaaacaa ggactaaagc gttacccact aaaaaagata gcgactttta      300 tcactttta gcaaagttgc actggacaaa aggtaccaca attggtgtac tgatactcga      360
cacagcatta gtgtcgattt ttcatataaa ggtaattttg                            400

<210> SEQ ID NO 3
<211> LENGTH: 400
<212> TYPE: DNA
<213> ORGANISM: Klebsiella variicola

<400> SEQUENCE: 3
gcccgctgac cgaccagaac ttccaccttg gactcggcta tacccttggc gtgacggcgc       60
gcgataactg ggactacatc cccattccgg tgatcttacc attggcgtca ataggttacg      120
gtccggcgac tttccagatg acctatattc ccggcaccta caataacggt aacgtttact      180
tcgcctgggc tcgtatacag ttttaattcg ctaagtctta gcaataaatg agataagcgg      240
tgtgtcttgt ggaaaaacaa ggactaaagc gttacccact aaaaaagata gcgactttta      300 tcactttta gcaaagttgc actggacaaa aggtaccaca attggtgtac tgatactcga      360
cacagcatta gtgtcgattt ttcatataaa ggtaattttg                            400

<210> SEQ ID NO 4
<211> LENGTH: 313
<212> TYPE: DNA
<213> ORGANISM: Kosakonia sacchari

<400> SEQUENCE: 4

-continued

```
ggacatcatc gcgacaaaca atattaatac cggcaaccac accggcaatt tacgagactg      60
cgcaggcatc ctttctcccg tcaatttctg tcaaataaag taaaagaggc agtctacttg     120
aattaccccc ggctggttga gcgtttgttg aaaaaaagta actgaaaaat ccgtagaata     180
gcgccactct gatggttaat taacctattc aattaagaat tatctggatg aatgtgccat     240
taaatgcgca gcataatggt gcgttgtgcg ggaaaactgc ttttttttga aagggttggt     300
cagtagcgga aac                                                       313
```

```
<210> SEQ ID NO 5
<211> LENGTH: 1997
<212> TYPE: DNA
<213> ORGANISM: Kosakonia sacchari

<400> SEQUENCE: 5
```

```
atgaccctga atatgatgat ggatgccggc ggacatcatc gcgacaaaca atattaatac      60
cggcaaccac accggcaatt tacgagactg cgcaggcatc ctttctcccg tcaatttctg     120
tcaaataaag taaaagaggc agtctacttg aattaccccc ggctggttga gcgtttgttg     180
aaaaaaagta actgaaaaat ccgtagaata gcgccactct gatggttaat taacctattc     240
aattaagaat tatctggatg aatgtgccat taaatgcgca gcataatggt gcgttgtgcg     300
ggaaaactgc ttttttttga aagggttggt cagtagcgga acaactcac ttcacacccc      360 gaaggggaa gttgcctgac cctacgattc ccgctatttc attcactgac cggaggttca     420
aaatgaccca gcgaaccgag tcgggtaata ccgtctggcg cttcgatttg tcccagcagt     480
tcactgcgat gcagcgcata agcgtggtac tcagccgggc gaccgaggtc gatcagacgc     540
tccagcaagt gctgtgcgta ttgcacaatg acgcctttt gcagcacggc atgatctgtc     600
tgtacgacag ccagcaggcg attttgaata ttgaagcgtt gcaggaagcc gatcagcagt     660
taatccccgg cagctcgcaa atccgctatc gtccgggcga agggctggtc gggacggtgc     720
tttcgcaggg ccaatcatta gtgctggcgc gcgttgctga cgatcagcgc tttcttgacc     780
ggctcgggtt gtatgattac aacctgccgt ttatcgccgt gccgctgata gggccagatg     840
cgcagacttt cggtgtgctg acggcacaac ccatggcgcg ttacgaagag cgattacccg     900
cctgcacccg ctttctggaa acggtcgcta acctggtcgc gcaaaccgtg cgtttgatgg     960
caccaccggc agtgcgccct tccccgcgcg ccgccataac acaggccgcc agcccgaaat    1020
cctgcacggc ctcacgcgca tttggttttg aaaatatggt cggtaacagt ccggcgatgc    1080
gccagaccat ggagattatc cgtcaggttt cgcgctggga caccaccgtt ctggtacgcg    1140
gcgagagtgg caccggcaag gagctgattg ccaacgccat ccaccaccat tcgccgcgtg    1200
ccggtgcgcc atttgtgaaa ttcaactgtg cggcgctgcc ggcacactg ctggaaagcg     1260 aattgttcgg tcacgagaaa ggggcattta ccggcgcggt acgccagcgt aaaggccgtt    1320
ttgagctggc cgatggcggc acgctgtttc ttgacgagat cggcgagagt agcgcctcgt    1380
ttcaggctaa gctgctgcgc attttgcagg aaggcgaaat ggaacgcgtc ggcggcgacg    1440
agacattgca agtgaatgtg cgcattattg ccgcgacgaa ccgcaatctt gaagatgaag    1500
tccggctggg gcactttcgc gaagatctct attatcgcct gaatgtgatg cccatcgccc    1560
tgccgccact acgcgaacgc caggaggaca ttgccgagct ggcgcacttt ctggtgcgta    1620
aaatcgccca taaccagagc cgtacgctgc gcattagcga gggcgctatc cgcctgctga    1680
tgagctacaa ctggcccggt aatgtgcgcg aactggaaaa ctgccttgag cgctcagcgg    1740
```

```
tgatgtcgga gaacggtctg atcgatcggg atgtgatttt gtttaatcat cgcgaccagc    1800
cagccaaacc gccagttatc agcgtctcgc atgatgataa ctggctcgat aacaaccttg    1860
acgagcgcca gcggctgatt gcggcgctgg aaaaagcggg atgggtacaa gccaaagccg    1920
cgcgcttgct ggggatgacg ccgcgccagg tcgcctatcg tattcagacg atggatataa    1980
ccctgccaag gctataa                                                    1997

<210> SEQ ID NO 6
<211> LENGTH: 2751
<212> TYPE: DNA
<213> ORGANISM: Klebsiella variicola

<400> SEQUENCE: 6
tgaaaagccg gcgcccgccg gctttttttat tagatagttt tttcttatgg tgacgcgatg      60
agcaactcat tacctgacac agcctcccct cttctgcccg tcccgccgga acatccggtg     120
agctggccgc agggcgatct gaactgtgct gcaattaagg cgcacatcga taccttccag     180
cactggctgg gcgaggcgtt tgactccggc atcgccgcgg agcagctcat tgcggcgcgc     240
accgaattta tcgaccagct gctgcagcgg ttgtggatcg cctacggttt tgaatccgtc     300
tgcgatctgg cgctggtggc cgtccttgat tatggccgcg cgcagctgca cccgctctct     360
gacgtcgcac tgctgatcct cagccgcaaa aaactgcctg acgaccaggc gcaaaaggtc     420
ggcgaactgc tgacgctact gtgggacgtc aagctggagg tgggccacag cgtgcgcacc     480
ctcgaagagt gtctgctcga aggactttcg gatctcaccg tcgccactaa cttgattgaa     540
tcgcgcctgc tgatcggcga cgtcgcgctg ttccttgaac tgcaaaaaca tattttttagc     600 gacggcttct ggccatcgga aaagttcttc gccgccaagg tggaagagca gaacgtccgt     660
catcaacgct atcacggcac cagctataac ctggagccgg acgtgaaaag cagccccggc     720
ggcctgcggg atatccatac gctacagtgg gtggctcgcc gtcattttgg cgccacctcg     780
atggatgaga tggtcggctt cggctttctg accgaagccg agcgcaatga gctcaacgag     840
tgtctgcatc agctgtggcg catccgtttc gcgctgcatc tcgagctcac tcgctatgac     900
aaccgtctgc ttttcgaccg ccagctcagc gtcgcccgcc ggctcggcta tgaaggcgac     960
ggcaaccagc cgattgagca tatgatgaag gacttcttcc gcgtcacccg ccgggtgagc    1020
gagctgaacc agatgctgct tcagctgttt gaagaggcta ttctcgccct gaccgaggat    1080
gaaaaaccgc gcccgataga cgatgacttc cagctgcgcg gcacccttat cgatctgcgt    1140
gacgacacgc tgtttattcg cgaaccgcag gccattctgc gcatgtttta tatgatggtg    1200
cgcaacagca ctatcaccgg catctactcc acgacgttgc gccatctgcg ccatgcccgg    1260
cgccatctga cccagccgct gtgctatatc ccggaggcgc gcacgctctt tctcagcatg    1320
ctgcgccatc aggggcggt cagccgcgga ctgctgccga tgcatcgcca tagcgtgctg    1380
tgggcctata tgccgcagtg gtcacatatc gtcggccaga tgcagttcga tctgtttcac    1440
gcctacaccg tcgatgaaca caccatccgc gtgatgctga agctggagag ctttgccaaa    1500
gaagaaaccc gcagccgcca cccgctgtgc gtggagctat ggccgcgctt aacgcacccg    1560
gagctgattt taatcgccgc cctgttccac gacattgcga aagggcgtgg cggcgaccac    1620
tcgatcctcg gcgcgcagga tgtgctgaag tttgccgagc tgcacggact gaactctcgc    1680
gaaacgcagt tggtcgcctg gctggtgcgt caccatctgc tgatgtcggt caccgcccag    1740
cggcgcgaca ttcaggatcc ggaggtgatt aagcagttcg ccgaggaagt gcaaacggaa    1800
aatcgcctgc gctatctggt gtgcctgacc gtcgccgaca tctgcgccac caacgaaacg    1860
```

-continued

```
ctgtggaaca gctggaagca gagtctgctg cgcgaactct atttcgccac cgagaaacag   1920
ctgcgtcggg gcatgcaaag cacccggat atgcgcgaac gggtgcgtca tcatcagctg   1980
caggcgctgg ccctgctgcg gatggacaat attaatgaag aggcgctgca tcagatctgg   2040
aaccgctgcc gcgccaacta tttcgtgcgg catacgccga cgcagctcgc ctggcacgcc   2100
cgcaacctgc tgcgtcacga tctgaataag ccgatgattc tgctgagttc gcaggccacc   2160
cgcggcggta cggagatttt tatctggagc ccggatcgcc cttatctgtt tgccgcggtg   2220
tgcggcgaac tggaccgccg caacctcagc gtccacgacg cgcagatctt caccacccgc   2280
gacggcatgg cgatggatac ctttattgtc ctcgaacccg acggcagccc gctttccgct   2340
gaccgccacg acgcgattcg ccacggtctt gaacagacga taactcagcg cagctgggaa   2400 ccccggccc cgcgtcgtca ggcggcaaaa ctgcgtcact tctctgtgcc gacagaggtg   2460
aatttcctgc cgacccatac cgatcgaaaa tcgtttctcg agctgattgc gctcgatcag   2520
ccagggctgc tcgcccgcgt cggccaggtg ttcgccgacc tcggtatttc gcttcacggg   2580
gcgcgaatta cgacaattgg tgagcgagta aagagtttat ttataatcgc caccgccgac   2640
cggcgtggcc ttaataatga gctacaacaa gaagtgcaac aacggttgac agaggccctc   2700
aatccaaacg ataaagggtg acgtattttt tttagtgaat ggaaagaaac a           2751

<210> SEQ ID NO 7
<211> LENGTH: 1410
<212> TYPE: DNA
<213> ORGANISM: Klebsiella variicola

<400> SEQUENCE: 7
atgcaacgag ggatagcctg gatcgttgat gacgatagct ccatccgctg ggtgcttgaa    60
cgcgcgctca ccggagccgg cttgagctgc acaacgttcg aaagcggcaa tgaggtgcta   120
gatgccctca ccaccaaaac cccggatgta ctgctgtcag ctatccgtat gccgggaatg   180
gatggtctgg cgctgctcaa acagattaag cagcgtcatc caatgcttcc ggtcatcata   240
atgaccgcac attccgatct ggacgctgcg gtcagcgctt atcagcaagg cgcgtttgat   300
tatctgccca aaccttttga tattgatgaa gccgtcgccc tggtcgaccg ggcgataagc   360
cactatcagg agcagcaaca gccgcgaaat gcgccaataa gcagcccaac tgccgacatc   420
atcggcgaag cgccggcaat gcaggatgtc tttcgcatta ttggccgttt gtcgcgatca   480
tccatcagcg tgctgattaa tggcgaatcc ggtaccggta agagctcgt cgctcacgcc   540 ctgcatcgtc atagcccacg ttcaaaagcg ccgtttatcg cactgaatat ggcggcaata   600
cccaaagacc tgattgagtc cgagctgttc gggcatgaaa aggggccctt taccggcgcc   660
aataccgtcc gccagggacg cttcgaacag gctgacggcg gcacgctatt cctggatgaa   720
attggcgata tgccgcttga tgtccagact cgtctgctgc gcgtgctggc ggatggccag   780
ttttatcgcg tgggcggtta cgcgccggtg aaggtcgatg tgcggatcat cgccgccacc   840
caccagaacc tggaacagcg cgtgcaggag gggaaattcc gtgaagattt gttccaccgc   900
ctgaacgtga tccgggtgca tttaccgccg ctgcgcgagc gccgggaaga tattccacgc   960
ctggcccgcc attttctgca gatagccgcc cgcgagctcg tgttgaagc caaacagctg   1020 catccggaaa cggagacagc gctgacacgc ctggcgtggc ctggcaacgt ccgtcagctg   1080
gaaaacacct gtcgctggct caccgtcatg gccgccggcc aggaggtact gacgcaggat   1140
ctgccgagcg aactgtttga gactacggtt ccggacagcc cgacgcagat gcagccgac   1200
```

-continued

```
agctgggcga cgctgctggg tcagtgggcc gatcgggcgt tgcgatccgg tcatcaaaac    1260
ctgctctcag aagcgcaacc cgaaatggag cgcacgctgc tgacgaccgc cctgcgccat    1320
acccaggggc acaagcagga ggctgcgcgt ctgctgggat ggggtcgtaa taccctgacg    1380
cgtaagctaa aagagctggg aatggagtag                                     1410

<210> SEQ ID NO 8
<211> LENGTH: 9
<212> TYPE: PRT
<213> ORGANISM: Artificial
<220> FEATURE:
<223> OTHER INFORMATION: synthetic polypeptide

<400> SEQUENCE: 8

Leu Ala Gly Leu Ile Asp Ala Asp Gly
1               5

<210> SEQ ID NO 9
<211> LENGTH: 1776
<212> TYPE: DNA
<213> ORGANISM: Artificial
<220> FEATURE:
<223> OTHER INFORMATION: encode truncated glnD

<400> SEQUENCE: 9
tgaaaagccg gcgcccgccg gcttttttat tagatagttt tttcttatgg tgacgcgatg     60
ctgcttcagc tgtttgaaga ggctattctc gccctgaccg aggatgaaaa accgcgcccg    120
atagacgatg acttccagct gcgcggcacc cttatcgatc tgcgtgacga cacgctgttt    180
attcgcgaac cgcaggccat tctgcgcatg ttttatatga tggtgcgcaa cagcactatc    240
accggcatct actccacgac gttgcgccat ctgcgccatg cccggcgcca tctgaccccag    300 ccgctgtgct atatcccgga ggcgcgcacg ctctttctca gcatgctgcg ccatcagggg    360
gcggtcagcc gcggactgct gccgatgcat cgccatagcg tgctgtgggc ctatatgccg    420
cagtggtcac atatcgtcgg ccagatgcag ttcgatctgt ttcacgccta caccgtcgat    480
gaacacacca tccgcgtgat gctgaagctg gagagctttg ccaaagaaga aacccgcagc    540
cgccacccgc tgtgcgtgga gctatggccg cgcttaacgc acccggagct gattttaatc    600
gccgccctgt tccacgacat tgcgaaaggg cgtggcggcg accactcgat cctcggcgcg    660
caggatgtgc tgaagtttgc cgagctgcac ggactgaact ctcgcgaaac gcagttggtc    720
gcctggctgg tgcgtcacca tctgctgatg tcggtcaccg cccagcggcg cgacattcag    780
gatccggagg tgattaagca gttcgccgag gaagtgcaaa cggaaaatcg cctgcgctat    840
ctggtgtgcc tgaccgtcgc cgacatctgc gccaccaacg aaacgctgtg gaacagctgg    900
aagcagagtc tgctgcgcga actctatttc gccaccgaga aacagctgcg tcggggcatg    960
caaagcaccc cggatatgcg cgaacgggtg cgtcatcatc agctgcaggc gctggccctg   1020
ctgcggatgg acaatattaa tgaagaggcg ctgcatcaga tctggaaccg ctgccgcgcc   1080
aactatttcg tgcggcatac gccgacgcag ctcgcctggc acgcccgcaa cctgctgcgt   1140
cacgatctga ataagccgat gattctgctg agttcgcagg ccacccgcgg cggtacggag   1200
atttttatct ggagcccgga tcgcccttat ctgtttgccg cggtgtgcgg cgaactggac   1260
cgccgcaacc tcagcgtcca cgacgcgcag atcttcacca cccgcgacgg catggcgatg   1320
gataccttta ttgtcctcga acccgacggc agccgcgcttt ccgctgaccg ccacgacgcg   1380
attcgccacg gtcttgaaca gacgataact cagcgcagct gggaaccccc ggccccgcgt   1440
```

```
cgtcaggcgg caaaactgcg tcacttctct gtgccgacag aggtgaattt cctgccgacc    1500
cataccgatc gaaaatcgtt tctcgagctg attgcgctcg atcagccagg gctgctcgcc    1560
cgcgtcggcc aggtgttcgc cgacctcggt atttcgcttc acggggcgcg aattacgaca    1620
attggtgagc gagtagaaga tttatttata atcgccaccg ccgaccggcg tggccttaat    1680
aatgagctac aacaagaagt gcaacaacgg ttgacagagg ccctcaatcc aaacgataaa    1740
gggtgacgta ttttttttag tgaatggaaa gaaaca                            1776

<210> SEQ ID NO 10
<211> LENGTH: 2208
<212> TYPE: DNA
<213> ORGANISM: Artificial
<220> FEATURE:
<223> OTHER INFORMATION: encode truncated glnD

<400> SEQUENCE: 10
tgaaaagccg gcgcccgccg gcttttttat tagatagttt tttcttatgg tgacgcgatg      60
agcaactcat tacctgacac agcctcccct cttctgcccg tcccgccgga acatccggtg     120
agctggccgc agggcgatct gaactgtgct gcaattaagg cgcacatcga taccttccag     180
cactggctgg gcgaggcgtt tgactccggc atcgccgcgg agcagctcat tgcggcgcgc     240
accgaattta tcgaccagct gctgcagcgg ttgtggatcg cctacggttt tgaatccgtc     300
tgcgatctgg cgctggtggc cgtcggcggc tatggccgcg gcgagctgca cccgctctct     360
gacgtcgacc tgctgatcct cagccgcaaa aaactgcctg acgaccaggc gcaaaaggtc     420
ggcgaactgc tgacgctact gtgggacgtc aagctggagg tgggccacag cgtgcgcacc     480
ctcgaagagt gtctgctcga aggactttcg gatctcaccg tcgccactaa cttgattgaa     540
tcgcgcctgc tgatcggcga cgtcgcgctg ttccttgaac tgcaaaaaca tatttttagc     600
gacggcttct ggccatcgga aaagttcttc gccgccaagg tggaagagca gaacgtccgt     660
catcaacgct atcacggcac cagctataac ctggagccgg acgtgaaaag cagcccggc     720 ggcctgcggg atatccatac gctacagtgg gtggctcgcc gtcattttgg cgccacctcg     780
atggatgaga tggtcggctt cggctttctg accgaagccg agcgcaatga gctcaacgag     840
tgtctgcatc agctgtggcg catccgtttc gcgctgcatc tcgagctcac tcgctatgac     900
aaccgtctgc ttttcgaccg ccagctcagc gtcgcccgcc ggctcggcta tgaaggcgac     960
ggcaaccagc cgattgagca tatgatgaag gacttcttcc gcgtcacccg ccgggtgagc    1020
gagctgaacc agatgctgct tcagctgttt gaagaggcta ttctcgccct gaccgaggat    1080
gaaaaaccgc gcccgataga cgatgacttc cagctgcgcg gcacccttat cgatctgcgt    1140
gacgacacgt gtttattcg cgaaccgcag gccattctgc gcatgtttta tatgatggtg    1200
cgcaacagca ctatcaccgg catctactcc acgacgttgc gccatctgcg ccatgcccgg    1260
cgccatctga cccagccgct gtgctatatc ccggaggcgc gcacgctctt tctcagcatg    1320
ctgcgccatc aggggggcggt cagccgcgga ctgctgccga tgcatcgcca tagcgtgctg    1380
tgggcctata tgccgcagtg gtcacatatc gtcggccaga tgcagttcga tctgtttcac    1440
gcctacaccg tcgatgaaca caccatccgc gtgatgctga agctggagag ctttgccaaa    1500
gaagaaaccc gcagccgcca cccgctgtgc gtggagctat ggccgcgctt aacgcacccg    1560
gagctgattt taatcgccgc cctgttccac gacattgcga aagggcgtgg cggcgaccac    1620
tcgatcctcg cgcgcagga tgtgctgaag tttgccgagc tgcacggact gaactctcgc    1680
gaaacgcagt tggtcgcctg gctggtgcgt caccatctgc tgatgtcggt caccgcccag    1740
```

-continued

```
cggcgcgaca ttcaggatcc ggaggtgatt aagcagttcg ccgaggaagt gcaaacggaa    1800
aatcgcctgc gctatctggt gtgcctgacc gtcgccgaca tctgcgccac caacgaaacg    1860
ctgtggaaca gctggaagca gagtctgctg cgcgaactct atttcgccac cgagaaacag    1920
ctgcgtcggg gcatgcaaag caccccggat atgcgcgaac gggtgcgtca tcatcagctg    1980
caggcgctgg ccctgctgcg gatggacaat attaatgaag aggcgctgca tcagatctgg    2040
aaccgctgcc gcgccaacta tttcgtgcgg catacgccga cgcagctcgc ctggcacgcc    2100
cgcaacctgc tgcgtcacga tctgaataag ccgatgattc tgctgagttc gcaggccacc    2160
cgcggcggta cggagtgacg tatttttttt agtgaatgga aagaaaca              2208
```

MODIFIED BACTERIAL STRAINS FOR IMPROVED FIXATION OF NITROGEN

CROSS-REFERENCE TO RELATED APPLICATIONS

This application is a National Stage application under 35 U.S.C. § 371 of International Application No. PCT/US2021/029895 having an International Filing Date of Apr. 29, 2021, which claims priority to U.S. Provisional Application No. 63/019,247, filed May 1, 2020, to PCT/US2020/031201, filed May 1, 2020, and to PCT/US2021/13120, filed on Jan. 12, 2021, the disclosures of which are incorporated by reference in their entirety.

DESCRIPTION OF THE TEXT FILE SUBMITTED ELECTRONICALLY

This application contains a Sequence Listing that has been submitted electronically as an ASCII text file named "48624-0027US1_SL.txt." The ASCII text file, created on Mar. 27, 2023, is 16,957 bytes in size. The material in the ASCII text file is hereby incorporated by reference in its entirety.

TECHNICAL FIELD

The present disclosure is related to genetically-engineered bacterial strains, and compositions thereof. Such bacterial strains, and compositions thereof, are useful for providing nitrogen to plants.

BACKGROUND

Approaches to agriculture and food production that are economically, environmentally, and socially sustainable will help to meet the needs of a growing global population. By 2050, the United Nations' Food and Agriculture Organization projects that total food production must increase by 70% to meet the needs of the growing population, a challenge that can be exacerbated by numerous factors, including diminishing freshwater resources, increasing competition for arable land, rising energy prices, increasing input costs, and the likely need for crops to adapt to the pressures of a drier, hotter, and more extreme global climate.

One area of interest is in the improvement of nitrogen fixation. Nitrogen gas ($N_2$) is a major component of the atmosphere of Earth. In addition, elemental nitrogen (N) is an important component of many chemical compounds which make up living organisms. However, many organisms cannot use $N_2$ directly to synthesize the chemicals used in physiological processes, such as growth and reproduction. $N_2$ must be combined with hydrogen to be utilized. This process of combining of hydrogen with $N_2$ is referred to as nitrogen fixation. Nitrogen fixation, whether accomplished chemically or biologically, requires an investment of large amounts of energy. In biological systems, the enzyme known as nitrogenase catalyzes the reaction which results in nitrogen fixation. An important goal of nitrogen fixation research is the extension of this phenotype to non-leguminous plants, particularly to important agronomic grasses such as wheat, rice, and maize. Despite enormous progress in understanding the development of the nitrogen-fixing symbiosis between *rhizobia* and legumes, the path to use that knowledge to induce nitrogen-fixing nodules on non-leguminous crops is still not clear. Meanwhile, the challenge of providing sufficient supplemental sources of nitrogen, such as in fertilizer, will continue to increase with the growing need for increased food production.

SUMMARY

This document is based, at least in part, on identification of one or more targeted genomic modifications that can be used to produce genetically engineered bacteria that can fix nitrogen under both nitrogen limiting and non-nitrogen limiting conditions as well as in the presence of oxygen (e.g., at least 0.5% oxygen), Such genetically engineered bacteria can be used to increase the amount of atmospheric derived nitrogen in plants (e.g., non-leguminous plants such as corn, wheat, *sorghum*, and rice).

Provided herein are methods of increasing the amount of atmospheric derived nitrogen in a plant, the method comprising contacting the plant, a part of the plant, or soil into which the plant is planted with a plurality of genetically engineered *Klebsiella variicola* bacteria and a plurality of genetically engineered *Kosakonia sacchari* bacteria.

Also provided herein are methods of increasing colonization in at least two different niches of the rhizosphere of a plant, the method comprising contacting the plant, a part of the plant, or soil into which the plant is planted with a plurality of a genetically engineered *Klebsiella variicola* bacteria and a plurality of a genetically engineered *Kosakonia sacchari* bacteria.

Also provided herein are methods of increasing the total space on the root surface of a plant occupied by bacteria that can fix nitrogen in the presence of nitrogen, the method comprising contacting the plant, a part of the plant, or soil into which the plant is planted with a plurality of genetically engineered *Klebsiella variicola* bacteria and a plurality of genetically engineered *Kosakonia sacchari* bacteria.

In some embodiments, the plurality of genetically engineered *Klebsiella variicola* bacteria utilize at least one carbon source that is different than the carbon sources utilized by the plurality of genetically engineered *Kosakonia sacchari* bacteria. In some embodiments, the plurality of genetically engineered *Kosakonia sacchari* bacteria utilize at least one carbon source that is different than the carbon sources utilized by the plurality of genetically engineered *Klebsiella variicola* bacteria. In some embodiments, the plurality of genetically engineered *Klebsiella variicola* bacteria utilize at least one carbon source at a different rate than the carbon sources utilized by the plurality of genetically engineered *Kosakonia sacchari* bacteria.

Also provided herein are methods of increasing the amount of atmospheric derived nitrogen in a plant, the method comprising contacting the plant, a part of the plant, or soil into which the plant is planted with a plurality of genetically engineered *Klebsiella variicola* bacteria and a plurality of genetically engineered *Kosakonia sacchari* bacteria, wherein the plurality of genetically engineered *Klebsiella variicola* bacteria and the plurality of genetically engineered *Kosakonia sacchari* bacteria each comprise at least one modification in a gene regulating nitrogen fixation or assimilation; and wherein the soil into which the plant is planted has at least about 0.5% oxygen.

In some embodiments, at least 50% of the plurality of genetically engineered *Klebsiella variicola* bacteria and at least 50% of the plurality of genetically engineered *Kosakonia sacchari* bacteria each comprise at least one modification in a gene regulating nitrogen fixation or assimilation. In some embodiments, at least 75% of the plurality of genetically engineered *Klebsiella variicola* bacteria and at least 75% of the plurality of genetically engineered *Kosa-*

*konia sacchari* bacteria each comprise at least one modification in a gene regulating nitrogen fixation or assimilation.

In some embodiments, the soil into which the plant is planted has at least about 1% oxygen. In some embodiments, the soil into which the plant is planted has at least about 2% oxygen. In some embodiments, the soil into which the plant is planted has at least about 3% oxygen.

In some embodiments, a genetically engineered bacterium of the plurality produces fixed N of at least about $1\times10^{-17}$ mmol N per bacterial cell per hour. In some embodiments, the plurality of genetically engineered *Kosakonia sacchari* bacteria produce fixed N of at least about $2\times10^{-13}$ mmol of N per CFU per hour. In some embodiments, the plurality of genetically engineered *Klebsiella variicola* bacteria produce fixed N of at least about $3\times10^{-13}$ mmol of N per CFU per hour. In some embodiments, the plurality of genetically engineered *Klebsiella variicola* bacteria colonize the root surface of the plant.

In some embodiments, the plurality of genetically engineered *Kosakonia sacchari* bacteria colonize the root surface of the plant. In some embodiments, the plurality of genetically engineered *Klebsiella variicola* bacteria and the plurality of genetically engineered *Kosakonia sacchari* bacteria produce 1% or more of the fixed nitrogen in the plant. In some embodiments, the plurality of genetically engineered *Klebsiella variicola* bacteria and the plurality of genetically engineered *Kosakonia sacchari* bacteria are capable of fixing atmospheric nitrogen in the presence of exogenous nitrogen.

In some embodiments, the plurality of genetically engineered *Klebsiella variicola* bacteria and the plurality of genetically engineered *Kosakonia sacchari* bacteria are contacted to the plant simultaneously. In some embodiments, the plurality of genetically engineered *Klebsiella variicola* bacteria and the plurality of genetically engineered *Kosakonia sacchari* bacteria are contacted to the plant sequentially.

Also provided here are methods of increasing the amount of atmospheric derived nitrogen in a plant, comprising contacting the plant, a part of the plant, or soil into which the plant is planted with any of the composition as described herein.

Also provided here are methods of increasing biomass in a plant, comprising contacting the plant, a part of the plant, or soil into which the plant is planted with the composition of any of the composition as described herein.

Also provided here are methods of increasing the amount of atmospheric derived nitrogen in a plant, the method comprising contacting the plant, a part of the plant, or soil into which the plant is planted with a plurality of genetically engineered *Klebsiella variicola* bacteria or a plurality of genetically engineered *Kosakonia sacchari* bacteria, and wherein the soil comprises at least about 0.5% oxygen.

Also provided here are methods of increasing the amount of nitrogen available to a plant, the method comprising contacting the plant, a part of the plant, or soil into which the plant is planted with a plurality of genetically engineered *Klebsiella variicola* bacteria or a plurality of genetically engineered *Kosakonia sacchari* bacteria; wherein the soil comprises at least about 0.5% oxygen; and wherein the genetically engineered *Klebsiella variicola* bacteria or the genetically engineered *Kosakonia sacchari* bacteria exhibits increased nitrogen excretion compared to a non-engineered diazotrophic bacteria of the same species.

In some embodiments, the soil comprises at least about 1% oxygen. In some embodiments, the soil comprises at least about 2% oxygen. In some embodiments, the soil comprises at least about 3% oxygen.

In some embodiments, a genetically engineered bacterium of the plurality produces fixed N of at least about $1\times10^{-17}$ mmol N per bacterial cell per hour. In some embodiments, the plurality of genetically engineered *Klebsiella variicola* bacteria or the plurality of genetically engineered *Kosakonia sacchari* bacteria produce fixed N of at least about $2\times10^{-13}$ mmol of N per CFU per hour.

In some embodiments, the plurality of genetically engineered *Klebsiella variicola* bacteria or the plurality of genetically engineered *Kosakonia sacchari* bacteria colonize the root surface of the plant. In some embodiments, the plurality of genetically engineered bacterium exhibit colonization levels of at least about $10^4$ CFU/g root fresh weight (FW). In some embodiments, the plurality of genetically engineered *Klebsiella variicola* bacteria or the plurality of genetically engineered *Kosakonia sacchari* bacteria exhibit colonization levels of at least about $10^5$ CFU/g root fresh weight (FW). In some embodiments, the plurality of genetically engineered *Klebsiella variicola* bacteria or the plurality of genetically engineered *Kosakonia sacchari* bacteria exhibit colonization levels of at least about $10^6$ CFU/g root fresh weight (FW).

In some embodiments, the plurality of genetically engineered *Klebsiella variicola* bacteria or the plurality of genetically engineered *Kosakonia sacchari* bacteria produce 1% or more of the fixed nitrogen in the plant.

In some embodiments, the nitrogen excreted by the plurality of genetically engineered *Klebsiella variicola* bacteria or the plurality of genetically engineered *Kosakonia sacchari* bacteria comprises ammonia.

In some embodiments, the plurality of genetically engineered *Klebsiella variicola* bacteria are capable of excreting at least about 2 mM $NH_4^+$ at 3% oxygen as measured by an ammonium excretion assay.

In some embodiments, the at least one modification in a gene regulating nitrogen fixation or assimilation results in expression of nifA in non-nitrogen limiting conditions in the genetically engineered *Klebsiella variicola* bacteria or the genetically engineered *Kosakonia sacchari* bacteria. In some embodiments, the at least one modification in a gene regulating nitrogen fixation or assimilation comprises a deletion of all or a portion of the coding sequence of the nifL gene in the genetically engineered *Klebsiella variicola* bacteria or the genetically engineered *Kosakonia sacchari* bacteria. In some embodiments, all or a portion of the nifL coding sequence is replaced by a promoter. In some embodiments, the promoter is a non-intergeneric promoter. In some embodiments, the promoter is a constitutive promoter. In some embodiments, the promoter is an infC gene promoter or a cspE gene promoter in the genetically engineered *Klebsiella variicola* bacteria. In some embodiments, the infC gene promoter comprises a sequence that has at least 95% sequence identity to SEQ ID NO: 1. In some embodiments, the cspE gene promoter comprises a sequence that has at least 95% sequence identity to SEQ ID NO: 2. In some embodiments, the promoter is an ompX gene promoter in the genetically engineered *Kosakonia sacchari* bacteria. In some embodiments, be promoter comprises a sequence that has at least 95% sequence identity to SEQ ID NO: 4.

In some embodiments, the at least one modification in a gene regulating nitrogen fixation or assimilation results in decreased uridylyl-transferase activity of GlnD in the genetically engineered *Klebsiella variicola* bacteria or the genetically engineered *Kosakonia sacchari* bacteria.

In some embodiments, the at least one modification in a gene regulating nitrogen fixation or assimilation comprises a deletion of all or a portion of the coding sequence of the glnD gene in the genetically engineered *Klebsiella variicola* bacteria or the genetically engineered *Kosakonia sacchari* bacteria. In some embodiments, the at least one modification in a gene regulating nitrogen fixation or assimilation in the genetically engineered *Klebsiella variicola* bacteria comprises a deletion of the N-terminal glnD-UTase domain. In some embodiments, the at least one modification in a gene regulating nitrogen fixation or assimilation in the genetically engineered *Klebsiella variicola* bacteria comprises a deletion of all or a portion of the coding sequence of the nifL gene and a deletion of the N-terminal glnD-UTase domain.

In some embodiments, the genetically engineered bacteria comprise a bacterium that is represented by bacteria deposited as ATCC Accession No. PTA-126740 (referred to as PTA-126740 herein).

In some embodiments, the at least one modification in a gene regulating nitrogen fixation or assimilation in the genetically engineered *Kosakonia sacchari* bacteria comprises a deletion of all of the coding sequence of the glnD gene.

In some embodiments, the at least one modification in a gene regulating nitrogen fixation or assimilation in the genetically engineered *Klebsiella variicola* bacteria comprises mutations in the coding sequence of the glnD gene. In some embodiments, the mutations in the coding sequence of the glnD gene encode a GlnD protein with amino acid substitutions comprising G90L, G91D, and D104A.

In some embodiments, the at least one modification in a gene regulating nitrogen fixation or assimilation results in decreased adenylyl-removing activity of GlnE in the genetically engineered *Klebsiella variicola* bacteria or the genetically engineered *Kosakonia sacchari* bacteria. In some embodiments, the at least one modification in a gene regulating nitrogen fixation or assimilation comprises a deletion of a portion of the coding sequence of the glnE gene in the genetically engineered *Klebsiella variicola* bacteria or the genetically engineered *Kosakonia sacchari* bacteria.

In some embodiments, the at least one modification in a gene regulating nitrogen fixation or assimilation results in a truncated GlnE protein lacking an adenylyl-removing (AR) domain in the genetically engineered *Klebsiella variicola* bacteria or the genetically engineered *Kosakonia sacchari* bacteria.

In some embodiments, the at least one modification in a gene regulating nitrogen fixation or assimilation in the genetically engineered *Kosakonia sacchari* bacteria comprises a deletion of all or a portion of the coding sequence of the nifL gene, a deletion of all of the coding sequence of the glnD gene, and a deletion of a portion of the coding sequence of the glnE gene.

In some embodiments, the genetically engineered bacteria comprise a bacterium that is represented by bacteria deposited as ATCC Accession No. PTA-126743 (referred to as PTA-126743 herein).

In some embodiments, the at least one modification in a gene regulating nitrogen fixation or assimilation results in increased extracellular ammonium in the genetically engineered *Klebsiella variicola* bacteria. In some embodiments, the at least one modification in a gene regulating nitrogen fixation or assimilation comprises a point mutation in the coding sequence of the ntrC gene in the genetically engineered *Klebsiella variicola* bacteria. In some embodiments, the mutation in the coding sequence of the ntrC gene encode NtrC protein comprising a D54A amino acid substitution.

In some embodiments, the at least one modification in a gene regulating nitrogen fixation or assimilation in the genetically engineered *Klebsiella variicola* bacteria comprises a deletion of all or a portion of the coding sequence of the nifL gene, a deletion of a portion of the coding sequence of the glnE gene, and a point mutation in the coding sequence of the ntrC gene.

In some embodiments, the genetically engineered bacteria comprise a bacterium that is represented by bacteria deposited as ATCC Accession No. PTA-126749 (referred to as PTA-126749 herein).

In some embodiments, the at least one modification in a gene regulating nitrogen fixation or assimilation results in constitutive expression of a nifA gene in nitrogen deplete and replete conditions in the genetically engineered *Klebsiella variicola* bacteria. In some embodiments, the at least one modification in a gene regulating nitrogen fixation or assimilation comprises an insertion of the coding sequence of the nifA gene in the genome of the genetically engineered *Klebsiella variicola* bacteria.

In some embodiments, the at least one modification in a gene regulating nitrogen fixation or assimilation comprises an insertion of the coding sequence of the nifA gene and a promoter in the genome of the genetically engineered *Klebsiella variicola* bacteria. In some embodiments, the promoter is a cspE gene promoter. In some embodiments, the cspE gene promoter comprises a sequence that has at least 95% sequence identity to SEQ ID NO: 2.

In some embodiments, the at least one modification in a gene regulating nitrogen fixation or assimilation in the genetically engineered *Klebsiella variicola* bacteria comprises a deletion of all or a portion of the coding sequence of the nifL gene, comprises point mutations in the coding sequence of the glnD gene, and insertion of the coding sequence of the nifA gene and a promoter in a non-coding region in the genome of the genetically engineered *Klebsiella variicola* bacteria.

In some embodiments, the genetically engineered bacteria comprise a bacterium that is represented by bacteria deposited as ATCC Accession No. PTA-126741 (referred to as PTA-herein).

In some embodiments, at least one of the genetically engineered *Klebsiella variicola* bacteria and the genetically engineered *Kosakonia sacchari* bacteria are non-intergeneric. In some embodiments, the plurality of genetically engineered *Klebsiella variicola* bacteria or the plurality of genetically engineered *Kosakonia sacchari* bacteria are capable of fixing atmospheric nitrogen in the presence of exogenous nitrogen.

In some embodiments, the composition comprising the genetically engineered bacteria is in the form of a liquid, a foam, or a dry product. In some embodiments, the composition further comprises an agriculturally acceptable carrier.

In some embodiments, at least 50% of the plurality of genetically engineered *Klebsiella variicola* bacteria or at least 50% of the plurality of genetically engineered *Kosakonia sacchari* bacteria comprise at least one modification in a gene regulating nitrogen fixation or assimilation.

In some embodiments, at least 75% of the plurality of genetically engineered *Klebsiella variicola* bacteria or at least 75% of the plurality of genetically engineered *Kosakonia sacchari* bacteria comprise at least one modification in a gene regulating nitrogen fixation or assimilation.

Also provided is a *Kosakonia sacchari* bacterium represented by bacteria deposited as ATCC Accession No. PTA-126743. Also provided is a *Klebsiella variicola* bacterium represented by bacteria deposited as ATCC Accession No.

PTA-126740. Also provided is a *Klebsiella variicola* bacterium represented by bacteria deposited as ATCC Accession No. PTA-126749. Also provided is a *Klebsiella variicola* bacterium represented by bacteria deposited as ATCC Accession No. PTA-126741.

Also provided is a genetically engineered bacterium comprising a modification in a gene regulating nitrogen fixation or assimilation, wherein the modification in the gene regulating nitrogen fixation or assimilation results in one or more of: constitutive expression of a nifA gene in nitrogen limiting and non-nitrogen limiting conditions, activity of nifA in non-nitrogen limiting conditions, decreased uridylyl-transferase activity of GlnD, decreased adenylyl-removing activity of GlnE, and increased ammonium excretion.

Also provided is a genetically engineered bacterium comprising a modification in a gene regulating nitrogen fixation or assimilation that results in constitutive expression of a nifA gene in nitrogen limiting and non-nitrogen limiting conditions and optionally wherein the genetically engineered bacterium further comprises a modification in a gene regulating nitrogen fixation or assimilation that results in one or more of: activity of nifA in non-nitrogen limiting conditions, decreased uridylyl-transferase activity of GlnD, decreased adenylyl-removing activity of GlnE, and increased ammonium excretion.

Also provided is a genetically engineered bacterium comprising a modification in a gene regulating nitrogen fixation or assimilation that results in constitutive expression of a nifA gene in nitrogen limiting and non-nitrogen limiting conditions and wherein the genetically engineered bacterium further comprises a modification in a gene regulating nitrogen fixation or assimilation that results in one or more of: activity of nifA in non-nitrogen limiting conditions, decreased uridylyl-transferase activity of GlnD, decreased adenylyl-removing activity of GlnE, and increased ammonium excretion.

Also provided is a genetically engineered bacterium comprising a mutation in the coding sequence of the bacterium's ntrC gene, wherein the coding sequence of the ntrC gene comprising the mutation encodes a NtrC protein with a D54A amino acid substitution, and wherein the genetically engineered bacterium is a genetically engineered diazotroph.

Also provided is a genetically engineered bacterium comprising a mutation in the coding sequence of the bacterium's ntrC gene, wherein the coding sequence of the ntrC gene comprising the mutation encodes a NtrC protein with a D54A amino acid substitution, and wherein the genetically engineered bacterium further comprises at least one modification in a gene regulating nitrogen fixation or assimilation that results in one or more of constitutive expression of a nifA gene in nitrogen limiting and non-nitrogen limiting conditions, activity of nifA in non-nitrogen limiting conditions, decreased uridylyl-transferase activity of GlnD, decreased adenylyl-removing activity of GlnE, and increased ammonium excretion.

In some embodiments, the mutation in the coding sequence of the ntrC results in increased ammonium excretion.

Also provided is a genetically engineered bacterium comprising a deletion of all or a portion of the entire coding sequence of glnD and wherein the genetically engineered bacterium further comprises at least one modification that results in one or more of: constitutive expression of a nifA gene in nitrogen limiting and non-nitrogen limiting conditions, activity of nifA in non-nitrogen limiting conditions, decreased adenylyl-removing activity of GlnE, and increased ammonium excretion.

In some embodiments, the deletion of all or a portion of the entire coding sequence of glnD results in the decreased uridylyl-transferase activity of GlnD.

In some embodiments, the modification in a gene regulating nitrogen fixation or assimilation that results in activity of nifA in non-nitrogen limiting conditions comprises a deletion of all or a portion of the coding sequence of the nifL gene. In some embodiments, the deletion of all or a portion of the coding sequence of the nifL gene results in the decreased expression of nifL. In some embodiments, all or a portion of the nifL coding sequence is replaced by a promoter. In some embodiments, the promoter is a non-intergeneric promoter. In some embodiments, the promoter is a constitutive promoter. In some embodiments, the promoter is an infC gene promoter, an ompX gene promoter, or a cspE gene promoter. In some embodiments, the infC gene promoter comprises a sequence that has at least 95% sequence identity to SEQ ID NO: 1. In some embodiments, the cspE gene promoter comprises a sequence that has at least 95% sequence identity to SEQ ID NO: 2. In some embodiments, the ompX gene promoter comprises a sequence that has at least 95% sequence identity to SEQ ID NO: 4.

In some embodiments, the modification in a gene regulating nitrogen fixation or assimilation that results in decreased uridylyl-transferase activity of GlnD comprises a deletion of all or a portion of the coding sequence of the glnD gene. In some embodiments, the deletion of all or a portion of the coding sequence of the glnD gene comprises a deletion of the N-terminal glnD-UTase domain. In some embodiments, all of the coding sequence of the glnD gene is deleted. In some embodiments, the decreased uridylyl-transferase activity of GlnD is the result of at least one mutation in the coding sequence of the glnD gene. In some embodiments, the coding sequence of the glnD gene comprising the at least one mutation encodes a GlnD protein with amino acid substitutions comprising G90L, G91D, and D104A.

In some embodiments, the modification in a gene regulating nitrogen fixation or assimilation that results in the decreased adenylyl-removing activity of GlnE comprises a deletion of a portion of the coding sequence of the glnE gene. In some embodiments, the deletion of a portion of the coding sequence of the glnE gene results in a truncated GlnE protein lacking an adenylyl-removing (AR) domain.

In some embodiments, the modification in a gene regulating nitrogen fixation or assimilation that results in increased ammonium excretion comprises a mutation in the coding sequence of the ntrC gene. In some embodiments, the coding sequence of the ntrC gene comprising the point mutation encodes a NtrC protein comprising a D54A amino acid substitution.

In some embodiments, the modification in a gene regulating nitrogen fixation or assimilation that results in constitutive expression of a nifA gene in nitrogen limiting and non-nitrogen limiting conditions comprises an insertion of the coding sequence of the nifA gene in the genome of the genetically engineered bacterium.

In some embodiments, the modification in a gene regulating nitrogen fixation or assimilation that results in constitutive expression of the nifA gene in nitrogen limiting and non-nitrogen limiting conditions comprises an insertion of the coding sequence of the nifA gene and a constitutive promoter in the genome of the genetically engineered *Klebsiella variicola* bacterium.

In some embodiments, the engineered bacterium is *Agrobacterium radiobacter, Bacillus acidocaldarius, Bacillus*

*acidoterrestris, Bacillus agri, Bacillus aizamwai, Bacillus albolactis, Bacillus alcalophilus, Bacillus alvei, Bacillus aninoglucosidicus, Bacillus aninovorans, Bacillus amylolyticus* (also known as *Paenibacillus amylolyticus*) *Bacillus amyloliquefaciens, Bacillus aneurinolyticus, Bacillus atrophaeus, Bacillus azotofbrmans, Bacillus badius, Bacillus cereus* (synonyms *Bacillus endorhythmos, Bacillus medusa*), *Bacillus chitinosporus, Bacillus circulans, Bacillus coagulans, Bacillus endoparasiticus, Bacillus fastidiosus, Bacillus firmus, Bacillus kurstaki, Bacillus lacticola, Bacillus lactimorbus, Bacillus lactis, Bacillus laterosporus* (also known as *Brevibacillus laterosporis*), *Bacillus lautus, Bacillus lentimorbus, Bacillus lentus, Bacillus licheniformis, Bacillus maroccanus, Bacillus megaterium, Bacillus metiens, Bacillus mYcoides, Bacillus natto, Bacillus nematocida, Bacillus nigrificans, Bacillus nigrum, Bacillus pantothenticus, Bacillus popillae, Bacillus psychrosaccharolyticus, Bacillus pumilus, Bacillus siamensis, Bacillus smnithii, Bacillus sphaericus, Bacillus subtilis, Bacillus thuringiensis, Bacillus uniflagellatus, Bradyrhizobium japonicum, Brevibacillus brevis, Brevibacillus laterosporus* (formerly *Bacillus laterosporus*), *Chromobacterium subtsugae, Delftia acidovorans, Lactobacillus acidophilus, Lysobacter antibioticus, Lysobacter enzymogenes, Paenibacillus alvei, Paenibacillus polymyxa, Paenibacillus popilliae* (formerly *Bacillus popilliae*), *Pantoea agglomerans, Pasteuria penetrans* (formerly *Bacillus penetrans*), *Pasteuria usgae, Pectobacterium carotovorum* (formerly *Erwinia carolovora*), *Pseudomonas aeruginosa, Pseudoimonas aureofaciens, Pseudomonas cepacia* (formerly known as *Burkholdieria cepacia*), *Pseudomonas chlororaphis, Pseudomonas fluorescens, Pseudomonas proradix, Pseudomonas putida, Pseudomonas syriigae, Serratia entomophila, Serratia marcescens, Streptomyces colombiensis, Streptomyces galbus, Streptomyces goshikiensis, Streptoimyces griseoviridis, Streptomvces lavendulae, Streptomyces prasinus, Streptomyces saraceticus, Streptomyces venezuelae, Xanthomonas campestris, Xenorhabdus luminescens, Xenorhabdus nematophila, Rhodococcus globerulus* AQ719 (NRRL Accession No. B-21663), *Bacillus* sp. AQ175 (ATTCC Accession No. 55608). *Bacillus* sp. AQ 177 (ATCC Accession No. 55609), *Bacillus* sp. AQ178 (ATCC Accession No. 53522), or *Streptomyces* sp. strain NRRL Accession No. 13-30145.

In some embodiments, the engineered bacterium is a *Kosakonia sacchari* bacterium or a *Klebsiella variicola* bacterium.

In some embodiments, the genetically engineered bacterium comprises a deletion of all or a portion of the coding sequence of the nifL gene and a deletion of the N-terminal glnD-UTase domain.

In some embodiments, the genetically engineered bacterium is represented by bacteria deposited as ATCC Accession No. PTA-126740.

In some embodiments, the genetically engineered bacterium comprises a deletion of all or a portion of the coding sequence of the nifL gene, a deletion of all of the coding sequence of the glnD gene, and a deletion of a portion of the coding sequence of the glnE gene.

In some embodiments, the genetically engineered bacterium is represented by bacteria deposited as ATCC Accession No. PTA-126743.

In some embodiments, the genetically engineered bacterium comprises a deletion of all or a portion of the coding sequence of the nifL gene, a deletion of a portion of the coding sequence of the glnE gene, and a point mutation in the coding sequence of the ntrC gene.

In some embodiments, the genetically engineered bacterium is represented by bacteria deposited as ATCC Accession No. PTA-126749.

In some embodiments, the genetically engineered bacterium comprises a deletion of all or a portion of the coding sequence of the nifL gene, point mutations in the coding sequence of the glnD gene, and insertion of the coding sequence of the nifA gene and a promoter in a non-coding region in the genome of the genetically engineered bacterium.

In some embodiments, wherein the genetically engineered bacterium is represented by bacteria deposited as ATCC Accession No. PTA-126741.

In some embodiments, the genetically engineered bacterium is non-intergeneric.

Also provided are methods of increasing the amount of atmospheric derived nitrogen in a plant, comprising contacting the plant, a part of the plant, or soil into which the plant is planted with a plurality of any of the genetically engineered bacterium described herein.

In some embodiments, a genetically engineered bacterium of the plurality produces fixed N of at least about $1 \times 10^{-17}$ mmol N per bacterial cell per hour. In some embodiments, the plurality of genetically engineered bacterium produce fixed N of at least about $2 \times 10^{-13}$ mmol of N per CFU per hour. In some embodiments, the plurality of genetically engineered bacterium produce fixed N of at least about $3 \times 10^{-13}$ mmol of N per CFU per hour.

In some embodiments, the plurality of genetically engineered bacterium colonize the root surface of the plant. In some embodiments, the plurality of genetically engineered bacterium exhibit colonization levels of at least about $10^4$ CFU/g root fresh weight (FW). In some embodiments, the plurality of genetically engineered bacterium exhibit colonization levels of at least about $10^5$ CFU/g root fresh weight (FW). In some embodiments, the plurality of genetically engineered bacteria exhibit colonization levels of at least about $10^6$ CFU/g root fresh weight (FW). In some embodiments, the plurality of genetically engineered bacterium produce 1% or more of the fixed nitrogen in the plant. In some embodiments, the plurality of genetically engineered bacterium are capable of fixing atmospheric nitrogen in the presence of exogenous nitrogen.

The terms "polynucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides can have any three dimensional structure, and can perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide can comprise one or more modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component.

"Hybridization" refers to the annealing of one or more polynucleotides to form a complex that is stabilized via hydrogen bonding between the bases of the nucleotide residues. The hydrogen bonding can occur by Watson Crick base pairing, Hoogstein binding, or in any other sequence specific manner according to base complementarity. The complex can comprise two strands forming a duplex structure, three or more strands forming a multi stranded complex, a single self-hybridizing strand, or any combination of thereof. Hybridization can be a step in a more extensive process, such as the initiation of PCR, or the enzymatic cleavage of a polynucleotide by an endonuclease. A second sequence that is complementary to a first sequence is referred to as the "complement" of the first sequence. The term "hybridizable" as applied to a polynucleotide refers to the ability of the polynucleotide to form a complex that is stabilized via hydrogen bonding between the bases of the nucleotide residues.

"Complementarity" refers to the ability of a nucleic acid to form hydrogen bond(s) with another nucleic acid sequence by base pairing such as Watson-Crick base-pairing. A percent complementarity indicates the percentage of residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

In general, "sequence identity" refers to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby, and comparing these sequences to a second nucleotide or amino acid sequence. Two or more sequences (polynucleotide or amino acid) can be compared by determining their "percent identity." The percent identity of two sequences, whether nucleic acid or amino acid sequences, can be calculated as the number of exact matches between two aligned sequences divided by the length of the shorter sequences and multiplied by 100. In some embodiments, the percent identity of a test sequence and a reference sequence, whether nucleic acid or amino acid sequences, can be calculated as the number of exact matches between two aligned sequences divided by the length of the reference sequence and multiplied by 100. Percent identity can also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul, et al., J. Mol. Biol. 215:403-410 (1990); Karlin And Altschul, Proc. Natl. Acad. Sci. USA 90:5873-5877 (1993); and Altschul et al., Nucleic Acids Res. 25:3389-3402 (1997). Briefly, the BLAST program defines identity as the number of identical aligned symbols (generally nucleotides or amino acids), divided by the total number of symbols in the shorter of the two sequences. The program can be used to determine percent identity over the entire length of the proteins being compared. Default parameters are provided to optimize searches with short query sequences in, for example, with the blastp program. The program also allows use of an SEG filter to mask-off segments of the query sequences as determined by the SEG program of Wootton and Federhen, Computers and Chemistry 17:149-163 (1993). Ranges of desired degrees of sequence identity are approximately 80% to 100% and integer values there between. Typically, the percent identities between a disclosed sequence and a claimed sequence are at least 80%, at least 85%, at least 90%, at least 95%, at least 98% or at least 99%.

Sequences can be aligned using an algorithm including but not limited to the Needleman-Wunsch algorithm (see e.g. the EMBOSS Needle aligner available at ebi.ac.uk/Tools/psa/emboss_needle/nucleotide.html on the World Wide Web, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at ebi.ac.uk/Tools/psa/emboss_water/nucleotide.html on the World Wide Web, optionally with default settings). Optimal alignment can be assessed using any suitable parameters of a chosen algorithm, including default parameters.

In general, "stringent conditions" for hybridization refer to conditions under which a nucleic acid having complementarity to a target sequence predominantly hybridizes with a target sequence, and substantially does not hybridize to non-target sequences. Stringent conditions are generally sequence-dependent and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

As used herein, "expression" refers to the process by which a polynucleotide is transcribed from a DNA template (such as into a mRNA or other RNA transcript) and/or the process by which a transcribed mRNA is subsequently translated into a peptide, polypeptide, or protein. Transcripts and encoded polypeptides can be collectively referred to as "gene product." If the polynucleotide is derived from genomic DNA, expression can include splicing of the mRNA in a eukaryotic cell.

The terms "polypeptide", "peptide" and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural (e.g., alpha-amino acids) and unnatural or synthetic amino acids, including both the D or L optical isomers, amino acid analogs, and peptidomimetics. Non-limiting examples of unnatural amino acids include beta-amino acids, homo-amino acids, proline and pyruvic acid derivatives, 3-substituted alanine derivatives, glycine derivatives, ring substituted phenylalanine and tyrosine derivatives, linear core amino acids, and N-methyl amino acids. An amino acid analog can be an amino acid resulting from a reaction at an amino group, carboxy group, side-chain functional group, or from the replacement of any hydrogen by a heteroatom.

As used herein, the term "about" is used synonymously with the term "approximately." Illustratively, the use of the term "about" with regard to an amount indicates that values slightly outside the cited values, e.g., plus or minus 0.1% to 10%.

The term "biologically pure culture" or "substantially pure culture" refers to a culture of a bacterial species described herein containing no other bacterial species in quantities sufficient to interfere with the replication of the culture or be detected by normal bacteriological techniques.

As used herein the term "plant" can include plant parts such as tissues, leaves, roots, root hairs, rhizomes, stems, seeds, ovules, pollen, flowers, fruit, etc.

As used herein, "in planta" may refer to in the plant, on the plant, or intimately associated with the plant, depending upon context of usage (e.g. endophytic, epiphytic, or rhizospheric associations). The plant may comprise plant parts such as tissue, leaves, roots, root hairs, rhizomes, stems, seed, ovules, pollen, flowers, fruit, etc.

"Plant productivity" refers generally to any aspect of growth or development of a plant that is a reason for which the plant is grown. For food crops, such as grains or vegetables, "plant productivity" can refer to the yield of grain or fruit harvested from a particular crop. As used herein, improved plant productivity refers broadly to improvements in yield of grain, fruit, flowers, or other plant parts harvested for various purposes, improvements in growth of plant parts, including stems, leaves and roots, promotion of plant growth, maintenance of high chlorophyll content in leaves, increasing fruit or seed numbers, increasing fruit or seed unit weight, reducing $NO_2$ emission due to reduced nitrogen fertilizer usage and similar improvements of the growth and development of plants.

Microbes in and around food crops can influence the traits of those crops. Plant traits that may be influenced by microbes include: yield (e.g., grain production, biomass generation, fruit development, flower set); nutrition (e.g., nitrogen, phosphorus, potassium, iron, micronutrient acquisition); abiotic stress management (e.g., drought tolerance, salt tolerance, heat tolerance); and biotic stress management (e.g., pest, weeds, insects, fungi, and bacteria). Strategies for altering crop traits include: increasing key metabolite concentrations; changing temporal dynamics of microbe influence on key metabolites; linking microbial metabolite production/degradation to new environmental cues; reducing negative metabolites; and improving the balance of metabolites or underlying proteins.

In some embodiments, "applying to the plant a plurality of genetically engineered bacteria," such as non-intergeneric bacteria includes any means by which the plant (including plant parts such as a seed, root, stem, tissue, etc.) is made to come into contact (i.e., exposed) with said bacteria at any stage of the plant's life cycle. Consequently, "applying to the plant a plurality genetically engineered bacteria," includes any of the following means of exposing the plant (including plant parts such as a seed, root, stem, tissue, etc.) to said bacteria: spraying onto plant, dripping onto plant, applying as a seed coat, applying to a field that will then be planted with seed, applying to a field already planted with seed, applying to a field with adult plants, etc.

As used herein "MRTN" is an acronym for maximum return to nitrogen and is utilized as an experimental treatment in the Examples. MRTN was developed by Iowa State University and information can be found at: cnrc.agron.iastate.edu/. The MRTN is the nitrogen rate where the economic net return to nitrogen application is maximized. The approach to calculating the MRTN is a regional approach for developing corn nitrogen rate guidelines in individual states. The nitrogen rate trial data was evaluated for Illinois, Iowa, Michigan, Minnesota, Ohio, and Wisconsin where an adequate number of research trials were available for corn plantings following soybean and corn plantings following corn The trials were conducted with spring, sidedress, or split preplant/sidedress applied nitrogen, and sites were not irrigated except for those that were indicated for irrigated sands in Wisconsin. MRTN was developed by Iowa State University due to apparent differences in methods for determining suggested nitrogen rates required for corn production, misperceptions pertaining to nitrogen rate guidelines, and concerns about application rates. By calculating the MRTN, practitioners can determine the following: (1) the nitrogen rate where the economic net return to nitrogen application is maximized, (2) the economic optimum nitrogen rate, which is the point where the last increment of nitrogen returns a yield increase large enough to pay for the additional nitrogen, (3) the value of corn grain increase attributed to nitrogen application, and the maximum yield, which is the yield where application of more nitrogen does not result in a corn yield increase. Thus the MRTN calculations provide practitioners with the means to maximize corn crops in different regions while maximizing financial gains from nitrogen applications.

In some embodiments, the increase of nitrogen fixation and/or the production of 1% or more of the nitrogen in the plant are measured relative to control plants, which have not been exposed to the bacteria of the present disclosure. All increases or decreases in bacteria are measured relative to control bacteria (e.g., a non-engineered bacteria of the same species). All increases or decreases in plants are measured relative to control plants.

As used herein, a "control sequence" refers to an operator, promoter, silencer, or terminator.

In some embodiments, native or endogenous control sequences of genes of the present disclosure are replaced with one or more intrageneric control sequences.

As used herein, a "constitutive promoter" is a promoter that is active under most conditions and/or during most developmental stages. There can be several advantages to using constitutive promoters in expression vectors used in biotechnology. Such advantages can include a high level of production of proteins used to select transgenic cells or organisms; a high level of expression of reporter proteins or scorable markers that can allow easy detection and quantification; a high level of production of a transcription factor that is part of a regulatory transcription system; production of compounds that requires ubiquitous activity in the organism; and production of compounds that are required during all stages of development. Non-limiting exemplary constitutive promoters include, CaMV 35S promoter, opine promoters, ubiquitin promoter, alcohol dehydrogenase promoter, etc.

As used herein, a "non-constitutive promoter" is a promoter which is active under certain conditions, in certain types of cells, and/or during certain development stages. For example, tissue-specific promoters, tissue-preferred promoters, cell type-specific promoters, cell type-preferred promoters, inducible promoters, and promoters under developmental control are non-constitutive promoters. Examples of promoters under developmental control include promoters that preferentially initiate transcription in certain tissues.

As used herein, an "inducible" promoter or a "repressible" promoter is a promoter that is under the control of chemical or environmental factors. Examples of environmental conditions that can affect transcription by inducible promoters include anaerobic conditions, certain chemicals, the presence of light, acidic or basic conditions, etc.

As used herein, a "tissue-specific" promoter is a promoter that initiates transcription only in certain tissues. Unlike constitutive expression of genes, tissue-specific expression is the result of several interacting levels of gene regulation. It can be advantageous to use promoters from homologous or closely related species to achieve efficient and reliable expression of transgenes in particular tissues. This is a reason for the large amount of tissue-specific promoters isolated from particular tissues found in both scientific and patent literature.

As used herein, the term "operably linked" refers to the association of nucleic acid sequences on a single nucleic acid fragment such that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In some embodiments, complementary RNA regions of the disclosure are operably linked either directly or indirectly, for example, 5' to the target mRNA, 3' to the target mRNA, or within the target mRNA. In some embodiments, a first complementary region is 5' and its complement is 3' to the target mRNA.

As used herein, "introduced" refers to the introduction by means of modern biotechnology, and not a naturally occurring introduction.

As used herein, "introduced genetic material" means genetic material that is added to, and remains as a component of, the genome of the recipient.

As used herein the terms "microorganism" or "microbe" should be taken broadly. These terms, used interchangeably, include but are not limited to, the two prokaryotic domains, Bacteria and Archaea. The term may also encompass eukaryotic fungi.

As used herein, an "intergeneric microorganism" is a microorganism that is formed by the deliberate combination of genetic material originally isolated from organisms of different taxonomic genera. An "intergeneric mutant" can be used interchangeably with "intergeneric microorganism". An exemplary "intergeneric microorganism" includes a microorganism containing a mobile genetic element which was first identified in a microorganism in a genus different from the recipient microorganism In some embodiments, microbes disclosed herein are "non-intergeneric," which means that the microbes are not intergeneric.

As used herein, an "intrageneric microorganism" is a microorganism that is formed by the deliberate combination of genetic material originally isolated from organisms of the same taxonomic genera. An "intrageneric mutant" can be used interchangeably with "intrageneric microorganism."

As used herein, in the context of non-intergeneric microorganisms, the term "remodeled" is used synonymously with the term "engineered". Consequently, a "non-intergeneric remodeled microorganism" has a synonymous meaning to "non-intergeneric engineered microorganism," and will be utilized interchangeably. Further, the disclosure may refer to an "engineered strain" or "engineered derivative" or "engineered non-intergeneric microbe," these terms are used synonymously with "remodeled strain" or "remodeled derivative" or "remodeled non-intergeneric microbe."

In some embodiments, the bacteria of the present disclosure have been modified such that they are not naturally occurring bacteria.

As used herein, when the disclosure discusses a particular microbial deposit by accession number, it is understood that the disclosure also contemplates a microbial strain having all of the identifying characteristics of said deposited microbe and/or a mutant thereof.

The term "microbial consortia" or "microbial consortium" refers to a subset of a microbial community of individual microbial species, or strains of a species, which can be described as carrying out a common function, or can be described as participating in, or leading to, or correlating with, a recognizable parameter, such as a phenotypic trait of interest.

The term "microbial community" means a group of microbes comprising two or more species or strains. Unlike microbial consortia, a microbial community does not have to be carrying out a common function, or does not have to be participating in, or leading to, or correlating with, a recognizable parameter, such as a phenotypic trait of interest.

As used herein, "isolate," "isolated," "isolated microbe," and like terms, are intended to mean that the one or more microorganisms has been separated from at least one of the materials with which it is associated in a particular environment (for example soil, water, plant tissue, etc.). Thus, an "isolated microbe" does not exist in its naturally-occurring environment; rather, it is through the various techniques described herein that the microbe has been removed from its natural setting and placed into a non-naturally occurring state of existence. Thus, the isolated strain or isolated microbe may exist as, for example, a biologically pure culture, or as spores (or other forms of the strain).

In some embodiments, the isolated microbe may be in association with an acceptable carrier, which may be an agriculturally acceptable carrier.

In some embodiments, the isolated microbes exist as "isolated and biologically pure cultures." It will be appreciated by one of skill in the art that an isolated and biologically pure culture of a particular microbe, denotes that said culture is substantially free of other living organisms and contains only the individual microbe in question. The culture can contain varying concentrations of said microbe. The present disclosure notes that isolated and biologically pure microbes often "necessarily differ from less pure or impure materials."

In some embodiments, wherein a plurality of genetically engineered microbes comprising at least one modification in a gene regulating nitrogen fixation or assimilation are provided, at least about 25% of the plurality comprises the at least one modification in a gene regulating nitrogen fixation or assimilation. In some embodiments, at least about 50% of the plurality of genetically engineered microbes comprises the at least one modification in a gene regulating nitrogen fixation or assimilation. For example, at least about 55%, about 60%, about 65%, about 70%, about 75%, about 80%, about 85%, about 90%, about 95%, about 98%, or about 99% of the plurality of genetically engineered microbes comprises the at least one modification in a gene regulating nitrogen fixation or assimilation. In some embodiments, every member of the plurality of genetically engineered microbes comprises the at least one modification.

In some embodiments, the disclosure provides for certain quantitative measures of the concentration, or purity limitations that must be found within an isolated and biologically pure microbial culture. The presence of these purity values, in certain embodiments, is a further attribute that distinguishes the presently disclosed microbes from those microbes existing in a natural state.

As used herein, "individual isolates" should be taken to mean a composition, or culture, comprising a predominance of a single genera, species, or strain, of microorganism, following separation from one or more other microorganisms.

Microbes of the present disclosure can include spores and/or vegetative cells. In some embodiments, microbes of the present disclosure include microbes in a viable but non-culturable (VBNC) state. As used herein, "spore" or "spores" refer to structures produced by bacteria and fungi that are adapted for survival and dispersal. Spores are generally characterized as dormant structures; however, spores are capable of differentiation through the process of germination. Germination is the differentiation of spores into vegetative cells that are capable of metabolic activity, growth, and reproduction. The germination of a single spore results in a single fungal or bacterial vegetative cell. Fungal spores are units of asexual reproduction, and in some cases are necessary structures in fungal life cycles. Bacterial spores are structures for surviving conditions that may ordinarily be non-conducive to the survival or growth of vegetative cells.

As used herein, a "microbial composition" refers to a composition comprising one or more microbes of the present disclosure. In some embodiments, a microbial composition is administered to plants (including various plant parts) and/or in agricultural fields.

As used herein, "carrier," "acceptable carrier," or "agriculturally acceptable carrier" refers to a diluent, adjuvant, excipient, or vehicle with which the microbe can be administered, which does not detrimentally effect the microbe.

In some embodiments, the bacteria of the present disclosure are present in the plant in an amount of at least $10^3$ cfu, $10^4$ cfu, $10^5$ cfu, $10^6$ cfu, $10^7$ cfu, $10^8$ cfu, $10^9$ cfu, $10^{10}$ cfu, $10^{11}$ cfu, or $10^{12}$ cfu per gram of fresh or dry weight of the plant. In some embodiments, the bacteria of the present disclosure are present in the plant in an amount of at least about $10^3$ cfu, about $10^4$ cfu, about $10^5$ cfu, about $10^6$ cfu, about $10^7$ cfu, about $10^8$ cfu, about $10^9$ cfu, about $10^{10}$ cfu, about $10^{11}$ cfu, or about $10^{12}$ cfu per gram of fresh or dry weight of the plant. In some embodiments, the bacteria of the present disclosure are present in the plant in an amount of at least $10^3$ to $10^9$, $10^3$ to $10^7$, $10^3$ to $10^5$, $10^5$ to $10^1$, $10^5$ to $10^7$, $10^6$ to $10^{10}$, $10^6$ to $10^7$ cfu per gram of fresh or dry weight of the plant.

As used herein, "exogenous nitrogen" refers to non-atmospheric nitrogen readily available in the soil, field, or growth medium that is present under non-nitrogen limiting conditions, including ammonia, ammonium, nitrate, nitrite, urea, uric acid, ammonium acids, etc.

Fertilizers and exogenous nitrogen of the present disclosure may comprise the following nitrogen-containing molecules: ammonium, nitrate, nitrite, ammonia, glutamine, etc. Nitrogen sources of the present disclosure may include anhydrous ammonia, ammonia sulfate, urea, diammonium phosphate, urea-form, monoammonium phosphate, ammonium nitrate, nitrogen solutions, calcium nitrate, potassium nitrate, sodium nitrate, etc.

As used herein, "non-nitrogen limiting conditions" refers to non-atmospheric nitrogen available in the soil, field, or culture media at concentrations greater than about 4 mM nitrogen, as disclosed by Kant et al. (2010. *J. Exp. Biol.* 62(4):1499-1509), which is incorporated herein by reference.

In some embodiments, fertilizer of the present disclosure comprises at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% nitrogen by weight.

In some embodiments, fertilizer of the present disclosure comprises at least about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% nitrogen by weight.

In some embodiments, fertilizer of the present disclosure comprises about 5% to 50%, about 5% to 75%, about 10% to 50%, about 10% to 75%, about 15% to 50%, about 15% to 75%, about 20% to 50%, about 20% to 75%, about 25% to 50%, about 25% to 75%, about 30% to 50%, about 30% to 75%, about 35% to 50%, about 35% to 75%, about 40% to 50%, about 40% to 75%, about 45% to 50%, about 45% to 75%, or about 50% to 75% nitrogen by weight.

In general, the term "genetic modification" refers to any change introduced into a polynucleotide sequence relative to a reference polynucleotide, such as a reference genome or portion thereof, or reference gene or portion thereof. A genetic modification may be referred to as a "mutation," and a sequence or organism comprising a genetic modification may be referred to as a "genetic variant" or "mutant".

Genetic modifications introduced into microbes can be classified as transgenic, cisgenic, intragenomic, intrageneric, intergeneric, synthetic, evolved, rearranged, or SNPs.

Genetic modification may be introduced into numerous metabolic pathways within microbes to elicit improvements in the traits described above. Representative pathways include sulfur uptake pathways, glycogen biosynthesis, the glutamine regulation pathway, the molybdenum uptake pathway, the nitrogen fixation pathway, ammonia assimilation, ammonia excretion or secretion. Nitrogen uptake, glutamine biosynthesis, annamox, phosphate solubilization, organic acid transport, organic acid production, agglutinins production, reactive oxygen radical scavenging genes, Indole Acetic Acid biosynthesis, trehalose biosynthesis, plant cell wall degrading enzymes or pathways, root attachment genes, exopolysaccharide secretion, glutamate synthase pathway, iron uptake pathways, siderophore pathway, chitinase pathway, ACC deaminase, glutathione biosynthesis, phosphorous signalig genes, quorum quenching pathway, cytochrome pathways, hemoglobin pathway, bacterial hemoglobin-like pathway, small RNA rsmZ, rhizobitoxine biosynthesis, lapA adhesion protein, AHL quorum sensing pathway, phenazine biosynthesis, cyclic lipopeptide biosynthesis, and antibiotic production.

In some embodiments, the microbes and/or genetic modifications disclosed herein are not the microbes taught in International Publication No. WO 2018/132774 A1), filed Jan. 12, 2018, and entitled: Methods and Compositions for Improving Plant Traits. In some embodiments, the methods disclosed herein are not the methods taught in PCT/US2018/013671 (WO 2018/132774 A1), filed Jan. 12, 2018, and entitled: Methods and Compositions for Improving Plant Traits. Thus, the present disclosure contemplates embodiments, which have a negative proviso of the microbes, methods, and gene modifications disclosed in said application.

Unless otherwise defined, all technical and scientific terms used herein have the same meaning as commonly understood by one of ordinary skill in the art to which this disclosure pertains. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 10A and 10B show the compiled results of several acetylate reduction assays (ARAs) with *K. variicola* 201708001 strains at 0 mM, 5 mM and 10 mM ammonium phosphate, expressed both as titer of ethylene produced (mmol) (FIG. 10A) and rate of ethylene produced per cell over time (mmol/CFU·hr) (FIG. 10B).

21 tives, with log 10 CFU/g root fresh weight (FW). Not all strains were tested in each experiment.

Figure 17A:
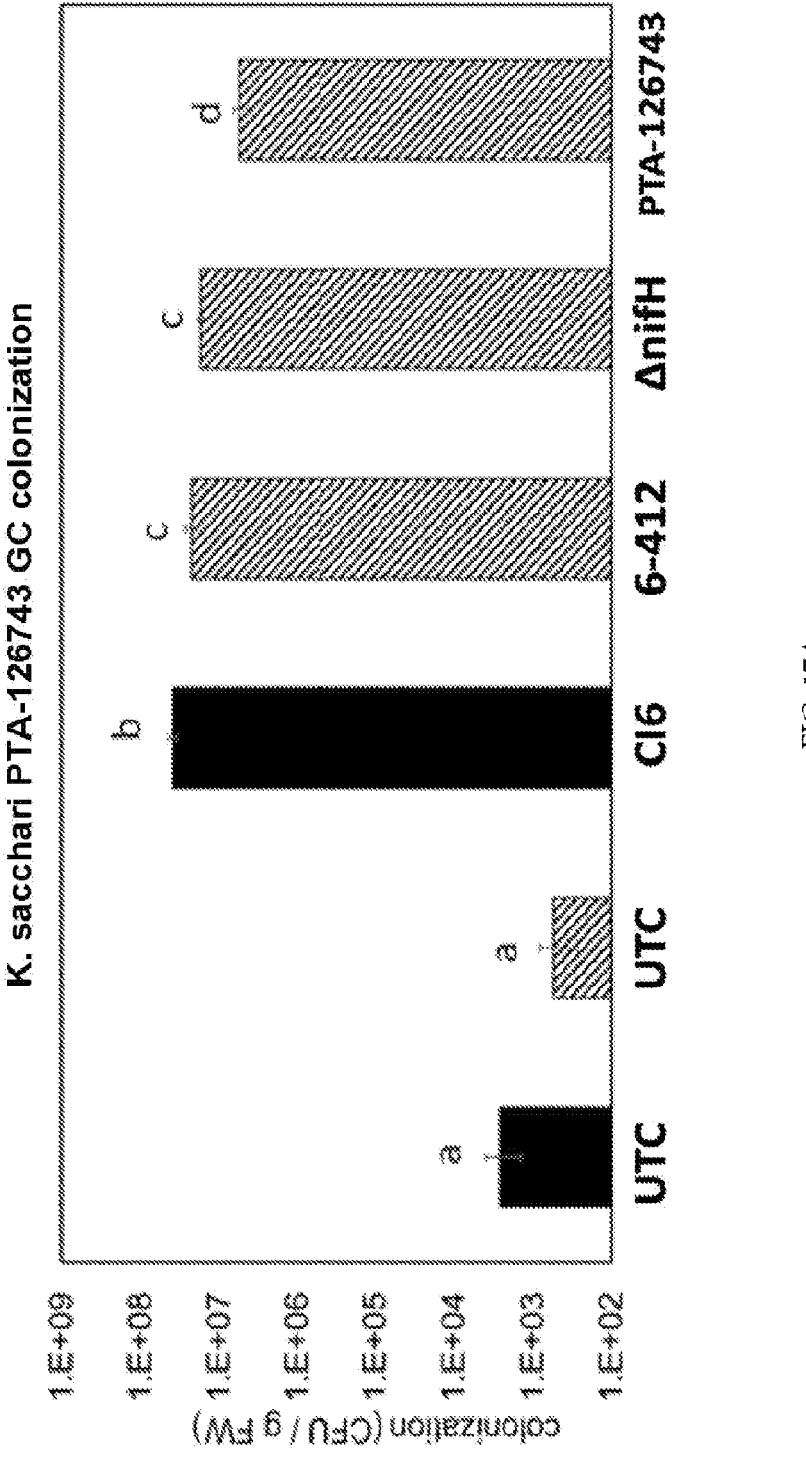
Figure 17B:
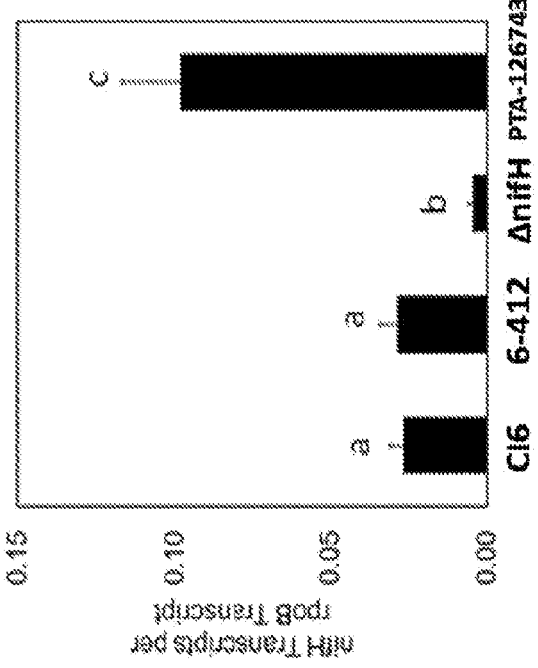

FIGS. 17A and 17B show the results of a growth chamber colonization experiment of *K. sacchari* 6 strains. In FIG. 17A, colonization is expressed as CFU/g root fresh weight (FW). In FIG. 17B, in the left panel, nifA transcripts per rpoB transcript is reported, while in the right panel, nifH transcripts per rpoB transcript is reported.

Figure 18A:
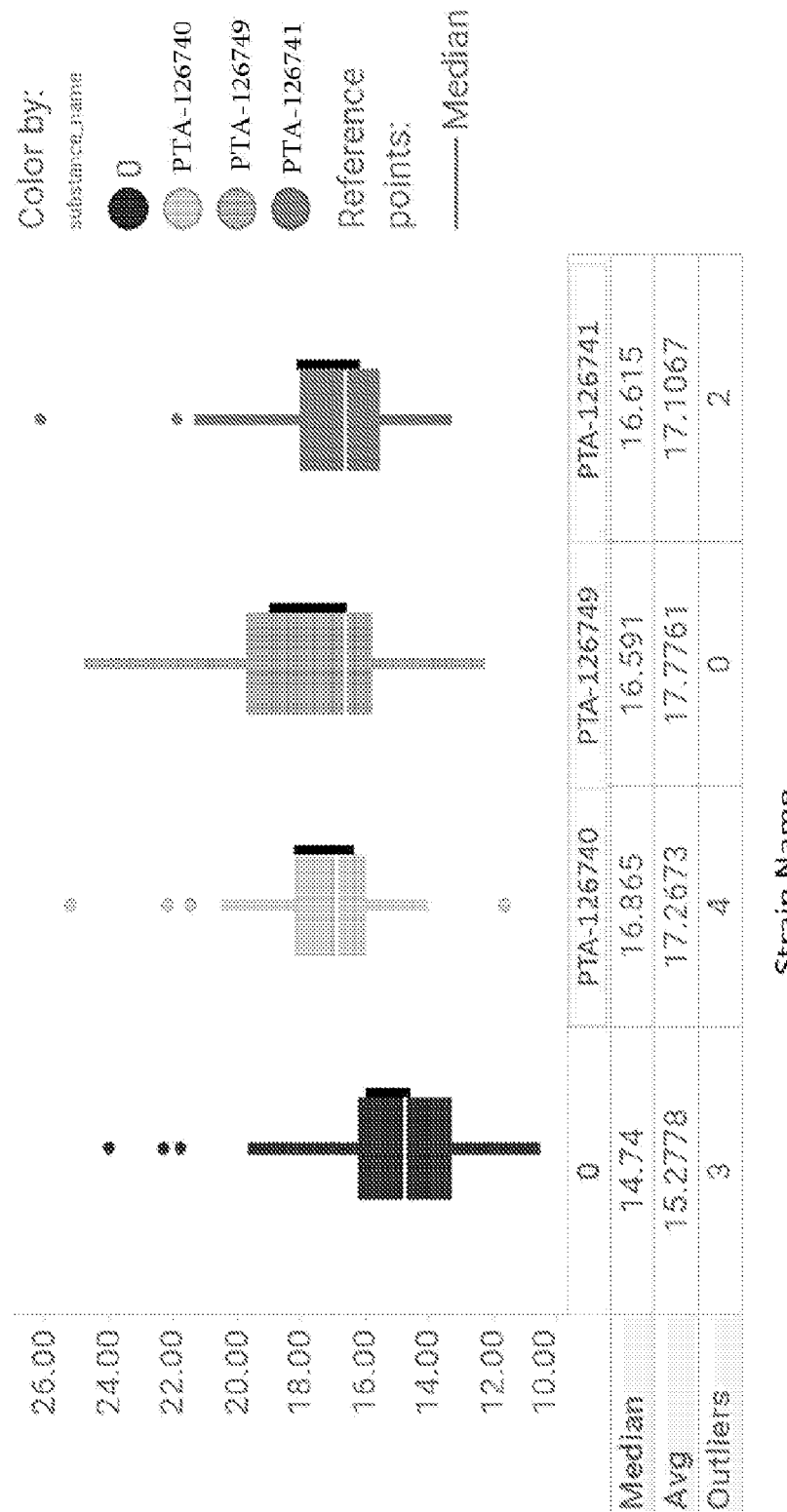
Figure 18B:
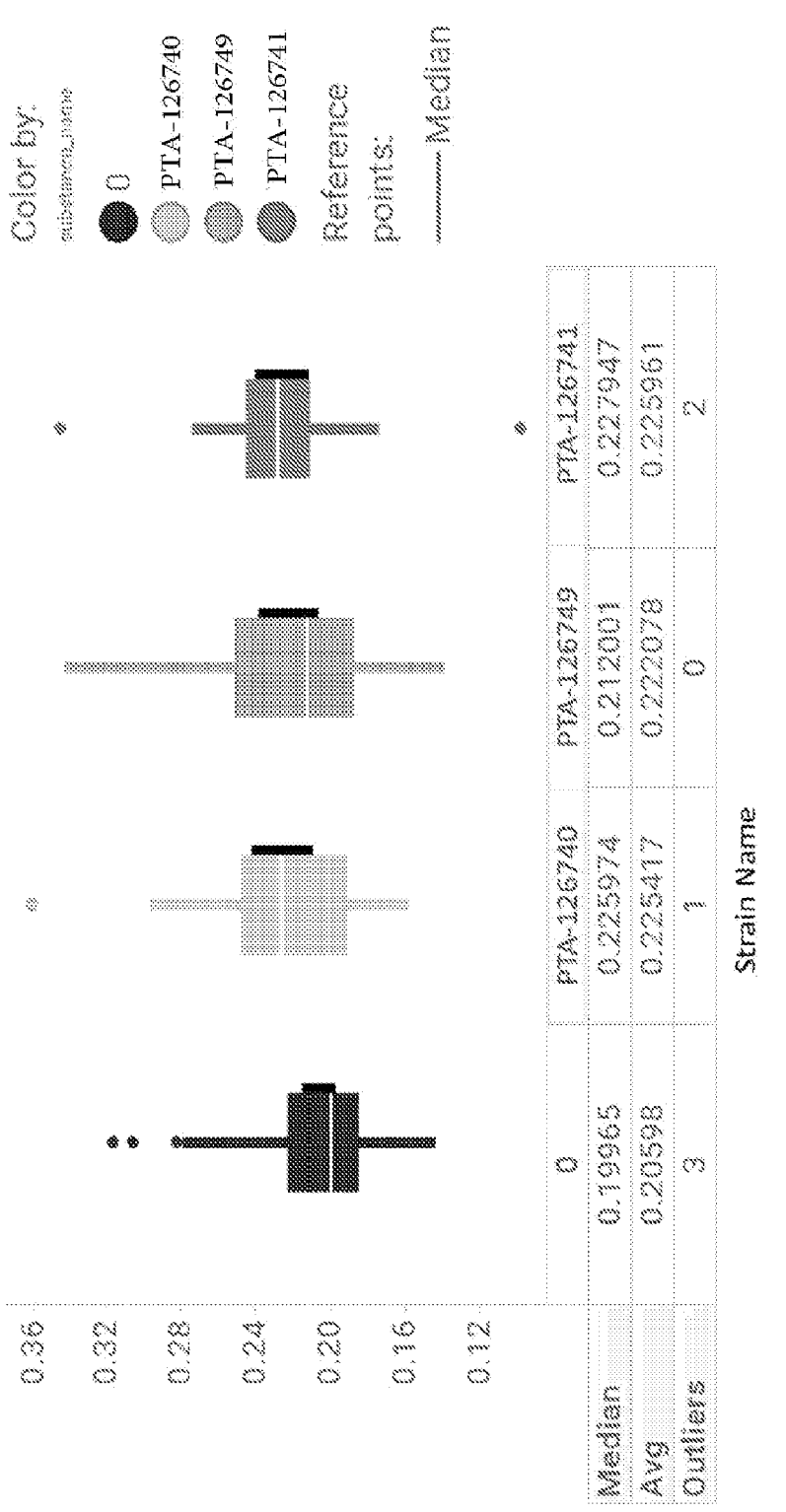

FIGS. 18A and 18B show the dry weights (FIG. 187A) and total N (FIG. 18B) of corn inoculated with Kv137 strains and grown with 2 mM N fertigation.

Figure 19A:
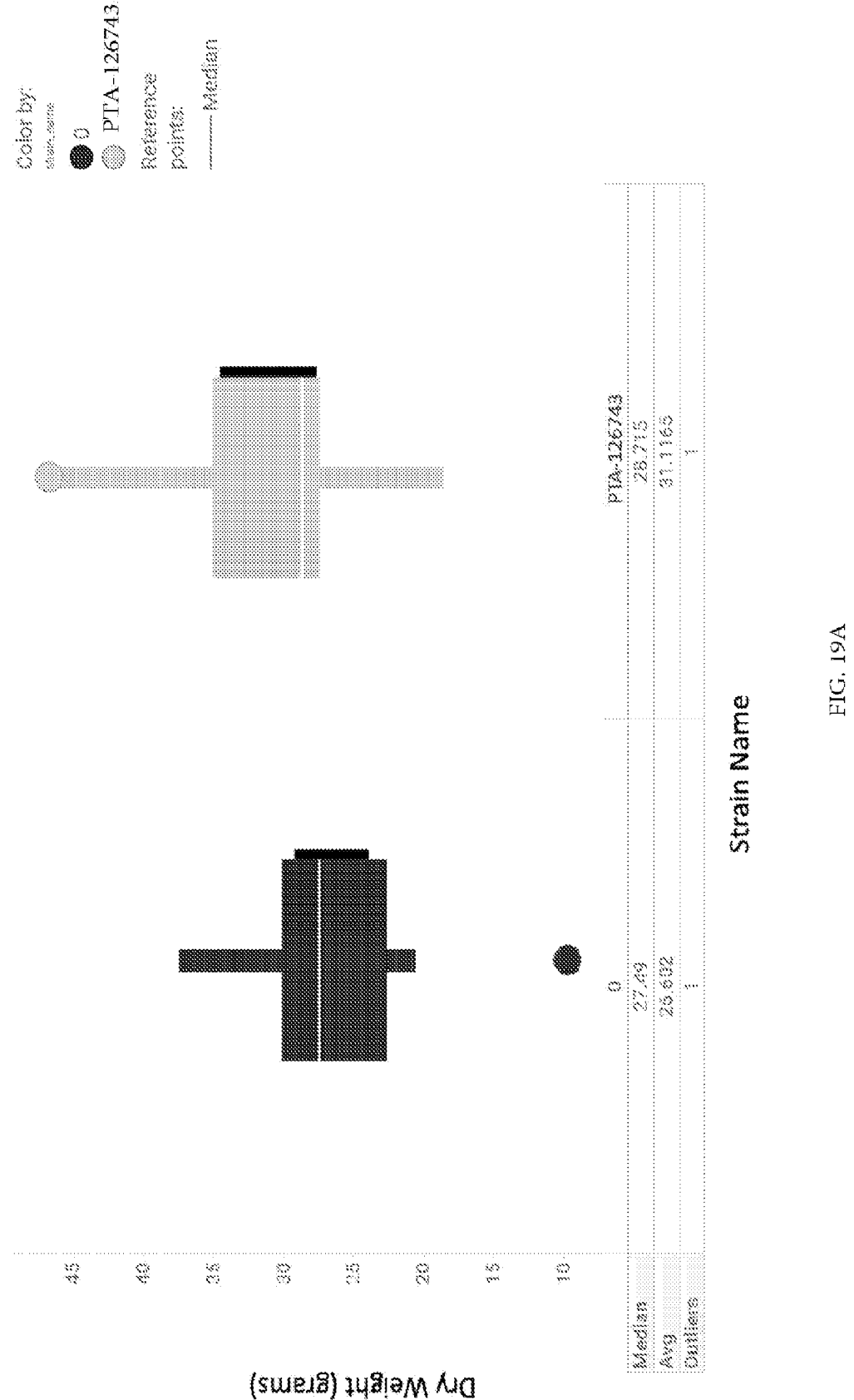
Figure 19B:
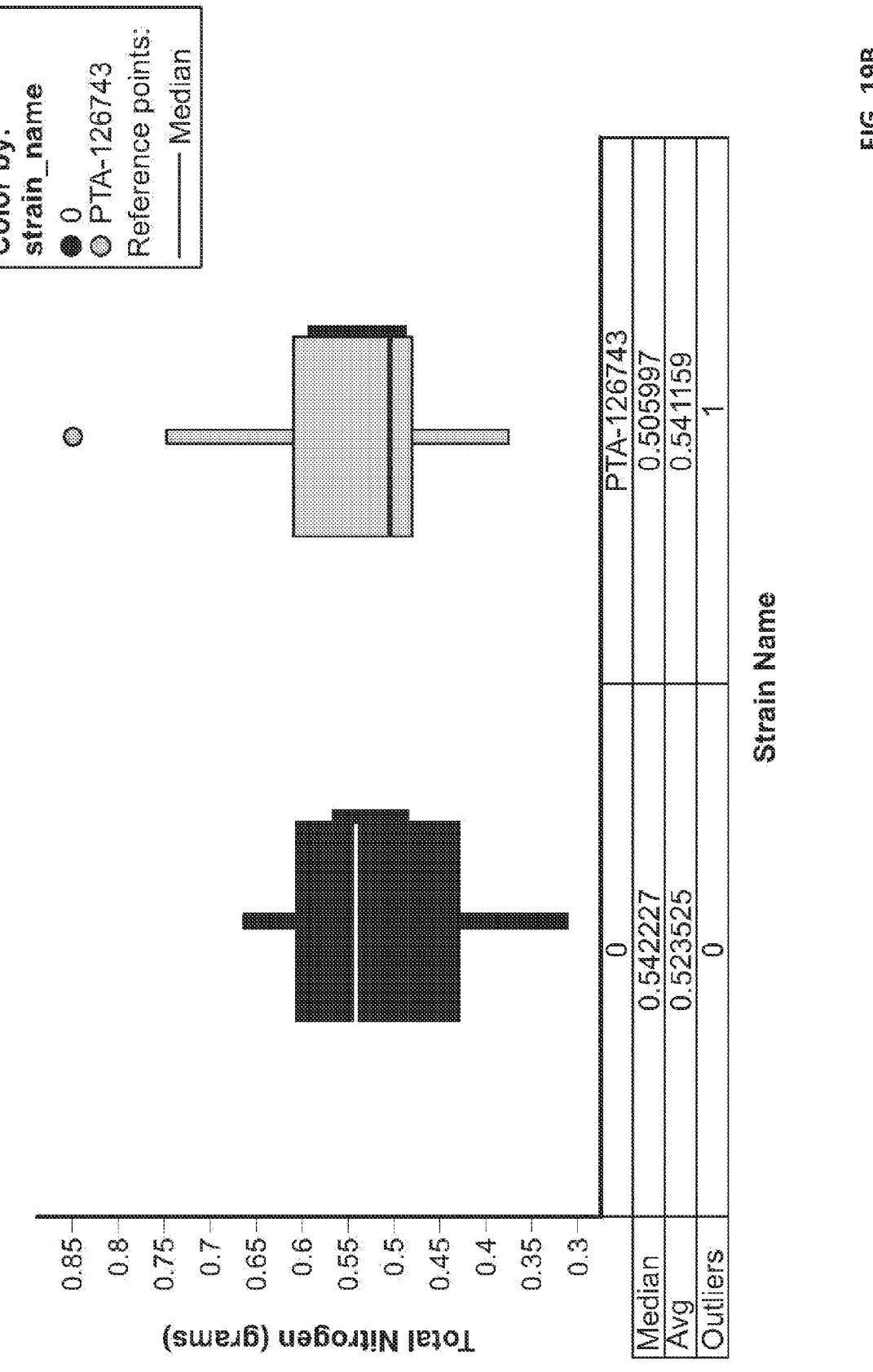

FIGS. 19A and 19B show the dry weights (FIG. 19A) and total N (FIG. 19B) of corn inoculated with PTA-126743 and grown with 8 mM N fertigation.

Figure 20:
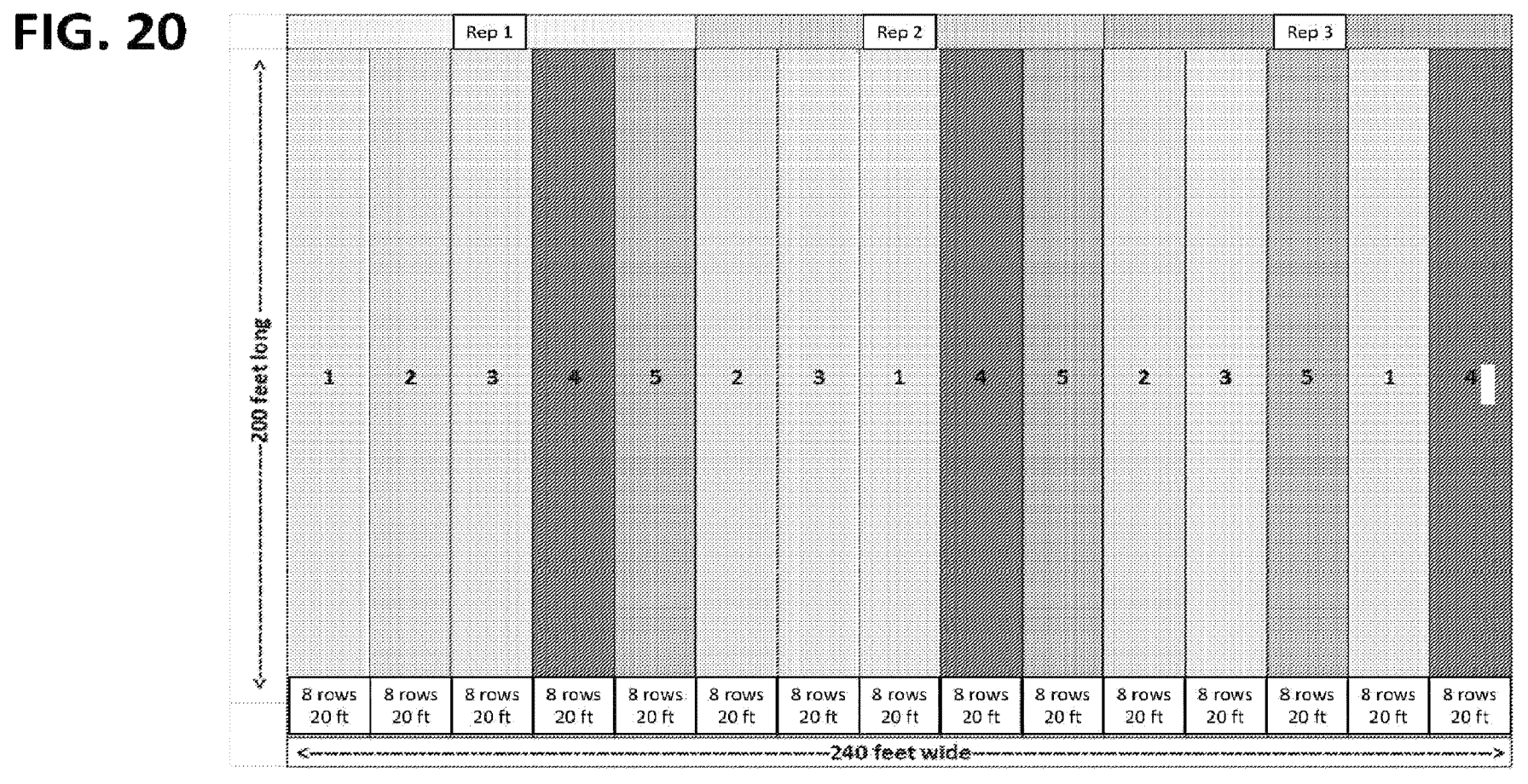

FIG. 20 depicts the layout of a field trial set up with plots that were 8 rows wide and 200 feet long.

Figure 21:
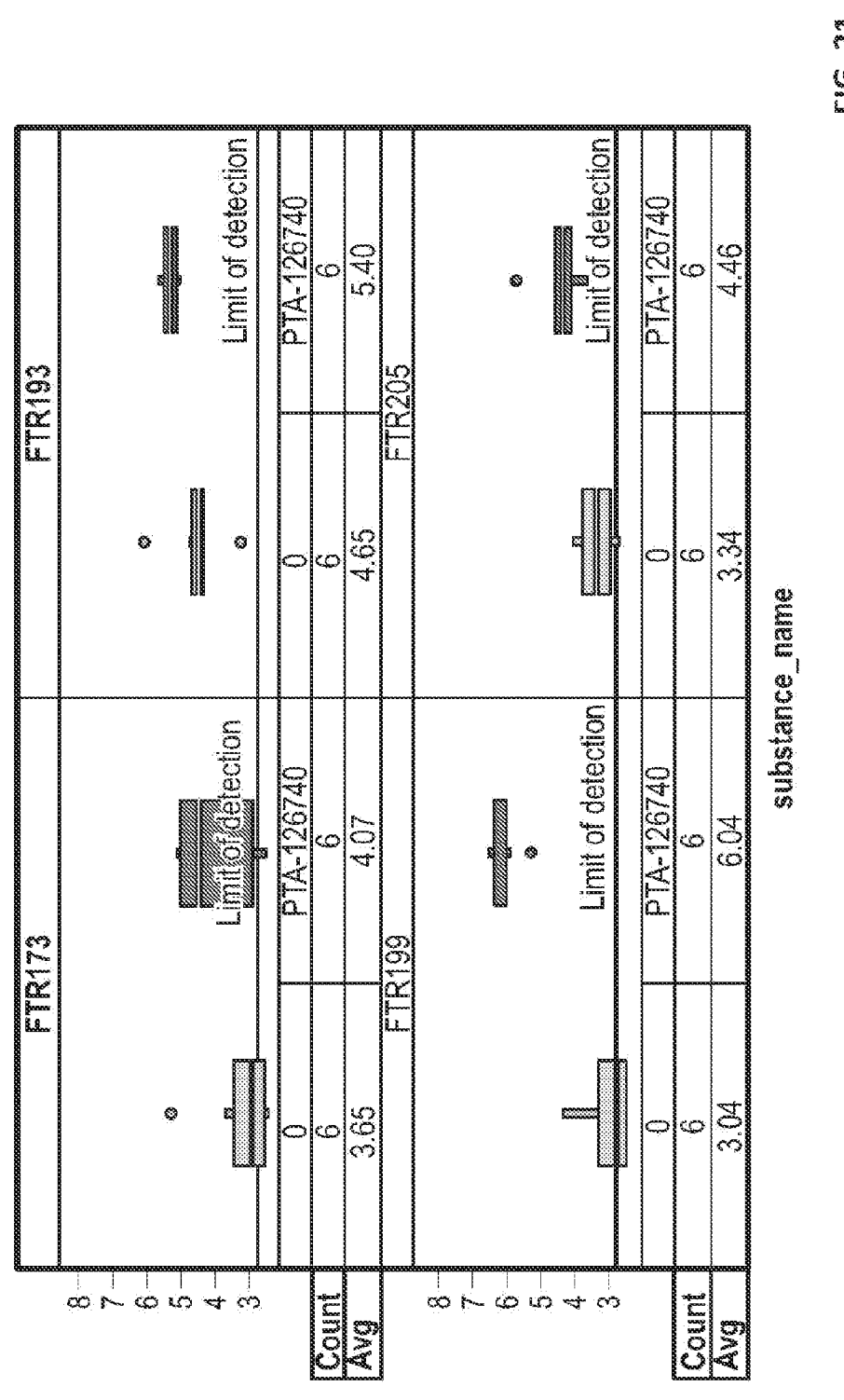

FIG. 21 shows colonization of *K. variicola* PTA-126740 from field trials, expressed as log 10 CFU/g root fresh weight (FW).

Figure 22A:
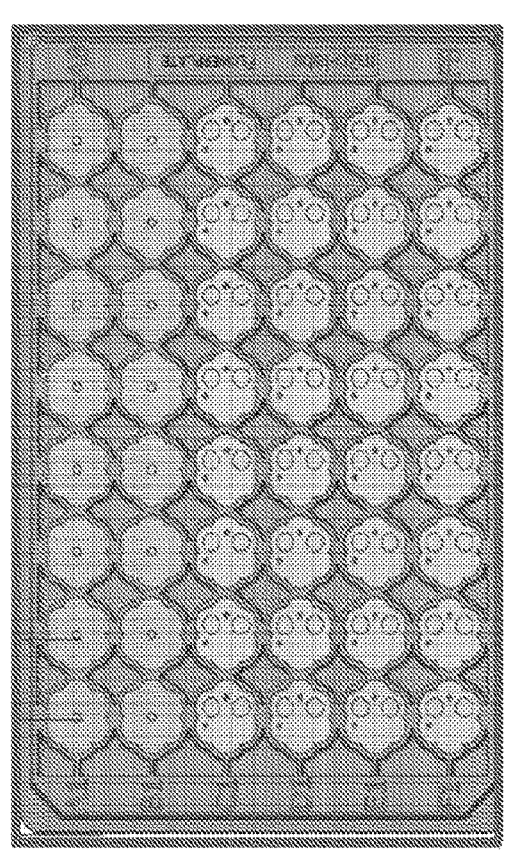
Figure 22B:
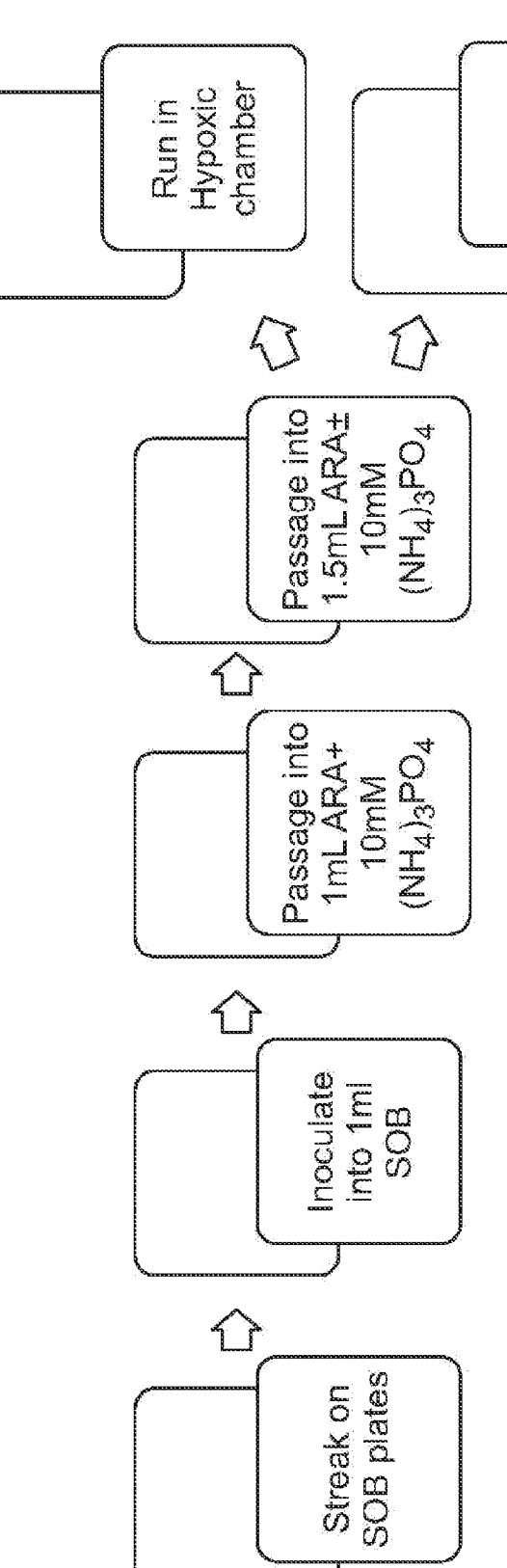

FIGS. 22A-22C provide details of a microbioreactor experiment to investigate the growth of *K. variicola* 201708001 and *K. sacchari* 201701001 strains at different levels of oxygen.

Figure 23A:
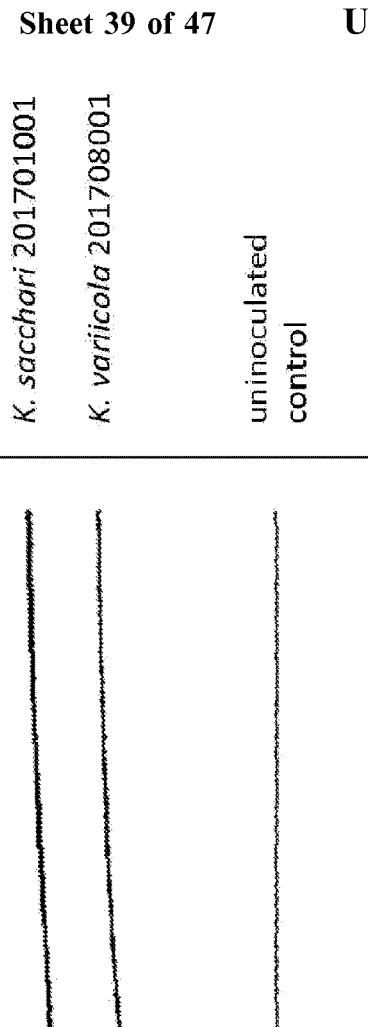
Figure 23B:
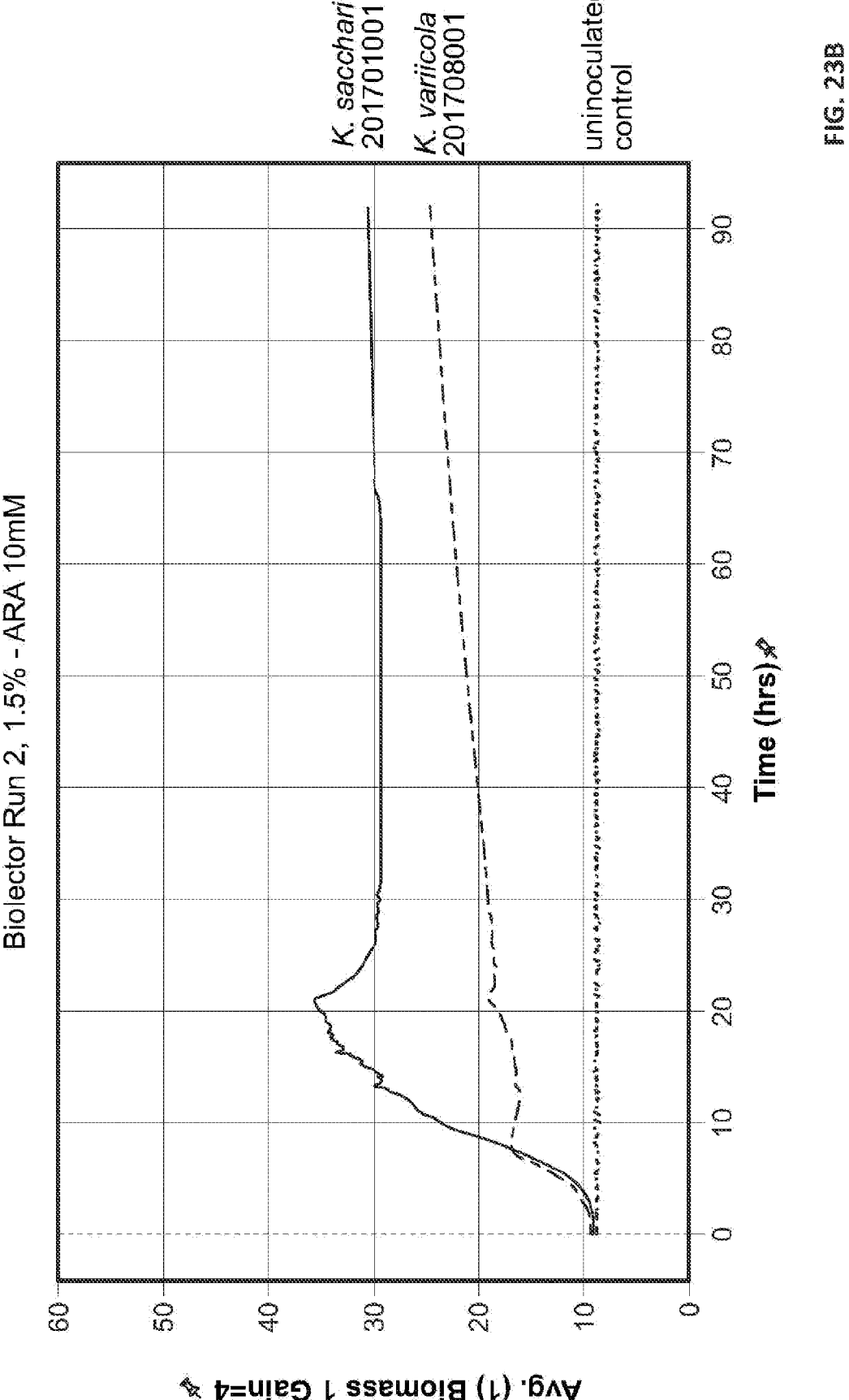
Figure 23C:
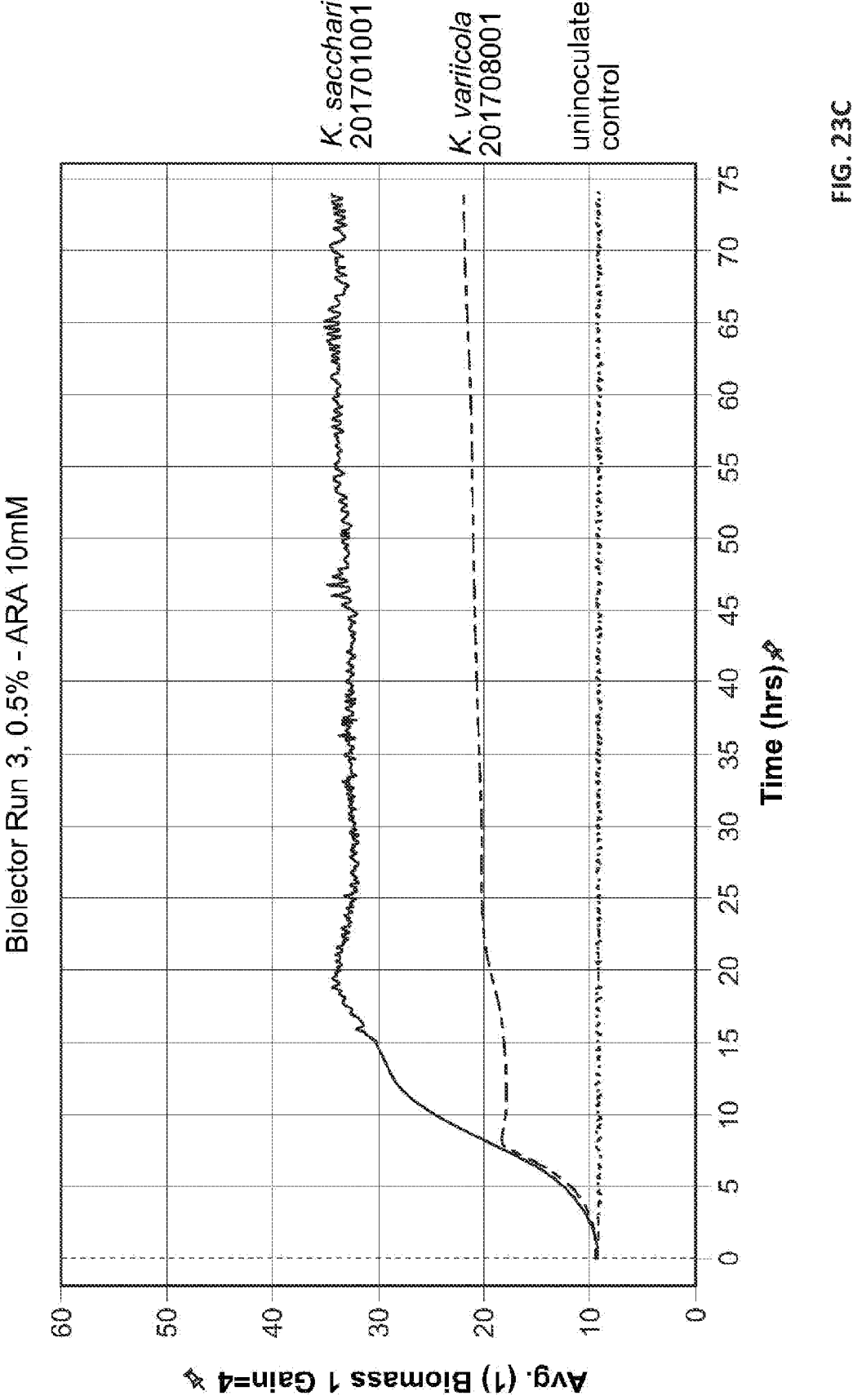

FIG. 23A-23C show the results of the microbioreactor experiment detailed in FIGS. 22A-C.

Figure 24:
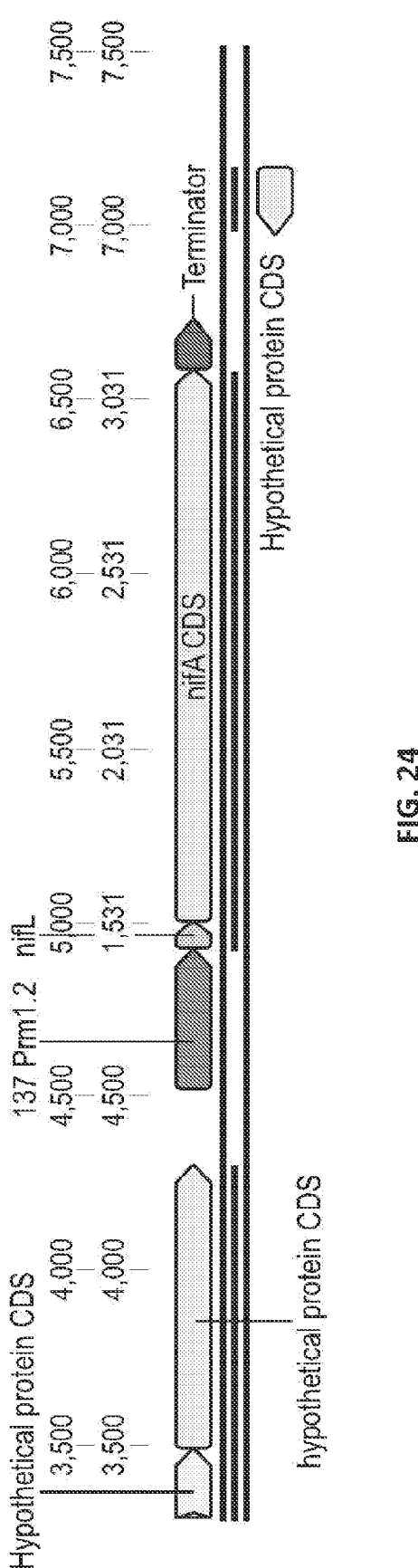

FIG. 24 depicts the nifA gene inserted into a non-coding region of the genome between two hypothetical genes that are transcribed in convergent fashion.

Figure 25A:
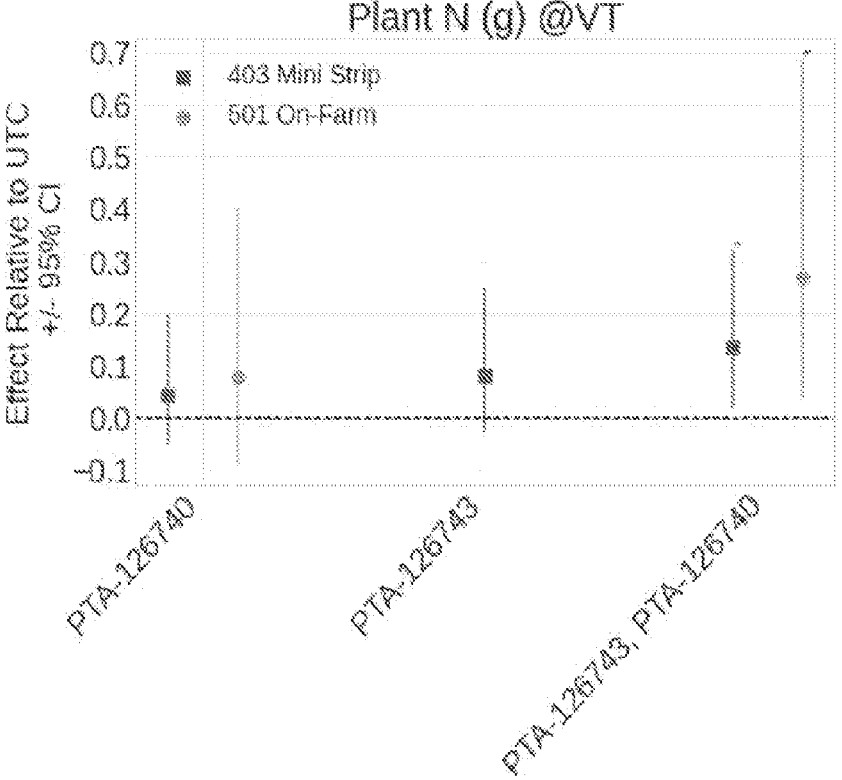
Figure 25B:
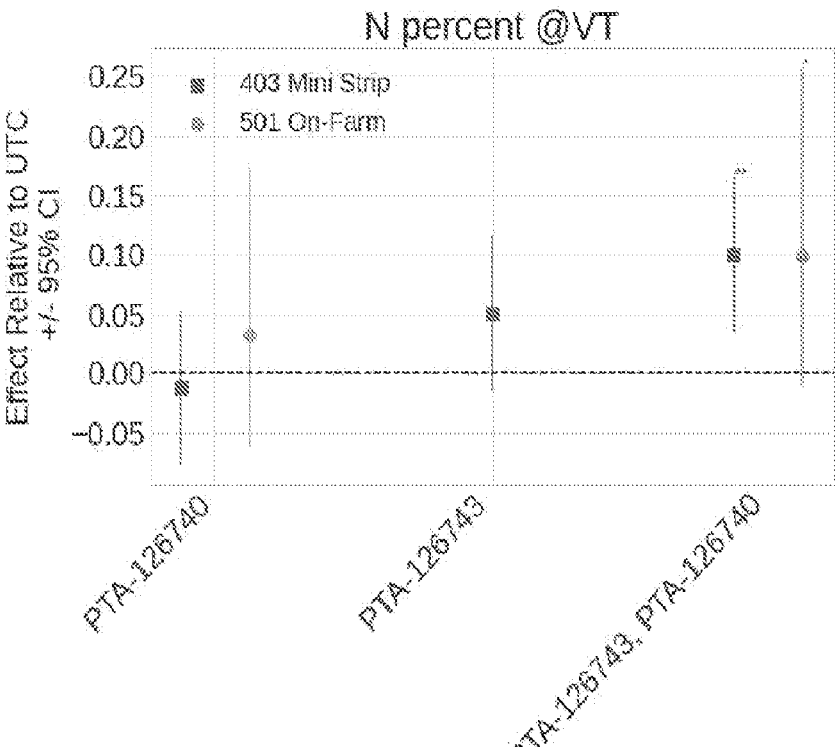

FIG. 25A depicts the nitrogen percent at the reproductive growth stage of corn, referred to as VT and FIG. 25B depicts the whole plant nitrogen at VT, where *p<0.1; p<0.05; *p<0.01.

Figure 26:
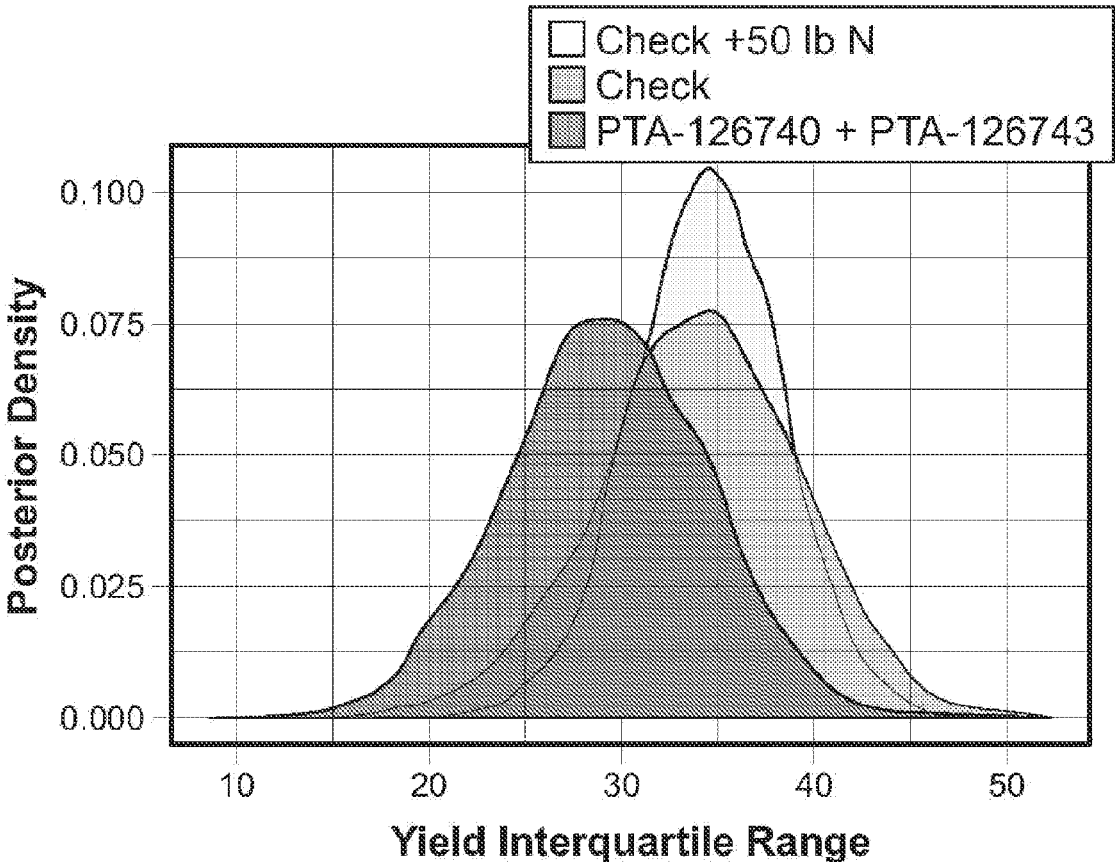

FIG. 26 is a graph of the conditional mean posterior values for each treatment type (x axis) and their associated frequency (posterior density) in a 4000-iteration monte-carlo sample, with results only using locations with proven X.

Figure 27A:
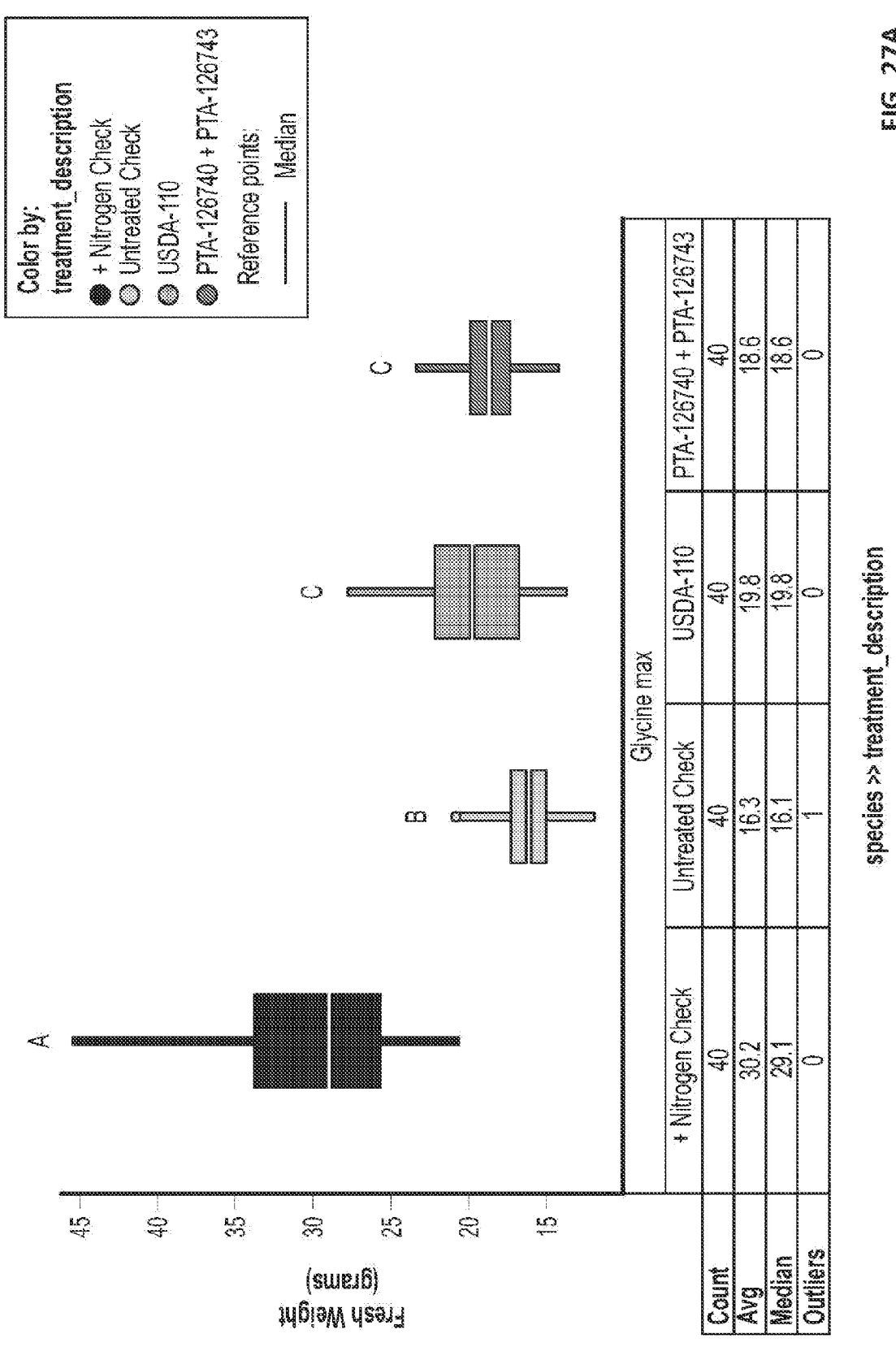
Figure 27B:
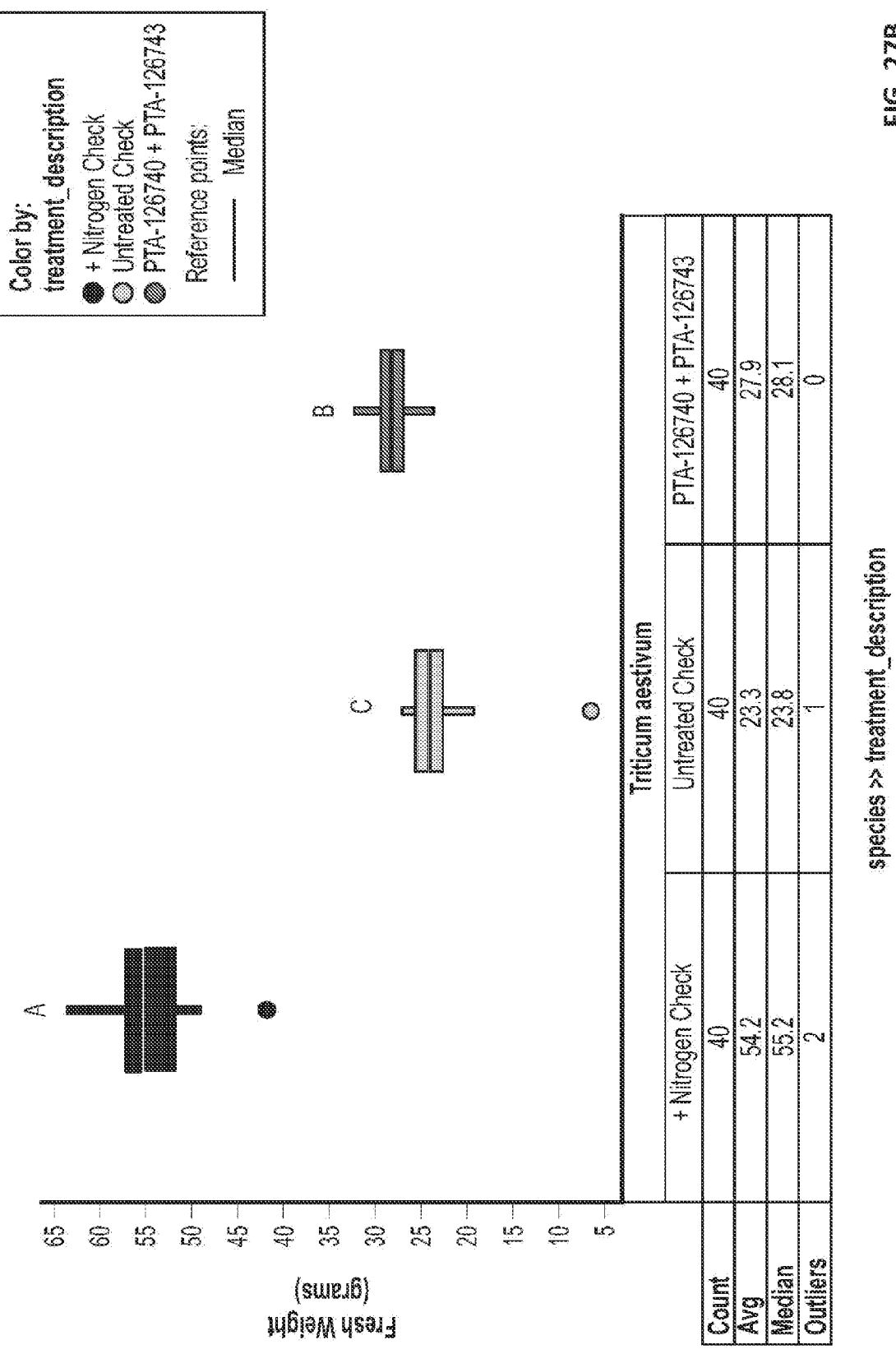
Figure 27C:
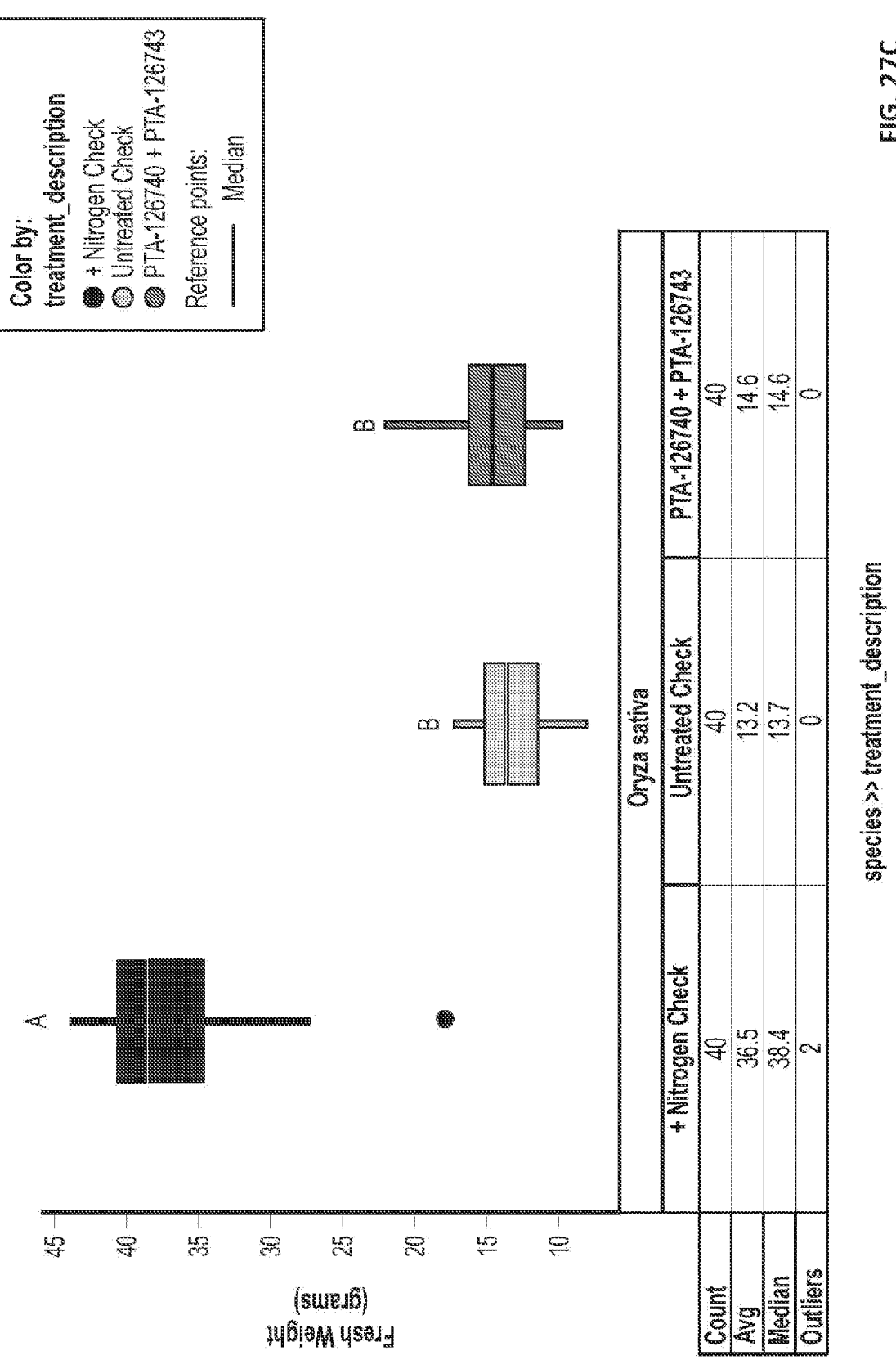

FIGS. 27A, 27B, and 27C are graphs of the fresh weight (grams) of *Glycine max, Triticum aestivum,* and *Oryza sativa* plants treated with either a combined bacterial sus-pension of PTA-126740 and PTA-126743 or a control with no inoculated cells in three greenhouse growth experiments. Additionally, soybean plants treated with USDA-110 *Bra-dyrhizobiom japonicum* (NRRL No. B-4361, USDA-ARS) as a positive control for biological nitrogen fixation. All plants were grown under nitrogen limiting conditions except a positive control (+ Nitrogen Check) to test for nitrogen response under these assay conditions.

DETAILED DESCRIPTION

Nitrogen fertilizer can be the largest operational expense on a farm and the biggest driver of higher yields in row crops like corn and wheat. Described herein are microbial products that can deliver renewable forms of nitrogen in non-legu-minous crops. While some endophytes have the genetics necessary for fixing nitrogen in pure culture, the fundamen-tal technical challenge is that wild-type endophytes of cereals and grasses stop fixing nitrogen in fertilized fields. The application of chemical fertilizers and residual nitrogen levels in field soils signal the microbe to shut down the biochemical pathway for nitrogen fixation. The genetically engineered bacteria and compositions provided herein can fix nitrogen under both nitrogen limiting and non-nitrogen limiting conditions as well as in the presence of oxygen (e.g., at least 0.5% oxygen). Accordingly, such genetically engineered bacteria and compositions can be applied to a plant and used to increase the amount of atmospheric derived nitrogen in plants (e.g., non-leguminous plants such as corn, wheat, and rice), even in fertilized fields.

Microbes in and around food crops can influence the traits of those crops. Plant traits that can be influenced by microbes include: yield (e.g., grain production, biomass generation, fruit development, flower set); nutrition (e.g., nitrogen, phosphorus, potassium, iron, micronutrient acqui-sition); abiotic stress management (e.g., drought tolerance, salt tolerance, heat tolerance); and biotic stress management (e.g., pest, weeds, insects, fungi, and bacteria). Strategies for altering crop traits include: increasing key metabolite con-centrations; changing temporal dynamics of microbe influ-ence on key metabolites; linking microbial metabolite pro-duction/degradation to new environmental cues; reducing negative metabolites; and improving the balance of metabo-lites or underlying proteins.

In some embodiments, provided herein are genetically engineered bacteria comprising at least one modification in a gene regulating nitrogen fixation or assimilation and the use thereof, for example, for increasing nitrogen uptake in a plant. The modification in a gene regulating nitrogen fixation or assimilation can be in any of the genes comprising the nitrogen fixation and assimilation genetic regulatory net-work. In some embodiments, the nitrogen fixation and assimilation genetic regulatory network includes polynucle-otides encoding genes and non-coding sequences that direct, modulate, and/or regulate microbial nitrogen fixation and/or assimilation and can comprise polynucleotide sequences of the nif cluster (e.g., nifA, nifB, nifC, . . . nifZ), polynucle-otides encoding nitrogen regulatory protein C, polynucle-otides encoding nitrogen regulatory protein B, polynucle-otide sequences of the gln cluster (e.g. glnA and glnD), draT, and ammonia transporters/permeases. In some cases, the Nif cluster may comprise NifB, NifH, NifD, NifK, NifE, NifN, NifX, hesa, and NifV. In some cases, the Nif cluster may comprise a subset of NifB, NifH, NifD, NifK, NifE, NifN, NifX, hesa, and NifV.

In some embodiments, a trait that can be targeted for regulation by the methods described herein is nitrogen fixation. In some embodiments, a trait that can be targeted for regulation by the methods described herein is nitrogen assimilation.

In some embodiments, a trait that can be targeted for regulation by the methods described herein is colonization potential.

In some embodiments, the at least one modification in the gene regulating nitrogen fixation or assimilation can result in one or more of: constitutive expression of the nifA gene in nitrogen limiting and non-nitrogen limiting condition, activ-ity of nifA in non-nitrogen limiting conditions, decreased uridylyl-transferase activity of GlnD, decreased adenylyl-removing activity of GlnE, and increased nitrogen excretion.

In some embodiments, genetically engineered bacteria as provided herein can comprise at least one modification in one or more genes regulating nitrogen fixation or assimila-tion selected from nifL, glnD, glnE, NtrC, and nifA.

In order to utilize elemental nitrogen (N) for chemical synthesis, life forms combine nitrogen gas ($N_2$) available in the atmosphere with hydrogen in a process known as nitro-gen fixation. Diazotrophs (i.e., bacteria and archaea that fix atmospheric nitrogen gas) have evolved sophisticated and tight regulation of the nif gene cluster in response to environmental oxygen and available nitrogen. Nif genes encode enzymes involved in nitrogen fixation, such as the nitrogenase complex, and proteins that regulate nitrogen fixation. See, e.g., Shamseldin (2013. Global J. Biotechnol.

Biochem. 8(4):84-94), which discloses detailed descriptions of nif genes and their products, and is incorporated herein by reference. Described herein are methods of producing a plant with an improved trait comprising isolating bacteria from a first plant, introducing a genetic modification into a nif gene of the isolated bacteria, exposing a second plant to the variant bacteria, isolating bacteria from the second plant having an improved trait relative to the first plant, and repeating the steps with bacteria isolated from the second plant.

Changes to the transcriptional and post-translational levels of components of the nitrogen fixation regulatory network can be beneficial to the development of a microbe capable of fixing and transferring nitrogen to corn in the presence of fertilizer. To that end, described herein is Host-Microbe Evolution (HoME) technology to precisely evolve regulatory networks and elicit novel phenotypes. Also described herein are unique, proprietary libraries of nitrogen-fixing endophytes isolated from corn, paired with extensive omics data surrounding the interaction of microbes and host plant under different environmental conditions like nitrogen stress and excess. In some embodiments, this technology enables precision evolution of the genetic regulatory network of endophytes to produce microbes that actively fix nitrogen even in the presence of fertilizer in the field. Also described herein are evaluations of the technical potential of evolving microbes that colonize corn root tissues and produce nitrogen for fertilized plants and evaluations of the compatibility of endophytes with standard formulation practices and diverse soils to determine feasibility of integrating the microbes into modern nitrogen management strategies.

In proteobacteria, regulation of nitrogen fixation centers on the σ54-dependent enhancer-binding protein NifA, the positive transcriptional regulator of the nif cluster. NifA upregulates the nif gene complex and drives nitrogen fixation when there is insufficient fixed nitrogen available to the microbe. NifL inhibits NifA when there is sufficient fixed N available to the microbe. Intracellular levels of active NifA are controlled by two key factors: transcription of the nifLA operon, and inhibition of NifA activity by protein-protein interaction with NifL. Both of these processes are responsive to intraceullar glutamine levels via the PII protein signaling cascade. This cascade is mediated by GlnD, which directly senses glutamine and catalyzes the uridylylation or deuridylylation of two PII regulatory proteins—GlnB and GlnK—in response the absence or presence, respectively, of bound glutamine. Under conditions of nitrogen excess, unmodified GlnB signals the deactivation of the nifLA promoter. However, under conditions of nitrogen limitation, GlnB is post-translationally modified, which inhibits its activity and leads to transcription of the nifLA operon. In this way, nifLA transcription is tightly controlled in response to environmental nitrogen via the PII protein signaling cascade. On the post-translational level of NifA regulation, GlnK inhibits the NifL/NifA interaction in a matter dependent on the overall level of free GlnK within the cell.

NifA is transcribed from the nifLA operon, whose promoter is activated by phosphorylated NtrC, another σ54-dependent regulator. The phosphorylation state of NtrC is mediated by the histidine kinase NtrB, which interacts with deuridylylated GlnB but not uridylylated GlnB. Under conditions of nitrogen excess, a high intracellular level of glutamine leads to deuridylylation of GlnB, which then interacts with NtrB to deactivate its phosphorylation activity and activate its phosphatase activity, resulting in dephosphorylation of NtrC and the deactivation of the nifLA promoter. However, under conditions of nitrogen limitation, a low level of intracellular glutamine results in uridylylation of GlnB, which inhibits its interaction with NtrB and allows the phosphorylation of NtrC and transcription of the nifLA operon. In this way, nifLA expression is tightly controlled in response to environmental nitrogen via the PII protein signaling cascade. nifA, ntrB, ntrC, and glnB, are all genes that can be mutated in the methods described herein. These processes can also be responsive to intracellular levels of ammonia, urea or nitrates.

The activity of NifA is also regulated post-translationally in response to environmental nitrogen, most typically through NifL-mediated inhibition of NifA activity. In general, the interaction of NifL and NifA is influenced by the PII protein signaling cascade via GlnK, although the nature of the interactions between GlnK and NifL/NifA varies significantly between diazotrophs. In *Klebsiella pneumoniae*, both forms of GlnK inhibit the NifL/NifA interaction, and the interaction between GlnK and NifL/NifA is determined by the overall level of free GlnK within the cell. Under nitrogen-excess conditions, deuridylylated GlnK interacts with the ammonium transporter AmtB, which serves to both block ammonium uptake by AmtB and sequester GlnK to the membrane, allowing inhibition of NifA by NifL. On the other hand, in *Azotobacter vinelandii*, interaction with deuridylylated GlnK is required for the NifL/NifAinteraction and NifA inhibition, while uridylylation of GlnK inhibits its interaction with NifL. In diazotrophs lacking the nifL gene, there is evidence that NifA activity is inhibited directly by interaction with the deuridylylated forms of both GlnK and GlnB under nitrogen-excess conditions. In some bacteria the Nif cluster can be regulated by glnR, which can comprise negative regulation. Regardless of the mechanism, post-translational inhibition of NifA is an important regulator of the nif cluster in most known diazotrophs. In some embodiments, one or more of nifL, amtB, glnK, and glnR can be mutated in the bacterial strains described herein.

Loss of NifL function can remove repression of NifA in nitrogen-limiting conditions. In some embodiments, at least one modification in a gene regulating nitrogen fixation or assimilation results in decreased expression of nifL. In some embodiments, at least one modification in a gene regulating nitrogen fixation or assimilation comprises a deletion of all or a portion of the coding sequence of the nifL gene. In some embodiments, at least one modification in a gene regulating nitrogen fixation or assimilation comprises a deletion of a portion of the coding sequence of the nifL gene. For example, a middle portion of the coding sequence of the nifL gene can be deleted. In some embodiments, the first 30 base pairs and the last 83 base pairs of the nifL coding sequence can be retained and the remaining base pairs can be deleted. In some embodiments, the deleted portion of the nifL coding sequence is replaced by a promoter, e.g., any of the promoters as described herein. For example, the promoter can be the infC gene promoter (PinfC, SEQ ID NO: 1), the cspE gene promoter (SEQ ID NO:2 and SEQ TD NO: 3), or the ompX gene promoter (Prm5; SEQ ID NOA4). For additional promoters see International Publication No. WO/2019/084059, which is incorporated herein by reference in its entirety. In some embodiments, the promoter has at least about 70%, about 75%, about 80%, about 85%, about 90%, about 95%, about 97%, about 98%, about 99%, or about 100% sequence identity to any one of SEQ ID Nos: 1-4.

| Description | SEQ ID NO | Sequence |
|---|---|---|
| PinfC | 1 | AGCGTCAGGTACCGGTCATGATTCACCGTGCGATTCTCGGTTCCCTGGAGC<br>GCTTCATTGGCATCCTGACCGAAGAGTTCGCTGGCTTCTTCCCAACCTGGAT<br>TGCACCAGTGCAGGTAGTGGTCATGAATATTACCGATTCTCAGGCTGAATA<br>CGTTAACGAATTGACGCGTAAACTACAAAATGCGGGCATTCGTGTAAAAGC<br>AGACTTGAGAAATGAGAAGATTGGCTTTAAAATCCGCGAGCACACTTTACG<br>TCGTGTCCCGTATATGTTGGTCTGTGGCGACAAAGAAGTCGAAGCCGGCAA<br>AGTGGCCGTGCGCACCCGTCGCGGGAAAGACCTCGGCAGCATGGACGTAA<br>GTGAAGTGATTGAGAAGCTGCAACAAGAGATTCGCAGCCGCAGTCTTCAAC<br>AACTGGAGGAATAAGGTATTAAAGGCGGAAAACGAGTTCAAACGGCACGT<br>CCGAATCGTATCAATGGCGAGATTCGCGCCCTGGAAGTTCGC |
| cspE promoter | 2 | GCCCGCTGACCGACCAGAACTTCCACCTTGGACTCGGCTATACCCTTGGCG<br>TGACGGCGCGCGATAACTGGGACTACATCCCCATTCCGGTGATCTTACCAT<br>TGGCGTCAATAGGTTACGGTCCGGCGACTTTCCAGATGACCTATATTCCCG<br>GCACCTACAATAACGGTAACGTTTACTTCGCCTGGGCTCGTATACAGTTTTA<br>ATTCGCTAAGTCTTAGCAATAAATGAGATAAGCGGTGTGTCTTGTGGAAAA<br>ACAAGGACTAAAGCGTTACCCACTAAAAAAGATAGCGACTTTTATCACTTT<br>TTAGCAAAGTTGCACTGGACAAAAGGTACCACAATTGGTGTACTGATACTC<br>GACACAGCATTAGTGTCGATTTTTCATATAAAGGTAATTTTG |
| cspE promoter | 3 | GCCCGCTGACCGACCAGAACTTCCACCTTGGACTCGGCTATACCCTTGGCG<br>TGACGGCGCGCGATAACTGGGACTACATCCCCATTCCGGTGATCTTACCAT<br>TGGCGTCAATAGGTTACGGTCCGGCGACTTTCCAGATGACCTATATTCCCG<br>GCACCTACAATAACGGTAACGTTTACTTCGCCTGGGCTCGTATACAGTTTTA<br>ATTCGCTAAGTCTTAGCAATAAATGAGATAAGCGGTGTGTCTTGTGGAAAA<br>ACAAGGACTAAAGCGTTACCCACTAAAAAAGATAGCGACTTTTATCACTTT<br>TTAGCAAAGTTGCACTGGACAAAAGGTACCACAATTGGTGTACTGATACTC<br>GACACAGCATTAGTGTCGATTTTTCATATAAAGGTAATTTTG |
| Prm5 | 4 | GGACATCATCGCGACAAACAATATTAATACCGGCAACCACACCGGCAATTT<br>ACGAGACTGCGCAGGCATCCTTTCTCCCGTCAATTTCTGTCAAATAAAGTA<br>AAAGAGGCAGTCTACTTGAATTACCCCCGGCTGGTTGAGCGTTTGTTGAAA<br>AAAAGTAACTGAAAAATCCGTAGAATAGCGCCACTCTGATGGTTAATTAAC<br>CTATTCAATTAAGAATTATCTGGATGAATGTGCCATTAAATGCGCAGCATA<br>ATGGTGCGTTGTGCGGGAAAACTGCTTTTTTTTGAAAGGGTTGGTCAGTAG<br>CGGAAAC |
| ΔnifL::Prm5 | 5 | ATGACCCTGAATATGATGATGGATGCCGGCGGACATCATCGCGACAAACAA<br>TATTAATACCGGCAACCACACCGGCAATTTACGAGACTGCGCAGGCATCCT<br>TTCTCCCGTCAATTTCTGTCAAATAAAGTAAAAGAGGCAGTCTACTTGAATT<br>ACCCCCGGCTGGTTGAGCGTTTGTTGAAAAAAAGTAACTGAAAAATCCGTA<br>GAATAGCGCCACTCTGATGGTTAATTAACCTATTCAATTAAGAATTATCTGG<br>ATGAATGTGCCATTAAATGCGCAGCATAATGGTGCGTTGTGCGGGAAAACT<br>GCTTTTTTTTGAAAGGGTTGGTCAGTAGCGGAAACAACTCACTTCACACCCC<br>GAAGGGGGAAGTTGCCTGACCCTACGATTCCCGCTATTTCATTCACTGACC<br>GGAGGTTCAAAATGACCCAGCGAACCGAGTCGGGTAATACCGTCTGGCGCT<br>TCGATTTGTCCCAGCAGTTCACTGCGATGCAGCGCATAAGCGTGGTACTCA<br>GCCGGGCGACCGAGGTCGATCAGACGCTCCAGCAAGTGCTGTGCGTATTGC<br>ACAATGACGCCTTTTTGCAGCACGGCATGATCTGTCTGTACGACAGCCAGC<br>AGGCGATTTTGAATATTGAAGCGTTGCAGGAAGCCGATCAGCAGTTAATCC<br>CCGGCAGCTCGCAAATCCGCTATCGTCCGGGCGAAGGGCTGGTCGGGACGG<br>TGCTTTCGCAGGGCCAATCATTAGTGCTGGCGCGCGTTGCTGACGATCAGC<br>GCTTTCTTGACCGGCTCGGGTTGTATGATTACAACCTGCCGTTTATCGCCGT<br>GCCGCTGATAGGGCCAGATGCGCAGACTTTCGGTGTGCTGACGGCACAACC<br>CATGGCGCGTTACGAAGAGCGATTACCCGCCTGCACCCGCTTTCTGGAAAC<br>GGTCGCTAACCTGGTCGCGCAAACCGTGCGTTTGATGGCACCACCGGCAGT<br>GCGCCCTTCCCCGCGCGCCGCCATAACACAGGCCGCCAGCCCGAAATCCTG<br>CACGGCCTCACGCGCATTTGGTTTTGAAAATATGGTCGGTAACAGTCCGGC<br>GATGCGCCAGACCATGGAGATTATCCGTCAGGTTTCGCGCTGGGACACCAC<br>CGTTCTGGTACGCGGCGAGAGTGGCACCGGCAAGGAGCTGATTGCCAACGC<br>CATCCACCACCATTCGCCGCGTGCCGGTGCGCCATTTGTGAAATTCAACTGT<br>GCGGCGCTGCCGGACACACTGCTGGAAAGCGAATTGTTCGGTCACGAGAA<br>AGGGGCATTTACCGGCGCGGTACGCCAGCGTAAAGGCCGTTTTGAGCTGGC<br>CGATGGCGGCACGCTGTTTCTTGACGAGATCGGCGAGAGTAGCGCCTCGTT<br>TCAGGCTAAGCTGCTGCGCATTTTGCAGGAAGGCGAAATGGAACGCGTCGG<br>CGGCGACGAGACATTGCAAGTGAATGTGCGCATTATTGCCGCGACGAACCG<br>CAATCTTGAAGATGAAGTCCGGCTGGGGCACTTTCGCGAAGATCTCTATTA<br>TCGCCTGAATGTGATGCCCATCGCCCTGCCGCCACTACGCGAACGCCAGGA<br>GGACATTGCCGAGCTGGCGCACTTTCTGGTGCGTAAAATCGCCCATAACCA<br>GAGCCGTACGCTGCGCATTAGCGAGGGCGCTATCCGCCTGCTGATGAGCTA<br>CAACCTGGCCCGGTAATGTGCGCGAACTGGAAAACTGCCTTGAGCGCTCAGC<br>GGTGATGTCGGAGAACGGTCTGATCGATCGGGATGTGATTTTGTTTAATCA<br>TCGCGACCAGCCAGCCAAACCGCCAGTTATCAGCGTCTCGCATGATGATAA<br>CTGGCTCGATAACAACCTTGACGAGCGCCAGCGGCTGATTGCGGCGCTGGA |

-continued

| Description | SEQ ID NO | Sequence |
|---|---|---|
| | | AAAAGCGGGATGGGTACAAGCCAAAGCCGCGCGCTTGCTGGGGATGACGC CGCGCCAGGTCGCCTATCGTATTCAGACGATGGATATAACCCTGCCAAGGC TATAA |

An additional target for genetic modification to facilitate field-based nitrogen fixation using the methods described herein is the NifA protein. The NifA protein is an activator for expression of nitrogen fixation genes. Increasing the expression of NifA (either constitutively or during high ammonia condition) circumvents the native ammonia-sensing pathway. Reducing the production of NifL proteins, a known inhibitor of NifA, can also lead to an increased level of freely active NifA. Increasing the transcription level of the nifAL operon (either constitutively or during high ammonia condition) can also lead to an overall higher level of NifA proteins. An elevated level of nifAL expression can be achieved by altering the promoter itself or by reducing the expression of NtrB (part of ntrB and ntrC signaling cascade that originally would result in the shutoff of nifAL operon during high nitrogen condition). A high level of NifA achieved by these or any other methods described herein increases the nitrogen fixation activity of the endophytes.

In some embodiments, the coding sequence of the nifA gene can be inserted into a non-coding site of the genome of a genetically engineered bacterium described herein. In some embodiments, inserting the coding sequence of the nifA gene into a non-coding site of the genome of a genetically engineered bacterium results in expression of the nifA gene in nitrogen limiting and non-nitrogen limiting conditions. In some embodiments, the expression is constitutive. In some embodiments, the nifA gene is inserted into a non-coding region of the genome between two hypothetical genes that are transcribed in convergent fashion (see, e.g., FIG. 16). In some embodiments, the coding sequence of the nifA gene and a promoter (e.g., any of the promoters described herein) are inserted into a non-coding site of the genome of a genetically engineered bacterium. For example, the promoter can be the cspE gene promoter (e.g., PcspE, also known as Prm1.2; SEQ ID NO: 2 and SEQ ID NO:3). In some embodiments, the promoter has at least about 70%, about 75%, about 80%, about 85%, about 90%, about 95%, about 97%, about 98%, about 99%, or about 100% sequence identity to any one of SEQ ID Nos: 2-3.

In addition to regulating the transcription of the nif gene cluster, many diazotrophs have evolved a mechanism for the direct post-translational modification and inhibition of the nitrogenase enzyme itself, known as nitrogenase shutoff. This is mediated by ADP-ribosylation of the Fe protein (NifH) under nitrogen-excess conditions, which disrupts its interaction with the MoFe protein complex (NifDK) and abolishes nitrogenase activity. DraT catalyzes the ADP-ribosylation of the Fe protein and shutoff of nitrogenase, while DraG catalyzes the removal of ADP-ribose and reactivation of nitrogenase. As with nifLA transcription and NifA inhibition, nitrogenase shutoff is also regulated via the PII protein signaling cascade. Under nitrogen-excess conditions, deuridylylated GlnB interacts with and activates DraT, while deuridylylated GlnK interacts with both DraG and AmtB to form a complex, sequestering DraG to the membrane. Under nitrogen-limiting conditions, the uridylylated forms of GlnB and GlnK do not interact with DraT and DraG, respectively, leading to the inactivation of DraT and the diffusion of DraG to the Fe protein, where it removes the ADP-ribose and activates nitrogenase. The methods described herein also contemplate introducing genetic modification into the nifH, nifD, nifK, and draT genes.

Another target for genetic modification to facilitate field-based nitrogen fixation using the methods described herein is the GlnD/GlnB/GlnK PII signaling cascade. The intracellular glutamine level is sensed through the GlnD/GlnB/GlnK PII signaling cascade. Active site mutations in GlnD that abolish the uridylyl-transferase activity of GlnD disrupt the nitrogen-sensing cascade. In addition, reduction of the GlnB concentration short circuits the glutamine-sensing cascade. These mutations "trick" the cells into perceiving a nitrogen-limited state, thereby increasing the nitrogen fixation level activity. These processes can also be responsive to intracellular or extracellular levels of ammonia, urea, or nitrates.

The amtB protein can also be a target for genetic modification to facilitate field-based nitrogen fixation using the methods described herein. Ammonia uptake from the environment can be reduced by decreasing the expression level of amtB protein. Without intracellular ammonia, the endophyte is not able to sense the high level of ammonia, preventing the down-regulation of nitrogen fixation genes. Any ammonia that manages to get into the intracellular compartment is converted into glutamine. Intracellular glutamine level is the major currency of nitrogen sensing. Decreasing the intracellular glutamine level can prevent the cells from sensing high ammonium levels in the environment. This effect can be achieved by increasing the expression level of glutaminase, an enzyme that converts glutamine into glutamate. In addition, intracellular glutamine can also be reduced by decreasing glutamine synthase (an enzyme that converts ammonia into glutamine). In diazotrophs, fixed ammonia is quickly assimilated into glutamine and glutamate to be used for cellular processes. Disruptions to ammonia assimilation can enable diversion of fixed nitrogen to be exported from the cell as ammonia. The fixed ammonia is predominantly assimilated into glutamine by glutamine synthetase (GS), encoded by glnA, and subsequently into glutamine by glutamine oxoglutarate aminotransferase (GOGAT). In some examples, glnS encodes a glutamine synthetase. GS is regulated post-translationally by GS adenylyl transferase (GlnE), a bi-functional enzyme encoded by glnE that catalyzes both the adenylylation and de-adenylylation of GS through activity of its adenylyl-transferase (AT) and adenylyl-removing (AR) domains, respectively. Under nitrogen limiting conditions, glnA is expressed, and GlnE's AR domain de-adenylylates GS, allowing it to be active. Under conditions of nitrogen excess, glnA expression is turned off, and GlnE's AT domain is activated allosterically by glutamine, causing the adenylylation and deactivation of GS.

In some embodiments, modification of glnE can increase ammonium excretion. In some embodiments, a conserved aspartate-amino acid-aspartate (DXD) motif on AR domain of glnE can be changed. In some embodiments, changing a conserved DXD residue on AR domain of glnE can be used to remove de-adenylylation activity from glnE. In some embodiments, a D residue can be replaced on a DXD motif in the AR region of glnE. In some embodiments, the replacement of a D residue on a DXD motif in the AR region of glnE can leave the GlnB binding site intact so as to allow for regulation of adenylation activity while decreasing or preventing AR activity. In some embodiments, strains that can be utilized in this process of increasing ammonium excretion can include, but are not limited to, *Rahnella aquatilis, Kosakonia sacchari*, and *Klebsiella variicola* strains.

In some embodiments, at least one modification in a gene regulating nitrogen fixation or assimilation results in decreased adenylyl-removing activity of GlnE. In some embodiments, a modification in a gene regulating nitrogen fixation or assimilation comprises a deletion of a portion of the coding sequence of the glnE gene. For example, in some embodiments, 1290 base pairs following the ATG start codon of the glnE gene are deleted. In some embodiments, a deletion of a portion of the coding sequence of the glnE gene results in decreased adenylyl-removing activity of GlnE. In some embodiments, a modification in a gene regulating nitrogen fixation or assimilation results in a truncated GlnE protein lacking an adenylyl-removing (AR) domain. In some embodiments, the GlnE protein lacking the AR domain has a functional ATase domain Furthermore, the draT gene can also be a target for genetic modification to facilitate field-based nitrogen fixation using the methods described herein. Once nitrogen fixing enzymes are produced by the cell, nitrogenase shut-off represents another level in which cell downregulates fixation activity in high nitrogen condition. This shut-off can be removed by decreasing the expression level of DraT.

Methods for imparting new microbial phenotypes can be performed at the transcriptional, translational, and post-translational levels. The transcriptional level includes changes at the promoter (such as changing sigma factor affinity or binding sites for transcription factors, including deletion of all or a portion of the promoter) or changing transcription terminators and attenuators. The translational level includes changes at the ribosome binding sites and changing mRNA degradation signals. The post-translational level includes mutating an enzyme's active site and changing protein-protein interactions. These changes can be achieved in a multitude of ways. Reduction of expression level (or complete abolishment) can be achieved by swapping the native ribosome binding site (RBS) or promoter with another with lower strength/efficiency. ATG start sites can be swapped to a GTG, TTG, or CTG start codon, which results in reduction in translational activity of the coding region. Complete abolishment of expression can be done by knocking out (deleting) the coding region of a gene. Frame-shifting the open reading frame (ORF) can result in a premature stop codon along the ORF, thereby creating a non-functional truncated product. Insertion of in-frame stop codons can also similarly create a non-functional truncated product. Addition of a degradation tag at the N or C terminal can also be done to reduce the effective concentration of a particular gene.

Conversely, expression level of the genes described herein can be achieved by using a stronger promoter. To ensure high promoter activity during high nitrogen level condition (or any other condition), a transcription profile of the whole genome in a high nitrogen level condition could be obtained and active promoters with a desired transcription level can be chosen from that dataset to replace the weak promoter. Weak start codons can be swapped out with an ATG start codon for better translation initiation efficiency. Weak ribosomal binding sites (RBS) can also be swapped out with a different RBS with higher translation initiation efficiency. In addition, site specific mutagenesis can also be performed to alter the activity of an enzyme.

Increasing the level of nitrogen fixation that occurs in a plant can lead to a reduction in the amount of chemical fertilizer needed for crop production and reduce greenhouse gas emissions (e.g., nitrous oxide).

Nitrogenases are enzymes responsible for catalyzing nitrogen fixation. There are three types of nitrogenase found in various nitrogen-fixing bacteria: molybdenum (Mo) nitro-genase, vanadium (V) nitrogenase, and iron-only (Fe) nitro-genase. Nitrogenases are two-component systems made up of Component I (also known as dinitrogenase) and Compo-nent II (also known as dinitrogenase reductase). Component I is a MoFe protein in molybdenum nitrogenase, a VFe protein in vanadium nitrogenase, and a Fe protein in iron-only nitrogenase. Component II is a Fe protein that contains an iron-sulfur (Fe—S) cluster.

In some embodiments, varying the supply of cofactors can result in an increase of nitrogen fixation. For example, increasing sulfur uptake can provide a larger pool of cofac-tors for nitrogenase enzymes, thus increasing the number of functional nitrogenase complexes. In some embodiments, sulfur uptake can be increased by upregulating sulfate transport genes. Some examples of sulfate transport genes can include, but are not limited to, cysPTWA, sbp, sbp, cysZK.

In some embodiments, varying the supply of cofactors can result in an increase in nitrogen fixation. For example, increasing molybdenum (Mo) uptake can increase the num-ber of functional nitrogenase complexes. In some embodi-ments, Mo uptake can be increased by upregulating Mo transport genes. Examples of Mo transport genes can include, but are not limited to, modEBA, modEB and modA.

In some embodiments, cofactor supply can be affected by iron uptake. Iron uptake can be influenced by the tonB transport system. In some embodiments, influencing iron uptake can be achieved by upregulating tonB transport system genes. Some examples of tonB transport system genes can include, but are not limited to, tonB, and exbAB. In some embodiments, iron uptake can be influenced by siderophores which increase iron uptake in microbes and plants. In some embodiments, influencing iron uptake can be achieved by upregulating siderophore biosynthesis genes. Some examples of siderophore biosynthesis genes can include, but are not limited to, yhfA, yusV, sbnA, fiu, yfiZ, and fur.

Varying the metabolic flux to ATP can result in an increase of nitrogen fixation. For example, the metabolic flux to ATP can be increased by targeting glycogen biosynthesis. Gly-cogen biosynthesis can be influenced by shunting carbon to glycolysis, the TCA cycle and/or oxidative phosphorylation rather than glycogen synthesis. In some embodiments, gly-cogen biosynthesis can be influenced by deleting or down-regulating the relevant gene for glycogen synthase. An example of a glycogen synthase gene can be, but is not limited to, glgA.

Varying the number of nitrogenase enzymes per cell can result in an increase in nitrogen fixation. For example, the number of nitrogenase enzymes per cell can be affected by nif derepression. Nif derepression can be achieved by con-stitutively signaling nitrogen starvation. In some embodi-ments, nif derepression can be achieved by deleting the UR-domain of relevant genes. An example of a gene which can be targeted to derepress nif genes can be, but is not limited to, glnD. In some embodiments, the transcription of the nif cluster(s) can be increased by inserting strong promoters upstream of a nifHDK or nifDK operon.

Another way to increase nitrogen fixation can be to increase the number of nitrogenase enzymes per cell by increasing nif cluster transcription. Nif cluster transcription can be increased by increasing nifA transcription. In some embodiments, nif cluster transcription can be influenced by increasing the copy number of a nifA gene in the genome.

Nif cluster transcription can also be increased by increasing NifA translation. In some embodiments, NifA translation can be increased by increasing the strength of the ribosome binding site in the nifA gene.

Altering the oxygen sensitivity of nitrogenase can result in an increase of nitrogen fixation. Oxygen sensitivity can be influenced by reducing oxygen sensing. In some embodiments, reducing oxygen sensing can be by disrupting oxygen-sensing genes. Some examples of oxygen-sensing genes can include, but are not limited to, nifT/fixU, fixJ and fixL.

In some embodiments, oxygen sensitivity can be influenced by keeping cytosolic oxygen levels low by promoting cytochrome bd-mediated respiration. In some embodiments, oxygen sensitivity can be influenced by upregulating genes encoding cytochrome bd oxidase and/or knocking out alternative cytochrome systems. Some examples of genes encoding cytochrome bd genes can include, but are not limited to, cydABX, cydAB, and cydX. In some embodiments, nitrogenase can be protected from oxidation by altering redox balance in the cell. Redox balance can be altered through ROS scavenging. One strategy for accomplishing ROS scavenging would be to upregulate relevant genes. Some examples of ROS scavenging genes can be, but are not limited, to grxABCD, trxA, trxC, and tpx.

In some embodiments, oxygen sensitivity can be influenced by scavenging free oxygen. In some embodiments, scavenging free oxygen can be achieved by upregulating bacterial hemoglobin genes.

An example of a hemoglobin gene can be, but is not limited to, glbN. In some embodiments, scavenging free oxygen can be achieved by upregulating fixNOPQ genes which code for a high-affinity heme-copper cbb3-type oxidase.

Modifying IHFa can result in an increase of nitrogenase expression. In some embodiments, nitrogenase expression can be increased by facilitating interaction between nifA and 654 at the upstream activation sequence upstream of certain genes. In particular, upregulation of IHIF can increase nitrogenase transcription. In some embodiments, upregulation of IHIF in combination with nifA and σ54 can increase transcription of nitrogenase operon. In some embodiments, strains that can be utilized in this process of increasing nitrogen expression can include, but is not limited to, *Rahnella aquatilis, Kosakonia sacchari*, and/or *Klebsiella variicola* strains. In some embodiments, the upregulation of a nitrogenase operon can be more effective when stacked with mutation in a gene encoding σ54.

Modifying a gene encoding σ54 can result in an increase of nitrogenase expression. In some embodiments, upregulation of a gene for σ54 can increase nitrogenase transcription. An example of a gene encoding σ54 includes, but is not limited to, rpoN. In some embodiments, strains that can be utilized in this process of increasing nitrogen expression can include, but are not limited to, *Rahnella aquatilis, Kosakonia sacchari*, and/or *Klebsiella variicola* strains. In some embodiments, upregulation of σ54 in combination with nifA and IHF can increase transcription of a nitrogenase operon. In some embodiments, the transcription of the nitrogenase operon can be further improved by stacking the upregulation of σ54 with an IHF mutation.

In some embodiments, deleting a protein such as DraT in a strain, such as a *kosakonia* strain, can increase nitrogenase activity. In some embodiments, DraT can post-translationally modify a nitrogenase enzyme to inhibit its activity. In some embodiments, strains that can be utilized in this process of increasing nitrogenase activity can include, but are not limited to, *Kosakonia* strains.

In some embodiments, modification of an asnB gene can increase ammonium excretion. In particular, truncation and upregulation of an asnB gene can convert glutamine back to ammonium. The AsnB enzymes contain two domains; one can deaminate glutamine to release ammonium, and the other uses the ammonium to generate asparagine. Truncating AsnB to delete the asparagine synthase domain and/or upregulating the glutamine deaminase domain can help to convert back cellular glutamine to ammonium, thereby increasing ammonium excretion. In some embodiments, strains that can be utilized in this process of increasing ammoniumexcretion can include, but are not limited to, *Rahnella aquatilis, Kosakonia sacchari*, and *Klebsiella variicola* strains.

In some embodiments, modification of an asnB gene can increase ammonium excretion. In particular, deletion of an asnB gene can reduce ammonium sinks in a cell. asnB is able to use cytosolic ammonium instead of glutamine as an N donor. In some embodiments, deleting, truncating, or upregulating asnB can increase the amount of ammonium excreted from a cell. In some embodiments, strains that can be utilized in this process of increasing ammonium excretion can include, but are not limited to, *Rahnella aquatilis, Kosakonia sacchari*, and *Klebsiella variicola* strains.

The GlnD protein has four domains: an N-terminal uridyltransferase (UTase) domain; a central uridyl-removal (UR) domain, and two C-terminal ACT domains. The UTase activity is localized to the N-terminal NT domain. This domain has a distinct amino acid residue pattern with conserved glycine (G) and aspartate (D) residues that are important for nucleotidyltransferase activity and binding of metal ions respectively. Most substitutions for conserved glycine and aspartate residues in this domain abolish glnD's UTase activity, preventing this enzyme from activating PII dependent nitrogen fixation and assimilation pathways. In some embodiments, modification of glnD can be beneficial in modifying regulation of nitrogen assimilation. In some embodiments, modifications of glnD can be used to optimize regulation of nitrogen assimilation pathways through the PII protein signaling pathway. The glnD gene encodes a bifunctional enzyme that can uridylate and deuridylate downstream signaling proteins based on cell's nitrogen status. For example, the enzyme encoded by glnD modifies the PII proteins GlnK and GlnB. The GlnD enzyme reversibly uridylylates and de-uridylylates the PII proteins in conditions of nitrogen limitation and excess, respectively. The PII proteins confer signaling cascades to nitrogen metabolic pathways. Examples of nitrogen metabolism genes influenced by PII protein signaling include but are not limited to, glnA encoding glutamine synthetase, ntrB/glnL encoding sensory histidine kinase/phosphatase ntrB, glnG/ntrC DNA-binding transcriptional regulator ntrC and the nifLA operon. In some embodiments, glnD can be deleted so as to decrease the transcription of nitrogen assimilation genes and the amount of nitrogen assimilated within a cell. In some embodiments, glnD can be modified by deleting the ACT12 region, deleting the UR region and/or by deactivating the UR region by mutating specific amino acid residues (for example residues 90, 91 and/or 104). In some embodiments, strains that can be utilized in this process of decreasing nitrogen assimilation can include, but are not limited to, *Rahnella aquatilis, Kosakonia sacchari,* and *Klebsiella variicola* strains.

In some embodiments, modification of glnD can be beneficial in increasing nitrogenase activity, ammonium excretion and/or plant growth. In particular, removal of a nitrogen sensing region can increase nitrogenase activity and/or plant growth. In some embodiments, an ACT domain of glnD can be deleted. In some embodiments, ACT domain is involved in sensing nitrogen status via allosteric regulation by glutamine. Removing an ACT domain can decrease uridylyl-transferase activity, thereby signaling nitrogen excess and downregulating nitrogen assimilation genes, leading to an increase in ammonium excretion. In some embodiments, strains that can be utilized in this process of increasing nitrogenase activity, ammonium excretion and/or plant growth can include, but are not limited to, *Kosakonia sacchari* and *Klebsiella variicola* strains.

In some embodiments, modification of glnD can be beneficial in increasing nitrogenase activity, ammonium excretion and/or plant growth. In particular, removal or deactivation of an uridylyl-transferase (UT) region within a domain of glnD can increase nitrogenase activity, ammonium excretion and/or plant growth. Removing or deactivating a UT domain can decrease uridylyl-transferase activity, thereby signaling nitrogen excess and downregulating nitrogen assimilation genes, leading to an increase in ammonium excretion. In some embodiments, strains that can be utilized in this process of increasing nitrogenase activity, ammonium excretion and/or plant growth can include, but are not limited to, *Rahnella aquatilis, Kosakonia sacchari,* and *Klebsiella variicola* strains.

In some embodiments, at least one modification in a gene regulating nitrogen fixation or assimilation comprises a deletion of all or a portion of the coding sequence of the glnD gene. In some embodiments, the at least one modification in a gene regulating nitrogen fixation or assimilation comprises a deletion of the N-terminal glnD-UTase domain. For example, the NT glnD-UTase domain can be deleted by removing 975 nucleotides after the start codon. In some embodiments, at least one modification in a gene regulating nitrogen fixation or assimilation comprises a deletion of all of the coding sequence of the glnD gene. For example, all 2,676 nucleotides of the glnD gene can be deleted from the genome of the genetically engineered bacteria. In some embodiments, the at least one modification in a gene regulating nitrogen fixation or assimilation comprises at least one point mutation in the coding sequence of the glnD gene. In some embodiments, the coding sequence of the glnD gene comprising at least one point mutation encodes a GlnD protein with amino acid substitutions comprising G90L, G91D, and D104A. In some embodiments, seven point mutations are incorporated into the glnD gene sequence (SEQ ID NO:6) to encode the following amino-acid changes: G90L, G91D, D104A in the UTase domain.

TABLE 1

| GlnD Sequences | | |
| --- | --- | --- |
| Description | SEQ ID NO | Sequence |
| Mutated glnD gene including promoter and terminator sequences | 6 | tgaaaagccggcgcccgccggctttttttattagatagttttttcttatggtgacgcgATGAGCAACTCATTACCTGA CACAGCCTCCCCTCTTCTGCCCGTCCCGCCGGAACATCCGGTGAGCTGGCCGCA GGGCGATCTGAACTGTGCTGCAATTAAGGCGCACATCGATACCTTCCAGCACTG GCTGGGCGAGGCGTTTGACTCCGGCATCGCCGCGGAGCAGCTCATTGCGGCGCG CACCGAATTTATCGACCAGCTGCTGCAGCGGTTGTGGATCGCCTACGGTTTTGA ATCCGTCTGCGATCTGGCGCTGGTGGCCGTCCTTGATTATGGCCGCGGCGAGCT GCACCCGCTCTCTGACGTCGCACTGCTGATCCTCAGCCGCAAAAAACTGCCTGA CGACCAGGCGCAAAAGGTCGGCGAACTGCTGACGCTACTGTGGGACGTCAAGC TGGAGGTGGGCCACAGCGTGCGCACCCTCGAAGAGTGTCTGCTCGAAGGACTTT CGGATCTCACCGTCGCCACTAACTTGATTGAATCGCGCCTGCTGATCGGCGACG TCGCGCTGTTCCTTGAACTGCAAAAACATATTTTTAGCGACGGCTTCTGGCCATC GGAAAAGTTCTTCGCCGCCAAGGTGGAAGAGCAGAACGTCCGTCATCAACGCT ATCACGGCACCAGCTATAACCTGGAGCCGGACGTGAAAAGCAGCCCCGGCGGC CTGCGGGATATCCATACGCTACAGTGGGTGGCTCGCCGTCATTTTGGCGCCACC TCGATGGATGAGATGGTCGGCTTCGGCTTTCTGACCGAAGCCGAGCGCAATGAG CTCAACGAGTGTCTGCATCAGCTGTGGCGCATCCGTTTCGCGCTGCATCTCGAG CTCACTCGCTATGACAACCGTCTGCTTTTCGACCGCCAGCTCAGCGTCGCCCGCC GGCTCGGCTATGAAGGCGACGGCAACCAGCCGATTGAGCATATGATGAAGGAC TTCTTCCGCGTCACCCGCCGGGTGAGCGAGCTGAACCAGATGCTGCTTCAGCTG TTTGAAGAGGCTATTCTCGCCCTGACCGAGGATGAAAAACCGCGCCCGATAGAC GATGACTTCCAGCTGCGCGGCACCCTTATCGATCTGCGTGACGACACGCTGTTT ATTCGCGAACCGCCAGGCCATTCTGCGCATGTTTTATATGATGGTGCGCAACAGC ACTATCACCGGCATCTACTCCACGACGTTGCGCCATCTGCGCCATGCCCGGCGC CATCTGACCCAGCCGCTGTGCTATATCCCGGAGGCGCGCACGCTCTTTCTCAGC ATGCTGCGCCATCAGGGGGCGGTCAGCCGCGGACTGCTGCCGATGCATCGCCAT AGCGTGCTGTGGGCCTATATGCCGCAGTGGTCACATATCGTCGGCCAGATGCAG TTCGATCTGTTTCACGCCTACACCGTCGATGAACACACCATCCGCGTGATGCTG AAGCTGGAGAGCTTTGCCAAAGAAGAAACCCGCAGCCGCCACCCGCTGTGCGT GGAGCTATGGCCGCGCTTAACGCACCCGGAGCTGATTTTAATCGCCGCCCTGTT CCACGACATTGCGAAAGGGCGTGGCGGCGACCACTCGATCCTCGGCGCGCAGG ATGTGCTGAAGTTTGCCGAGCTGCACGGACTGAACTCTCGCGAAACGCAGTTGG TCGCCTGGCTGGTGCGTCACCATCTGCTGATGTCGGTCACCGCCCAGCGGCGCG ACATTCAGGATCCGGAGGTGATTAAGCAGTTCGCCGAGGAAGTGCAAACGGAA AATCGCCTGCGCTATCTGGTGTGCCTGACCGTCGCCGACATCTGCGCCACCAAC GAAACGCTGTGGAACAGCTGGAAGCAGAGTCTGCTGCGCGAACTCTATTTCGCC ACCGAGAAACAGCTGCGTCGGGGCATGCAAAGCACCCCGGATATGCGCGAACG |

TABLE 1-continued

| | | |
|---|---|---|
| | | GlnD Sequences |

| Description | SEQ ID NO | Sequence |
|---|---|---|
| | | GGTGCGTCATCATCAGCTGCAGGCGCTGGCCCTGCTGCGGATGGACAATATTAA<br>TGAAGAGGCGCTGCATCAGATCTGGAACCGCTGCCGCGCCAACTATTTCGTGCG<br>GCATACGCCGACGCAGCTCGCCTGGCAGCCCGCCAACCTGCTGCGTCACGATCT<br>GAATAAGCCGATGATTCGCTGAGTTCGCAGGCCACCCGCGGCGGTACGGAGA<br>TTTTTATCTGGAGCCCGGATCGCCCTTATCTGTTTGCCCGCGGTGTGCGGCGAACT<br>GGACCGCCGCAACCTCAGCGTCCACGACGCGCAGATCTTCACCACCCGCGACG<br>GCATGGCGATGGATACCTTTATTGTCCTCGAACCCGACGGCAGCCCGCTTTCCG<br>CTGACCGCCACGACGCGATTCGCCACGGTCTTGAACAGACGATAACTCAGCGCA<br>GCTGGGAACCCCCGGCCCCGCGTCGTCAGGCGGCAAAACTGCGTCACTTCTCTG<br>TGCCGACAGAGGTGAATTTCCTGCCGACCCATACCGATCGAAAATCGTTTCTCG<br>AGCTGATTGCGCTCGATCAGCCAGGGCTGCTCGCCCGCGTCGGCCAGGTGTTCG<br>CCGACCTCGGTATTTCGCTTCACGGGGCGCGAATTACGACAATTGGTGAGCGAG<br>TAGAAGATTTATTTATAATCGCCACCGCCGACCGGCGTGGCCTTAATAATGAGC<br>TACAACAAGAAGTGCAACAACGGTTGACAGAGGCCCTCAATCCAAACGATAAA<br>GGGTGAcgtattttttttttagtgaatggaaagaaaca |
| Truncated glnD gene including promoter and terminator sequences | 9 | tgaaaagccggcgcccgccggctttttttattagatagtttttttcttatggtgacgcgATGCTGCTTCAGCTGTTTGAA<br>GAGGCTATTCTCGCCCTGACCGAGGATGAAAAACCGCGCCCGATAGACGATGA<br>CTTCCAGCTGCGCGGCACCCTTATCGATCTGCGTGACGACACGCTGTTTATTCGC<br>GAACCGCAGGCCATTCTGCGCATGTTTTATATGATGGTGCGCAACAGCACTATC<br>ACCGGCATCTACTCCACGACGTTGCGCCATCTGCGCCATGCCCGGCGCCATCTG<br>ACCCAGCCGCTGTGCTATATCCCGGAGGCGCGCACGCTCTTTCTCAGCATGCTG<br>CGCCATCAGGGGGCGGTCAGCCGCGGACTGCTGCCGATGCATCGCCATAGCGT<br>GCTGTGGGCCTATATGCCGCAGTGGTCACATATCGTCGGCCAGATGCAGTTCGA<br>TCTGTTTCACGCCTACACCGTCGATGAACACACCATCCGCGTGATGCTGAAGCT<br>GGAGAGCTTTGCCAAAGAAGAAACCCGCAGCCGCCACCCGCTGTGCGTGGAGC<br>TATGGCCGCGCTTAACGCACCCGGAGCTGATTTTAATCGCCGCCCTGTTCCACG<br>ACATTGCGAAAGGGCGTGGCGGCGACCACTCGATCCTCGGCGCGCAGGATGTG<br>CTGAAGTTTGCCGAGCTGCACGGACTGAACTCTCGCGAAACGCAGTTGGTCGCC<br>TGGCTGGTGCGTCACCATCTGCTGATGTCGGTCACCGCCCAGCGGCGCGACATT<br>CAGGATCCGGAGGTGATTAAGCAGTTCGCCGAGGAAGTGCAAACGGAAAATCG<br>CCTGCGCTATCTGGTGTGCCTGACCGTCGCCGACATCTGCGCCACCAACGAAAC<br>GCTGTGGAACAGCTGGAAGCAGAGTCTGCTGCGCGAACTCTATTTCGCCACCGA<br>GAAACAGCTGCGTCGGGGCATGCAAAGCACCCCGGATATGCGCGAACGGGTGC<br>GTCATCATCAGCTGCAGGCGCTGGCCCTGCTGCGGATGGACAATATTAATGAAG<br>AGGCGCTGCATCAGATCTGGAACCGCTGCCGCGCCAACTATTTCGTGCGCATA<br>CGCCGACGCAGCTCGCCTGGCACGCCCGCAACCTGCTGCGTCACGATCTGAATA<br>AGCCGATGATTCTGCTGAGTTCGCAGGCCACCCGCGGCGGTACGGAGATTTTTA<br>TCTGGAGCCCGGATCGCCCTTATCTGTTTGCCCGCGGTGTGCGGCGAACTGGACC<br>GCCGCAACCTCAGCGTCCACGACGCGCAGATCTTCACCACCCGCGACGGCATGG<br>CGATGGATACCTTTATTGTCCTCGAACCCGACGGCAGCCCGCTTTCCGCTGACC<br>GCCACGACGCGATTCGCCACGGTCTTGAACAGACGATAACTCAGCGCAGCTGG<br>GAACCCCCGGCCCCGCGTCGTCAGGCGGCAAAACTGCGTCACTTCTCTGTGCCG<br>ACAGAGGTGAATTTCCTGCCGACCCATACCGATCGAAAATCGTTTCTCGAGCTG<br>ATTGCGCTCGATCAGCCAGGGCTGCTCGCCCGCGTCGGCCAGGTGTTCGCCGAC<br>CTCGGTATTTCGCTTCACGGGGCGCGAATTACGACAATTGGTGAGCGAGTAGAA<br>GATTTATTTATAATCGCCACCGCCGACCGGCGTGGCCTTAATAATGAGCTACAA<br>CAAGAAGTGCAACAACGGTTGACAGAGGCCCTCAATCCAAACGATAAAGGGTG<br>Acgtattttttttttagtgaatggaaagaaaca |
| glnD-ACT1, 2 truncation including promoter and terminator sequences | 10 | tgaaaagccggcgcccgccggctttttttattagatagtttttttcttatggtgacgcgATGAGCAACTCATTACCTGA<br>CACAGCCTCCCCTCTTCTGCCCGTCCCGCCGGAACATCCGGTGAGCTGGCCGCA<br>GGGCGATCTGAACTGTGCTGCAATTAAGGCGCACATCGATACCTTCCAGCACTG<br>GCTGGGCGAGGCGTTTGACTCCGGCATCGCCGCGGAGCAGCTCATTGCGGCGCG<br>CACCGAATTTATCGACCAGCTGCTGCAGCGGTTGTGGATCGCCTACGGTTTTGA<br>ATCCGTCTGCGATCTGGCGCTGGTGGCCGTCGGCGGCTATGGCCGCGGCGAGCT<br>GCACCCGCTCTCTGACGTCGACCTGCTGATCCTCAGCCGCAAAAAACTGCCTGA<br>CGACCAGGCGCAAAAGGTCGGCGAACTGCTGACGCTACTGTGGGACGTCAAGC<br>TGGAGGTGGGCCACAGCGTGCGCACCCTCGAAGAGTGTCTGCTCGAAGGACTTT<br>CGGATCTCACCGTCGCCACTAACTTGATTGAATCGCGCCTGCTGATCGGCGACG<br>TCGCGCTGTTCCTTGAACTGCAAAAACATATTTTTAGCGACGGCTTCTGGCCATC<br>GGAAAAGTTCTTCGCCGCCAAGGTGGAAGAGCAGAACGTCCGTCATCAACGCT<br>ATCACGGCACCAGCTATAACCTGGAGCCGGACGTGAAAAGCAGCCCCGGCGGC<br>CTGCGGGATATCCATACGCTACAGTGGGTGGCTCGCCGTCATTTTGGCGCCACC<br>TCGATGGATGAGATGGTCGGCTTCGGCTTTCTGACCGAAGCCGAGCGCAATGAG<br>CTCAACGAGTGTCTGCATCAGCTGTGGCGCATCCGTTTCGCGCTGCATCTCGAG<br>CTCACTCGCTATGACAACCGTCTGCTTTTCGACCGCCAGCTCAGCGTCGCCCGCC<br>GGCTCGGCTATGAAGGCGACGGCAACCAGCCGATTGAGCATATGATGAAGGAC<br>TTCTTCCCGCGTCACCCGCCGGGTGAGCGAGCTGAACCAGATGCTGCTTCAGCTG<br>TTTGAAGAGGCTATTCTCGCCCTGACCGAGGATGAAAAACCGCGCCCGATAGAC<br>GATGACTTCCAGCTGCGCGGCACCCTTATCGATCTGCGTGACGACACGCTGTTT<br>ATTCGCGAACCGCAGGCCATTCTGCGCATGTTTTATATGATGGTGCGCAACAGC<br>ACTATCACCGGCATCTACTCCACGACGTTGCGCCATCTGCGCCATGCCCGGCGC<br>CATCTGACCCAGCCGCTGTGCTATATCCCGGAGGCGCGCACGCTCTTTCTCAGC |

TABLE 1-continued

GlnD Sequences

| Description | SEQ ID NO | Sequence |
|---|---|---|
| | | ATGCTGCGCCATCAGGGGGCGGTCAGCCGCGGACTGCTGCCGATGCATCGCCAT |
| | | AGCGTGCTGTGGGCCTATATGCCGCAGTGGTCACATATCGTCGGCCAGATGCAG |
| | | TTCGATCTGTTTCACGCCTACACCGTCGATGAACACACCATCCGCGTGATGCTG |
| | | AAGCTGGAGAGCTTTGCCAAAGAAGAACCCGCAGCCGCCACCCGCTGTGCGT |
| | | GGAGCTATGGCCGCGCTTAACGCACCCGGAGCTGATTTTAATCGCCGCCCTGTT |
| | | CCACGACATTGCGAAAGGGCGTGGCGGCGACCACTCGATCCTCGGCGCGCAGG |
| | | ATGTGCTGAAGTTTGCCGAGCTGCACGGACTGAACTCTCGCGAAACGCAGTTGG |
| | | TCGCCTGGCTGGTGCGTCACCATCTGCTGATGTCGGTCACCGCCCAGCGGCGCG |
| | | ACATTCAGGATCCGGAGGTGATTAAGCAGTTCGCCGAGGAAGTGCAAACGGAA |
| | | AATCGCCTGCGCTATCTGGTGTGCCTGACCGTCGCCGACATCTGCGCCACCAAC |
| | | GAAACGCTGTGGAACAGCTGGAAGCAGAGTCTGCTGCGCGAACTCTATTTCGCC |
| | | ACCGAGAAACAGCTGCGTCGGGGCATGCAAAGCACCCCGGATATGCGCGAACG |
| | | GGTGCGTCATCATCAGCTGCAGGCGCTGGCCCTGCTGCGGATGGACAATATTAA |
| | | TGAAGAGGCGCTGCATCAGATCTGGAACCGCTGCCGCGCCAACTATTTCGTGCG |
| | | GCATACGCCGACGCAGCTCGCCTGGCACGCCCGCAACCTGCTGCGTCACGATCT |
| | | GAATAAGCCGATGATTCTGCTGAGTTCGCAGGCCACCCGCGGCGGTACGGAGT |
| | | GACgtattttttttagtgaatggaaagaaaca |

In some embodiments, modification of GlnB can be beneficial in increasing nitrogen compound excretion. In some embodiments, the uridylyl transferase (UTase) domain of GlnD modifies GlnB at tyrosine-51. In some embodiments, by modifying the UTase domain of GlnD, GlnB-UMP production can be decreased. In some embodiments, by removing the UTase domain of GlnD, GlnB-UMP production can be decreased. In some embodiments, by changing the UTase domain of GlnD, GlnB-UMP production can be prevented. In some embodiments, by removing the UTase domain of GlnD, GlnB-UMP production can be prevented. In some embodiments, GlnB can be modified by deleting tyrosine-51. In some embodiments, GlnB can be modified by modifying GlnB at tyrosine-51. In some embodiments, strains that can be utilized in this process of increasing ammonium excretion can include, but are not limited to, *Rahnella aquatilis, Kosakonia sacchari*, and *Klebsiella variicola* strains.

In some embodiments, modification of GlnK can be beneficial in increasing ammonium excretion. In some embodiments, GlnK can behave within a strain as a GlnB analogue based on a similarity of structure between GlnK and GlnB. In some embodiments, modifying GlnK can increase ammonium excretion by removing inhibitory effects that can be based on GlnK. In some embodiments, by changing GlnK, inhibitory effects on ammonium excretion can be decreased. In some embodiments, by removing GlnK, inhibitory effects on ammonium excretion can be decreased. In some embodiments, by changing GlnK, inhibitory effects on ammonium excretion based on GlnK can be prevented. In some embodiments, by removing the glnK gene, inhibitory effects on ammonium excretion based on GlnK can be prevented. In some embodiments, strains that can be utilized in this process of increasing ammonium excretion can include, but are not limited to, *Rahnella aquatilis, Kosakonia sacchari*, and *Klebsiella variicola* strains.

In some embodiments, modification of glnK can be beneficial in increasing ammonium excretion. In some embodiments, the UTase domain of GlnD modifies glnK at tyrosine-51. In some embodiments, by modifying the UTase domain of GlnD, glnK-UMP production can be decreased. In some embodiments, by removing the UTase domain of GlnD, glnK-UMP production can be decreased. In some embodiments, by changing the UTase domain of GlnD, glnK-UMP production can be prevented. In some embodiments, by removing the UTase domain of GlnD, glnK-UMP production can be prevented. In some embodiments, GlnK can be modified by deleting tyrosine-51. In some embodiments, GlnK can be modified by modifying GlnK at tyrosine-51. In some embodiments, strains that can be utilized in this process of increasing ammonium excretion can include, but are not limited to, *Rahnella aquatilis, Kosakonia sacchari*, and *Klebsiella variicola* strains.

In some embodiments, modification of the glnL encoding the NtrB protein can be beneficial in increasing ammonium excretion. In particular, modification of NtrB can be beneficial in controlling glnA transcription independent of nitrogen status. In some embodiments, modification of ntrB can be achieved by deleting specific resides to titrate activity. In some embodiments, strains that can be utilized in this process of increasing ammonium excretion can include, but are not limited to, *Rahnella aquatilis, Kosakonia sacchari*, and *Klebsiella variicola* strains.

In some embodiments, modification of glnA can be beneficial in increasing ammonium excretion. In some embodiments, modification of NtrC can be beneficial in modifying the level of GlnA protein in the cell. NtrC is the member of the two-component regulatory system NtrB/NtrC, which controls expression of the nitrogen-regulated (ntr) genes in response to nitrogen limitation. Under nitrogen limited conditions, PII signaling proteins initiate a phosphorylation cascade that leads to the phosphorylation of the aspartate (D54) residue of NtrC. The phosphorylated form of NtrC binds upstream of multiple nitrogen metabolism genes it regulates and activates their transcription. Changing aspartate residue to a more negatively charged amino acid residue, glutamate (D54E), led NtrC to behave like phosphorylated and constitutively activated the transcription of its downstream target genes (Klose et al., *J Mol Biol.*, 232(1): 67-78, 1993). On the other hand, changing aspartate to alanine (D54A), prohibited phosphorylation of this residue, and hence activation of NtrC, resulting in lack of transcriptional response even under nitrogen limited conditions. In some embodiments, modification of NtrC can be beneficial by preventing the phosphorylization of NtrC. Phosphorylated NtrC can lead to transcriptional activation of glnA. As such, modification of ntrC so as to prevent the phosphorylization of ntrC can be beneficial in decreasing transcription of glnA. In some embodiments, modification of NtrC can be achieved by replacing asparate 54.

In some embodiments of the genetically engineered bacteria described herein, the NtrC binding site upstream of nifA is replaced by a constitutive promoter. This can remove NtrC for transcriptional activation of nifA. In some embodiments, the at least one modification in a gene regulating nitrogen fixation or assimilation comprises a mutation in the coding sequence of the ntrC gene. In some embodiments, at least one modification in a gene regulating nitrogen fixation or assimilation comprises changing the 161st nucleotide of the ntrC coding sequence from A to C (SEQ ID NO:7). In some embodiments, the mutation in the coding sequence of the ntrC gene encode NtrC protein comprising a D54A amino acid substitution. In some embodiments, the mutation in NtrcC results in increased ammonium excretion. In some embodiments, strains that can be utilized in this process of increasing ammonium excretion can include, but are not limited to, *Rahnella aquatilis, Kosakonia sacchari*, and *Klebsiella variicola* strains.

some embodiments, attaching a nifA gene copy to one or more housekeeping operons can increase an overall number of nifA genes in a cell. In some embodiments, strains that can be utilized in this process of increasing nitrogenase expression can include, but are not limited to, *Rahnella aquatilis* and *Klebsiella variicola* strains.

In some embodiments, modification of a nitrogenase operon can be beneficial in increasing nitrogenase expression. In some embodiments, it can be beneficial to upregulate nitrogenase operons so as to increase nitrogenase transcription. In some embodiments, promoters from within the bacterium that are active when the bacterium is colonizing the rhizosphere can be inserted in front of nitrogenase operons to upregulate nitrogenase operons. In some embodiments, nifL can be deleted within nitrogenase operons to upregulate nitrogenase operons. In some embodiments, nifA can be deleted within nitrogenase operons to upregulate nitrogenase operons. In some embodiments, nifA and nifL can be deleted within nitrogenase operons to upregulate nitrogenase operons. In some embodiments, multiple promoters can be placed directly in front of nifHDK genes so

TABLE 2

NtrC Sequence

| Description | SEQ ID NO | Sequence |
|---|---|---|
| Mutated NtrC | 7 | ATGCAACGAGGGATAGCCTGGATCGTTGATGACGATAGCTCCATCCGCTGGGT GCTTGAACGCGCGCTCACCGGAGCCGGCTTGAGCTGCACAACGTTCGAAAGC GGCAATGAGGTGCTAGATGCCCTCACCACCAAAACCCCGGATGTACTGCTGTC AGCTATCCGTATGCCGGGAATGGATGGTCTGGCGCTGCTCAAACAGATTAAGC AGCGTCATCCAATGCTTCCGGTCATCATAATGACCGCACATTCCGATCTGGAC GCTGCGGTCAGCGCTTATCAGCAAGGCGCGTTTGATTATCTGCCCAAACCTTT TGATATTGATGAAGCCGTCGCCCTGGTCGACCGGGCGATAAGCCACTATCAGG AGCAGCAACAGCCGCGAAATGCGCCAATAAGCAGCCCAACTGCCGACATCAT CGGCGAAGCGCCGGCAATGCAGGATGTCTTTCGCATTATTGGCCGTTTGTCGC GATCATCCATCAGCGTGCTGATTAATGGCGAATCCGGTACCGGTAAAGAGCTC GTCGCTCACGCCCTGCATCGTCATAGCCCACGTTCAAAAGCGCCGTTTATCGC ACTGAATATGGCGGCAATACCCAAAGACCTGATTGAGTCCGAGCTGTTCGGGC ATGAAAAAGGGGCCTTTACCGGCGCCAATACCGTCCGCCAGGGACGCTTCGA ACAGGCTGACGGCGGCACGCTATTCCTGGATGAAATTGGCGATATGCCGCTTG ATGTCCAGACTCGTCTGCTGCGCGTGCTGGCGGATGGCCAGTTTTATCGCGTG GGCGGTTACGCGCCGGTGAAGGTCGATGTGCGGATCATCGCCGCCACCCACC AGAACCTGGAACAGCGCGTGCAGGAGGGGAAATTCCGTGAAGATTTGTTCCA CCGCCTGAACGTGATCCGGGTGCATTTACCGCCGCTGCGCGAGCGCCGGGAA GATATTCCACGCCTGGCCCGCCATTTTCTGCAGATAGCCGCCCGCGAGCTCGG TGTTGAAGCCAAACAGCTGCATCCGGAAACGGAGACAGCGCTGACACGCCTG GCGTGGCCTGGCAACGTCCGTCAGCTGGAAAACACCTGTCGCTGGCTCACCGT CATGGCCGCCGGCCAGGAGGTACTGACGCAGGATCTGCCGAGCGAACTGTTT GAGACTACGGTTCCGGACAGCCCGACGCAGATGCAGCCCGACAGCTGGGCGA CGCTGCTGGGTCAGTGGGCCGATCGGGCGTTGCGATCCGGTCATCAAAACCTG CTCTCAGAAGCGCAACCCGAAATGGAGCGCACGCTGCTGACGACCGCCCTGC GCCATACCCAGGGGCACAAGCAGGAGGCTGCGCGTCTGCTGGGATGGGGTCG TAATACCCTGACGCGTAAGCTAAAAGAGCTGGGAATGGAGTAG |

In some embodiments, modification of Glutaminase B can be beneficial in increasing ammonium excretion. In some embodiments, the conversion of glutamine back to glutamate and ammonia by Glutaminase B can be upregulated so as to increase ammonium excretion. In some embodiments, strains that can be utilized in this process of increasing nitrogen excretion can include, but are not limited to, *Rahnella aquatilis, Kosakonia sacchari*, and *Klebsiella variicola* strains.

In some embodiments, modification of nifA can be beneficial in increasing nitrogenase expression. In some embodiments, it can be beneficial to modify nifA so as to increase nifA gene copy numbers in a cell. nifA gene copy numbers can be increased by insert multiple copies of a nifA gene in front of constitutively expressing promoters. In as to circumvent nifA transcription control. In some embodiments, strains that can be utilized in this process of increasing nitrogenase expression can include, but are not limited to, *Rahnella aquatilis* and *Klebsiella variicola* strains.

In some embodiments, modification of glnE can be beneficial in increasing ammonium excretion. In some embodiments, a conserved aspartate-amino acid-aspartate (DXD) motif on AR domain of glnE can be changed. In some embodiments, changing a conserved DXD residue on AR domain of glnE can be used to remove de-adenylylation activity from glnE. In some embodiments, a D residue can be replaced on a DXD motif in the AR region of glnE. In some embodiments, the replacement of a D residue on a DXD motif in the AR region of glnE can leave the GlnB binding site intact so as to allow for regulation of adenylation activity while decreasing or preventing AR activity. In some embodiments, strains that can be utilized in this process of increasing ammonium excretion can include, but are not limited to, *Rahnella aquatilis, Kosakonia sacchari*, and *Klebsiella variicola* strains.

In some embodiments, modification of glnA can be beneficial in increasing AMM excretion. In some embodiments, glnA can be downregulated by inserting the promoters of glnB, glnD, and/or glnE upstream of the glnA gene. In some embodiments, modification of glnA can decouple glnA expression from an N-status signaling cascade and decrease expression to a basal level so that more fixed nitrogen remains unassimilated. In some embodiments, strains that can be utilized in this process of increasing ammonium excretion can include, but are not limited to, *Rahnella aquatilis, Kosakonia sacchari*, and *Klebsiella variicola* strains.

In some embodiments, modification of GOGAT can be beneficial in increasing ammonium excretion. In some embodiments, GOGAT can be downregulated by inserting upstream of the GOGAT genes a promoter that controls glnB, glnD, and/or glnE. Downregulation of GOGAT can, in turn, lead to lowering glutamine oxyglutarate aminotransferase expression. In some embodiments, modification of GOGAT can decouple GOGAT expression from an N-status signaling cascade and decrease expression to a basal level so that more fixed nitrogen remains unassimilated. In some embodiments, strains that can be utilized in this process of increasing ammonium excretion can include, but are not limited to, *Rahnella aquatilis, Kosakonia sacchari*, and *Klebsiella variicola* strains.

In some embodiments, modification of GDH can be beneficial in increasing ammonium excretion. In some embodiments, GDH can be downregulated by inserting upstream of the GDH gene a promoter that controls glnB, glnD, and/or glnE. Downregulation of GDH can, in turn, lead to lowering NAD-specific glutamate dehydrogenase expression. In some embodiments, modification of GDH can decouple GDH expression from an N-status signaling cascade and decrease expression to a basal level so that more fixed nitrogen remains unassimilated. In some embodiments, strains that can be utilized in this process of increasing ammonium excretion can include, but are not limited to, *Rahnella aquatilis, Kosakonia sacchari*, and *Klebsiella variicola* strains.

In some embodiments, the amount of nitrogen provided to a microbe-associated plant is increased by decreasing the nitrogen assimilation in the microbe. Assimilation can be influenced by the excretion rate of ammonia. By targeting the assimilation of ammonia, nitrogen availability can be increased. In some embodiments, ammonia assimilation is influenced by decreasing the rate of ammonia reuptake after excretion. To decrease the rate of ammonia reuptake after excretion, any relevant gene can be knocked out. An example of an ammonia reuptake genes can be, but is not limited to, amtB.

In some embodiments, the assimilation can be influenced by the plant uptake rate. By targeting the plant nitrogen assimilation genes and pathways, nitrogen availability can be increased. In some embodiments, ammonia assimilation by a plant can be altered through inoculation with N-fixing plant growth promoting microbes. A screen can be carried out to identify microbes which induce ammonia assimilation in plants.

Although some endophytes have the ability to fix nitrogen in vitro, genes associated with nitrogen fixation can be silenced in the field by high levels of exogenous chemical fertilizers. The sensing of exogenous nitrogen can be decoupled from expression of the nitrogenase enzyme to facilitate field-based nitrogen fixation. Improving the integral of nitrogenase activity across time further serves to augment the production of nitrogen for utilization by the crop. Specific targets for genetic modification to facilitate field-based nitrogen fixation using the methods described herein include one or more genes selected from the group consisting of nifA, nifL, ntrB, ntrC, glnA, glnB, glnK, draT, amtB, glnD, glnE, nifJ, nifH, nifD, nifK, nifY, nifE, nifN, nifU, nifS, nifV, nifW, nifZ, nifM, nifF, nifB, and nifQ.

Increasing the colonization capacity of the microbes can increase the amount of fixed nitrogen provided to a plant. The colonization can be influenced by altering carrying capacity (the abundance of microbes on the root surface) and/or microbe fitness. In some embodiments, influencing carrying capacity and microbe fitness can be achieved through altering organic acid transport. Organic acid transport can be improved by upregulating relevant genes. An example of an organic acid transport gene can be, but is not limited to, dctA.

For example, the colonization capacity can be affected by expression of agglutinins. Increased expression of agglutinins can help the microbes stick to plant roots. Examples of agglutinin genes can include, but are not limited to, fhaB and fhaC.

The colonization capacity can be affected by an increase in endophytic entry. For example, endophytic entry can be affected by plant cell wall-degrading enzymes (CDWE). Increasing CDWE expression and/or secretion can increase the colonization and endophytic entry of the microbes. Some examples of CDWEs are, but are not limited to, polygalacturonases and cellulases. An example of a polygalacturonases gene is pehA. In some embodiments, export of polygalacturonases and cellulases can be increased by providing an export signal with the enzymes.

Varying the carrying capacity can result in an increased amount of nitrogen being provided to an associated plant. Carrying capacity can be affected by biofilm formation. In some embodiments, carrying capacity can be affected by small RNA rsmZ. Small RNA rsmZ is a negative regulator of biofilm formation. In some embodiments, biofilm formation can be promoted by deleting or downregulating rsmZ, leading to increased translation of rsmA (a positive regulator of secondary metabolism) and biofilm formation.

In some embodiments, biofilm formation can be influenced by enhancing the ability of strains to adhere to the root surface. In some embodiments, biofilm formation can be promoted by upregulating large adhesion proteins. An example of a large adhesion protein can be, but is not limited to, lapA.

In some embodiments, carrying capacity can be affected by quorum sensing. In some embodiments, quorum sensing can be enhanced by increasing the copy number of AHL biosynthesis genes.

In some embodiments, the colonization of the rhizosphere can be influenced by root mass. For example, root mass can be affected by microbial IAA biosynthesis. Increased IAA biosynthesis by the microbe can stimulate root biomass formation. In some embodiments, influencing IAA biosynthesis can be achieved through upregulation (at a range of levels) of IAA biosynthesis genes. An example of an IAA biosynthesis gene can be, but is not limited to, ipdC.

In some embodiments ethylene signaling can induce systemic resistance in the plant and affect the colonization capacity of the microbe. Ethylene is a plant signaling molecule that elicits a wide range of responses based on plant tissue and ethylene level. The prevailing model for root ethylene response is that plants that are exposed to stress quickly respond by producing a small peak of ethylene that initiates a protective response by the plant, for example, transcription of genes encoding defensive proteins. If the stress persists or is intense, a second much larger peak of ethylene occurs, often several days later. This second ethylene peak induces processes such as senescence, chlorosis, and abscission that can lead to a significant inhibition of plant growth and survival. In some embodiments, plant growth promoting bacteria can stimulate root growth by producing the auxin IAA, which stimulates a small ethylene response in the roots. At the same time, the bacteria can prevent the second large ethylene peak by producing an enzyme (ACC deaminase) that slows ethylene production in the plant, thus maintaining an ethylene level that's conducive to stimulating root growth. Induction of systemic resistance in the plant can be influenced by bacterial IAAs. In some embodiments, stimulating IAAbiosynthesis can be achieved through upregulation (at a range of levels) of IAA biosynthesis genes. An example of a biosynthesis gene can be, but is not limited to, ipdC.

In some embodiments, colonization can be affected by ACC Deaminase. ACC Deaminase can be decrease ethylene production in the root by shunting ACC to a side product. In some embodiments, influencing ACC Deaminase can be achieved through upregulation of ACC Deaminase genes. Some examples of ACC Deaminase genes can include, but are not limited to, dcyD.

In some embodiments, the colonization can be influenced by carrying capacity and/or microbe fitness. For example, carrying capacity and/or microbe fitness can be affected by trehalose overproduction. Trehalose overproduction can increase of drought tolerance. In some embodiments, influencing trehalose overproduction can be achieved through upregulation (at a range of levels) of trehalose biosynthesis genes. Some examples of trehalose biosynthesis genes can include, but are not limited to, otsA, otsB, treZ and treY In some embodiments, upregulation of otsB can also increase nitrogen fixation activity.

In some embodiments, carrying capacity can be affected by root attachment. Root attachment can be influenced by exopolysaccharide secretion. In some embodiments, influencing exopolysaccharide secretion can be achieved through upregulation of exopolysaccharide production proteins. Some examples of exopolysaccharide production proteins can include, but are not limited to, yjbE and pssM. In some embodiments, influencing exopolysaccharide secretion can be achieved through upregulation of cellulose biosynthesis. Some examples of cellulose biosynthesis genes can include, but are not limited to, acs genes, and bcs gene clusters.

In some embodiments, carrying capacity and/or the microbe's fitness can be affected by fungal inhibition. Fungal inhibition can be influenced by chitinases which can break down fungal cell walls and can lead to biocontrol of rhizosphere fungi. In some embodiments, influencing fungal inhibition can be achieved through upregulation of chitinase genes. Some examples of chitinase genes can include, but are not limited to, chitinase class 1 and chiA.

In some embodiments, efficient iron uptake can help microbes to survive in the rhizosphere where they have to compete with other soil microbes and the plant for iron uptake. In some embodiments, high-affinity chelation (siderophores) and transport systems can help with rhizosphere competency by 1) ensuring the microbes obtains enough iron and 2) reducing the iron pool for competing species. Increasing the microbe's ability to do this could increase its competitive fitness in the rhizosphere. In some embodiments, influencing iron uptake can be by upregulating siderophore genes. Some examples of siderophore genes can include, but are not limited to, yhfA, yusV, sbnA, fiu, yfiZ, and fur. In some embodiments iron uptake can be influenced by the tonB transport system. In some embodiments, influencing iron uptake can be by upregulating tonB transport system genes. Some examples of tonB transport system genes can include, but are not limited to, tonB, and exbAB.

In some embodiments, carrying capacity and/or microbe fitness can be affected by redox balance and/or ROS scavenging. Redox balance and/or ROS scavenging can be influenced by bacterial glutathione (GSH) biosynthesis. In some embodiments, influencing bacterial glutathione (GSH) biosynthesis can be through upregulation of bacterial glutathione biosynthesis genes. Some examples of bacterial glutathione biosynthesis genes can include, but are not limited to, gshA, gshAB, and gshB.

In some embodiments, Redox balance can be influenced by ROS scavenging. In some embodiments, influencing ROS scavenging can be through upregulation of catalases. Some examples of catalases genes can include, but are not limited to, katEG, and Mn catalase.

In some embodiments, biofilm formation can be influenced by phosphorus signaling. In some embodiments, influencing phosphorus signaling can be by altering the expression of phosphorous signaling genes. Some examples of phosphorous signaling genes can include, but are not limited to, phoR and phoB.

In some embodiments, carrying capacity can be affected by root attachment. Root attachment can be influenced by surfactin biosynthesis. In some embodiments, influencing surfactin biosynthesis can be achieved by upregulating surfactin biosynthesis to improve biofilm formation. An example of surfactin biosynthesis genes can be, but is not limited to, srfAA.

In some embodiments, the colonization and/or microbe fitness can be influenced by carrying capacity, competition with other microbes and/or crop protection from other microbes. In some embodiments, competition with other microbes and/or crop protection from other microbes can be influenced by quorum sensing and/or quorum quenching. Quorum quenching can influence colonization by inhibiting quorum-sensing of potential pathogenic/competing bacteria. In some embodiments, influencing quorum quenching can be achieved by inserting and/or upregulating genes encoding quorum quenching enzymes. Some examples of quorum quenching genes can include, but are not limited to, ahlD, Y2-aiiA, aiiA, ytnP and attM. In some embodiments, modification of enzymes involved in quorum quenching, such as Y2-aiiA and/or ytnP can be beneficial for colonization. In some embodiments, upregulation of Y2-aiiA and/or ytnP can result in hydrolysis of extracellular acyl-homoserine lactone (AHL). aiiA is an N-acyl homoserine lactonase that is an enzyme that breaks down homoserine lactone. Breaking down AHL can stop or slow the quorum signaling ability of competing gram negative bacteria. In some embodiments, strains that can be utilized in this process of increasing colonization can include, but are not limited to, *Rahnella aquatilis, Kosakonia sacchari*, and *Klebsiella variicola* strains.

In some embodiments, carrying capacity and/or microbes fitness can be affected by rhizobitoxine biosynthesis. Rhizobitoxine biosynthesis can decrease ethylene production in the root by inhibiting ACC synthase. In some embodiments, influencing rhizobitoxine biosynthesis can be achieved by upregulating rhizobitoxine biosynthesis genes.

In some embodiments, carrying capacity can be affected by root attachment. Root attachment can be influenced by exopolysaccharide secretion. In some embodiments, influencing exopolysaccharide secretion can be achieved by generating hypermucoid mutants by deleting mucA.

In some embodiments, root attachment can be influenced by phenazine biosynthesis. In some embodiments, influencing phenazine biosynthesis can be achieved by upregulating phenazine biosynthesis genes to improve biofilm formation.

In some embodiments, root attachment can be influenced by cyclic lipopeptide (CLP) biosynthesis. In some embodiments, influencing cyclic lipopeptide (CLP) biosynthesis can be achieved by upregulating CLP biosynthesis to improve biofilm formation.

In some embodiments, carrying capacity and/or competition can be affected by antibiotic synthesis. Antibiotic synthesis can increase antibiotic production to kill competing microbes. In some embodiments, increasing antibiotic production can be achieved by mining genomes for antibiotic biosynthesis pathways and upregulation.

In some embodiments, colonization can be affected by desiccation tolerance. In some embodiments, modification of rpoE can be beneficial for colonization. In some embodiments, upregulation of rpoE can result in increasing expression of stress tolerance genes and pathways. In some embodiments, rpoE can be upregulated using a unique switchable promoter. In some embodiments, rpoE can be upregulated using an arabinose promoter. rpoE is a sigma factor similar to phyR. When expressed, rpoE can cause upregulation of multiple stress tolerance genes. As stress tolerance enzymes may not be useful during a colonization cycle, a switchable promoter can be used. In some embodiments, the promoter can be active during biomass growth and/or during seed coating. In some embodiments, a switchable promoter can be used where the sugar or chemical can be spiked in during the log phase of biomass growth but can also have the promoter not turned on during one or more other applications of the microbe. In some embodiments, rpoE can be upregulated while also downregulating rseA. In some embodiments, strains that can be utilized in this process of increasing colonization can include, but are not limited to, *Rahnella aquatilis, Kosakonia sacchari*, and *Klebsiella variicola* strains.

In some embodiments, colonization can be affected by desiccation tolerance. In some embodiments, modification of rseA can be beneficial for colonization. In some embodiments, rseA can be downregulated using a unique switchable promoter. In some embodiments, rseA can be downregulated using an arabinose promoter. rseA is an anti-sigma factor coexpressed with rpoE. In some embodiments, the enzymes remain bound to each other, which can decrease or disable rpoE's ability to act as a transcription factor. However, during stress conditions, resA can be cleaved and rpoE can be free to up/down regulate stress tolerance genes. By breaking co-transcription with rpoE, levels of rpoE and resA can be titered independently, which can be beneficial in optimizing colonization of engineered strains. In some embodiments, strains that can be utilized in this process of increasing colonization can include, but are not limited to, *Rahnella aquatilis, Kosakonia sacchari*, and *Klebsiella variicola* strains.

In some embodiments, a trait that can be targeted for regulation by the methods described herein is colonization potential. Accordingly, in some embodiments, pathways and genes involved in colonization can act as a target for genetic engineering and optimization.

In some cases, exopolysaccharides can be involved in bacterial colonization of plants. In some cases, plant colonizing microbes can produce a biofilm. In some cases, plant colonizing microbes secrete molecules which can assist in adhesion to the plant, or in evading a plant immune response. In some cases, plant colonizing microbes can excrete signaling molecules which alter the plants response to the microbes. In some cases, plant colonizing microbes can secrete molecules which alter the local microenvironment. In some cases, a plant colonizing microbe can alter expression of genes to adapt to a plant said microbe is in proximity to. In some cases, a plant colonizing microbe can detect the presence of a plant in the local environment and can change expression of genes in response.

In some embodiments, to improve colonization, a gene involved in a pathway selected from the group consisting of: exopolysaccharide production, endo-polygalaturonase production, trehalose production, and glutamine conversion can be targeted for genetic engineering and optimization.

In some embodiments, an enzyme or pathway involved in production of exopolysaccharides can be genetically modified to improve colonization. Exemplary genes encoding an exopolysaccharide producing enzyme that can be targeted to improve colonization include, but are not limited to, bcsii, bcsiii, andyjbE.

In some embodiments, an enzyme or pathway involved in production of a filamentous hemagglutinin can be genetically modified to improve colonization. For example, ajhaB gene encoding a filamentous hemagglutinin can be targeted to improve colonization.

In some embodiments, an enzyme or pathway involved in production of an endo-polygalaturonase can be genetically modified to improve colonization. For example, a pehA gene encoding an endo-polygalaturonase precursor can be targeted to improve colonization.

In some embodiments, an enzyme or pathway involved in production of trehalose can be genetically modified to improve colonization. Exemplary genes encoding a trehalose producing enzyme that can be targeted to improve colonization include, but are not limited to, otsB and treZ.

In some embodiments, an enzyme or pathway involved in conversion of glutamine can be genetically modified to improve colonization. For example, the glsA2 gene encodes a glutaminase which converts glutamine into ammonium and glutamate. Upregulating glsA2 improves fitness by increasing the cell's glutamate pool, thereby increasing available N to the cells. Accordingly, in some embodiments, the glsA2 gene can be targeted to improve colonization.

In some embodiments, colonization genes selected from the group consisting of: bcsii, bcsiii, yjbE, jhaB, pehA, otsB, treZ, glsA2, and combinations thereof, can be genetically modified to improve colonization.

Colonization genes that can be targeted to improve the colonization potential are also described in a PCT publication, WO/2019/032926, which is incorporated by reference herein in its entirety.

Methods of Use

Also provided herein are methods of increasing nitrogen fixation in a plant, comprising exposing the plant, a part of the plant, or soil into which the plant is planted or will be planted to bacteria comprising one or more genetic modifications introduced into one or more genes regulating nitrogen fixation. Also provided herein are methods of increasing the amount of atmospheric derived nitrogen in a plant, the method comprising contacting the plant, a part of the plant, or soil into which the plant is planted with a plurality of any of the genetically engineered bacteria described herein.

In some embodiments, provided herein are methods of increasing the total space on the root surface of a plant occupied by bacteria that can fix nitrogen in the presence of nitrogen, the method comprising contacting the plant, a part of the plant, or soil into which the plant is planted with a plurality of any of the genetically engineered bacteria described herein.

In some embodiments, the amount of atmospheric derived nitrogen in a plant is increased under conditions in which the genetically engineered bacteria are exposed to oxygen. For example, in some embodiments, the genetically engineered bacteria can produce about 1% or more of nitrogen in the plant under conditions in which the genetically engineered bacteria are exposed to oxygen. Such conditions can include, but are not limited to, when the soil into which the plant is planted, or will be planted into, can have at least about 0.5% oxygen. For example, at least about 0.75%, about 1%, about 1.25%, about 1.5%, about 1.75%, about 2%, about 2%, about 2.25%, about 2.5%, about 2.75%, or about 3% or more oxygen. In some embodiments, the at least one modification in a gene regulating nitrogen fixation or assimilation in the genetically engineered bacteria results in an increased level of nitrogenase activity in the presence of at least about 0.5% oxygen than in non-engineered bacteria of the same species. For example, at least about 0.75%, about 1%, about 1.25%, about 1.5%, about 1.75%, about 2%, about 2%, about 2.25%, about 2.5%, about 2.75%, or about 3% oxygen. An exemplary method for measuring nitrogen fixation of bacteria in the presence of oxygen is described in Example 3.

Also provided herein are methods of increasing the biomass of a plant (e.g., overall biomass, root and/or shoot biomass), comprising contacting the plant, a part of the plant, or soil into which the plant is planted or will be planted, with a plurality of any of the genetically engineered bacteria described herein.

In some embodiments, a combination of genetically engineered bacteria can be used. For example, in some embodiments, methods of increasing the amount of atmospheric derived nitrogen in a plant can include contacting the plant, a part of the plant, or soil into which the plant is planted with a plurality of genetically engineered *Klebsiella variicola* bacteria and a plurality of genetically engineered *Kosakonia sacchari* bacteria. In some embodiments, the *Klebsiella variicola* bacterium has a higher nitrogenase activity than the *Kosakonia sacchari* bacterium. In some embodiments, the *Kosakonia sacchari* bacterium has a higher growth rate than the *Klebsiella variicola* bacterium. In some embodiments, the a plurality of genetically engineered *Klebsiella variicola* bacteria and a plurality of genetically engineered *Kosakonia sacchari* bacteria are applied to the plant, a part of the plant, or soil into which the plant is planted, or will be planted, simultaneously. In some embodiments, the a plurality of genetically engineered *Klebsiella variicola* bacteria and a plurality of genetically engineered *Kosakonia sacchari* bacteria are applied to the plant, a part of the plant, or soil into which the plant is planted or will be planted, sequentially.

In some embodiments, provided herein are methods of increasing colonization in at least two different niches of the rhizosphere of a plant, the method comprising contacting the plant, a part of the plant, or soil into which the plant is planted with a plurality of any of the genetically engineered bacteria described herein. A "niche" as used herein can refer to the ecological space a microbe (e.g., a genetically engineered bacterium) occupies. For example, a niche can describe how a microbe responds to the distribution of resources, physical parameters (e.g., host tissue space) and competitors (e.g., by growing when resources are abundant) and how it in turn alters those same factors (e.g., limiting access to resources by other organisms). In some embodiments, at least two pluralities of genetically engineered bacteria are contacted with the plant, a part of the plant, or soil into which the plant is planted, wherein the first plurality occupies a different niche than the second plurality. In some embodiments, the first plurality is a plurality of genetically engineered *Klebsiella variicola* bacteria and the second plurality is a plurality of genetically engineered *Kosakonia sacchari* bacteria.

In some embodiments, genetically engineered bacteria from different niches have one or more of: different nutrient utilization; different temporal occupation; different oxygen adaptability; and different spatial occupation. In some embodiments, the nutrient is carbon. In some embodiments, a strain of bacteria in the rhizosphere of a plant utilize at least one carbon source that is different than the carbon source of a different strain of bacteria in the rhizosphere of the plant. In some embodiments, a strain of bacteria in the rhizosphere of a plant utilize at least one carbon source at a different rate than the carbon source of a different strain of bacteria in the rhizosphere of the plant. In some embodiments, a strain of bacteria in the rhizosphere of a plant is able to fixate nitrogen at a higher rate in the presence of oxygen (e.g., oxygen in the soil the plant is planted in) a different strain of bacteria in the rhizosphere of the plant.

In some embodiments, the bacteria cans produce about 1% or more of nitrogen in the plant (e.g. about 2%, about 5%, about 10%, or more). This can represent a nitrogen-fixation capability of at least 2-fold as compared to the plant in the absence of the bacteria. In some embodiments, the bacteria are capable of fixing atmospheric nitrogen in the presence of exogenous nitrogen In some embodiments, the bacteria can produce the nitrogen in the presence of fertilizer supplemented with glutamine, urea, nitrates or ammonia.

Genetic modifications can be any genetic modification described herein, including examples provided above, in any number and any combination. In some embodiments, the genetic modification introduced into a gene selected from the group consisting of nifA, nifL, ntrB, ntrC, glutamine synthetase, glnA, glnB, glnK, draT, amtB, glutaminase, glnD, glnE, nifJ, nifH, nifD, nifK, nifY, nifE, nifN, nifU, nifS, nifV, nifW, nifZ, nifM, nifF, nifB, and nifQ. The genetic modification may be a mutation that results in one or more of: increased expression or activity of nifA or glutaminase; decreased expression or activity of nifL, ntrB, glutamine synthetase, glnB, glnK, draT, amtB; decreased adenylyl-removing activity of GlnE; or decreased uridylyl-transfersae activity of GlnD.

In some embodiments, the at least one modification in the gene regulating nitrogen fixation or assimilation can result in one or more of: constitutive expression of the nifA gene in nitrogen limiting and non-nitrogen limiting condition, activity of nifA in non-nitrogen limiting conditions, decreased uridylyl-transferase activity of GlnD, decreased adenylyl-removing activity of GlnE, and increased nitrogen excretion.

In some embodiments, genetically engineered bacteria as provided herein can comprise at least one modification in one or more genes regulating nitrogen fixation or assimilation selected from nifL, glnD, glnE, NtrC, and nifA.

The genetic modification introduced into one or more bacteria of the methods disclosed herein may be a knock-out mutation or it may abolish a regulatory sequence of a target gene, or it may comprise insertion of a heterologous regulatory sequence, for example, insertion of a regulatory sequence found within the genome of the same bacterial species or genus. The regulatory sequence can be chosen based on the expression level of a gene in a bacterial culture or within plant tissue. The genetic modification may be produced by chemical mutagenesis. The plants grown in step (c) may be exposed to biotic or abiotic stressors.

In some embodiments, the genetically engineered bacteria colonize the root surface of the plant. In some embodiments, provided herein are methods of increasing the total space on the root surface of a plant occupied by bacteria that can fix nitrogen in the presence of nitrogen that include contacting the plant, a part of the plant, or soil into which the plant is planted with genetically engineered bacteria as described herein. In some embodiments, the genetically engineered bacteria exhibit colonization levels of at least about $10^3$ CFU/g root fresh weight (FW). For example, at least about $10^4$ CFU/g root fresh weight (FW), at least about $10^5$ CFU/g root fresh weight (FW), or at least about $10^6$ CFU/g root fresh weight (FW).

In some embodiments, genetically engineered bacteria of the present disclosure produce fixed N of at least about $2\times10^{-13}$ mmol of N per CFU per hour, about $2.5\times10^{-13}$ mmol of N per CFU per hour, about $3\times10^{-13}$ mmol of N per CFU per hour, about $3.5\times10^{-13}$ mmol of N per CFU per hour, about $4\times10^{-13}$ mmol of N per CFU per hour, about $4.5\times10^{-13}$ mmol of N per CFU per hour, about $5\times10^{-13}$ mmol of N per CFU per hour, about $5.5\times10^{-13}$ mmol of N per CFU per hour, about $6\times10^{-13}$ mmol of N per CFU per hour, about $6.5\times10^{-13}$ mmol of N per CFU per hour, about $7\times10^{-13}$ mmol of N per CFU per hour, about $7.5\times10^{-13}$ mmol of N per CFU per hour, about $8\times10^{-13}$ mmol of N per CFU per hour, about $8.5\times10^{-13}$ mmol of N per CFU per hour, about $9\times10^{-13}$ mmol of N per CFU per hour, about $9.5\times10^{-13}$ mmol of N per CFU per hour, or about $10\times10^{-13}$ mmol of N per CFU per hour.

In some embodiments, genetically engineered bacteria of the present disclosure produce fixed N of at least about $2\times10^{-12}$ mmol of N per CFU per hour, about $2.25\times10^{-12}$ mmol of N per CFU per hour, about $2.5\times10^{-12}$ mmol of N per CFU per hour, about $2.75\times10^{-12}$ mmol of N per CFU per hour, about $3\times10^{-12}$ mmol of N per CFU per hour, about $3.25\times10^{-12}$ mmol of N per CFU per hour, about $3.5\times10^{-12}$ mmol of N per CFU per hour, about $3.75\times10^{-12}$ mmol of N per CFU per hour, about $4\times10^{-12}$ mmol of N per CFU per hour, about $4.25\times10^{-12}$ mmol of N per CFU per hour, about $4.5\times10^{-12}$ mmol of N per CFU per hour, about $4.75\times10^{-12}$ mmol of N per CFU per hour, about $5\times10^{-12}$ mmol of N per CFU per hour, about $5.25\times10^{-12}$ mmol of N per CFU per hour, about $5.5\times10^{-12}$ mmol of N per CFU per hour, about $5.75\times10^{-12}$ mmol of N per CFU per hour, about $6\times10^{-12}$ mmol of N per CFU per hour, about $6.25\times10^{-12}$ mmol of N per CFU per hour, about $6.5\times10^{-12}$ mmol of N per CFU per hour, about $6.75\times10^{-12}$ mmol of N per CFU per hour, about $7\times10^{-12}$ mmol of N per CFU per hour, about $7.25\times10^{-12}$ mmol of N per CFU per hour, about $7.5\times10^{-12}$ mmol of N per CFU per hour, about $7.75\times10^{-12}$ mmol of N per CFU per hour, about $8\times10^{-12}$ mmol of N per CFU per hour, about $8.25\times10^{-12}$ mmol of N per CFU per hour, about $8.5\times10^{-12}$ mmol of N per CFU per hour, about $8.75\times10^{-12}$ mmol of N per CFU per hour, about $9\times10^{-12}$ mmol of N per CFU per hour, about $9.25\times10^{-12}$ mmol of N per CFU per hour, about $9.5\times10^{-12}$ mmol of N per CFU per hour, about $9.75\times10^{-12}$ mmol of N per CFU per hour, or about $10\times10^{-12}$ mmol of N per CFU per hour.

In some embodiments, genetically engineered bacteria of the present disclosure produce fixed N of at least about $5.49\times10^{-13}$ mmol of N per CFU per hour. In some embodiments, genetically engineered bacteria of the present disclosure produce fixed N of at least about $4.03\times10^{-13}$ mmol of N per CFU per hour. In some embodiments, genetically engineered bacteria of the present disclosure produce fixed N of at least about $2.75\times10^{-13}$ mmol of N per CFU per hour.

In some embodiments, genetically engineered bacteria of the present disclosure produce fixed N of at least about $1\times10^{-17}$ mmol N per bacterial cell per hour. For example, at least about $2\times10^{-17}$ mmol N per bacterial cell per hour, at least about $2.5\times10^{-17}$ mmol N per bacterial cell per hour, at least about $3\times10^{-17}$ mmol N per bacterial cell per hour, at least about $3.5\times10^{-17}$ mmol N per bacterial cell per hour, at least about $4\times10^{-17}$ mmol N per bacterial cell per hour, at least about $4.5\times10^{-17}$ mmol N per bacterial cell per hour, or at least about $5\times10^{-17}$ mmol N per bacterial cell per hour.

In some embodiments, genetically engineered bacteria of the present disclosure in aggregate produce at least about 15 pounds of fixed N per acre, at least about 20 pounds of fixed N per acre, at least about 25 pounds of fixed N per acre, at least about 30 pounds of fixed N per acre, at least about 35 pounds of fixed N per acre, at least about 40 pounds of fixed N per acre, at least about 45 pounds of fixed N per acre, at least about 50 pounds of fixed N per acre, at least about 55 pounds of fixed N per acre, at least about 60 pounds of fixed N per acre, at least about 65 pounds of fixed N per acre, at least about 70 pounds of fixed N per acre, at least about 75 pounds of fixed N per acre, at least about 80 pounds of fixed N per acre, at least about 85 pounds of fixed N per acre, at least about 90 pounds of fixed N per acre, at least about 95 pounds of fixed N per acre, or at least about 100 pounds of fixed N per acre.

In some embodiments, genetically engineered bacteria of the present disclosure produce fixed N in the amounts disclosed herein over the course of at least about day 0 to about 80 days, at least about day 0 to about 70 days, at least about day 0 to about 60 days, at least about 1 day to about 80 days, at least about 1 day to about 70 days, at least about 1 day to about 60 days, at least about 2 days to about 80 days, at least about 2 days to about 70 days, at least about 2 days to about 60 days, at least about 3 days to about 80 days, at least about 3 days to about 70 days, at least about 3 days to about 60 days, at least about 4 days to about 80 days, at least about 4 days to about 70 days, at least about 4 days to about 60 days, at least about 5 days to about 80 days, at least about 5 days to about 70 days, at least about 5 days to about 60 days, at least about 6 days to about 80 days, at least about 6 days to about 70 days, at least about 6 days to about 60 days, at least about 7 days to about 80 days, at least about 7 days to about 70 days, at least about 7 days to about 60 days, at least about 8 days to about 80 days, at least about 8 days to about 70 days, at least about 8 days to about 60 days, at least about 9 days to about 80 days, at least about 9 days to about 70 days, at least about 9 days to about 60 days, at least about 10 days to about 80 days, at least about 10 days to about 70 days, at least about 10 days to about 60 days, at least about 15 days to about 80 days, at least about 15 days to about 70 days, at least about 15 days to about 60 days, at least about 20 days to about 80 days, at least about 20 days to about 70 days, or at least about 20 days to about 60 days.

In some embodiments, genetically engineered bacteria of the present disclosure produce fixed N in any of the amounts disclosed herein over the course of at least about 80 days: 5 days, at least about 80 days: 10 days, at least about 80 days: 15 days, at least about 80 days 20 days, at least about 75 days 5 days, at least about 75 days 10 days, at least about 75 days 15 days, at least about 75 days 20 days, at least about 70 days 5 days, at least about 70 days 10 days, at least about 70 days 15 days, at least about 70 days±20 days, at least about 60 days±5 days, at least about 60 days±10 days, at least about 60 days±15 days, at least about 60 days±20 days.

In some embodiments, genetically engineered bacteria of the present disclosure produce fixed N in any of the amounts disclosed herein over the course of at least about 10 days to about 80 days, at least about 10 days to about 70 days, or at least about 10 days to about 60 days.

The amount of nitrogen fixation that occurs in the plants described herein may be measured in several ways, for example by an acetylene-reduction (AR) assay. An acetylene-reduction assay can be performed in vitro or in vivo. Evidence that a particular bacterium is providing fixed nitrogen to a plant can include: 1) total plant N significantly increases upon inoculation, preferably with a concomitant increase in N concentration in the plant; 2) nitrogen deficiency symptoms are relieved under N-limiting conditions upon inoculation (which should include an increase in dry matter); 3) $N_2$ fixation is documented through the use of an $^{15}N$ approach (which can be isotope dilution experiments, $^{15}N_2$ reduction assays, or $^{15}N$ natural abundance assays); 4) fixed N is incorporated into a plant protein or metabolite; and 5) all of these effects are not be seen in non-inoculated plants or in plants inoculated with a mutant of the inoculum strain.

The wild-type nitrogen fixation regulatory cascade can be represented as a digital logic circuit where the inputs $O_2$ and $NH_4^+$ pass through a NOR gate, the output of which enters an AND gate in addition to ATP. In some embodiments, the methods disclosed herein disrupt the influence of $NH_4^+$ on this circuit, at multiple points in the regulatory cascade, so that microbes can produce nitrogen even in fertilized fields. However, the methods disclosed herein also envision altering the impact of ATP or $O_2$ on the circuitry, or replacing the circuitry with other regulatory cascades in the cell, or altering genetic circuits other than nitrogen fixation. Gene clusters can be re-engineered to generate functional products under the control of a heterologous regulatory system. By eliminating native regulatory elements outside of, and within, coding sequences of gene clusters, and replacing them with alternative regulatory systems, the functional products of complex genetic operons and other gene clusters can be controlled and/or moved to heterologous cells, including cells of different species other than the species from which the native genes were derived. Once re-engineered, the synthetic gene clusters can be controlled by genetic circuits or other inducible regulatory systems, thereby controlling the products' expression as desired. The expression cassettes can be designed to act as logic gates, pulse generators, oscillators, switches, or memory devices. The controlling expression cassette can be linked to a promoter such that the expression cassette functions as an environmental sensor, such as an oxygen, temperature, touch, osmotic stress, membrane stress, or redox sensor.

As an example, the nifL, nifA, nifT, and nifX genes can be eliminated from the nif gene cluster. Synthetic genes can be designed by codon randomizing the DNA encoding each amino acid sequence. Codon selection is performed, specifying that codon usage be as divergent as possible from the codon usage in the native gene. Proposed sequences are scanned for any undesired features, such as restriction enzyme recognition sites, transposon recognition sites, repetitive sequences, sigma 54 and sigma 70 promoters, cryptic ribosome binding sites, and rho independent terminators. Synthetic ribosome binding sites are chosen to match the strength of each corresponding native ribosome binding site, such as by constructing a fluorescent reporter plasmid in which the 150 bp surrounding a gene's start codon (from −60 to +90) is fused to a fluorescent gene. This chimera can be expressed under control of the Ptac promoter, and fluorescence measured via flow cytometry. To generate synthetic ribosome binding sites, a library of reporter plasmids using 150 bp (−60 to +90) of a synthetic expression cassette is generated. Briefly, a synthetic expression cassette can consist of a random DNA spacer, a degenerate sequence encoding an RBS library, and the coding sequence for each synthetic gene. Multiple clones are screened to identify the synthetic ribosome binding site that best matched the native ribosome binding site. Synthetic operons that consist of the same genes as the native operons are thus constructed and tested for functional complementation. A further exemplary description of synthetic operons is provided in US20140329326.

Systems for plant growth and measurement of nitrogen incorporation can include a chamber, a gas delivery apparatus, a nutrient delivery apparatus. The system includes a chamber with walls that enclose a spatial volume internal to chamber. System also includes a gas delivery apparatus and a nutrient delivery apparatus connected to a controller via control lines. System can optionally include a sampling apparatus.

Chamber can include any number of walls suitable for enclosing spatial volume, and the wall(a)s can define any shape for chamber. In some embodiments, for example, the wall(s) define a cubic or rectangular prismatic shape for chamber. In certain embodiments, the wall(s) define a spherical or elliptical shape for chamber. More generally, the wall(s) can define any regular or irregular shape for chamber.

At least one surface of at least one wall typically supports one or more plants within the enclosed spatial volume. The height h of chamber is the minimum distance between the plant-supporting surface and a wall surface opposite the plant supporting surface. Upward plant growth generally occurs in a direction parallel to height h, and so the height can be selected to accommodate such growth for one or more different plant types. In some embodiments, h can be 0.5 m or more (e.g., 0.6 m or more, 0.7 m or more, 0.8 m or more, 0.9 m or more, 1.0 m or more, 1.5 m or more, 2.0 m or more, 2.5 m or more, 3.0 m or more, 3.5 m or more, 4.0 m or more, 4.5 m or more, 5.0 m or more, 5.5 m or more, 6.0 m or more, 6.5 m or more, 7.0 m or more, 7.5 m or more, 8.0 m or more, 8.5 m or more, 9.0 m or more, 9.5 m or more, 10.0 m or more, or even more).

In certain embodiments, the height h is sufficiently large so that the entire plant is positioned within the enclosed spatial volume. This provides an important advantage relative to measurement systems in which just the plant roots are enclosed. By placing the entire plant within the enclosed spatial volume, direct assessment of the fixation of nitrogen surrounding the entire plant—as is typical under field growing conditions—and subsequent incorporation of reduced nitrogen by plant tissues can be performed.

In general, the enclosed spatial volume of chamber can be selected as desired to accommodate one or more plants and gases delivered to the plants. In some embodiments, for example, the enclosed spatial volume can be 100 L or more (e.g., 200 L or more, 300 L or more, 400 L or more, 500 L or more, 600 L or more, 700 L or more, 800 L or more, 900 L or more, 1000 L or more, 1500 L or more, 2000 L or more, 2500 L or more, 3000 L or more, 4000 L or more, 5000 L or more, 7000 L or more, 10,000 L or more, 15,000 L or more, 20,000 L or more, 30,000 L or more, 50,000 L or more, or even more).

In some embodiments, chamber is relatively airtight, such that a leakage rate of gases from chamber is relatively small. For example, when chamber is filled with a gas such as nitrogen at a pressure of 1.5 atmospheres (e.g., 152 kPa), a leakage rate of the gas from the chamber can be less than 0.5 L/day (e.g., less than 0.3 L/day, less than 0.1 L/day, less than 0.05 L/day, less than 0.01 L/day, less than 0.005 L/day, less than 0.001 L/day). More generally, when chamber is filled with a gas such as nitrogen at a pressure p at a first time, the gas pressure within the chamber at a second time at least 7 days after the first time can be 0.70p or more (e.g., 0.80p or more, 0.85p or more, 0.90p or more, 0.95p or more, 0.98p or more, 0.99p or more, 0.999p or more, 0.9999p or more, or even more).

The walls of chamber can generally be formed from a variety of materials including, but not limited to, various plastics and metals. Mating walls can be joined by bonding, welding, clamping, and other processes to form wall joints. A variety of structural supporting members can be used to reinforce the walls of chamber, and such members can be formed of the same or different materials than the walls.

During operation of system, controller activates the gas delivery apparatus to deliver one or more gases into the enclosed spatial volume of chamber. Gas delivery apparatus can be implemented in different ways. In some embodiments, gas delivery apparatus is positioned within chamber. Alternatively, in certain embodiments, gas delivery apparatus (or a portion thereof) is positioned external to chamber. Gas delivery apparatus can include one or more gas sources, one or more conduits, and one or more valves. Each of the valves can optionally be connected to controller, which activates the valve(s) to regulate gas delivery from the gas delivery apparatus.

Generation of Bacterial Populations

Isolation of Bacteria

Microbes useful in methods and compositions disclosed herein can be obtained by extracting microbes from surfaces or tissues of native plants. Microbes can be obtained by grinding seeds to isolate microbes. Microbes can be obtained by planting seeds in diverse soil samples and recovering microbes from tissues. Additionally, microbes can be obtained by inoculating plants with exogenous microbes and determining which microbes appear in plant tissues. Non-limiting examples of plant tissues may include a seed, seedling, leaf, cutting, plant, bulb, or tuber.

A method of obtaining microbes may be through the isolation of bacteria from soils. Bacteria may be collected from various soil types. In some example, the soil can be characterized by traits such as high or low fertility, levels of moisture, levels of minerals, and various cropping practices. For example, the soil may be involved in a crop rotation where different crops are planted in the same soil in successive planting seasons. The sequential growth of different crops on the same soil may prevent disproportionate depletion of certain minerals. The bacteria can be isolated from the plants growing in the selected soils. The seedling plants can be harvested at 2-6 weeks of growth. For example, at least 400 isolates can be collected in a round of harvest. Soil and plant types reveal the plant phenotype as well as the conditions, which allow for the downstream enrichment of certain phenotypes.

Microbes can be isolated from plant tissues to assess microbial traits. The parameters for processing tissue samples may be varied to isolate different types of associative microbes, such as rhizopheric bacteria, epiphytes, or endophytes. The isolates can be cultured in nitrogen-free media to enrich for bacteria that perform nitrogen fixation. Alternatively, microbes can be obtained from global strain banks.

In planta analytics are performed to assess microbial traits. In some embodiments, the plant tissue can be processed for screening by high throughput processing for DNA and RNA. Additionally, non-invasive measurements can be used to assess plant characteristics, such as colonization. Measurements on wild microbes can be obtained on a plant-by-plant basis. Measurements on wild microbes can also be obtained in the field using medium throughput methods. Measurements can be done successively over time. Model plant system can be used including, but not limited to, *Setaria*.

Microbes in a plant system can be screened via transcriptional profiling of a microbe in a plant system. Examples of screening through transcriptional profiling are using methods of quantitative polymerase chain reaction (qPCR), molecular barcodes for transcript detection, Next Generation Sequencing, and microbe tagging with fluorescent markers. Impact factors can be measured to assess colonization in the greenhouse including, but not limited to, microbiome, abiotic factors, soil conditions, oxygen, moisture, temperature, inoculum conditions, and root localization. Nitrogen fixation can be assessed in bacteria by measuring 15N gas/fertilizer (dilution) with IRMS or NanoSIMS as described herein NanoSIMS is high-resolution secondary ion mass spectrometry. The NanoSIMS technique is a way to investigate chemical activity from biological samples. The catalysis of reduction of oxidation reactions that drive the metabolism of microorganisms can be investigated at the cellular, subcellular, molecular and elemental level. NanoSIMS can provide high spatial resolution of greater than 0.1 μm. NanoSIMS can detect the use of isotope tracers such as $^{13}C$, $^{15}N$, and $^{18}O$. Therefore, NanoSIMS can be used to the chemical activity nitrogen in the cell.

Automated greenhouses can be used for planta analytics. Plant metrics in response to microbial exposure include, but are not limited to, biomass, chloroplast analysis, CCD camera, volumetric tomography measurements.

One way of enriching a microbe population is according to genotype. For example, a polymerase chain reaction (PCR) assay with a targeted primer or specific primer. Primers designed for the nifH gene can be used to identity diazotrophs because diazotrophs express the nifH gene in the process of nitrogen fixation. A microbial population can also be enriched via single-cell culture-independent approaches and chemotaxis-guided isolation approaches. Alternatively, targeted isolation of microbes can be performed by culturing the microbes on selection media. Premeditated approaches to enriching microbial populations for desired traits can be guided by bioinformatics data and are described herein.

Enriching for Microbes with Nitrogen Fixation Capabilities Using Bioinformatics

Bioinformatic tools can be used to identify and isolate plant growth promoting *rhizobacteria*, which are selected based on their ability to perform nitrogen fixation. Microbes with high nitrogen fixing ability can promote favorable traits in plants. Bioinformatic modes of analysis for the identification of *rhizobacteria* include, but are not limited to, genomics, metagenomics, targeted isolation, gene sequencing, transcriptome sequencing, and modeling.

Genomics analysis can be used to identify *rhizobacteria* and confirm the presence of mutations with methods of Next Generation Sequencing as described herein and microbe version control.

Metagenomics can be used to identify and isolate *rhizobacteria* using a prediction algorithm for colonization. Metadata can also be used to identify the presence of an engineered strain in environmental and greenhouse samples.

Transcriptomic sequencing can be used to predict genotypes leading to *rhizobacteria* phenotypes. Additionally, transcriptomic data is used to identify promoters for altering gene expression. Transcriptomic data can be analyzed in conjunction with the Whole Genome Sequence (WGS) to generate models of metabolism and gene regulatory networks.

Domestication of Microbes

Microbes isolated from nature can undergo a domestication process wherein the microbes are converted to a form that is genetically trackable and identifiable. One way to domesticate a microbe is to engineer it with antibiotic resistance. The process of engineering antibiotic resistance can begin by determining the antibiotic sensitivity in the wild type microbial strain. If the bacteria are sensitive to the antibiotic, then the antibiotic can be a good candidate for antibiotic resistance engineering. Subsequently, an antibiotic resistant gene or a counterselectable suicide vector can be incorporated into the genome of a microbe using recombineering methods. A counterselectable suicide vector may consist of a deletion of the gene of interest, a selectable marker, and the counterselectable marker sacB. Counterselection can be used to exchange native microbial DNA sequences with antibiotic resistant genes. A medium throughput method can be used to evaluate multiple microbes simultaneously allowing for parallel domestication. Alternative methods of domestication include the use of homing nucleases to prevent the suicide vector sequences from looping out or from obtaining intervening vector sequences.

DNA vectors can be introduced into bacteria via several methods including electroporation and chemical transformations. A standard library of vectors can be used for transformations. An example of a method of gene editing is CRISPR preceded by Cas9 testing to ensure activity of Cas9 in the microbes.

Non-Transgenic Engineering of Microbes

A microbial population with favorable traits can be obtained via directed evolution. Direct evolution is an approach wherein the process of natural selection is mimicked to evolve proteins or nucleic acids towards a user-defined goal. An example of direct evolution is when random mutations are introduced into a microbial population, the microbes with the most favorable traits are selected, and the growth of the selected microbes is continued. The most favorable traits in *rhizobacteria* can be in nitrogen fixation. The method of directed evolution may be iterative and adaptive based on the selection process after each iteration.

*Rhizobacteria* with high capability of nitrogen fixation can be generated. The evolution of *rhizobacteria* can be carried out via the introduction of genetic modification. Genetic modification can be introduced via polymerase chain reaction mutagenesis, oligonucleotide-directed mutagenesis, saturation mutagenesis, fragment shuffling mutagenesis, homologous recombination, CRISPR/Cas9 systems, chemical mutagenesis, and combinations thereof. These approaches can introduce random mutations into the microbial population. For example, mutants can be generated using synthetic DNA or RNA via oligonucleotide-directed mutagenesis. Mutants can be generated using tools contained on plasmids, which are later cured. Genes of interest can be identified using libraries from other species with improved traits including, but not limited to, improved

*rhizobacteria* properties, improved colonization of cereals, increased oxygen sensitivity, increased nitrogen fixation, and increased ammonia excretion. Intrageneric genes can be designed based on these libraries using software such as Geneious or Platypus design software. Mutations can be designed with the aid of machine learning. Mutations can be designed with the aid of a metabolic model. Automated design of the mutation can be done using a la Platypus and will guide RNAs for Cas-directed mutagenesis.

The intra-generic genes can be transferred into the host microbe. Additionally, reporter systems can also be transferred to the microbe. The reporter systems characterize promoters, determine the transformation success, screen mutants, and act as negative screening tools.

The microbes carrying the mutation can be cultured via serial passaging. A microbial colony contains a single variant of the microbe. Microbial colonies are screened with the aid of an automated colony picker and liquid handler. Mutants with gene duplication and increased copy number express a higher genotype of the desired trait.

Selection of Plant Growth Promoting Microbes Based on Nitrogen Fixation

The microbial colonies can be screened using various assays to assess nitrogen fixation. One way to measure nitrogen fixation is via a single fermentative assay, which measures nitrogen excretion. An alternative method is the acetylene reduction assay (ARA) with in-line sampling over time. ARA can be performed in high throughput plates of microtube arrays. ARA can be performed with live plants and plant tissues. The media formulation and media oxygen concentration can be varied in ARA assays. Another method of screening microbial variants is by using biosensors. The use of NanoSIMS and Raman microspectroscopy can be used to investigate the activity of the microbes. In some cases, bacteria can also be cultured and expanded using methods of fermentation in bioreactors. The bioreactors are designed to improve robustness of bacteria growth and to decrease the sensitivity of bacteria to oxygen. Medium to high TP plate-based microfermentors are used to evaluate oxygen sensitivity, nutritional needs, nitrogen fixation, and nitrogen excretion. The bacteria can also be co-cultured with competitive or beneficial microbes to elucidate cryptic pathways. Flow cytometry can be used to screen for bacteria that produce high levels of nitrogen using chemical, colorimetric, or fluorescent indicators. The bacteria may be cultured in the presence or absence of a nitrogen source. For example, the bacteria may be cultured with glutamine, ammonia, urea or nitrates.

Guided Microbial Remodeling—An Overview

Guided microbial remodeling is a method to systematically identify and improve the role of species within the crop microbiome. In some embodiments, and according to a particular methodology of grouping/categorization, the method comprises three steps: 1) selection of candidate species by mapping plant-microbe interactions and predicting regulatory networks linked to a particular phenotype, 2) pragmatic and predictable improvement of microbial phenotypes through intra-species crossing of regulatory networks and gene clusters within a microbe's genome, and 3) screening and selection of new microbial genotypes that produce desired crop phenotypes.

To systematically assess the improvement of strains, a model is created that links colonization dynamics of the microbial community to genetic activity by key species. The model is used to predict genetic targets for non-intergeneric genetic remodeling (i.e. engineering the genetic architecture of the microbe in a non-transgenic fashion). Rational improvement of the crop microbiome can be used to increase soil biodiversity, tune impact of keystone species, and/or alter timing and expression of important metabolic pathways.

The aforementioned "Guided Microbial Remodeling" process is further elaborated upon in International Publication Nos. WO 2020/006246 and WO 2020/014498, each of which are incorporated by reference herein in their entireties. The genetically engineered bacteria of the present disclosure can be generating using a suicide plasmid, e.g., as described in International Publication No. WO 2020/00624.

Serial Passage

Production of bacteria to improve plant traits (e.g., nitrogen fixation) can be achieved through serial passage. The production of this bacteria can be done by selecting plants, which have a particular improved trait that is influenced by the microbial flora, in addition to identifying bacteria and/or compositions that are capable of imparting one or more improved traits to one or more plants. One method of producing a bacteria to improve a plant trait includes the steps of: (a) isolating bacteria from tissue or soil of a first plant; (b) introducing a genetic modification into one or more of the bacteria to produce one or more variant bacteria; (c) exposing a plurality of plants to the variant bacteria; (d) isolating bacteria from tissue or soil of one of the plurality of plants, wherein the plant from which the bacteria is isolated has an improved trait relative to other plants in the plurality of plants; and (e) repeating steps (b) to (d) with bacteria isolated from the plant with an improved trait (step (d)). Steps (b) to (d) can be repeated any number of times (e.g., once, twice, three times, four times, five times, ten times, or more) until the improved trait in a plant reaches a desired level. Further, the plurality of plants can be more than two plants, such as 10 to 20 plants, or 20 or more, 50 or more, 100 or more, 300 or more, 500 or more, or 1000 or more plants.

In addition to obtaining a plant with an improved trait, a bacterial population comprising bacteria comprising one or more genetic modifications introduced into one or more genes (e.g., genes regulating nitrogen fixation) is obtained. By repeating the steps described above, a population of bacteria can be obtained that include the most appropriate members of the population that correlate with a plant trait of interest. The bacteria in this population can be identified and their beneficial properties determined, such as by genetic and/or phenotypic analysis. Genetic analysis may occur of isolated bacteria in step (a). Phenotypic and/or genotypic information may be obtained using techniques including: high through-put screening of chemical components of plant origin, sequencing techniques including high throughput sequencing of genetic material, differential display techniques (including DDRT-PCR, and DD-PCR), nucleic acid microarray techniques, RNA-sequencing (Whole Transcriptome Shotgun Sequencing), and qRT-PCR (quantitative real time PCR). Information gained can be used to obtain community profiling information on the identity and activity of bacteria present, such as phylogenetic analysis or microarray-based screening of nucleic acids coding for components of rRNA operons or other taxonomically informative loci. Examples of taxonomically informative loci include 16S rRNA gene, 23S rRNA gene, 5S rRNA gene, 5.8S rRNA gene, 12S rRNA gene, 18S rRNA gene, 28S rRNA gene, gyrB gene, rpoB gene, fusA gene, recA gene, coxl gene, nifD gene. Example processes of taxonomic profiling to determine taxa present in a population are described in US20140155283. Bacterial identification may comprise characterizing activity of one or more genes or one or more signaling pathways, such as genes associated with the nitrogen fixation pathway. Synergistic interactions (where two components, by virtue of their combination, increase a desired effect by more than an additive amount) between different bacterial species may also be present in the bacterial populations.

Genetic Modification—Locations and Sources of Genomic Alteration

The genetic modification may be a gene selected from the group consisting of: nifA, nifL, ntrB, ntrC, glnA, glnB, glnK, draT, amtB, glnD, glnE, nifJ, nifH, nifD, nifK, nifY, nifE, nifN, nifU, nifS, nifV, nifW, nifZ, nifM, niff, nifB, and nifQ. The genetic modification may be a modification in a gene encoding a protein with functionality selected from the group consisting of: glutamine synthetase, glutaminase, glutamine synthetase adenylyltransferase, transcriptional activator, anti-transcriptional activator, pyruvate flavodoxin oxidoreductase, flavodoxin, and NAD+-dinitrogen-reductase aDP-D-ribosyltransferase. The genetic modification may be a mutation that results in one or more of: increased expression or activity of NifA or glutaminase; decreased expression or activity of NifL, NtrB, glutamine synthetase, GlnB, GinK, DraT, AmtB; decreased adenylyl-removing activity of GlnE; or decreased uridylyl-transferase activity of GlnD. The genetic modification can be a modification in a gene selected from the group consisting of: bcsii, bcsiii, yjbE, jhaB, pehA, otsB, treZ, glsA2, and combinations thereof. In some embodiments, a genetic modification can be a modification in any of the genes described throughout this disclosure.

Introducing a genetic modification may comprise insertion and/or deletion of one or more nucleotides at a target site, such as 1, 2, 3, 4, 5, 10, 25, 50, 100, 250, 500, or more nucleotides. The genetic modification introduced into one or more bacteria of the methods disclosed herein may be a knock-out mutation (e.g. deletion of a promoter, insertion or deletion to produce a premature stop codon, deletion of an entire gene), or it may be elimination or abolishment of activity of a protein domain (e.g. point mutation affecting an active site, or deletion of a portion of a gene encoding the relevant portion of the protein product), or it may alter or abolish a regulatory sequence of a target gene. One or more regulatory sequences may also be inserted, including heterologous regulatory sequences and regulatory sequences found within a genome of a bacterial species or genus corresponding to the bacteria into which the genetic modification is introduced. Moreover, regulatory sequences may be selected based on the expression level of a gene in a bacterial culture or within a plant tissue. The genetic modification may be a pre-determined genetic modification that is specifically introduced to a target site. The genetic modification may be a random mutation within the target site. The genetic modification may be an insertion or deletion of one or more nucleotides. In some cases, a plurality of different genetic modifications (e.g. 2, 3, 4, 5, 10, or more) are introduced into one or more of the isolated bacteria before exposing the bacteria to plants for assessing trait improvement. The plurality of genetic modifications can be any of the above types, the same or different types, and in any combination. In some cases, a plurality of different genetic modifications are introduced serially, introducing a first genetic modification after a first isolation step, a second genetic modification after a second isolation step, and so forth so as to accumulate a plurality of genetic modifications in bacteria imparting progressively improved traits on the associated plants.

Genetic Modification—Methods of Introducing Genomic Alteration

Genetic modifications can have any number of effects, such as the increase or decrease of some biological activity, including gene expression, metabolism, and cell signaling. Genetic modifications can be specifically introduced to a target site, or introduced randomly. A variety of molecular tools and methods are available for introducing genetic modification. For example, genetic modification can be introduced via polymerase chain reaction mutagenesis, oligonucleotide-directed mutagenesis, saturation mutagenesis, fragment shuffling mutagenesis, homologous recombination, recombineering, lambda red mediated recombination, CRISPR/Cas9 systems, chemical mutagenesis, and combinations thereof. Chemical methods of introducing genetic modification include exposure of DNA to a chemical mutagen, e.g., ethyl methanesulfonate (EMS), methyl methanesulfonate (MMS), N-nitrosourea (EN U), N-methyl-N-nitro-N'-nitrosoguanidine, 4-nitroquinoline N-oxide, diethylsulfate, benzopyrene, cyclophosphamide, bleomycin, triethylmelamine, acrylamide monomer, nitrogen mustard, vincristine, diepoxyalkanes (for example, diepoxybutane), ICR-170, formaldehyde, procarbazine hydrochloride, ethylene oxide, dimethylnitrosamine, 7,12 dimethylbenz(a)anthracene, chlorambucil, hexamethylphosphoramide, bisulfan, and the like. Radiation mutation-inducing agents include ultraviolet radiation, γ-irradiation, X-rays, and fast neutron bombardment. Genetic modification can also be introduced into a nucleic acid using, e.g., trimethylpsoralen with ultraviolet light. Random or targeted insertion of a mobile DNA element, e.g., a transposable element, is another suitable method for generating genetic modification. Genetic modifications can be introduced into a nucleic acid during amplification in a cell-free in vitro system, e.g., using a polymerase chain reaction (PCR) technique such as error-prone PCR. Genetic modifications can be introduced into a nucleic acid in vitro using DNA shuffling techniques (e.g., exon shuffling, domain swapping, and the like). Genetic modifications can also be introduced into a nucleic acid as a result of a deficiency in a DNA repair enzyme in a cell, e.g., the presence in a cell of a mutant gene encoding a mutant DNA repair enzyme is expected to generate a high frequency of mutations (i.e., about 1 mutation/100 genes-1 mutation/10,000 genes) in the genome of the cell. Examples of genes encoding DNA repair enzymes include but are not limited to Mut H, Mut S, Mut L, and Mut U, and the homologs thereof in other species (e.g., MSH 1 6, PMS 1 2, MLH 1, GTBP, ERCC-1, and the like). Example descriptions of various methods for introducing genetic modifications are provided in e.g., Stemple (2004) Nature 5:1-7; Chiang et al. (1993) PCR Methods Appl 2(3): 210-217; Stemmer (1994) Proc. Natl. Acad. Sci. USA 91:10747-10751; and U.S. Pat. Nos. 6,033,861, and 6,773,900.

Genetic modifications introduced into microbes may be classified as transgenic, cisgenic, intragenomic, intrageneric, intergeneric, synthetic, evolved, rearranged, or SNPs.

Genetic modification may be introduced into numerous metabolic pathways within microbes to elicit improvements in the traits described above. Representative pathways include sulfur uptake pathways, glycogen biosynthesis, the glutamine regulation pathway, the molybdenum uptake pathway, the nitrogen fixation pathway, ammonia assimilation, ammonia excretion or secretion, Nitrogen uptake, glutamine biosynthesis, colonization pathways, annamox, phosphate solubilization, organic acid transport, organic acid production, agglutinins production, reactive oxygen radical scavenging genes, Indole Acetic Acid biosynthesis, trehalose biosynthesis, plant cell wall degrading enzymes or pathways, root attachment genes, exopolysaccharide secretion, glutamate synthase pathway, iron uptake pathways, siderophore pathway, chitinase pathway, ACC deaminase, glutathione biosynthesis, phosphorous signaling genes, quorum quenching pathway, cytochrome pathways, hemoglobin pathway, bacterial hemoglobin-like pathway, small RNA rsmZ, rhizobitoxine biosynthesis, lapA adhesion protein, AHL quorum sensing pathway, phenazine biosynthesis, cyclic lipopeptide biosynthesis, and antibiotic production.

CRISPR/Cas9 (Clustered regularly interspaced short palindromic repeats)/CRISPR-associated (Cas) systems can be used to introduce desired mutations. CRISPR/Cas9 provide bacteria and archaea with adaptive immunity against viruses and plasmids by using CRISPR RNAs (crRNAs) to guide the silencing of invading nucleic acids. The Cas9 protein (or functional equivalent and/or variant thereof, i.e., Cas9-like protein) naturally contains DNA endonuclease activity that depends on the association of the protein with two naturally occurring or synthetic RNA molecules called crRNA and tracrRNA (also called guide RNAs). In some cases, the two molecules are covalently link to form a single molecule (also called a single guide RNA ("sgRNA"). Thus, the Cas9 or Cas9-like protein associates with a DNA-targeting RNA (which term encompasses both the two-molecule guide RNA configuration and the single-molecule guide RNA configuration), which activates the Cas9 or Cas9-like protein and guides the protein to a target nucleic acid sequence. If the Cas9 or Cas9-like protein retains its natural enzymatic function, it will cleave target DNA to create a double-stranded break, which can lead to genome alteration (i.e., editing: deletion, insertion (when a donor polynucleotide is present), replacement, etc.), thereby altering gene expression. Some variants of Cas9 (which variants are encompassed by the term Cas9-like) have been altered such that they have a decreased DNA cleaving activity (in some cases, they cleave a single strand instead of both strands of the target DNA, while in other cases, they have severely reduced to no DNA cleavage activity). Further exemplary descriptions of CRISPR systems for introducing genetic modification can be found in, e.g. U.S. Pat. No. 8,795,965.

As a cyclic amplification technique, polymerase chain reaction (PCR) mutagenesis uses mutagenic primers to introduce desired mutations. PCR is performed by cycles of denaturation, annealing, and extension. After amplification by PCR, selection of mutated DNA and removal of parental plasmid DNA can be accomplished by: 1) replacement of dCTP by hydroxymethylated-dCTP during PCR, followed by digestion with restriction enzymes to remove non-hydroxymethylated parent DNA only; 2) simultaneous mutagenesis of both an antibiotic resistance gene and the studied gene changing the plasmid to a different antibiotic resistance, the new antibiotic resistance facilitating the selection of the desired mutation thereafter; 3) after introducing a desired mutation, digestion of the parent methylated template DNA by restriction enzyme Dpnl which cleaves only methylated DNA, by which the mutagenized unmethylated chains are recovered; or 4) circularization of the mutated PCR products in an additional ligation reaction to increase the transformation efficiency of mutated DNA. Further description of exemplary methods can be found in e.g. U.S. Pat. Nos. 7,132,265, 6,713,285, 6,673,610, 6,391,548, 5,789,166, 5,780,270, 5,354,670, 5,071,743, and US20100267147.

Oligonucleotide-directed mutagenesis, also called site-directed mutagenesis, typically utilizes a synthetic DNA primer. This synthetic primer contains the desired mutation and is complementary to the template DNA around the mutation site so that it can hybridize with the DNA in the gene of interest. The mutation may be a single base change (a point mutation), multiple base changes, deletion, or insertion, or a combination of these. The single-strand primer is then extended using a DNA polymerase, which copies the rest of the gene. The gene thus copied contains the mutated site, and may then be introduced into a host cell as a vector and cloned. Finally, mutants can be selected by DNA sequencing to check that they contain the desired mutation.

Genetic modifications can be introduced using error-prone PCR. In this technique the gene of interest is amplified using a DNA polymerase under conditions that are deficient in the fidelity of replication of sequence. The result is that the amplification products contain at least one error in the sequence. When a gene is amplified and the resulting product(s) of the reaction contain one or more alterations in sequence when compared to the template molecule, the resulting products are mutagenized as compared to the template. Another means of introducing random mutations is exposing cells to a chemical mutagen, such as nitrosogua-nidine or ethyl methanesulfonate (Nestmann, Mutat Res 1975 June; 28(3):323-30), and the vector containing the gene is then isolated from the host.

Saturation mutagenesis is another form of random muta-genesis, in which one tries to generate all or nearly all possible mutations at a specific site, or narrow region of a gene. In a general sense, saturation mutagenesis is com-prised of mutagenizing a complete set of mutagenic cas-settes (wherein each cassette is, for example, 1-500 bases in length) in defined polynucleotide sequence to be mutagen-ized (wherein the sequence to be mutagenized is, for example, from 15 to 100,000 bases in length). Therefore, a group of mutations (e.g. ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons, and groupings of particular nucleotide cassettes.

Fragment shuffling mutagenesis, also called DNA shuf-fling, is a way to rapidly propagate beneficial mutations. In an example of a shuffling process, DNAse is used to fragment a set of parent genes into pieces of e.g. about 50-100 bp in length. This is then followed by a polymerase chain reaction (PCR) without primers—DNA fragments with sufficient overlapping homologous sequence will anneal to each other and are then be extended by DNA polymerase. Several rounds of this PCR extension are allowed to occur, after some of the DNA molecules reach the size of the parental genes. These genes can then be amplified with another PCR, this time with the addition of primers that are designed to complement the ends of the strands. The primers may have additional sequences added to their 5' ends, such as sequences for restriction enzyme recognition sites needed for ligation into a cloning vector. Further examples of shuffling techniques are provided in US20050266541.

Homologous recombination mutagenesis involves recom-bination between an exogenous DNA fragment and the targeted polynucleotide sequence. After a double-stranded break occurs, sections of DNA around the 5' ends of the break are cut away in a process called resection. In the strand invasion step that follows, an overhanging 3' end of the broken DNA molecule then "invades" a similar or identical DNA molecule that is not broken. The method can be used to delete a gene, remove exons, add a gene, and introduce point mutations. Homologous recombination mutagenesis can be permanent or conditional. Typically, a recombination template is also provided. A recombination template may be a component of another vector, contained in a separate vector, or provided as a separate polynucleotide. In some embodiments, a recombination template is designed to serve as a template in homologous recombination, such as within or near a target sequence nicked or cleaved by a site-specific nuclease. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence. Non-limiting examples of site-directed nucleases useful in methods of homologous recombination include zinc finger nucleases, CRISPR nucleases, TALE nucleases, and meganuclease. For a further description of the use of such nucleases, see e.g. U.S. Pat. No. 8,795,965 and US20140301990.

Mutagens that create primarily point mutations and short deletions, insertions, transversions, and/or transitions, including chemical mutagens or radiation, may be used to create genetic modifications. Mutagens include, but are not limited to, ethyl methanesulfonate, methylmethane sulfonate, N-ethyl-N-nitrosurea, triethylmelamine, N-methyl-N-nitrosourea, procarbazine, chlorambucil, cyclophosphamide, diethyl sulfate, acrylamide monomer, melphalan, nitrogen mustard, vincristine, dimethylnitro-samine, N-methyl-N'-nitro-Nitrosoguanidine, nitrosoguani-dine, 2-aminopurine, 7,12 dimethyl-benz(a)anthracene, eth-ylene oxide, hexamethylphosphoramide, bisulfan, diepoxyalkanes (diepoxyoctane, diepoxybutane, and the like), 2-methoxy-6-chloro-9[3-(ethyl-2-chloro-ethyl)amino-propylamino]acridine dihydrochloride and formaldehyde.

Introducing genetic modification may be an incomplete process, such that some bacteria in a treated population of bacteria carry a desired mutation while others do not. In some cases, it is desirable to apply a selection pressure so as to enrich for bacteria carrying a desired genetic modifica-tion. Traditionally, selection for successful genetic variants involved selection for or against some functionality imparted or abolished by the genetic modification, such as in the case of inserting antibiotic resistance gene or abolishing a metabolic activity capable of converting a non-lethal compound into a lethal metabolite. It is also possible to apply a selection pressure based on a polynucleotide sequence itself, such that only a desired genetic modification need be introduced (e.g. without also requiring a selectable marker). In this case, the selection pressure can comprise cleaving genomes lacking the genetic modification intro-duced to a target site, such that selection is effectively directed against the reference sequence into which the genetic modification is sought to be introduced. Typically, cleavage occurs within 100 nucleotides of the target site (e.g. within 75, 50, 25, 10, or fewer nucleotides from the target site, including cleavage at or within the target site). Cleaving may be directed by a site-specific nuclease selected from the group consisting of a Zinc Finger nuclease, a CRISPR nuclease, a TALE nuclease (TALEN), and a meganuclease. Such a process is similar to processes for enhancing homologous recombination at a target site, except that no template for homologous recombination is provided. As a result, bacteria lacking the desired genetic modification are more likely to undergo cleavage that, left unrepaired, results in cell death. Bacteria surviving selection may then be isolated for use in exposing to plants for assessing conferral of an improved trait.

A CRISPR nuclease may be used as the site-specific nuclease to direct cleavage to a target site. An improved selection of mutated microbes can be obtained by using Cas9 to kill non-mutated cells. Plants are then inoculated with the mutated microbes to re-confirm symbiosis and create evolutionary pressure to select for efficient symbionts. Microbes can then be re-isolated from plant tissues. CRISPR nuclease systems employed for selection against non-variants can employ similar elements to those described above with respect to introducing genetic modification, except that no template for homologous recombination is provided. Cleavage directed to the target site thus enhances death of affected cells.

Other options for specifically inducing cleavage at a target site are available, such as zinc finger nucleases, TALE nuclease (TALEN) systems, and meganuclease. Zinc-finger nucleases (ZFNs) are artificial DNA endonucleases generated by fusing a zinc finger DNA binding domain to a DNA cleavage domain. ZFNs can be engineered to target desired DNA sequences and this enables zinc-finger nucleases to cleave unique target sequences. When introduced into a cell, ZFNs can be used to edit target DNA in the cell (e.g., the cell's genome) by inducing double stranded breaks. Transcription activator-like effector nucleases (TALENs) are artificial DNA endonucleases generated by fusing a TAL (Transcription activator-like) effector DNA binding domain to a DNA cleavage domain. TALENS can be quickly engineered to bind practically any desired DNA sequence and when introduced into a cell, TALENs can be used to edit target DNA in the cell (e.g., the cell's genome) by inducing double strand breaks. Meganucleases (homing endonuclease) are endodeoxyribonucleases characterized by a large recognition site (double-stranded DNA sequences of 12 to 40 base pairs. Meganucleases can be used to replace, eliminate or modify sequences in a highly targeted way. By modifying their recognition sequence through protein engineering, the targeted sequence can be changed. Meganucleases can be used to modify all genome types, whether bacterial, plant or animal and are commonly grouped into four families: the LAGLIDADG family (SEQ ID NO: 8), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII.

Genetic Modification—Methods of Identification

The microbes of the present disclosure can be identified by one or more genetic modifications or alterations, which have been introduced into the microbe. One method by which a genetic modification or alteration can be identified is via reference to a SEQ ID NO that contains a portion of the microbe's genomic sequence that is sufficient to identify the genetic modification or alteration.

Further, in the case of microbes that have not had a genetic modification or alteration (e.g. a wild type, WT) introduced into their genomes, the disclosure can utilize 16S nucleic acid sequences to identify said microbes. A 16S nucleic acid sequence is an example of a "molecular marker" or "genetic marker," which refers to an indicator that can be used in methods for visualizing differences in species of bacteria. Examples of other such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location. Markers further can include polynucleotide sequences encoding 16S or 18S rRNA, and internal transcribed spacer (ITS) sequences, which are sequences found between small-subunit and large-subunit rRNA genes that have proven to be especially useful in elucidating relationships or distinctions when compared against one another. Furthermore, the disclosure utilizes unique sequences found in genes of interest (e.g. nifH, nifD, nifK, nifL, nifA, glnE, amtB, etc.) to identify microbes disclosed herein.

The primary structure of the major rRNA subunit 16S comprises a particular combination of conserved, variable, and hypervariable regions that evolve at different rates and can enable the resolution of both very ancient lineages such as domains, and more modern lineages such as genera. The secondary structure of the 16S subunit includes approximately 50 helices that result in base pairing of about 67% of the residues. These highly conserved secondary structural features are of great functional importance and can be used to ensure positional homology in multiple sequence alignments and phylogenetic analysis. Over the previous few decades, the 16S rRNA gene has become the most sequenced taxonomic marker and is the cornerstone for the current systematic classification of bacteria and archaea (Yarza et al. 2014. Nature Rev. Micro. 12:635-45).

Genetic Modification—Methods of Detection: Primers, Probes, and Assays

The present disclosure provides primers, probes, and assays that are useful for detecting the microbes taught herein. In some embodiments, the disclosure provides for methods of detecting the WT parental strains. In some embodiments, the disclosure provides for methods of detecting the non-intergeneric engineered microbes derived from the WT strains. In some embodiments, the present disclosure provides methods of identifying non-intergeneric genetic alterations in a microbe.

In some embodiments, the genomic engineering methods of the present disclosure lead to the creation of non-natural nucleotide "junction" sequences in the derived non-intergeneric microbes. These non-naturally occurring nucleotide junctions can be used as a type of diagnostic that is indicative of the presence of a particular genetic alteration in a microbe taught herein.

The present techniques are able to detect these non-naturally occurring nucleotide junctions via the utilization of specialized quantitative PCR methods, including uniquely designed primers and probes. In some embodiments, the probes of the disclosure bind to the non-naturally occurring nucleotide junction sequences. In some embodiments, traditional PCR is utilized. In some embodiments, real-time PCR is utilized. In some embodiments, quantitative PCR (qPCR) is utilized.

Thus, the disclosure can cover the utilization of two common methods for the detection of PCR products in real-time: (1) non-specific fluorescent dyes that intercalate with any double-stranded DNA, and (2) sequence-specific DNA probes consisting of oligonucleotides that are labelled with a fluorescent reporter which permits detection only after hybridization of the probe with its complementary sequence. In some embodiments, only the non-naturally occurring nucleotide junction will be amplified via the taught primers, and consequently can be detected either via a non-specific dye, or via the utilization of a specific hybridization probe. In some embodiments, the primers of the disclosure are chosen such that the primers flank either side of a junction sequence, such that if an amplification reaction occurs, then said junction sequence is present.

Some embodiments of the disclosure involve non-naturally occurring nucleotide junction sequence molecules per se, along with other nucleotide molecules that are capable of binding to said non-naturally occurring nucleotide junction sequences under mild to stringent hybridization conditions. In some embodiments, the nucleotide molecules that are capable of binding to said non-naturally occurring nucleotide junction sequences under mild to stringent hybridization conditions are termed "nucleotide probes."

In some embodiments, genomic DNA can be extracted from samples and used to quantify the presence of microbes of the disclosure by using qPCR. The primers utilized in the qPCR reaction can be primers designed by Primer Blast (www.ncbi.nlm.nih.gov/tools/primer-blast/) to amplify unique regions of the wild-type genome or unique regions of the engineered non-intergeneric mutant strains. The qPCR reaction can be carried out using the SYBR GreenER qPCR SuperMix Universal (Thermo Fisher PIN 11762100) kit, using only forward and reverse amplification primers; alternatively, the Kapa Probe Force kit (Kapa Biosystems PIN KK4301) can be used with amplification primers and a TaqMan probe containing a FAM dye label at the 5' end, an internal ZEN quencher, and a minor groove binder and fluorescent quencher at the 3' end (Integrated DNA Technologies).

qPCR reaction efficiency can be measured using a standard curve generated from a known quantity of gDNA from the target genome. Data can be normalized to genome copies per g fresh weight using the tissue weight and extraction volume.

Quantitative polymerase chain reaction (qPCR) is a method of quantifying, in real time, the amplification of one or more nucleic acid sequences. The real time quantification of the PCR assay permits determination of the quantity of nucleic acids being generated by the PCR amplification steps by comparing the amplifying nucleic acids of interest and an appropriate control nucleic acid sequence, which can act as a calibration standard.

TaqMan probes are often utilized in qPCR assays that require an increased specificity for quantifying target nucleic acid sequences. TaqMan probes comprise an oligonucleotide probe with a fluorophore attached to the 5' end and a quencher attached to the 3' end of the probe. When the TaqMan probes remain as is with the 5' and 3' ends of the probe in close contact with each other, the quencher prevents fluorescent signal transmission from the fluorophore. TaqMan probes are designed to anneal within a nucleic acid region amplified by a specific set of primers. As the Taq polymerase extends the primer and synthesizes the nascent strand, the 5' to 3' exonuclease activity of the Taq polymerase degrades the probe that annealed to the template. This probe degradation releases the fluorophore, thus breaking the close proximity to the quencher and allowing fluorescence of the fluorophore. Fluorescence detected in the qPCR assay is directly proportional to the fluorophore released and the amount of DNA template present in the reaction.

The features of qPCR can allow the practitioner to eliminate the labor-intensive post-amplification step of gel electrophoresis preparation, which is generally required for observation of the amplified products of traditional PCR assays. The benefits of qPCR over conventional PCR can be considerable, and include increased speed, ease of use, reproducibility, and quantitative ability.

Improvement of Traits

Methods of the present disclosure may be employed to introduce or improve one or more of a variety of desirable traits. Examples of traits that may introduced or improved include: root biomass, root length, height, shoot length, leaf number, water use efficiency, overall biomass, yield, fruit size, grain size, photosynthesis rate, tolerance to drought, heat tolerance, salt tolerance, resistance to nematode stress, resistance to a fungal pathogen, resistance to a bacterial pathogen, resistance to a viral pathogen, level of a metabolite, and proteome expression. The desirable traits, including height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof, can be used to measure growth, and compared with the growth rate of reference agricultural plants (e.g., plants without the improved traits) grown under identical conditions.

In some embodiments, a trait to be introduced or improved is nitrogen fixation, as described herein. In some embodiments, a trait to be introduced or improved is colonization potential, as described herein. In some embodiments, a plant resulting from the methods described herein exhibits a difference in the trait that is at least about 5% greater, for example at least about 5%, at least about 8%, at least about 10%, at least about 15%, at least about 20%, at least about 25%, at least about 30%, at least about 40%, at least about 50%, at least about 60%, at least about 75%, at least about 80%, at least about 80%, at least about 90%, or at least 100%, at least about 200%, at least about 300%, at least about 400% or greater than a reference agricultural plant grown under the same conditions in the soil. In additional examples, a plant resulting from the methods described herein exhibits a difference in the trait that is at least about 5% greater, for example at least about 5%, at least about 8%, at least about 10%, at least about 15%, at least about 20%, at least about 25%, at least about 30%, at least about 40%, at least about 50%, at least about 60%, at least about 75%, at least about 80%, at least about 80%, at least about 90%, or at least 100%, at least about 200%, at least about 300%, at least about 400% or greater than a reference agricultural plant grown under similar conditions in the soil.

The trait to be improved may be assessed under conditions including the application of one or more biotic or abiotic stressors. Examples of stressors include abiotic stresses (such as heat stress, salt stress, drought stress, cold stress, and low nutrient stress) and biotic stresses (such as nematode stress, insect herbivory stress, fungal pathogen stress, bacterial pathogen stress, and viral pathogen stress).

The trait improved by methods and compositions of the present disclosure may be nitrogen fixation, including in a plant not previously capable of nitrogen fixation. In some cases, bacteria isolated according to a method described herein produce 1% or more (e.g. 2%, 3%, 4%, 5%, 6%, 7%, 8%, 9%, 10%, 15%, 20%, or more) of a plant's nitrogen, which may represent an increase in nitrogen fixation capability of at least 2-fold (e.g. 3-fold, 4-fold, 5-fold, 6-fold, 7-fold, 8-fold, 9-fold, 10-fold, 20-fold, 50-fold, 100-fold, 1000-fold, or more) as compared to bacteria isolated from the first plant before introducing any genetic modification. In some cases, the bacteria produce 5% or more of a plant's nitrogen. The desired level of nitrogen fixation may be achieved after repeating the steps of introducing genetic modification, exposure to a plurality of plants, and isolating bacteria from plants with an improved trait one or more times (e.g. 1, 2, 3, 4, 5, 10, 15, 25, or more times). In some cases, enhanced levels of nitrogen fixation are achieved in the presence of fertilizer supplemented with glutamine, ammonia, or other chemical source of nitrogen. Methods for assessing degree of nitrogen fixation are known, examples of which are described herein.

Measuring Nitrogen Delivered in an Agriculturally Relevant Field Context

In the field, the amount of nitrogen delivered can be determined by the function of colonization multiplied by the activity.

$$\text{Nitrogen delivered} = \int_{\text{Time \& Space}} \text{Colonization} \times \text{Activity}$$

The above equation requires (1) the average colonization per unit of plant tissue, and (2) the activity as either the amount of nitrogen fixed or the amount of ammonia excreted by each microbial cell. To convert to pounds of nitrogen per acre, corn growth physiology is tracked over time, e.g., size of the plant and associated root system throughout the maturity stages.

The pounds of nitrogen delivered to a crop per acre-season can be calculated by the following equation:

$$\text{Nitrogen delivered} = \text{Plant Tissue}(t) \times \text{Colonization} \times \text{Activity}(t)dt$$

The Plant Tissue(t) is the fresh weight of corn plant tissue over the growing time (t). Values for reasonably making the calculation are described in detail in the publication entitled Roots, Growth and Nutrient Uptake (Mengel. Dept. of Agronomy Pub. #AGRY-95-08 (Rev. May-95. p. 1-8.).

The Colonization (t) is the amount of the microbes of interest found within the plant tissue, per gram fresh weight of plant tissue, at any particular time, t, during the growing season. In the instance of only a single timepoint available, the single timepoint is normalized as the peak colonization rate over the season, and the colonization rate of the remaining timepoints are adjusted accordingly.

Activity(t) is the rate at which N is fixed by the microbes of interest per unit time, at any particular time, t, during the growing season. In the embodiments disclosed herein, this activity rate is approximated by in vitro acetylene reduction assay (ARA) in ARA media in the presence of 5 mM glutamine or ammonium excretion assay in ARA media in the presence of 5 mM ammonium ions.

The Nitrogen delivered amount is then calculated by numerically integrating the above function. In cases where the values of the variables described above are discretely measured at set timepoints, the values in between those timepoints are approximated by performing linear interpolation.

Bacterial Species

Microbes useful in the methods and compositions disclosed herein may be obtained from any source. In some cases, microbes may be bacteria, archaea, protozoa or fungi. The microbes of this disclosure may be nitrogen fixing microbes, for example a nitrogen fixing bacteria, nitrogen fixing archaea, nitrogen fixing fungi, nitrogen fixing yeast, or nitrogen fixing protozoa. Microbes useful in the methods and compositions disclosed herein may be spore forming microbes, for example spore forming bacteria. In some cases, bacteria useful in the methods and compositions disclosed herein may be Gram positive bacteria or Gram negative bacteria. In some cases, the bacteria may be an endospore forming bacteria of the Firmicute phylum. In some cases, the bacteria may be a diazatroph. In some cases, the bacteria may not be a diazotroph.

The methods and compositions of this disclosure may be used with an archaea, such as, for example, Methanothermobacter *thermoautotrophicus.*

In some cases, bacteria which may be useful include, but are not limited to, *Agrobacterium radiobacter, Bacillus acidocaldarius, Bacillus acidoterrestris, Bacillus agri, Bacillus aizawai, Bacillus albolactis, Bacillus alcalophilus, Bacillus alvei, Bacillus aminoglucosidicus, Bacillus aminovorans, Bacillus amylolyticus* (also known as *Paenibacillus amylolyticus*) *Bacillus amyloliquefaciens, Bacillus aneurinolyticus, Bacillus atrophaeus, Bacillus azotofirmans, Bacillus badius, Bacillus cereus* (synonyms: *Bacillus endorhythmos, Bacillus medusa), Bacillus chitinosporus, Bacillus circulans, Bacillus coagulans, Bacillus endoparasiticus Bacillus fastidiosus, Bacillus firmuis, Bacillus kurstaki, Bacillus lacticola, Bacillus lactimorbus, Bacillus lactis, Bacillus laterosporus* (also known as *Brevibacillus laterosporus), Bacillus lautus, Bacillus lentimorbus, Bacillus lentus, Bacillus licheniformis, Bacillus maroccanus, Bacillus megaterium, Bacillus metiens, Bacillus mycoides, Bacillus natto, Bacillus nemalocida, Bacillus nigrificans, Bacillus nigrum, Bacillus pantothenticus, Bacillus popillae, Bacillus psychrosaccharolyticus, Bacillus pumilus, Bacillus siamensis, Bacillus smithii, Bacillus sphaericus, Bacillus subtilis, Bacillus thuringiensis, Bacillus uniflagellatus, Bradyrhizobium japonicum, Brevibacillus brevis Brevibacillus laterosporus* (formerly *Bacillus laterosporus), Chromobacterium subtsugae, Delftia acidovorans, Lactobacillus acidophilus, Lysobacter antibioticus, Lysobacter enzymogenes, Paenibacillus alvei, Paenibacillus polymyxa, Paenibacillus popilliae* (formerly *Bacillus popioliae), Pantoea agglonerans, Pasteuria penetrans* (formerly *Bacillus penetrans), Pasteuria usgae, Pectobacterium carotovorum* (formerly *Erwinia carotovora), Pseudormonas aeruginosa, Pseudononas aureofaciens, Pseudononas cepacia* (formerly known as *Burkholderia cepacia), Pseudomonas chlororaphis, Pseudomonas fluorescens, Pseudomonas proradix, Pseudomonas putida, Pseudononas syringae, Serratia entomophila, Serratia marcescens, Streptomyces colombiensis, Streptomyces galbus, Streptomyces goshikiensis, Streptomyces griseoviridin, Streptomyces lavendulae, Streptomyces prasinus, Streptomyces saraceticus, Streptomyces venezuelae, Xanthomonas campestris, Xenorhabdus luminescens, Xenorhabdus nematophila, Rhodococcus globerulus* AQ719 (NRIL Accession No. B-21663), *Bacillus* sp. AQ175 (ATCC Accession No. 55608), *Bacillus* sp. AQ177 (ATCC Accession No. 55609), *Bacillus* sp. AQ178 (ATCC Accession No. 53522), and *Streptomyces* sp. strain NRRL Accession No. B-30145. In some cases the bacterium may be *Azotobacter chroococcum, Methanosarcina barkeri, Klesiella pneumoniae, Azotobacter vinelandii, Rhodobacter sphaeroides, Rhodobacter capsulatus, Rhodobacter palustris, Rhodospirillum rubrum, Rhizobium leguminosarum* or *Rhizobium etli.*

In some cases the bacterium may be a species of *Clostridium*, for example *Clostridium pasteurianum, Clostridium beijerinckii, Clostridium perfringens, Clostridium tetani, Clostridium acetobutylicum.*

In some cases, bacteria used with the methods and compositions of the present disclosure may be cyanobacteria. Examples of cyanobacterial genuses include *Anabaena* (for example *Anagaena* sp. PCC7120), *Nostoc* (for example *Nostoc punctiforme*), or *Synechocystis* (for example *Synechocystis* sp. PCC6803).

In some cases, bacteria used with the methods and compositions of the present disclosure may belong to the phylum Chlorobi, for example *Chlorobium tepidum.*

In some cases, microbes used with the methods and compositions of the present disclosure may comprise a gene homologous to a known NifH gene. Sequences of known NifH genes may be found in, for example, the Zehr lab NifH database, (wwwzehr.pmc.ucsc.edu/nifH_Database_Public/, Apr. 4, 2014), or the Buckley lab NifH database (www.css.cornell.edu/faculty/buckley/nifh.htm, and Gaby, John Christian, and Daniel H. Buckley. "A comprehensive aligned nifH gene database: a multipurpose tool for studies of nitrogen-fixing bacteria." Database 2014 (2014): bau001.). In some cases, microbes used with the methods and compositions of the present disclosure may comprise a sequence which encodes a polypeptide with at least 60%, 70%, 80%, 85%, 90%, 95%, 96%, 96%, 98%, 99% or more than 99% sequence identity to a sequence from the Zehr lab NifH database, (www.zehr.pmc.ucsc.edu/nifH_Database_Public/, Apr. 4, 2014). In some cases, microbes used with the methods and compositions of the present disclosure may comprise a sequence which encodes a polypeptide with at least 60%, 70%, 80%, 85%, 90%, 95%, 96%, 96%, 98%, 99% or more than 99% sequence identity to a sequence from the Buckley lab NifH database, (Gaby, John Christian, and Daniel H. Buckley. "A comprehensive aligned nif-1 gene database: a multipurpose tool for studies of nitrogen-fixing bacteria." *Database* 2014 (2014): bau001.).

Microbes useful in the methods and compositions disclosed herein can be obtained by extracting microbes from surfaces or tissues of native plants; grinding seeds to isolate microbes; planting seeds in diverse soil samples and recovering microbes from tissues; or inoculating plants with exogenous microbes and determining which microbes appear in plant tissues. Non-limiting examples of plant tissues include a seed, seedling, leaf, cutting, plant, bulb, tuber, root, and rhizosomes. In some cases, bacteria are isolated from a seed. The parameters for processing samples may be varied to isolate different types of associative microbes, such as rhizospheric, epiphytes, or endophytes. Bacteria may also be sourced from a repository, such as environmental strain collections, instead of initially isolating from a first plant. The microbes can be genotyped and phenotyped, via sequencing the genomes of isolated microbes; profiling the composition of communities in planta; characterizing the transcriptomic functionality of communities or isolated microbes; or screening microbial features using selective or phenotypic media (e.g., nitrogen fixation or phosphate solubilization phenotypes). Selected candidate strains or populations can be obtained via sequence data; phenotype data; plant data (e.g., genome, phenotype, and/or yield data); soil data (e.g., pH, N/P/K content, and/or bulk soil biotic communities); or any combination of these.

The bacteria and methods of producing bacteria described herein may apply to bacteria able to self-propagate efficiently on the leaf surface, root surface, or inside plant tissues without inducing a damaging plant defense reaction, or bacteria that are resistant to plant defense responses. The bacteria described herein may be isolated by culturing a plant tissue extract or leaf surface wash in a medium with no added nitrogen. However, the bacteria may be unculturable, that is, not known to be culturable or difficult to culture using standard methods known in the art. The bacteria described herein may be an endophyte or an epiphyte or a bacterium inhabiting the plant rhizosphere (rhizospheric bacteria). The bacteria obtained after repeating the steps of introducing genetic modification, exposure to a plurality of plants, and isolating bacteria from plants with an improved trait one or more times (e.g. 1, 2, 3, 4, 5, 10, 15, 25, or more times) may be endophytic, epiphytic, or rhizospheric. Endophytes are organisms that enter the interior of plants without causing disease symptoms or eliciting the formation of symbiotic structures, and are of agronomic interest because they can enhance plant growth and improve the nutrition of plants (e.g., through nitrogen fixation). The bacteria can be a seed-borne endophyte. Seed-borne endophytes include bacteria associated with or derived from the seed of a grass or plant, such as a seed-borne bacterial endophyte found in mature, dry, undamaged (e.g., no cracks, visible fungal infection, or prematurely germinated) seeds. The seed-borne bacterial endophyte can be associated with or derived from the surface of the seed; alternatively, or in addition, it can be associated with or derived from the interior seed compartment (e.g., of a surface-sterilized seed). In some cases, a seed-borne bacterial endophyte is capable of replicating within the plant tissue, for example, the interior of the seed. Also, in some cases, the seed-borne bacterial endophyte is capable of surviving desiccation.

The bacterial isolated according to methods of the disclosure, or used in methods or compositions of the disclosure, can comprise a plurality of different bacterial taxa in combination. By way of example, the bacteria may include Proteobacteria (such as *Pseudomonas, Enterobacter, Stenotrophomonas, Burkholderia, Rhizobium, Herbaspirillum, Pantoea, Serratia, Rahnella, Azospirillum, Azorhizobium, Azotobacter, Duganella, Delftia, Bradyrhizobiun, Sinorhizobium* and *Halomonas*), Firmicutes (such as *Bacillus, Paenibacillus, Lactobacillus, Mycoplasma*, and *Acetabacterium*), and Actinobacteria (such as *Streptomyces, Rhodacoccus, Microbacterium*, and *Curtobacterium*). The bacteria used in methods and compositions of this disclosure may include nitrogen fixing bacterial consortia of two or more species. In some cases, one or more bacterial species of the bacterial consortia may be capable of fixing nitrogen. In some cases, one or more species of the bacterial consortia may facilitate or enhance the ability of other bacteria to fix nitrogen. The bacteria which fix nitrogen and the bacteria which enhance the ability of other bacteria to fix nitrogen may be the same or different. In some examples, a bacterial strain may be able to fix nitrogen when in combination with a different bacterial strain, or in a certain bacterial consortia, but may be unable to fix nitrogen in a monoculture. Examples of bacterial genuses which may be found in a nitrogen fixing bacterial consortia include, but are not limited to, *Herbaspirillum, Azospirillum, Enterobacter*, and *Bacillus.*

Bacteria that can be produced by the methods disclosed herein include *Azotobacter* sp., *Bradyrhizobium* sp., *Klebsiella* sp., and *Sinorhizobium* sp. In some cases, the bacteria may be selected from the group consisting of: *Azotobacter vinelandii, Bradyrhizobium japonicum, Klebsiella pneumoniae*, and *Sinorhizobium meliloti*. In some cases, the bacteria may be of the genus *Enterobacter* or *Rahnella*. In some cases, the bacteria may be of the genus *Frankia*, or *Clostridium*. Examples of bacteria of the genus *Clostridium* include, but are not limited to, *Clostridium acetobutilicum*, *Clostridium pasteurianum*, *Clostridium beijerinckii*, *Clostridium perfringens*, and *Clostridium tetani*. In some cases, the bacteria may be of the genus *Paenibacillus*, for example *Paenibacillus azotofixans*, *PaenMbacillus boreais*, *Paenibacillus durus*, *Paenibacillus macerans*, *Paenibacillus polymyxa*, *Paenibacillus alvei*, *Paenibacillus amylolyticus*, *Paenibacillus campinasensis*, *Paenibacillus chibensis*, *Paenibacillus glucanolyticus*, *Paenibacillus illinoisensis*, *Paenibacillus larvae* subsp. *Larvae*, *Paenibacillus larvae* subsp. *Pulvifaciens*, *Paenibacillus lautus*, *Paenibacillus macerans*, *Paenibacillus macquariensis*, *Paenibacillus macquariensis*, *Paenibacillus pabuli*, *Paenibacillus peoriae*, or *Paenibacillus polymyxa*.

In some examples, bacteria isolated according to methods of the disclosure can be a member of one or more of the following taxa: *Achromobacter, Acidithiobacillus, Acidovorax, Acidovoraz, Acinetobacter, Actinoplanes, Adlercreutzia, Aerococcus, Aeromonas, Afipia, Agromyces, Ancylobacter, Arthrobacter, Atopostipes, Azospirillum, Bacillus, Bdellovibrio, Beijerinckia, Bosea, Bradyrhizobium, Brevibacillus, Brevundimonas, Burkholderia, Candidatus Haloredivivus, Caulobacter, Cellulomonas, Cellvibrio, Chryseobacterium, Citrobacter, Clostridium, Coraliomargarita, Corynebacterium, Cupriavidus, Curtobacterium, Curvibacter, Deinococcus, Delftia, Desemzia, Devosia, Dokdonella, Dyella, Enhydrobacter, Enterobacter, Enterococcus, Erwinia, Escherichia, Escherichia Shigella, Exiguobacterium, Ferroglobus, Filimonas, Finegoldia, Flavisolibacter, Flavobacterium, Frigoribacterium, Gluconacetobacter, Hafnia, Halobaculum, Halomonas, Halosimplex, Herbaspirillum, Hymenobacter, Klebsiella, Kocuria, Kosakonia, Lactobacillus, Leclercia, Lentzea, Luteibacter, Luteimonas, Massilia, Mesorhizobium, Methylobacterium, Microbacterium, Micrococcus, Microvirga, Mycobacterium, Neisseria, Nocardia, Oceanibaculum, Ochrobactrum, Okibacterium, Oligotropha, Oryzihumus, Oxalophagus, Paenibacillus, Panteoa, Pantoea, Pelomonas, Perlucidibaca, Plantibacter, Polynucleobacter, Propionibacterium, Propioniciclava, Pseudoclavibacter, Pseudomonas, Pseudonocardia, Pseudoxanthomonas, Psychrobacter, Ralstonia, Rheinheimera, Rhizobium, Rhodococcus, Rhodopseudomonas, Roseateles, Ruminococcus, Sebaldella, Sediminibacillus, Sediminibacterium, Serratia, Shigella, Shinella, Sinorhizobium, Sinosporangium, Sphingobacterium, Sphingomonas, Sphingopyxis, Sphingosinicella, Staphylococcus, 25 Stenotrophomonas, Strenotrophomonas, Streptococcus, Streptomyces, Stygiolobus, Sulfurisphaera, Tatumella, Tepidimonas, Thermomonas, Thiobacillus, Variovorax*, WPS-2 genera *Incertae sedis, Xanthomonas*, and *Zimmermannella*.

In some embodiments, a bacterial species selected from at least one of the following genera is utilized: *Enterobacter, Klebsiella, Kosakonia*, and *Rahnella*. In some cases, a combination of bacterial species from the following genera are utilized: *Enterobacter, Klebsiella, Kosakonia*, and *Rahnella*. In some cases, the species utilized can be one or more of: *Enterobacter sacchari, Klebsiella variicola, Kosakonia sacchari*, and *Rahnella aquatilis*.

In some cases, a Gram positive microbe can have a Molybdenum-Iron nitrogenase system comprising: nifH, nifD, nifK, nifB, nifE, nifN, nifX, hesA, nifV, nifW, nifU, nifS, nifl1, and nifl2. In some cases, a Gram positive microbe can have a vanadium nitrogenase system comprising: vnjDG, vnfK, vnjE, vnjN, vupC, vupB, vupA, vnjV, vnjRI, vnjH, vnjR2, vnfA (transcriptional regulator). In some cases, a Gram positive microbe can have an iron-only nitrogenase system comprising: anfK, anfG, anjD, anjH, anfA (transcriptional regulator). In some cases, a Gram positive microbe can have a nitrogenase system comprising glnB, and glnK (nitrogen signaling proteins). Some examples of enzymes involved in nitrogen metabolism in Gram positive microbes include glnA (glutamine synthetase), gdh (glutamate dehydrogenase), bdh (3-hydroxybutyrate dehydrogenase), glutaminase, gltAB/gltB/gltS (glutamate synthase), asnA/asnB (aspartate-ammonia ligase/asparagine synthetase), and ansA/ansZ (asparaginase). Some examples of proteins involved in nitrogen transport in Gram positive microbes include amtB (ammonium transporter), glnK (regulator of ammonium transport), glnPHQ/glnQHMP (ATP-dependent glutamine/glutamate transporters), glnT/alsT/yrbD/yjlA (glutamine-like proton symport transporters), and gltP/gltT/yhcllnqt (glutamate-like proton symport transporters).

Examples of Gram positive microbes that can be of particular interest include *Paenibacillus polymixa, Paenibacillus riograndensis, Paenibacillus* sp., *Frankia* sp., *Heliobacterium* sp., *Heliobacterium chlorum, Heliobacillus* sp., *Heliophilum* sp., *Heliorestis* sp., *Clostridium acetobutylicum, Clostridium* sp., *Mycobacterium jlaum, Mycobacterium* sp., *Arthrobacter* sp., *Agromyces* sp., *Corynebacterium autitrophicum, Corynebacterium* sp., *Micromonspora* sp., *Propionibacteria* sp., *Streptomyces* sp., and *Microbacterium* sp.

Some examples of genetic alterations that can be made in Gram positive microbes include: deleting glnR to remove negative regulation of BNF in the presence of environmental nitrogen, inserting different promoters directly upstream of the nif cluster to eliminate regulation by GlnR in response to environmental nitrogen, mutating glnA to reduce the rate of ammonium assimilation by the GS-GOGAT pathway, deleting amtB to reduce uptake of ammonium from the media, mutating glnA so it is constitutively in the feedback-inhibited (FBI-GS) state, to reduce ammonium assimilation by the GS-GOGAT pathway.

In some cases, glnR is the main regulator of N metabolism and fixation in *Paenibacillus* species. In some cases, the genome of a *Paenibacillus* species does not contain a gene to produce glnR. In some cases, the genome of a *Paenibacillus* species does not contain a gene to produce glnE or glnD. In some cases, the genome of a *Paenibacillus* species does not contain a gene to produce glnB or glnK. For example, *Paenibacillus* sp. WLY78 doesn't contain a gene for glnB, or its homologs found in the archaeon Methanococcus maripaludis, nifil and nifl2. In some cases, the genomes of *Paenibacillus* species can be variable. For example, *Paenibacillus* polymixa E68 1 lacks glnK and gdh, has several nitrogen compound transporters, but only amtB appears to be controlled by GlnR. In another example, *Paenibacillus* sp. JDR2 has glnK, gdh and most other central nitrogen metabolism genes, has many fewer nitrogen compound transporters, but does have glnPHQ controlled by GlnR. *Paenibacillus* riograndensis SBR5 contains a standard glnRA operon, anfdx gene, a main nif operon, a secondary nif operon, and an anf operon (encoding iron-only nitrogenase). Putative glnR/tnrA sites were found upstream of each of these operons. GlnR does regulate all of the above operons, except the anf operon. GlnR can bind to each of these regulatory sequences as a dimer.

*Paenibacillus* N-fixing strains can fall into two subgroups: Subgroup I, which contains only a minimal nif gene cluster and subgroup II, which contains a minimal cluster, plus an uncharacterized gene between nifX and hesA, and often other clusters duplicating some of the nif genes, such as nifH, nifHDK, nifBEN, or clusters encoding vanadaium nitrogenase (vnj) or iron-only nitrogenase (anj) genes.

In some cases, the genome of a *Paenibacillus* species does not contain a gene to produce glnB or glnK. In some cases, the genome of a *Paenibacillus* species contains a minimal nif cluster with 9 genes transcribed from a sigma-70 promoter. In some cases, a *Paenibacillus* nif cluster can be negatively regulated by nitrogen or oxygen. In some cases, the genome of a *Paenibacillus* species does not contain a gene to produce sigma-54. For example, *Paenibacillus* sp. WLY78 does not contain a gene for sigma-54. In some cases, a nif cluster can be regulated by glnR, and/or TnrA. In some cases, activity of a nif cluster can be altered by altering activity of glnR, and/or TnrA.

In Bacilli, glutamine synthetase (GS) is feedback-inhibited by high concentrations of intracellular glutamine, causing a shift in confirmation (referred to as FBI-GS). Nif clusters contain distinct binding sites for the regulators GlnR and TnrA in several Bacilli species. GlnR binds and represses gene expression in the presence of excess intracellular glutamine and AMP. A role of GlnR can be to prevent the influx and intracellular production of glutamine and ammonium under conditions of high nitrogen availability. TnrA can bind and/or activate (or repress) gene expression in the presence of limiting intracellular glutamine, and/or in the presence of FBI-GS. In some cases, the activity of a Bacilli nif cluster can be altered by altering the activity of GlnR.

Feedback-inhibited glutamine synthetase (FBI-GS) can bind GlnR and stabilize binding of GlnR to recognition sequences. Several bacterial species have a GlnR/TnrA binding site upstream of the nif cluster. Altering the binding of FBI-GS and GlnR can alter the activity of the nif pathway.

Sources of Microbes

The bacteria (or any microbe according to the disclosure) can be obtained from any general terrestrial environment, including its soils, plants, fungi, animals (including invertebrates) and other biota, including the sediments, water and biota of lakes and rivers; from the marine environment, its biota and sediments (for example, sea water, marine muds, marine plants, marine invertebrates (for example, sponges), marine vertebrates (for example, fish)); the terrestrial and marine geosphere (regolith and rock, for example, crushed subterranean rocks, sand and clays); the cryosphere and its meltwater; the atmosphere (for example, filtered aerial dusts, cloud and rain droplets); urban, industrial and other man-made environments (for example, accumulated organic and mineral matter on concrete, roadside gutters, roof surfaces, and road surfaces).

The plants from which the bacteria (or any microbe according to the disclosure) are obtained may be a plant having one or more desirable traits, for example a plant which naturally grows in a particular environment or under certain conditions of interest. By way of example, a certain plant may naturally grow in sandy soil or sand of high salinity, or under extreme temperatures, or with little water, or it may be resistant to certain pests or disease present in the environment, and it may be desirable for a commercial crop to be grown in such conditions, particularly if they are, for example, the only conditions available in a particular geographic location. By way of further example, the bacteria may be collected from commercial crops grown in such environments, or more specifically from individual crop plants best displaying a trait of interest amongst a crop grown in any specific environment: for example the fastest-growing plants amongst a crop grown in saline-limiting soils, or the least damaged plants in crops exposed to severe insect damage or disease epidemic, or plants having desired quantities of certain metabolites and other compounds, including fiber content, oil content, and the like, or plants displaying desirable colors, taste or smell. The bacteria may be collected from a plant of interest or any material occurring in the environment of interest, including fungi and other animal and plant biota, soil, water, sediments, and other elements of the environment as referred to previously.

The bacteria may be isolated from plant tissue. This isolation can occur from any appropriate tissue in the plant, including for example root, stem and leaves, and plant reproductive tissues. By way of example, conventional methods for isolation from plants typically include the sterile excision of the plant material of interest (e.g. root or stem lengths, leaves), surface sterilization with an appropriate solution (e.g. 2% sodium hypochlorite), after which the plant material is placed on nutrient medium for microbial growth. Alternatively, the surface-sterilized plant material can be crushed in a sterile liquid (usually water) and the liquid suspension, including small pieces of the crushed plant material spread over the surface of a suitable solid agar medium, or media, which may or may not be selective (e.g. contain only phytic acid as a source of phosphorus). This approach is especially useful for bacteria which form isolated colonies and can be picked off individually to separate plates of nutrient medium, and further purified to a single species by well-known methods. Alternatively, the plant root or foliage samples may not be surface sterilized but only washed gently thus including surface-dwelling epiphytic microorganisms in the isolation process, or the epiphytic microbes can be isolated separately, by imprinting and lifting off pieces of plant roots, stem or leaves onto the surface of an agar medium and then isolating individual colonies as above. This approach is especially useful for bacteria, for example. Alternatively, the roots may be processed without washing off small quantities of soil attached to the roots, thus including microbes that colonize the plant rhizosphere. Otherwise, soil adhering to the roots can be removed, diluted and spread out onto agar of suitable selective and non-selective media to isolate individual colonies of rhizospheric bacteria.

Biologically pure cultures of *Rahnella aquatilis* and *Enterobacter sacchari* were deposited on Jul. 14, 2015 with the American Type Culture Collection (ATCC; an International Depositary Authority), Manassas, VA, USA, and assigned ATTC Patent Deposit Designation numbers PTA-122293 and PTA-122294, respectively. These deposits were made under the provisions of the Budapest Treaty on the International Recognition of the Deposit of Microorganisms for the Purpose of Patent Procedure and the Regulations (Budapest Treaty).

*Enterobacter sacchari* has now been reclassified as *Kosakonia sacchari*, the name for the organism may be used interchangeably throughout the manuscript.

Many microbes of the present disclosure are derived from two wild-type strains. Strain CI006 is a bacterial species previously classified in the genus *Enterobacter* (see aforementioned reclassification into *Kosakonia*). Strain CI019 is a bacterial species classified in the genus *Rahnella*. It is noted that strains comprising CM in the name are mutants of the strains depicted immediately to the left of said CM strain. The deposit information for the CI006 *Kosakonia* wild type (WT) and CIO19 *Rahnella* WT are found in the below Table 3.

Some microorganisms described in this application were deposited on Jan. 6, 2017 or Aug. 11, 2017 with the Bigelow National Center for Marine Algae and Microbiota (NCMA), located at 60 Bigelow Drive, East Boothbay, Maine 04544, USA As aforementioned, all deposits were made under the terms of the Budapest Treaty on the International Recognition of the Deposit of Microorganisms for the Purposes of Patent Procedure. The Bigelow National Center for Marine Algae and Microbiota accession numbers and dates of deposit for the aforementioned Budapest Treaty deposits are provided in Table 3.

Biologically pure cultures of *Kosakonia sacchari* (WT), *Rahnella aquatilis* (WT), and a variant/remodeled *Kosakonia sacchari* strain were deposited on Jan. 6, 2017 with the NCMA, located at 60 Bigelow Drive, East Boothbay, Maine 04544, USA, and assigned NCMA Patent Deposit Designation numbers 201701001, 201701003, and 201701002, respectively. The applicable deposit information is found below in Table 3.

Biologically pure cultures of variant/remodeled *Kosakonia sacchari* strains were deposited on Aug. 11, 2017 with the NCMA, located at 60 Bigelow Drive, East Boothbay, sions of the Budapest Treaty. The applicable deposit information is found below in Table 3.

A biologically pure culture of *Klebsiella variicola* was deposited on Mar. 25, 2020, with the ATCC, Manassas, VA, USA, and assigned ATTC Patent Deposit Designation number PTA-126741. This deposit was made under the provisions of the Budapest Treaty. The applicable deposit information is found below in Table 3.

A biologically pure culture of *Klebsiella variicola* was deposited on Mar. 25, 2020, with the ATCC, Manassas, VA, USA, and assigned ATTC Patent Deposit Designation number PTA-126740. This deposit was made under the provisions of the Budapest Treaty. The applicable deposit information is found below in Table 3.

A biologically pure culture of *Klebsiella variicola* was deposited on Apr. 2, 2020, with the ATCC, Manassas, VA, USA, and assigned ATTC Patent Deposit Designation number PTA-126749. This deposit was made under the provisions of the Budapest Treaty. The applicable deposit information is (found below 2 in Table 3.

TABLE 3

| | Microorganisms Deposited under the Budapest Treaty | | | |
|---|---|---|---|---|
| Depository | Pivot Strain Designation (some strains have multiple designations) | Taxonomy | Accession Number | Date of Deposit |
| NCMA | CI006, PBC6.1, 6 | *Kosakonia sacchari* (WT) | 201701001 | Jan. 6, 2017 |
| NCMA | CI019, 19 | *Rahnella aquatilis* (WT) | 201701003 | Jan. 6, 2017 |
| NCMA | CM029, 6-412 | *Kosakonia sacchari* | 201701002 | Jan. 6, 2017 |
| NCMA | 6-403 CM037 | *Kosakonia sacchari* | 201708004 | Aug. 11, 2017 |
| NCMA | 6-404, CM38, PBC6.38 | *Kosakonia sacchari* | 201708003 | Aug. 11, 2017 |
| NCMA | CM094, 6-881, PBC6.94 | *Kosakonia sacchari* | 201708002 | Aug. 11, 2017 |
| NCMA | CI137, 137, PB137 | *Klebsiella variicola* (WT) | 201708001 | Aug. 11, 2017 |
| NCMA | 137-1034 | *Klebsiella variicola* | 201712001 | Dec. 20, 2017 |
| NCMA | 137-1036 | *Klebsiella variicola* | 201712002 | Dec. 20, 2017 |
| ATCC | 137-3890 | *Klebsiella variicola* | PTA-126749 | Apr. 2, 2020 |
| ATCC | 6-5687 | *Kosakonia sacchari* | PTA-126743 | Mar. 25, 2020 |
| ATCC | 137-3896 | *Klebsiella variicola* | PTA-126741 | Mar. 25, 2020 |
| ATCC | 137-2253 | *Klebsiella variicola* | PTA-126740 | Mar. 25, 2020 |

Maine 04544, USA, and assigned NCMA Patent Deposit Designation numbers 201708004, 201708003, and 201708002, respectively. The applicable deposit information is found below in Table 3.

A biologically pure culture of *Klebsiella variicola* (WT) was deposited on Aug. 11, 2017 with the NCMA, located at 60 Bigelow Drive, East Boothbay, Maine 04544, USA, and assigned NCMA Patent Deposit Designation number 201708001. Biologically pure cultures of two *Klebsiella variicola* variants/remodeled strains were deposited on Dec. 20, 2017 with the NCMA, located at 60 Bigelow Drive, East Boothbay, Maine 04544, USA, and assigned NCMA Patent Deposit Designation numbers 201712001 and 201712002, respectively. The applicable deposit information is found below in Table 3.

A biologically pure culture of *Kosokonia sacchari* was deposited on Mar. 25, 2020, with the ATCC, Manassas, VA, USA, and assigned ATTC Patent Deposit Designation number PTA-126743. This deposit was made under the provi- Isolated and Biologically Pure Microorganisms The present disclosure, in some embodiments, provides isolated and biologically pure microorganisms that have applications, inter alia, in agriculture. The disclosed microorganisms can be utilized in their isolated and biologically pure states, as well as being formulated into compositions (see below section for exemplary composition descriptions). Furthermore, the disclosure provides microbial compositions containing at least two members of the disclosed isolated and biologically pure microorganisms, as well as methods of utilizing said microbial compositions. Furthermore, the disclosure provides for methods of modulating nitrogen fixation in plants via the utilization of the disclosed isolated and biologically pure microbes.

In some embodiments, the isolated and biologically pure microorganisms of the disclosure are those from Table 3. In some embodiments, the isolated and biologically pure microorganisms of the disclosure are derived from a microorganism of Table 3. For example, a strain, child, mutant, or derivative, of a microorganism from Table 3 are provided herein. The disclosure contemplates all possible combinations of microbes listed in Table 3, said combinations sometimes forming a microbial consortia. The microbes from Table 3, either individually or in any combination, can be combined with any plant, active molecule (synthetic, organic, etc.), adjuvant, carrier, supplement, or biological, mentioned in the disclosure.

Agricultural Compositions

Compositions comprising bacteria or bacterial populations produced according to methods described herein and/or having characteristics as described herein can be in the form of a liquid, a foam, or a dry product. Compositions comprising bacteria or bacterial populations produced according to methods described herein and/or having characteristics as described herein can also be used to improve plant traits. In some examples, a composition comprising bacterial populations may be in the form of a dry powder, a slurry of powder and water, or a flowable seed treatment. The compositions comprising bacterial populations my be coated on a surface of a seed, and may be in liquid form In some embodiments, wherein a plant, a part of the plant, or soil into which the plant is planted is contacted with more than one plurality of genetically engineered bacteria, the different pluralities of genetically engineered bacteria can be formulated separately or together. In some embodiments, wherein the different pluralities of genetically engineered bacteria are in the same composition, the composition is in the form of a liquid, a foam, or a dry product. In some embodiments, wherein the different pluralities of genetically engineered bacteria are in separate compositions (e.g., each plurality is part of a different composition), each composition is in the form of a liquid, a foam, or a dry product. In some embodiments, wherein the different pluralities of genetically engineered bacteria are in separate compositions, the first composition is in the form of a liquid and the second composition is in the form of a dry product. In some embodiments, wherein the different pluralities of genetically engineered bacteria are in separate compositions, the compositions are mixed prior to contacting a plant, a part of the plant, or soil into which the plant is planted.

The composition can be fabricated in bioreactors such as continuous stirred tank reactors, batch reactors, and on the farm. In some examples, compositions can be stored in a container, such as a jug or in mini bulk. In some examples, compositions may be stored within an object selected from the group consisting of a bottle, jar, ampule, package, vessel, bag, box, bin, envelope, carton, container, silo, shipping container, truck bed, and/or case.

Compositions may also be used to improve plant traits. In some examples, one or more compositions may be coated onto a seed. In some examples, one or more compositions may be coated onto a seedling. In some examples, one or more compositions may be coated onto a surface of a seed. In some examples, one or more compositions may be coated as a layer above a surface of a seed. In some examples, a composition that is coated onto a seed may be in liquid form, in dry product form, in foam form, in a form of a slurry of powder and water, or in a flowable seed treatment. In some examples, one or more compositions may be applied to a seed and/or seedling by spraying, immersing, coating, encapsulating, and/or dusting the seed and/or seedling with the one or more compositions. In some examples, multiple bacteria or bacterial populations can be coated onto a seed and/or a seedling of the plant. In some examples, at least two, at least three, at least four, at least five, at least six, at least seven, at least eight, at least nine, at least ten, or more than ten bacteria of a bacterial combination can be selected from one of the following genera: Acidovorax, *Agrobacterium, Bacillus, Burkholderia, Chryseobacterium, Curtobacterium, Enterobacter, Escherichia, Methylobacterium, Paenibacillus, Pantoea, Pseudomonas, Ralstonia, Saccharibacillus, Sphingomonas*, and *Stenotrophomonas*.

In some examples, at least two, at least three, at least four, at least five, at least six, at least seven, at least eight, at least nine, at least ten, or more than ten bacteria and bacterial populations of an endophytic combination are selected from one of the following families: Bacillaceae, Burkholderiaceae, Comamonadaceae, Enterobacteriaceae, Flavobacteriaceae, Methylobacteriaceae, Microbacteriaceae, Paenibacillileae, Pseudomonnaceae, Rhizobiaceae, Sphingomonadaceae, Xanthomonadaceae, Cladosporiaceae, Gnomoniaceae, *Incertae sedis*, Lasiosphaeriaceae, Netriaceae, and Pleosporaceae.

In some examples, at least two, at least three, at least four, at least five, at least six, at least seven, at least eight, at least night, at least ten, or more than ten bacteria and bacterial populations of an endophytic combination are selected from one of the following families: Bacillaceae, Burkholderiaceae, Comamonadaceae, Enterobacteriaceae, Flavobacteriaceae, Methylobacteriaceae, Microbacteriaceae, Paenibacillileae, Pseudomonnaceae, Rhizobiaceae, Sphingomonadaceae, Xanthomonadaceae, Cladosporiaceae, Gnomoniaceae, *Incertae sedis*, Lasiosphaeriaceae, Netriaceae, Pleosporaceae.

The compositions comprising the bacterial populations described herein may be coated onto the surface of a seed. Examples of compositions may include seed coatings for commercially important agricultural crops, for example, *sorghum*, canola, tomato, strawberry, barley, rice, maize, and wheat. Examples of compositions can also include seed coatings for corn, soybean, canola, *sorghum*, potato, rice, vegetables, cereals, and oilseeds. Seeds as provided herein can be genetically modified organisms (GMO), non-GMO, organic, or conventional. In some examples, compositions may be sprayed on the plant aerial parts, or applied to the roots by inserting into furrows in which the plant seeds are planted, watering to the soil, or dipping the roots in a suspension of the composition. In some examples, compositions may be dehydrated in a suitable manner that maintains cell viability and the ability to artificially inoculate and colonize host plants. The bacterial species may be present in compositions at a concentration of between $10^8$ to $10^{10}$ CFU/ml. In some examples, compositions may be supplemented with trace metal ions, such as molybdenum ions, iron ions, manganese ions, or combinations of these ions. The concentration of ions in examples of compositions as described herein may between about 0.1 mM and about 50 mM. Some examples of compositions may also be formulated with a carrier, such as beta-glucan, carboxylmethyl cellulose (CMC), bacterial extracellular polymeric substance (EPS), sugar, animal milk, or other suitable carriers. In some examples, peat or planting materials can be used as a carrier, or biopolymers in which a composition is entrapped in the biopolymer can be used as a carrier. The compositions comprising the bacterial populations described herein can improve plant traits, such as promoting plant growth, maintaining high chlorophyll content in leaves, increasing fruit or seed numbers, and increasing fruit or seed unit weight.

Compositions comprising a seed coated with one or more bacteria described herein are also contemplated. The seed coating can be formed by mixing the bacterial population with a porous, chemically inert granular carrier. Alternatively, the compositions may be inserted directly into the furrows into which the seed is planted or sprayed onto the plant leaves or applied by dipping the roots into a suspension of the composition. An effective amount of the composition can be used to populate the sub-soil region adjacent to the roots of the plant with viable bacterial growth, or populate the leaves of the plant with viable bacterial growth. In general, an effective amount is an amount sufficient to result in plants with improved traits (e.g. a desired level of nitrogen fixation).

Bacterial compositions described herein can be formulated using an agriculturally acceptable carrier. The formulation useful for these embodiments may include at least one member selected from the group consisting of a tackifier, a microbial stabilizer, a fungicide, an antibacterial agent, a preservative, a stabilizer, a surfactant, an anti-complex agent, a pesticide, including a non-naturally occurring pesticide, or a biorational or biological pesticide, an herbicide, a nematicide, an insecticide, a plant growth regulator, a fertilizer, a rodenticide, a dessicant, a bactericide, a nutrient, or any combination thereof.

In some examples, compositions may be shelf-stable. For example, any of the compositions described herein can include an agriculturally acceptable carrier (e.g., one or more of a fertilizer such as a non-naturally occurring fertilizer, an adhesion agent such as a non-naturally occurring adhesion agent, and a pesticide such as a non-naturally occurring pesticide). A non-naturally occurring adhesion agent can be, for example, a polymer, copolymer, or synthetic wax. For example, any of the coated seeds, seedlings, or plants described herein can contain such an agriculturally acceptable carrier in the seed coating. In any of the compositions or methods described herein, an agriculturally acceptable carrier can be or can include a non-naturally occurring compound (e.g., a non-naturally occurring fertilizer, a non-naturally occurring adhesion agent such as a polymer, copolymer, or synthetic wax, or a non-naturally occurring pesticide). Non-limiting examples of agriculturally acceptable carriers are described below. Additional examples of agriculturally acceptable carriers are known in the art.

In some cases, bacteria are mixed with an agriculturally acceptable carrier. The carrier can be a solid carrier or liquid carrier, and in various forms including microspheres, powders, emulsions and the like. The carrier may be any one or more of a number of carriers that confer a variety of properties, such as increased stability, wettability, or dispersability. Wetting agents such as natural or synthetic surfactants, which can be nonionic or ionic surfactants, or a combination thereof can be included in the composition. Water-in-oil emulsions can also be used to formulate a composition that includes the isolated bacteria (see, for example, U.S. Pat. No. 7,485,451). Suitable formulations that may be prepared include wettable powders, granules, gels, agar strips or pellets, thickeners, and the like, micro-encapsulated particles, and the like, liquids such as aqueous flowables, aqueous suspensions, water-in-oil emulsions, etc. The formulation may include grain or legume products, for example, ground grain or beans, broth or flour derived from grain or beans, starch, sugar, or oil.

In some embodiments, the agricultural carrier may be soil or a plant growth medium. Other agricultural carriers that may be used include water, fertilizers, plant-based oils, humectants, or combinations thereof. Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers, such as but not limited to, pesta (flour and kaolin clay), agar or flour-based pellets in loam, sand, or clay, etc. Formulations may include food sources for the bacteria, such as barley, rice, or other biological materials such as seed, plant parts, sugar cane bagasse, hulls or stalks from grain processing, ground plant material or wood from building site refuse, sawdust or small fibers from recycling of paper, fabric, or wood.

For example, a fertilizer can be used to help promote the growth or provide nutrients to a seed, seedling, or plant. Non-limiting examples of fertilizers include nitrogen, phosphorous, potassium, calcium, sulfur, magnesium, boron, chloride, manganese, iron, zinc, copper, molybdenum, and selenium (or a salt thereof). Additional examples of fertilizers include one or more amino acids, salts, carbohydrates, vitamins, glucose, NaCl, yeast extract, $NH_4H_2PO_4$, $(NH_4)_2SO_4$, glycerol, valine, L-leucine, lactic acid, propionic acid, succinic acid, malic acid, citric acid, KH tartrate, xylose, lyxose, and lecithin. In one embodiment, the formulation can include a tackifier or adherent (referred to as an adhesive agent) to help bind other active agents to a substance (e.g., a surface of a seed). Such agents are useful for combining bacteria with carriers that can contain other compounds (e.g., control agents that are not biologic), to yield a coating composition. Such compositions help create coatings around the plant or seed to maintain contact between the microbe and other agents with the plant or plant part. In one embodiment, adhesives are selected from the group consisting of: alginate, gums, starches, lecithins, formononetin, polyvinyl alcohol, alkali formononetinate, hesperetin, polyvinyl acetate, cephalins, Gum Arabic, Xanthan Gum, Mineral Oil, Polyethylene Glycol (PEG), Polyvinyl pyrrolidone (PVP), Arabino-galactan, Methyl Cellulose, PEG 400, Chitosan, Polyacrylamide, Polyacrylate, Polyacrylonitrile, Glycerol, Triethylene glycol, Vinyl Acetate, Gellan Gum, Polystyrene, Polyvinyl, Carboxymethyl cellulose, Gum Ghatti, and polyoxyethylene-polyoxybutylene block copolymers.

In some embodiments, the adhesives can be, e.g. a wax such as carnauba wax, beeswax, Chinese wax, shellac wax, spermaceti wax, candelilla wax, castor wax, ouricury wax, and rice bran wax, a polysaccharide (e.g., starch, dextrins, maltodextrins, alginate, and chitosans), a fat, oil, a protein (e.g., gelatin and zeins), gum arables, and shellacs. Adhesive agents can be non-naturally occurring compounds, e.g., polymers, copolymers, and waxes. For example, non-limiting examples of polymers that can be used as an adhesive agent include: polyvinyl acetates, polyvinyl acetate copolymers, ethylene vinyl acetate (EVA) copolymers, polyvinyl alcohols, polyvinyl alcohol copolymers, celluloses (e.g., ethylcelluloses, methylcelluloses, hydroxymethylcelluloses, hydroxypropylcelluloses, and carboxymethylcelluloses), polyvinylpyrolidones, vinyl chloride, vinylidene chloride copolymers, calcium lignosulfonates, acrylic copolymers, polyvinylacrylates, polyethylene oxide, acylamide polymers and copolymers, polyhydroxyethyl acrylate, methylacrylamide monomers, and polychloroprene.

In some examples, one or more of the adhesion agents, anti-fungal agents, growth regulation agents, and pesticides (e.g., insecticide) are non-naturally occurring compounds (e.g., in any combination). Additional examples of agriculturally acceptable carriers include dispersants (e.g., polyvinylpyrrolidone/vinyl acetate PVPIVA S-630), surfactants, binders, and filler agents.

The formulation can also contain a surfactant. Non-limiting examples of surfactants include nitrogen-surfactant blends such as Prefer 28 (Cenex), Surf-N(US), Inhance (Brandt), P-28 (Wilfarm) and Patrol (Helena); esterified seed oils include Sun-It II (AmCy), MSO (UAP), Scoil (Agsco), Hasten (Wilfarm) and Mes-100 (Drexel); and organo-silicone surfactants include Silwet L77 (UAP), Silikin (Terra), Dyne-Amic (Helena), Kinetic (Helena), Sylgard 309 (Wilbur-Ellis) and Century (Precision). In one embodiment, the surfactant is present at a concentration of between 0.01% v/v to 10% v/v. In another embodiment, the surfactant is present at a concentration of between 0.1% v/v to 1% v/v.

In certain cases, the formulation includes a microbial stabilizer. Such an agent can include a desiccant, which can include any compound or mixture of compounds that can be classified as a desiccant regardless of whether the compound or compounds are used in such concentrations that they in fact have a desiccating effect on a liquid inoculant. Such desiccants are ideally compatible with the bacterial population used, and should promote the ability of the microbial population to survive application on the seeds and to survive desiccation. Examples of suitable desiccants include one or more of trehalose, sucrose, glycerol, and Methylene glycol. Other suitable desiccants include, but are not limited to, non reducing sugars and sugar alcohols (e.g., mannitol or sorbitol). The amount of desiccant introduced into the formulation can range from about 5% to about 50% by weight/ volume, for example, between about 10% to about 40%, between about 15% to about 35%, or between about 20% to about 30%. In some cases, it is advantageous for the formulation to contain agents such as a fungicide, an antibacterial agent, an herbicide, a nematicide, an insecticide, a plant growth regulator, a rodenticide, bactericide, or a nutrient. In some examples, agents may include protectants that provide protection against seed surface-borne pathogens. In some examples, protectants may provide some level of control of soil-borne pathogens. In some examples, protectants may be effective predominantly on a seed surface.

In some cases, a bacterial composition can include one or more pesticides. Suitable pesticides can target economically important agronomic, forest, greenhouse, nursery ornamentals, food and fiber, public and animal health, domestic and commercial structure, household, or stored product pests. For example, the one or more pesticides can target insects, fungi, bacteria, nematodes, mites, ticks and the like. Insect pests include insects selected from the orders Coleoptera, Diptera, Hymenoptera, Lepidoptera, Mallophaga, Homoptera, Hemiptera Orthroptera, Thysanoptera, Dermaptera, Isoptera, Anoplura, Siphonaptera, Trichoptera, etc., particularly Lepidoptera and Coleoptera. In some cases, a biorational pesticide can be used. Such biorational pesticides include (1) biochemicals (hormones, enzymes, pheromones and natural agents, such as insect and plant growth regulators), (2) microbial (viruses, bacteria, fungi, protozoa, and nematodes), or (3) Plant-Incorporated protectants (PIPs)— primarily transgenic plants, e.g., Bt corn.

Bacteria, fungi, oomycetes, viruses and protozoa are all used for the biological control of insect pests. The most widely used microbial biopesticide is the insect pathogenic bacteria *Bacillus thuringiensis* (Bt), which produces a protein crystal (the Bt 8-endotoxin) during bacterial spore formation that is capable of causing lysis of gut cells when consumed by susceptible insects. Microbial Bt biopesticides consist of bacterial spores and 8-endotoxin crystals mass-produced in fermentation tanks and formulated as a sprayable product. Bt does not harm vertebrates and is safe to people, beneficial organisms and the environment. Thus, Bt sprays are a growing tactic for pest management on fruit and vegetable crops where their high level of selectivity and safety are considered desirable, and where resistance to synthetic chemical insecticides is a problem Bt sprays have also been used on commodity crops such as maize, soybean and cotton, but with the advent of genetic modification of plants, farmers are increasingly growing Bt transgenic crop varieties.

In some embodiments, fungicidal compositions may be included in the compositions set forth herein, and can be applied to a plant(s) or a part(s) thereof simultaneously or in succession, with other compounds. In some examples, a fungicide may include a compound or agent, whether chemical or biological, that can inhibit the growth of a fungus or kill a fungus. In some examples, a fungicide may include compounds that may be fungistatic or fungicidal. In some examples, fungicide can be a protectant, or agents that are effective predominantly on the seed surface, providing protection against seed surface-borne pathogens and providing some level of control of soil-borne pathogens. Non-limiting examples of protectant fungicides include captan, maneb, thiram, or fludioxonil. In some examples, a fungicide can be a systemic fungicide, which can be absorbed into the emerging seedling and inhibit or kill the fungus inside host plant tissues. Systemic fungicides used for seed treatment include, but are not limited to the following: azoxystrobin, carboxin, mefenoxam, metalaxyl, thiabendazole, trifloxystrobin, and various triazole fungicides, including difenoconazole, ipconazole, tebuconazole, and triticonazole. Mefenoxam and metalaxyl are primarily used to target the water mold fungi *Pythium* and *Phytophthora*. Some fungicides are preferred over others, depending on the plant species, either because of subtle differences in sensitivity of the pathogenic fungal species, or because of the differences in the fungicide distribution or sensitivity of the plants. In some examples, fungicide can be a biological control agent, such as a bacterium or fungus. Such organisms may be parasitic to the pathogenic fungi, or secrete toxins or other substances which can kill or otherwise prevent the growth of fungi. Any type of fungicide, particularly ones that are commonly used on plants, can be used as a control agent in a seed composition. In some cases, a fungicide can be azoxystrobin, captan, carboxin, ethaboxam, fludioxonil, mefenoxam, fludioxonil, thiabendazole, thiabendaz, ipconazole, mancozeb, cyazofamid, zoxamide, metalaxyl, PCNB, metaconazole, pyraclostrobin, *Bacillus subtilis* strain QST 713, sedaxane, thiamethoxam, fludioxonil, thiram, tolclofos-methyl, trifloxystrobin, *Bacillus subtilis* strain MBI 600, pyraclostrobin, fluoxastrobin, *Bacillus pumilus* strain QST 2808, chlorothalonil, copper, flutriafol, fluxapyroxad, mancozeb, gludioxonil, penthiopyrad, triazole, propiconaozole, prothioconazole, tebuconazole, fluoxastrobin, pyraclostrobin, picoxystrobin, qols, tetraconazole, trifloxystrobin, cyproconazole, flutriafol, SDHI, EBDCs, sedaxane, MAXIM QUATTRO (gludioxonil, mefenoxam, azoxystrobin, and thiabendaz), RAXIL (tebuconazole, prothioconazole, metalaxyl, and ethoxylated tallow alkyl amines), or benzovindiflupyr.

In some examples, the seed coating composition comprises a control agent which has antibacterial properties. In one embodiment, the control agent with antibacterial properties is selected from the compounds described herein elsewhere. In another embodiment, the compound is Streptomycin, oxytetracycline, oxolinic acid, or gentamicin. Other examples of antibacterial compounds which can be used as part of a seed coating composition include those based on dichlorophene and benzylalcohol hemi formal (Proxel® from ICI or Acticide® RS from Thor Chemie and Kathon® MK 25 from Rohm & Haas) and isothiazolinone derivatives such as alkylisothiazolinones and benzisothiazolinones (Acticide® MBS from Thor Chemie).

In some examples, growth regulator is selected from the group consisting of: Abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione phosphorotrithioate, 2,3,5-tri-iodobenzoic acid, trinexapac-ethyl and uniconazole. Additional non-limiting examples of growth regulators include brassinosteroids, cytokinines (e.g., kinetin and zeatin), auxins (e.g., indolylacetic acid and indolylacetyl aspartate), flavonoids and isoflavanoids (e.g., formononetin and diosmetin), phytoaixins (e.g., glyceolline), and phytoalexin-inducing oligosaccharides (e.g., pectin, chitin, chitosan, polygalacuronic acid, and oligogalacturonic acid), and gibellerins. Such agents are ideally compatible with the agricultural seed or seedling onto which the formulation is applied (e.g., it should not be deleterious to the growth or health of the plant). Furthermore, the agent is ideally one which does not cause safety concerns for human, animal or industrial use (e.g., no safety issues, or the compound is sufficiently labile that the commodity plant product derived from the plant contains negligible amounts of the compound).

Some examples of nematode-antagonistic biocontrol agents include ARF18; 30 *Arthrobotrys* spp.; *Chaetomium* spp.; *Cylindrocarpon* spp.; *Exophilia* spp.; *Fusarium* spp.; *Gliocladium* spp.; *Hirsutella* spp.; *Lecanicillium* spp.; *Monacrosporium* spp.; *Myrothecium* spp.; *Neocosmospora* spp.; *Paecilomyces* spp.; *Pochonia* spp.; *Stagonospora* spp.; *vesicular-arbuscular mycorrhizal fungi, Burkholderia* spp.; *Pasteuria* spp., *Brevibacillus* spp.; *Pseudomonas* spp.; and *Rhizobacteria*. Particularly preferred nematode-antagonistic biocontrol agents include ARF18, *Arthrobotrys oligospora, Arthrobotrys dactyloides, Chaetomium globosum, Cylindrocarpon heteronema, Exophilia jeanselmei, Exophilia pisciphila, Fusarium aspergilus, Fusarium solani, Gliocladium catenulatum, Gliocladium roseum, Gliocladium vixens, Hirsutella rhossiliensis, Hirsutella minnesotensis, Lecanicillium lecanii, Monacrosporium drechsleri, Monacrosporium gephyropagum, Myrotehcium verrucaria, Neocosmospora vasinfecta, Paecilomyces lilacinus, Pochonia chlamydosporia, Stagonospora heteroderae, Stagonospora phaseoli, vesicular-arbuscular mycorrhizal fungi, Burkholderia cepacia, Pasteuria penetrans, Pasteuria thornei, Pasteuria nishizawae, Pasteuria ramosa, Pastrueia usage, Brevibacillus laterosporus* strain G4, *Pseudomonas fluorescens* and *Rhizobacteria*.

Some examples of nutrients can be selected from the group consisting of a nitrogen fertilizer including, but not limited to Urea, Ammonium nitrate, Ammonium sulfate, Non-pressure nitrogen solutions, Aqua ammonia, Anhydrous ammonia, Ammonium thiosulfate, Sulfur-coated urea, Urea-formaldehydes, IBDU, Polymer-coated urea, Calcium nitrate, Ureaform, and Methylene urea, phosphorous fertilizers such as Diammonium phosphate, Monoammonium phosphate, Ammonium polyphosphate, Concentrated superphosphate and Triple superphosphate, and potassium fertilizers such as Potassium chloride, Potassium sulfate, Potassium-magnesium sulfate, Potassium nitrate. Such compositions can exist as free salts or ions within the seed coat composition. Alternatively, nutrients/fertilizers can be complexed or chelated to provide sustained release over time.

Some examples of rodenticides may include selected from the group of substances consisting of 2-isovalerylindan-1, 3-dione, 4-(quinoxalin-2-ylamino) benzenesulfonamide, alpha-chlorohydrin, aluminum phosphide, antu, arsenous oxide, barium carbonate, bisthiosemi, brodifacoum, bromadiolone, bromethalin, calcium cyanide, chloralose, chlorophacinone, cholecalciferol, coumachlor, coumafuryl, coumatetralyl, crimidine, difenacoum, difethialone, diphacinone, ergocalciferol, flocoumafen, fluoroacetamide, flupropadine, flupropadine hydrochloride, hydrogen cyanide, iodomethane, lindane, magnesium phosphide, methyl bromide, norbormide, phosacetim, phosphine, phosphorus, pindone, potassium arsenite, pyrinuron, scilliroside, sodium arsenite, sodium cyanide, sodium fluoroacetate, strychnine, thallium sulfate, warfarin and zinc phosphide.

Compositions comprising bacteria as described herein can include one or more herbicides. In some embodiments, herbicidal compositions are applied to the plants and/or plant parts. In some embodiments, herbicidal compositions may be included in the compositions set forth herein, and can be applied to a plant(s) or a part(s) thereof simultaneously or in succession, with other compounds. Herbicides can include 2,4-D, 2,4-DB, acetochlor, acifluorfen, alachlor, ametryn, atrazine, aminopyralid, benefin, bensulfuron, bensulide, bentazon, bicyclopyrone, bromacil, bromoxynil, butylate, carfentrazone, chlorimuron, chlorsulfuron, clethodim, clomazone, clopyralid, cloransulam, cycloate, DCPA, desmedipham, dicamba, dichlobenil, diclofop, diclosulam, diflufenzopyr, dimethenamid, diquat, diuron, DSMA, endothall, EPTC, ethalfluralin, ethofumesate, fenoxaprop, fluazifop-P, flucarbzone, flufenacet, flumetsulam, flumiclorac, flumioxazin, fluometuron, fluroxypyr, fomesafen, foramsulfuron, glufosinate, glyphosate, halosulfuron, hexazinone, imazamethabenz, imazamox, imazapic, imazaquin, imazethapyr, isoxaflutole, lactofen, linuron, MCPA, MCPB, mesotrione, metolachlor-s, metribuzin, indaziflam, metsulfuron, molinate, MSMA, napropamide, naptalam, nicosulfuron, norflurazon, oryzalin, oxadiazon, oxyfluorfen, paraquat, pelargonic acid, pendimethalin, phenmedipham, picloram, primisulfuron, prodiamine, prometryn, pronamide, propanil, prosulfuron, pyrazon, pyrithioac, quinclorac, quizalofop, rimsulfuron, S-metolachlor, sethoxydim, siduron, simazine, sulfentrazone, sulfometuron, sulfosulfuron, tebuthiuron, tembotrione, terbacil, thiazopyr, thifensulfuron, thiobencarb, topramezone, tralkoxydim, triallate, triasulfuron, tribenuron, triclopyr, trifluralin, and triflusulfuron. Herbicidal products may include CORVUS, BALANCE FLEXX, CAPRENO, DIFLEXX, LIBERTY, LAUDIS, AUTUMN SUPER, and DIFLEXX DUO.

In the liquid form, for example, solutions or suspensions, bacterial populations can be mixed or suspended in water or in aqueous solutions. Suitable liquid diluents or carriers include water, aqueous solutions, petroleum distillates, or other liquid carriers.

Solid compositions can be prepared by dispersing the bacterial populations in and on an appropriately divided solid carrier, such as peat, wheat, bran, vermiculite, clay, talc, bentonite, diatomaceous earth, fuller's earth, pasteurized soil, and the like. When such formulations are used as wettable powders, biologically compatible dispersing agents such as non-ionic, anionic, amphoteric, or cationic dispersing and emulsifying agents can be used.

The solid carriers used upon formulation include, for example, mineral carriers such as kaolin clay, pyrophyllite, bentonite, montmorillonite, diatomaceous earth, acid white soil, vermiculite, and pearlite, and inorganic salts such as ammonium sulfate, ammonium phosphate, ammonium nitrate, urea, ammonium chloride, and calcium carbonate. Also, organic fine powders such as wheat flour, wheat bran, and rice bran may be used. The liquid carriers include vegetable oils such as soybean oil and cottonseed oil, glycerol, ethylene glycol, polyethylene glycol, propylene glycol, polypropylene glycol, etc.

In some embodiments, the pesticides/microbial combinations can be applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time release or biodegradable carrier formulations that permit long term dosing of a target area following a single application of the formulation. They can also be selective herbicides, chemical insecticides, virucides, microbicides, amoebicides, pesticides, fungicides, bacteriocides, nematicides, molluscicides or mixtures of several of these preparations, if desired, together with further agriculturally acceptable carriers, surfactants or application promoting adjuvants customarily employed in the art of formulation. Suitable carriers (i.e. agriculturally acceptable carriers) and adjuvants can be solid or liquid and correspond to the substances ordinarily employed in formulation technology, e.g. natural or regenerated mineral substances, solvents, dispersants, wetting agents, sticking agents, tackifiers, binders or fertilizers. Likewise, the formulations may be prepared into edible baits or fashioned into pest traps to permit feeding or ingestion by a target pest of the pesticidal formulation.

In some cases, a composition provided here can include a microbial insecticide based on entomopathogenic baculoviruses. Baculoviruses that are pathogenic to arthropods belong to the virus family and possess large circular, covalently closed, and double-stranded DNA genomes that are packaged into nucleocapsids. More than 700 baculoviruses have been identified from insects of the orders Lepidoptera, Hymenoptera, and Diptera. Baculoviruses are usually highly specific to their host insects and thus, are safe to the environment, humans, other plants, and beneficial organisms. Over 50 baculovirus products have been used to control different insect pests worldwide. In the US and Europe, the *Cydia pomonella* granulovirus (CpGV) is used as an inundative biopesticide against codlingmoth on apples. Washington State, as the biggest apple producer in the US, uses CpGV on 13% of the apple crop. In Brazil, the nucleopolyhedrovirus of the soybean caterpillar *Anticarsia gemmatalis* was used on up to 4 million ha (approximately 35%) of the soybean crop in the mid-1990s. Viruses such as Gemstar® (Certis USA) are available to control larvae of *Heliothis* and *Helicoverpa* species.

At least 170 different biopesticide products based on entomopathogenic fungi have been developed for use against at least five insect and acarine orders in glasshouse crops, fruit and field vegetables as well as commodity crops. The majority of products are based on the ascomycetes *Beauveria bassiana* or *Metarhizium anisopliae. M anisopliae* has also been developed for the control of locust and grasshopper pests in Africa and Australia and is recommended by the Food and Agriculture Organization of the United Nations (FAO) for locust management.

A number of microbial pesticides registered in the United States are listed in Table 16 of Kabaluk et al. 2010 (Kabaluk, J. T. et al. (ed.). 2010. The Use and Regulation of Microbial Pesticides in Representative Jurisdictions Worldwide. IOBC Global. 99 pp.) and microbial pesticides registered in selected countries are listed in Annex 4 of Hoeschle-Zeledon et al. 2013 (Hoeschle-Zeledon, I., P. Neuenschwander and L. Kumar. (2013). Regulatory Challenges for biological control. SP-IPM Secretariat, International Institute of Tropical Agriculture (IITA), Ibadan, Nigeria. 43 pp.), each of which is incorporated herein in its entirety.

Plants produce a wide variety of secondary metabolites that deter herbivores from feeding on them. Some of these can be used as biopesticides. They include, for example, pyrethrins, which are fast-acting insecticidal compounds produced by *Chrysanthemum cinerariaefolium*. They have low mammalian toxicity but degrade rapidly after application. This short persistence prompted the development of synthetic pyrethrins (pyrethroids). The most widely used botanical compound is neem oil, an insecticidal chemical extracted from seeds of *Azadirachta indica*. Two highly active pesticides are available based on secondary metabolites synthesized by soil actinomycetes, but they have been evaluated by regulatory authorities as if they were synthetic chemical pesticides. Spinosad is a mixture of two macrolide compounds from *Saccharopolyspora spinosa*. It has a very low mammalian toxicity and residues degrade rapidly in the field. Farmers and growers used it widely following its introduction in 1997 but resistance has already developed in some important pests such as western flower *thrips*. Abamectin is a macrocyclic lactone compound produced by *Streptomyces avermitilis*. It is active against a range of pest species but resistance has developed to it also, for example, in tetranychid mites.

Peptides and proteins from a number of organisms have been found to possess pesticidal properties. Perhaps most prominent are peptides from spider venom (King, G. F. and Hardy, M. C. (2013) Spider-venom peptides: structure, pharmacology, and potential for control of insect pests. Annu. Rev. Entomol. 58: 475-496). A unique arrangement of disulfide bonds in spider venom peptides render them extremely resistant to proteases. As a result, these peptides are highly stable in the insect gut and hemolymph and many of them are orally active. The peptides target a wide range of receptors and ion channels in the insect nervous system Other examples of insecticidal peptides include: sea anemone venom that act on voltage-gated Na+ channels (Bosmans, F. and Tytgat, J. (2007) Sea anemone venom as a source of insecticidal peptides acting on voltage-gated Na+ channels. Toxicon. 49(4): 550-560); the PAlb (Pea Albumin 1, subunit b) peptide from Legume seeds with lethal activity on several insect pests, such as mosquitoes, some aphids and cereal weevils (Eyraud, V. et al. (2013) Expression and Biological Activity of the Cystine Knot Bioinsecticide PAlb (Pea Albumin 1 Subunit b). PLoS ONE 8(12): e81619); and an internal 10 kDa peptide generated by enzymatic hydrolysis of *Canavalia ensiformis* Gack bean) urease within susceptible insects (Martinelli, A. H. S., et al. (2014) Structure-function studies on jaburetox, a recombinant insecticidal peptide derived from jack bean (*Canavalia ensiformis*) urease. Biochimica et Biophysica Acta 1840: 935-944). Examples of commercially available peptide insecticides include Spear™-T for the treatment of *thrips* in vegetables and ornamentals in greenhouses, Spear™-P to control the Colorado Potato Beetle, and Spear™-C to protect crops from lepidopteran pests (Vestaron Corporation, Kalamazoo, MI). A novel insecticidal protein from *Bacillus bombysepticus*, called parasporal crystal toxin (PC), shows oral pathogenic activity and lethality towards silkworms and Cry1Ac-resistant *Helicoverpa armigera* strains (Lin, P. et al. (2015)

PC, a novel oral insecticidal toxin from *Bacillus bombysepticus* involved in host lethality via APN and BtR-175. Sci. Rep. 5: 11101).

A semiochemical is a chemical signal produced by one organism that causes a behavioral change in an individual of the same or a different species. The most widely used semiochemicals for crop protection are insect sex pheromones, some of which can now be synthesized and are used for monitoring or pest control by mass trapping, lure-and-kill systems and mating disruption. Worldwide, mating disruption is used on over 660,000 ha and has been particularly useful in orchard crops.

As used herein, "transgenic insecticidal trait" refers to a trait exhibited by a plant that has been genetically engineered to express a nucleic acid or polypeptide that is detrimental to one or more pests. In one embodiment, the plants of the present disclosure are resistant to attach and/or infestation from any one or more of the pests of the present disclosure. In one embodiment, the trait comprises the expression of vegetative insecticidal proteins (VIPs) from *Bacillus thuringiensis*, lectins and proteinase inhibitors from plants, terpenoids, cholesterol oxidases from *Streptomyces* spp., insect chitinases and fungal chitinolytic enzymes, bacterial insecticidal proteins and early recognition resistance genes. In another embodiment, the trait comprises the expression of a *Bacillus thuringiensis* protein that is toxic to a pest. In one embodiment, the Bt protein is a Cry protein (crystal protein). Bt crops include Bt corn, Bt cotton and Bt soy. Bt toxins can be from the Cry family (see, for example, Crickmore et al., 1998, Microbiol. Mol. Biol. Rev. 62: 807-812), which are particularly effective against Lepidoptera, Coleoptera and Diptera.

Bt Cry and Cyt toxins belong to a class of bacterial toxins known as pore-forming toxins (PFT) that are secreted as water-soluble proteins undergoing conformational changes in order to insert into, or to translocate across, cell membranes of their host. There are two main groups of PFT: (i) the a-helical toxins, in which a-helix regions form the trans-membrane pore, and (ii) the P-barrel toxins, that insert into the membrane by forming a P-barrel composed of Psheet hairpins from each monomer. See, Parker M W, Feil S C, "Pore-forming protein toxins: from structure to function," Prog. Biophys. Mol. Biol. 2005 May; 88(1):91-142.

The first class of PFT includes toxins such as the colicins, exotoxin A, diphtheria toxin and also the Cry three-domain toxins. On the other hand, aerolysin, a-hemolysin, anthrax protective antigen, cholesterol-dependent toxins as the perfringolysin O and the Cyt toxins belong to the P-barrel toxins. Id. In general, PFT producing-bacteria secrete their toxins and these toxins interact with specific receptors located on the host cell surface. In most cases, PFT are activated by host proteases after receptor binding inducing the formation of an oligomeric structure that is insertion competent. Finally, membrane insertion is triggered, in most cases, by a decrease in pH that induces a molten globule state of the protein. Id.

The development of transgenic crops that produce Bt Cry proteins has allowed the substitution of chemical insecticides by environmentally friendly alternatives. In transgenic plants the Cry toxin is produced continuously, protecting the toxin from degradation and making it reachable to chewing and boring insects. Cry protein production in plants has been improved by engineering cry genes with a plant biased codon usage, by removal of putative splicing signal sequences and deletion of the carboxy-terminal region of the protoxin. See, Schuler T H, et al., "Insect-resistant transgenic plants," Trends Biotechnol. 1998; 16:168-175. The use of insect resistant crops has diminished considerably the use of chemical pesticides in areas where these transgenic crops are planted. See, Qaim M, Zilberman D, "Yield effects of genetically modified crops in developing countries," Science. 2003 Feb. 7; 299(5608):900-2.

Known Cry proteins include: 8-endotoxins including but not limited to: the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry 28, Cry 29, Cry 30, Cry31, Cry32, Cry33, Cry34, Cry35, Cry36, Cry37, Cry38, Cry39, Cry40, Cry41, Cry42, Cry43, Cry44, Cry45, Cry 46, Cry47, Cry49, Cry 51, Cry52, Cry 53, Cry 54, Cry55, Cry56, Cry57, Cry58, Cry59. Cry60, Cry61, Cry62, Cry63, Cry64, Cry65, Cry66, Cry67, Cry68, Cry69, Cry70 and Cry71 classes of 8-endotoxin genes and the *B. thuringiensis* cytolytic cyt1 and cyt2 genes.

Examples of 8-endotoxins also include but are not limited to Cry1A proteins of U.S. Pat. Nos. 5,880,275, 7,858,849, 8,530,411, 8,575,433, and 8,686,233; a DIG-3 or DIG-11 toxin (N-terminal deletion of a-helix 1 and/or a-helix 2 variants of cry proteins such as Cry1A, Cry3 A) of U.S. Pat. Nos. 8,304,604, 8,304,605 and 8,476,226; Cry1B of U.S. patent application Ser. No. 10/525,318; Cry1C of U.S. Pat. No. 6,033,874; Cry1F of U.S. Pat. Nos. 5,188,960 and 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including butnot limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as such as members of the Cry9A, Cry9B, Cry9C, Cry9D, Cry9E and Cry9F families. Other Cry proteins are well known to one skilled in the art. See, N. Crickmore, et al., "Revision of the Nomenclature for the *Bacillus thuringiensis* Pesticidal Crystal Proteins," Microbiology and Molecular Biology Reviews," (1998) Vol 62: 807-813; see also, N. Crickmore, et al., "*Bacillus thuringiensis* toxin nomenclature" (2016), at www.btnomenclature.info/.

The use of Cry proteins as transgenic plant traits is well known to one skilled in the art and Cry-transgenic plants including but not limited to plants expressing Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bbl, Cry34Abl, Cry35Abl, Vip3A, mCry3A, Cry9c and CBI-Bt have received regulatory approval. See, Sanahuja et al., "*Bacillus thuringiensis*: a century of research, development and commercial applications," (2011) Plant Biotech Journal, April 9(3):283-300 and the CERA (2010) GM Crop Database Center for Environmental Risk Assessment (CERA), ILS Research Foundation, Washington D.C. at cera-gmc.org/index.php?action=gm_crop_database, which can be accessed on the world-wide web using the "www" prefix). More than one pesticidal proteins well known to one skilled in the art can also be expressed in plants such as Vip3Ab & Cry1Fa (US2012/0317682); Cry1BE & Cry1F (US2012/0311746); Cry1CA & Cry1AB (US2012/0311745); Cry1F & CryCa (US2012/0317681); Cry1DA& Cry1BE (US2012/0331590); Cry1DA & Cry1Fa (US2012/0331589); Cry1AB & Cry1BE (US2012/0324606); Cry1Fa & Cry2Aa and Cry1I & Cry1E (US2012/0324605); Cry34Ab/35Ab and Cry6Aa (US20130167269); Cry34Ab/

VCry35Ab & Cry3Aa (US20130167268); Cry1Ab & Cry1F (US20140182018); and Cry3A and Cry1Ab or Vip3Aa (US20130116170). Pesticidal proteins also include insecticidal lipases including lipid acyl hydrolases of U.S. Pat. No. 7,491,869, and cholesterol oxidases such asfromStreptomyces (Purcell et al. (1993) Biochem Biophys Res Commun 15:1406-1413).

Pesticidal proteins also include VIP (vegetative insecticidal proteins) toxins. Entomopathogenic bacteria produce insecticidal proteins that accumulate in inclusion bodies or parasporal crystals (such as the aforementioned Cry and Cyt proteins), as well as insecticidal proteins that are secreted into the culture medium Among the latter are the Vip proteins, which are divided into four families according to their amino acid identity. The Vip1 and Vip2 proteins act as binary toxins and are toxic to some members of the Coleoptera and Hemiptera. The Vip1 component is thought to bind to receptors in the membrane of the insect midgut, and the Vip2 component enters the cell, where it displays its ADP-ribosyltransferase activity against actin, preventing microfilament formation. Vip3 has no sequence similarity to Vip1 or Vip2 and is toxic to a wide variety of members of the Lepidoptera. Its mode of action has been shown to resemble that of the Cry proteins in terms of proteolytic activation, binding to the midgut epithelial membrane, and pore formation, although Vip3A proteins do not share binding sites with Cry proteins. The latter property makes them good candidates to be combined with Cry proteins in transgenic plants (*Bacillus thuringiensis*-treated crops [Bt crops]) to prevent or delay insect resistance and to broaden the insecticidal spectrum. There are commercially grown varieties of Bt cotton and Bt maize that express the Vip3Aa protein in combination with Cry proteins. For the most recently reported Vip4 family, no target insects have been found yet. See, Chakroun et al., "Bacterial Vegetative Insecticidal Proteins (Vip) from Entomopathogenic Bacteria," Microbiol Mol Biol Rev. 2016 Mar. 2; 80(2):329-50. VIPs can be found in U.S. Pat. Nos. 5,877,012, 6,107,279, 6,137, 033, 7,244,820, 7,615,686, and 8,237,020 and the like. Other VIP proteins are well known to one skilled m the art (see, lifesci.sussex.ac.uk/home/Neil_Crickmore/Bt/vip.html, which can be accessed on the world-wide web using the "www" prefix).

Pesticidal proteins also include toxin complex (TC) proteins, obtainable from organisms such as *Xenorhabdus, Photorhabdus* and *Paenibacillus* (see, U.S. Pat. Nos. 7,491, 698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptCl Wi. Examples of Class C proteins are TccC, XptClXb and XptBl Wi. Pesticidal proteins also include spider, snake and scorpion venom proteins. Examples of spider venom peptides include, but are not limited to lycotoxin-1 peptides and mutants thereof (U.S. Pat. No. 8,334,366).

Transgenic plants have also been engineered to express dsRNA directed against insect genes (Baum, J. A. et al.

(2007) Control of coleopteran insect pests through RNA interference. Nature Biotechnology 25: 1322-1326; Mao, Y. B. et al. (2007) Silencing a cotton bollworm P450 monooxygenase gene by plant-mediated RNAi impairs larval tolerance of gossypol. Nature Biotechnology 25: 1307-1313). RNA interference can be triggered in the pest by feeding of the pest on the transgenic plant. Pest feeding thus causes injury or death to the pest.

In some embodiments, any one or more of the pesticides set forth herein may be utilized with any one or more of the microbes of the disclosure and can be applied to plants or parts thereof, including seeds.

Nematicides

As aforementioned, agricultural compositions of the disclosure, which may comprise any microbe taught herein, are sometimes combined with one or more nematicides.

Compositions comprising bacteria or bacterial populations produced according to methods described herein and/ or having characteristics as described herein may further include one or more nematicide. In some embodiments, nematicidal compositions may be included in the compositions set forth herein, and can be applied to a plant(s) or a part(s) thereof simultaneously or in succession, with other compounds. The nematicides may be selected from D-D, 1,3-dichloropropene, ethylene dibromide, 1,2-dibromo-3-chloropropane, methyl bromide, chloropicrin, metam sodium, dazomet, methylisothiocyanate, sodium tetrathiocarbonate, aldicarb, aldoxycarb, carbofuran, oxamyl, ethoprop, fenamiphos, cadusafos, fosthiazate, terbufos, fensulfothion, phorate, DiTera, clandosan, sincocin, methyl iodide, propargyl bromide, 2,5-dihydroxymethyl-3,4-dihydroxypyrrolidine (DMDP), any one or more of the avermectins, sodium azide, furfural, *Bacillus jirmus*, abamectrin, thiamethoxam, fludioxonil, clothiandin, salicylic acid, and benzo-(1,2,3)-thiadiazole-7-carbothioic acid S-methyl ester.

In some embodiments, any one or more of the nematicides set forth herein may be utilized with any one or more of the plants or parts thereof set forth herein.

In some embodiments, any one or more of the nematicides, fungicides, herbicides, insecticides, and/or pesticides set forth herein may be utilized with any one or more of the plants or parts thereof set forth herein.

Fertilizers, Nitrogen Stabilizers, and Urease Inhibitors

As aforementioned, agricultural compositions of the disclosure, which may comprise any microbe taught herein, are sometimes combined with one or more of a: fertilizer, nitrogen stabilizer, or urease inhibitor.

In some embodiments, fertilizers are used in combination with the methods and bacteria of the present disclosure. Fertilizers include anhydrous ammonia, urea, ammonium nitrate, and urea-ammonium nitrate (UAN) composition, among many others. In some embodiments, pop-up fertilization and/or starter fertilization is used in combination with the methods and bacteria of the present disclosure.

In some embodiments, nitrogen stabilizers are used in combination with the methods and bacteria of the present disclosure. Nitrogen stabilizers include nitrapyrin, 2-chloro-6-(trichloromethyl) pyridine, N-SERVE 24, INSTINCT, dicyandiamide (DCD).

In some embodiments, urease inhibitors are used in combination with the methods and bacteria of the present disclosure. Urease inhibitors include N-(n-butyl)-thiophosphoric triamide (NBPT), AGROTAIN, AGROTAIN PLUS, and AGROTAIN PLUS SC. Further, the disclosure contemplates utilization of AGROTAIN ADVANCED 1.0, AGROTAIN DRI-MAXX, and AGROTAIN ULTRA.

Further, stabilized forms of fertilizer can be used. For example, a stabilized form offertilizer is SUPER U, containing 46% nitrogen in a stabilized, urea-based granule, SUPERU contains urease and nitrification inhibitors to guard from dentrification, leaching, and volatilization. Stabilized and targeted foliar fertilizer such as NITAMIN may also be used herein.

Pop-up fertilizers are commonly used in corn fields. Pop-up fertilization comprises applying a few pounds of nutrients with the seed at planting. Pop-up fertilization is used to increase seedling vigor.

Slow- or controlled-release fertilizer that may be used herein entails: A fertilizer containing a plant nutrient in a form which delays its availability for plant uptake and use after application, or which extends its availability to the plant significantly longer than a reference 'rapidly available nutrient fertilizer' such as ammonium nitrate or urea, ammonium phosphate or potassium chloride. Such delay of initial availability or extended time of continued availability may occur by a variety of mechanisms. These include controlled water solubility of the material by semi-permeable coatings, occlusion, protein materials, or other chemical forms, by slow hydrolysis of water-soluble low molecular weight compounds, or by other unknown means.

Stabilized nitrogen fertilizer that may be used herein entails: A fertilizer to which a nitrogen stabilizer has been added. A nitrogen stabilizer is a substance added to a fertilizer which extends the time the nitrogen component of the fertilizer remains in the soil in the urea-Nor ammoniacal-Nform Nitrification inhibitor that may be used herein entails: A substance that inhibits the biological oxidation of ammoniacal-N to nitrate-N. Some examples include: (1) 2-chloro-6-(trichloromethyl-pyridine), common name Nitrapyrin, manufactured by Dow Chemical; (2) 4-amino-1,2,4-6-triazole-HCl, common name ATC, manufactured by Ishihada Industries; (3) 2,4-diamino-6-trichloro-methyltriazine, common name CI-1580, manufactured by American Cyanamid; (4) Dicyandiamide, common name DCD, manufactured by Showa Denko; (5) Thiourea, common name TU, manufactured by Nitto Ryuso; (6) 1-mercapto-1,2,4-triazole, common name MT, manufactured by Nippon; (7) 2-amino-4-chloro-6-methyl-pyramidine, common name AM, manufactured by Mitsui Toatsu; (8) 3,4-dimethylpyrazole phosphate (DMPP), from BASF; (9) 1-amide-2-thiourea (ASU), from Nitto Chemical Ind.; (10) Ammoniumthiosulphate (ATS); (11) 1H-1,2,4-triazole (HPLC); (12) 5-ethylene oxide-3-trichloro-methlyl,2,4-thiodiazole (Terrazole), from Olin Mathieson; (13) 3-methylpyrazole (3-MP); (14) 1-carbamoyle-3-methyl-pyrazole (CMP); (15) Neem; and (16) DMPP.

Urease inhibitor that may be used herein entails: A substance that inhibits hydrolytic action on urea by the enzyme urease. Thousands of chemicals have been evaluated as soil urease inhibitors (see, e.g., Kiss and Simihaian, "Improving Efficiency of Urea Fertilizers by Inhibition of Soil Urease Activity," 2002, Springer Netherlands). However, only a few of the many compounds tested meet the necessary requirements of being non toxic, effective at low concentration, stable, and compatible with urea (solid and solutions), degradable in the soil and inexpensive. They can be classified according to their structures and their assumed interaction with the enzyme urease (Watson, "Urease Activity and inhibition—Principles and Practice, 2000, The International Fertiliser Society; Watson, "Urease Inhibitors" in "IFA International Workshop on Enhanced-Efficiency Fertilizers" 2005, Frankfurt, Germany, International Fertiliser Industry Association). Four main classes of urease inhibitors have been proposed: (a) reagents which interact with the sulphydryl groups (sulphydryl reagents), (b) hydroxamates, (c) agricultural crop protection chemicals, and (d) structural analogues of urea and related compounds. N-(n-Butyl) thiophosphoric triamide (NBPT), phenylphosphorodiamidate (PPD/PPDA), and hydroquinone are probably the most thoroughly studied urease inhibitors (Kiss and Simihaian, 2002, supra). Research and practical testing has also been carried out with N-(2-nitrophenyl) phosphoric acid triamide (2-NPT) and ammonium thiosulphate (ATS). The organo-phosphorus compounds are structural analogues of urea and are some of the most effective inhibitors of urease activity, blocking the active site of the enzyme (Watson, 2005).

Insecticidal Seed Treatments (ISTs) for Corn

Corn seed treatments normally target three spectrums of pests: nematodes, fungal seedling diseases, and insects. Insecticide seed treatments are usually the main component of a seed treatment package. Most corn seed available today comes with a base package that includes a fungicide and insecticide. In some aspects, the insecticide options for seed treatments include PONCHO (clothianidin), CRUISER/CRUISER EXTREME (thiamethoxam) and GAUCHO (Imidacloprid). All three of these products are neonicotinoid chemistries. CRUISER and PONCHO at the 250 (0.25 mg AI/seed) rate are some of the most common base options available for corn. In some aspects, the insecticide options for treatments include CRUISER 250 thiamethoxam, CRUISER 250 (thiamethoxam) plus LUMIVIA (chlorantraniliprole), CRUISER 500 (thiamethoxam), and PONCHO VOTIVO 1250 (Clothianidin & *Bacillus jirmus* 1-1582).

Application of Bacterial Populations on Crops

The composition of the bacteria or bacterial population described herein can be applied in furrow, in talc, or as seed treatment. The composition can be applied to a seed package in bulk, mini bulk, in a bag, or in talc.

The planter can plant the treated seed and grows the crop according to conventional ways, twin row, or ways that do not require tilling. The seeds can be distributed using a control hopper or an individual hopper. Seeds can also be distributed using pressurized air or manually. Seed placement can be performed using variable rate technologies. Additionally, application of the bacteria or bacterial population described herein may be applied using variable rate technologies. In some examples, the bacteria can be applied to seeds of corn, soybean, canola, *sorghum*, potato, rice, vegetables, cereals, pseudocereals, and oilseeds. Examples of cereals may include barley, fonio, oats, palmer's grass, rye, pearl millet, *sorghum*, spelt, teff, triticale, and wheat. Examples of pseudocereals may include breadnut, buckwheat, cattail, chia, flax, grain amaranth, hanza, *quinoa*, and sesame. In some examples, seeds can be genetically modified organisms (GMO), non-GMO, organic or conventional.

Additives such as micro-fertilizer, PGR, herbicide, insecticide, and fungicide can be used additionally to treat the crops. Examples of additives include crop protectants such as insecticides, nematicides, fungicide, enhancement agents such as colorants, polymers, pelleting, priming, and disinfectants, and other agents such as inoculant, PGR, softener, and micronutrients. PGRs can be natural or synthetic plant hormones that affect root growth, flowering, or stem elongation. PGRs can include auxins, gibberellins, cytokinins, ethylene, and abscisic acid (ABA).

The composition can be applied in furrow in combination with liquid fertilizer. In some examples, the liquid fertilizer may be held in tanks. NPK fertilizers contain macronutrients of sodium, phosphorous, and potassium.

The composition may improve plant traits, such as promoting plant growth, maintaining high chlorophyll content in leaves, increasing fruit or seed numbers, and increasing fruit or seed unit weight. Methods of the present disclosure may be employed to introduce or improve one or more of a variety of desirable traits. Examples of traits that may introduced or improved include: root biomass, root length, height, shoot length, leaf number, water use efficiency, overall biomass, yield, fruit size, grain size, photosynthesis rate, tolerance to drought, heat tolerance, salt tolerance, tolerance to low nitrogen stress, nitrogen use efficiency, resistance to nematode stress, resistance to a fungal pathogen, resistance to a bacterial pathogen, resistance to a viral pathogen, level of a metabolite, modulation in level of a metabolite, proteome expression. The desirable traits, including height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof, can be used to measure growth, and compared with the growth rate of reference agricultural plants (e.g., plants without the introduced and/or improved traits) grown under identical conditions. In some examples, the desirable traits, including height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof, can be used to measure growth, and compared with the growth rate of reference agricultural plants (e.g., plants without the introduced and/or improved traits) grown under similar conditions.

An agronomic trait to a host plant may include, but is not limited to, the following: altered oil content, altered protein content, altered seed carbohydrate composition, altered seed oil composition, and altered seed protein composition, chemical tolerance, cold tolerance, delayed senescence, disease resistance, drought tolerance, ear weight, growth improvement, health e4nhancement, heat tolerance, herbicide tolerance, herbivore resistance improved nitrogen fixation, improved nitrogen utilization, improved root architecture, improved water use efficiency, increased biomass, increased root length, increased seed weight, increased shoot length, increased yield, increased yield under water-limited conditions, kernel mass, kernel moisture content, metal tolerance, number of ears, number of kernels per ear, number of pods, nutrition enhancement, pathogen resistance, pest resistance, photosynthetic capability improvement, salinity tolerance, stay-green, vigor improvement, increased dry weight of mature seeds, increased fresh weight of mature seeds, increased number of mature seeds per plant, increased chlorophyll content, increased number of pods per plant, increased length of pods per plant, reduced number of wilted leaves per plant, reduced number of severely wilted leaves per plant, and increased number of non-wilted leaves per plant, a detectable modulation in the level of a metabolite, a detectable modulation in the level of a transcript, and a detectable modulation in the proteome, compared to an isoline plant grown from a seed without said seed treatment formulation.

In some cases, plants are inoculated with bacteria or bacterial populations that are isolated from the same species of plant as the plant element of the inoculated plant. For example, an bacteria or bacterial population that is normally found in one variety of *Zea mays* (corn) is associated with a plant element of a plant of another variety of *Zea mays* that in its natural state lacks said bacteria and bacterial populations. In one embodiment, the bacteria and bacterial populations is derived from a plant of a related species of plant as the plant element of the inoculated plant. For example, an bacteria and bacterial populations that is normally found in *Zea diploperennis* Iltis et al., (diploperennial teosinte) is applied to a *Zea mays* (corn), or vice versa. In some cases, plants are inoculated with bacteria and bacterial populations that are heterologous to the plant element of the inoculated plant. In one embodiment, the bacteria and bacterial populations is derived from a plant of another species. For example, an bacteria and bacterial populations that is normally found in dicots is applied to a monocot plant (e.g., inoculating corn with a soybean-derived bacteria and bacterial populations), or vice versa. In other cases, the bacteria and bacterial populations to be inoculated onto a plant is derived from a related species of the plant that is being inoculated. In one embodiment, the bacteria and bacterial populations is derived from a related taxon, for example, from a related species. The plant of another species can be an agricultural plant. In another embodiment, the bacteria and bacterial populations is part of a designed composition inoculated into any host plant element.

In some examples, the bacteria or bacterial population is exogenous wherein the bacteria and bacterial population is isolated from a different plant than the inoculated plant. For example, in one embodiment, the bacteria or bacterial population can be isolated from a different plant of the same species as the inoculated plant. In some cases, the bacteria or bacterial population can be isolated from a species related to the inoculated plant.

In some examples, the bacteria and bacterial populations described herein are capable of moving from one tissue type to another. For example, the present invention's detection and isolation of bacteria and bacterial populations within the mature tissues of plants after coating on the exterior of a seed demonstrates their ability to move from seed exterior into the vegetative tissues of a maturing plant. Therefore, in one embodiment, the population of bacteria and bacterial populations is capable of moving from the seed exterior into the vegetative tissues of a plant. In one embodiment, the bacteria and bacterial populations that is coated onto the seed of a plant is capable, upon germination of the seed into a vegetative state, of localizing to a different tissue of the plant. For example, bacteria and bacterial populations can be capable of localizing to any one of the tissues in the plant, including: the root, adventitious root, seminal 5 root, root hair, shoot, leaf, flower, bud, tassel, meristem, pollen, pistil, ovaries, stamen, fruit, stolon, rhizome, nodule, tuber, trichome, guard cells, hydathode, petal, sepal, glume, rachis, vascular cambium, phloem, and xylem. In one embodiment, the bacteria and bacterial populations is capable of localizing to the root and/or the root hair of the plant. In another embodiment, the bacteria and bacterial populations is capable of localizing to the photosynthetic tissues, for example, leaves and shoots of the plant. In other cases, the bacteria and bacterial populations is localized to the vascular tissues of the plant, for example, in the xylem and phloem. In still another embodiment, the bacteria and bacterial populations is capable of localizing to the reproductive tissues (flower, pollen, pistil, ovaries, stamen, fruit) of the plant. In another embodiment, the bacteria and bacterial populations is capable of localizing to the root, shoots, leaves and reproductive tissues of the plant. In still another embodiment, the bacteria and bacterial populations colonizes a fruit or seed tissue of the plant. In still another embodiment, the bacteria and bacterial populations is able to colonize the plant such that it is present in the surface of the plant (i.e., its presence is detectably present on the plant exterior, or the episphere of the plant). In still other embodiments, the bacteria and bacterial populations is capable of localizing to substantially all, or all, tissues of the plant. In certain embodiments, the bacteria and bacterial populations is not localized to the root of a plant. In other cases, the bacteria and bacterial populations is not localized to the photosynthetic tissues of the plant.

The effectiveness of the compositions can also be assessed by measuring the relative maturity of the crop or the crop heating unit (CHU). For example, the bacterial population can be applied to corn, and corn growth can be assessed according to the relative maturity of the corn kernel or the time at which the corn kernel is at maximum weight. The CHU can also be used to predict the maturation of the corn crop. The CHU determines the amount of heat accumulation by measuring the daily maximum temperatures on crop growth.

In examples, bacterial may localize to any one of the tissues in the plant, including: the root, adventitious root, seminal root, root hair, shoot, leaf, flower, bud tassel, meristem, pollen, pistil, ovaries, stamen, fruit, stolon, rhizome, nodule, tuber, trichome, guard cells, hydathode, petal, sepal, glume, rachis, vascular cambium, phloem, and xylem. In another embodiment, the bacteria or bacterial population is capable of localizing to the photosynthetic tissues, for example, leaves and shoots of the plant. In other cases, the bacteria and bacterial populations is localized to the vascular tissues of the plant, for example, in the xylem and phloem. In another embodiment, the bacteria or bacterial population is capable of localizing to reproductive tissues (flower, pollen, pistil, ovaries, stamen, or fruit) of the plant. In another embodiment, the bacteria and bacterial populations is capable of localizing to the root, shoots, leaves and reproductive tissues of the plant. In another embodiment, the bacteria or bacterial population colonizes a fruit or seed tissue of the plant. In still another embodiment, the bacteria or bacterial population is able to colonize the plant such that it is present in the surface of the plant. In another embodiment, the bacteria or bacterial population is capable of localizing to substantially all, or all, tissues of the plant. In certain embodiments, the bacteria or bacterial population is not localized to the root of a plant. In other cases, the bacteria and bacterial populations is not localized to the photosynthetic tissues of the plant.

The effectiveness of the bacterial compositions applied to crops can be assessed by measuring various features of crop growth including, but not limited to, planting rate, seeding vigor, root strength, drought tolerance, plant height, dry down, and test weight.

Plant Species

The methods and bacteria described herein are suitable for any of a variety of plants, such as plants in the genera *Hordeum, Oryza, Zea,* and *Triticeae.* Other non-limiting examples of suitable plants include mosses, lichens, and algae. In some cases, the plants have economic, social and/or environmental value, such as food crops, fiber crops, oil crops, plants in the forestry or pulp and paper industries, feedstock for biofuel production and/or ornamental plants. In some examples, plants may be used to produce economically valuable products such as a grain, a flour, a starch, a syrup, a meal, an oil, a film, a packaging, a nutraceutical product, a pulp, an animal feed, a fish fodder, a bulk material for industrial chemicals, a cereal product, a processed human-food product, a sugar, an alcohol, and/or a protein. Non-limiting examples of crop plants include maize, rice, wheat, barley, *sorghum,* millet, oats, rye triticale, buckwheat, sweet corn, sugar cane, onions, tomatoes, strawberries, and asparagus. In some embodiments, the methods and bacteria described herein are suitable for any of a variety of transgenic plants, non-transgenic plants, and hybrid plants thereof.

In some examples, plants that may be obtained or improved using the methods and composition disclosed herein may include plants that are important or interesting for agriculture, horticulture, biomass for the production of biofuel molecules and other chemicals, and/or forestry. Some examples of these plants may include pineapple, banana, coconut, lily, grasspeas, and grass; and dicotyledonous plants, such as, for example, peas, alfalfa, tomatillo, melon, chickpea, chicory, clover, kale, lentil, soybean, tobacco, potato, sweet potato, radish, cabbage, rape, apple trees, grape, cotton, sunflower, thale cress, canola, citrus (including orange, mandarin, kumquat, lemon, lime, grapefruit, tangerine, tangelo, citron, and pomelo), pepper, bean, lettuce, *Panicum virgatum* (switch), *Sorghum* spp., *Sorghum bicolor* (sorghum, sudan), *Miscanthus* spp., *Miscanthus giganteus* (miscanthus), *Saccharum* spp. (energycane), *Populus balsamifera* (poplar), *Zea mays* (corn), *Glycine max* (soybean), *Brassica napus* (canola), *Brassica juncea, Brassica oleracea* (broccoli, cauliflower, brussel sprouts), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), *Pennisetum glaucum* (pearl millet), *Panicum* spp., *Erianthus* spp., *Populus* spp., *Secale cereale* (rye), *Salix* spp. (willow), *Eucalyptus* spp. (eucalyptus), *Triticosecale* spp. (triticum-25 wheat X rye), Bamboo, *Carthamus tinctorius* (safflower), *Jatropha curcas* (Jatropha), *Ricinus communis* (castor), *Elaeis guineensis* (oil palm), *Phoenix dactylfera* (date palm), *Archontophoenix cunninghamiana* (king palm), *Syagrus romanzoffiana* (queen palm), *Linum usitatissimum* (flax), *Manihot esculenta* (cassaya), *Lycopersicon esculentum* (tomato), *Lactuca saliva* (lettuce), *Musa paradisiaca* (banana), *Solanum tuberosum* (potato), *Camellia sinensis* (tea), *Fragaria ananassa* (strawberry), *Theobroma cacao* (cocoa), *Coffea arabica* (coffee), *Vitis vinfera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Papaver somniferum* (opium poppy), *Papaver orientale, Taxus baccata, Taxus brevifolia, Artemisia annua, Cannabis saliva, Camptotheca acuminate, Catharanthus roseus, Vinca rosea, Cinchona officinalis, Coichicum autumnale, Veratrum calfornica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (*Huperzia serrata*), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii, Tanacetum parthenium, Parthenium argentatum* (guayule), *Hevea* spp. (rubber), *Mentha spicata* (mint), *Mentha piperita* (mint), *Bixa orellana, Alstroemeria* spp., *Rosa* spp. (rose), *Dianthus caryophyllus* (carnation), *Petunia* spp. (petunia), *Poinsettia pulcherrima* (poinsettia), *Nicotiana tabacum* (tobacco), *Lupinus albus* (lupin), *Uniola paniculata* (oats), *Hordeum vulgare* (barley), and *Lolium* spp. (rye).

In some examples, a monocotyledonous plant may be used. Monocotyledonous plants belong to the orders of the Alismatales, Arales, Arecales, Bromeliales, Commelinales, Cyclanthales, Cyperales, Eriocaulales, Hydrocharitales, Juncales, Lilliales, Najadales, Orchidales, Pandanales, Poales, Restionales, Triuridales, Typhales, and Zingiberales. Plants belonging to the class of the Gymnospermae are Cycadales, Ginkgoales, Gnetales, and Pinales. In some examples, the monocotyledonous plant can be selected from the group consisting of a maize, rice, wheat, barley, and sugarcane.

In some examples, a dicotyledonous plant may be used, including those belonging to the orders of the Aristochiales, Asterales, Batales, Campanulales, Capparales, Caryophyllales, Casuarinales, Celastrales, Cornales, Diapensales, Dilleniales, Dipsacales, Ebenales, Ericales, Eucomiales, Euphorbiales, Fabales, Fagales, Gentianales, Geraniales, Haloragales, Hamamelidales, Middles, Juglandales, Lamiales, Laurales, Lecythidales, Leitneriales, Magniolales, Malvales, Myricales, Myrtales, Nymphaeales, Papeverales, Piperales, Plantaginales, Plumb aginales, Podostemales, Polemoniales, Polygalales, Polygonales, Primulales, Proteales, Rafflesiales, Ranunculales, Rhamnales, Rosales, Rubiales, Salicales, Santales, Sapindales, Sarraceniaceae, Scrophulariales, Theales, Trochodendrales, Umbellales, Urticales, and Violates. In some examples, the dicotyledonous plant can be selected from the group consisting of cotton, soybean, pepper, and tomato.

In some cases, the plant to be improved is not readily amenable to experimental conditions. For example, a crop plant may take too long to grow enough to practically assess an improved trait serially over multiple iterations. Accordingly, a first plant from which bacteria are initially isolated, and/or the plurality of plants to which genetically manipulated bacteria are applied may be a model plant, such as a plant more amenable to evaluation under desired conditions. Non-limiting examples of model plants include *Setaria*, Brachypodium, and *Arabidopsis*. Ability of bacteria isolated according to a method of the disclosure using a model plant may then be applied to a plant of another type (e.g. a crop plant) to confirm conferral of the improved trait.

Traits that may be improved by the methods disclosed herein include any observable characteristic of the plant, including, for example, growth rate, height, weight, color, taste, smell, changes in the production of one or more compounds by the plant (including for example, metabolites, proteins, drugs, carbohydrates, oils, and any other compounds). Selecting plants based on genotypic information is also envisaged (for example, including the pattern of plant gene expression in response to the bacteria, or identifying the presence of genetic markers, such as those associated with increased nitrogen fixation). Plants may also be selected based on the absence, suppression or inhibition of a certain feature or trait (such as an undesirable feature or trait) as opposed to the presence of a certain feature or trait (such as a desirable feature or trait).

The invention will be further described in the following examples, which do not limit the scope of the invention described in the claims.

EXAMPLES

Example 1—ginD Mutations Increase Nitrogen Excretion

Figure 1:
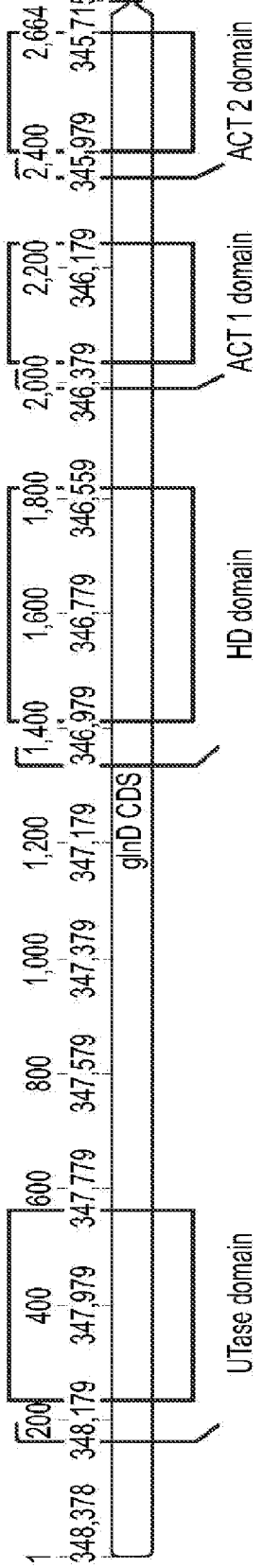
FIG. 1 illustrates a schematic of the glnD gene, showing regions corresponding to the functional domains of the GlnD protein.

GlnD is a bifunctional uridylyltransferase/uridylyl-removing enzyme which acts as the central "switch" for nitrogen sensing in the cell. It contains three distinct domains: the UTase domain, which uridylylates the PII proteins GlnB and GlnK; the uridylyl-reoving (UR) domain, also known as the HD domain, which removes the uriylyl group from the PII proteins; and two ACT domains, which regulate the activity of the other two domains in response to glutamine binding (FIG. 1). In nitrogen excess, glutamine binds the ACT domain and the UR domain is activated; in nitrogen starvation, ACT is unbound and the UTase domain is active. Subsequent PII protein signaling affects transcription of several gene clusters, including nitrogenase and nitrogen assimilation genes.

Figure 2:
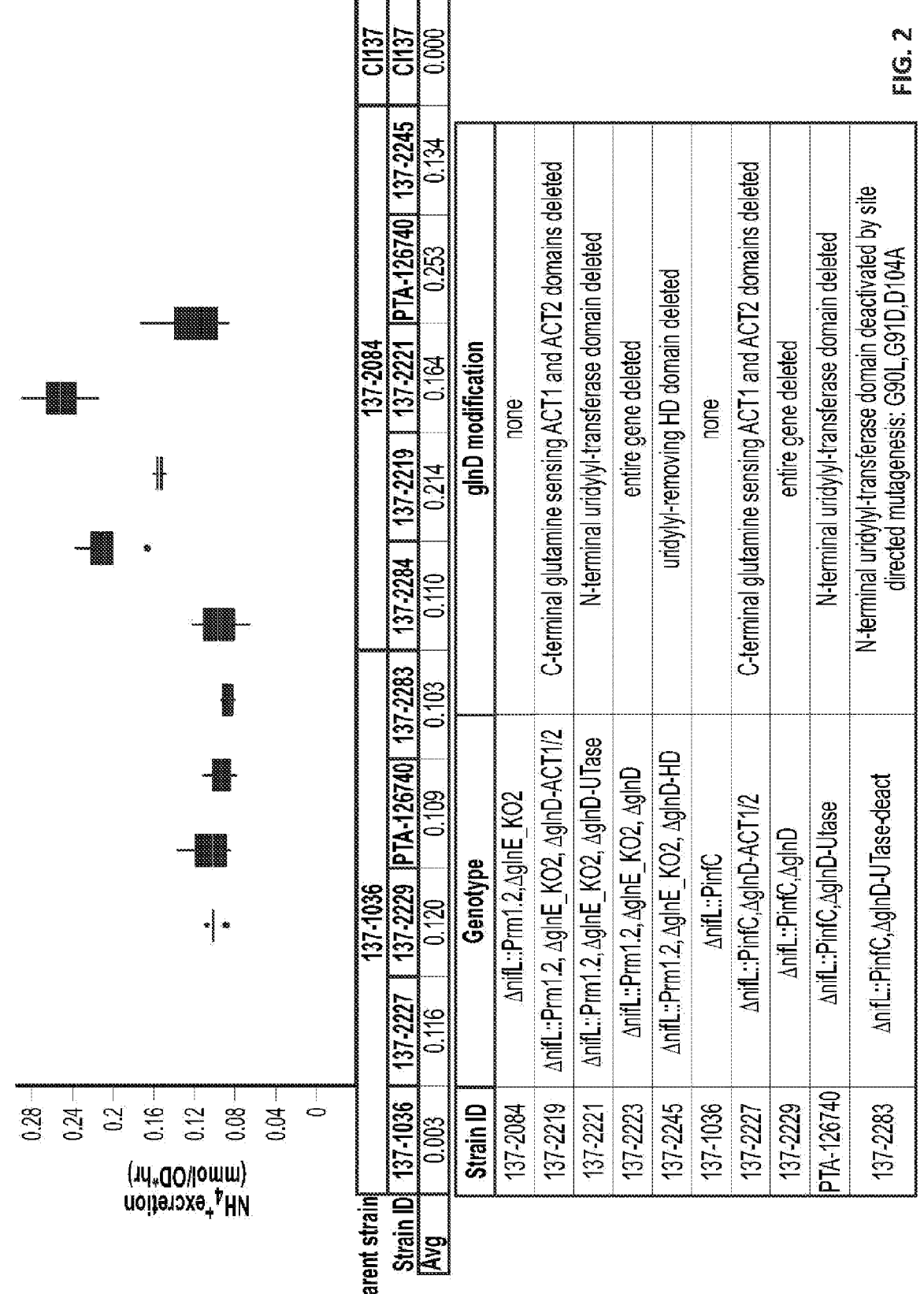
FIG. 2 depicts increased ammonium excretion in minimal nitrogen-free media in mutants of *K. variicola* strain 201708001 with modifications in the glnD gene.
Figure 3:
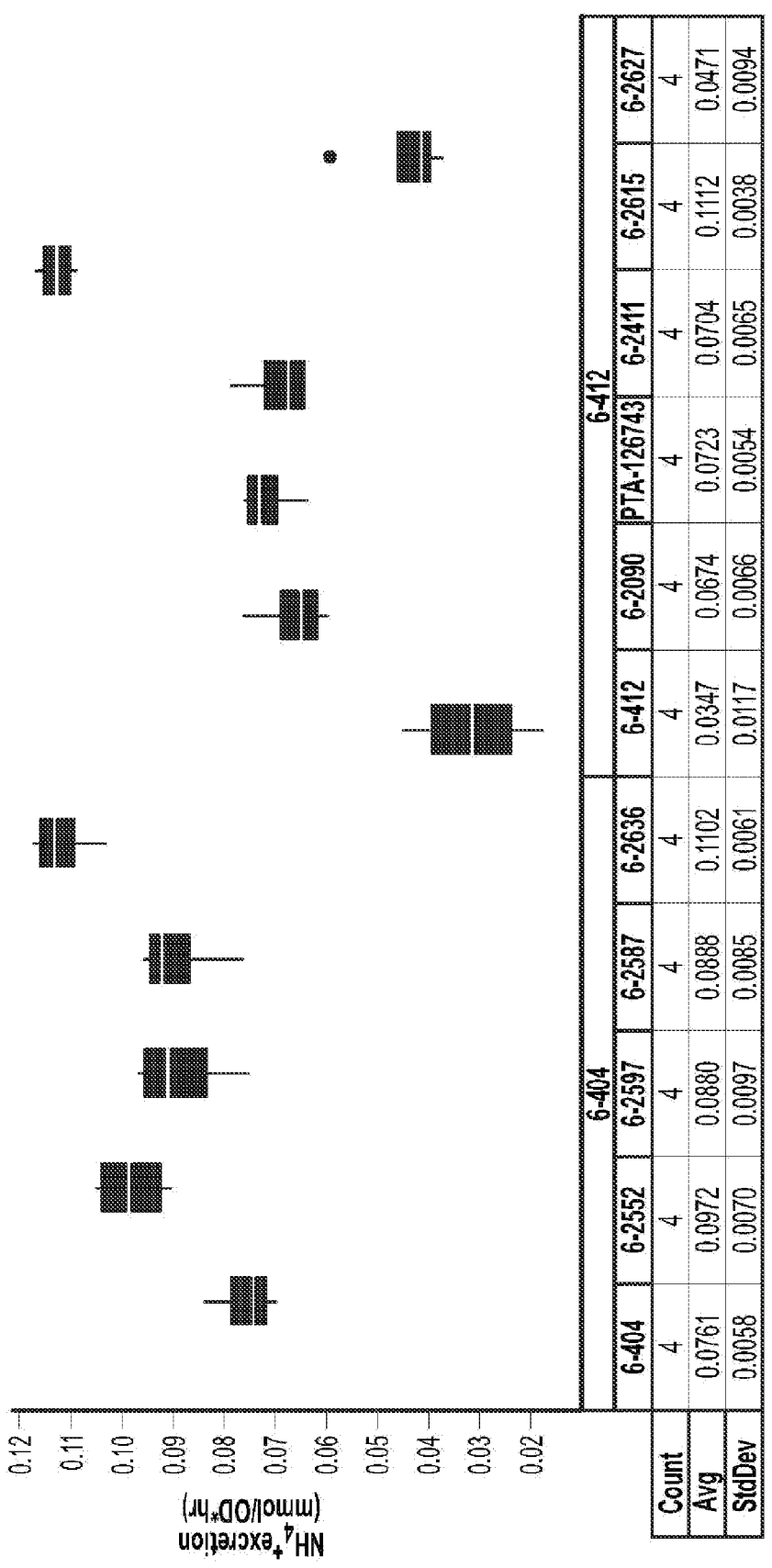
FIG. 3 depicts increased ammonium excretion in the indicated mutants of *K. sacchari* strain 201701001 with modifications in the glnD gene and a table of strains describing the genetic variations in the glnD gene. All strains are derived from *K. sacchari* strain 201701001. Ammonium excretion was measured in minimal nitrogen-free media.

Various truncations and deletions were performed to see how they impact fixation and excretion of nitrogen. Several glnD mutations modifying the UTase, UR and ACT1/2 (glutamine-sensing) domains lead to increases in activity as measured in ARA and ammonium excretion assays. FIG. 2 demonstrates several glnD modifications which lead to increased ammonium excretion in *K. variicola* CI137; FIG. 3 demonstrates several glnD modifications which lead to increases ammonium excretion in *K. sacchari*. FIG. 3 also contains a table that describes the strains with the genetic variations in the glnD gene.

Figure 4:
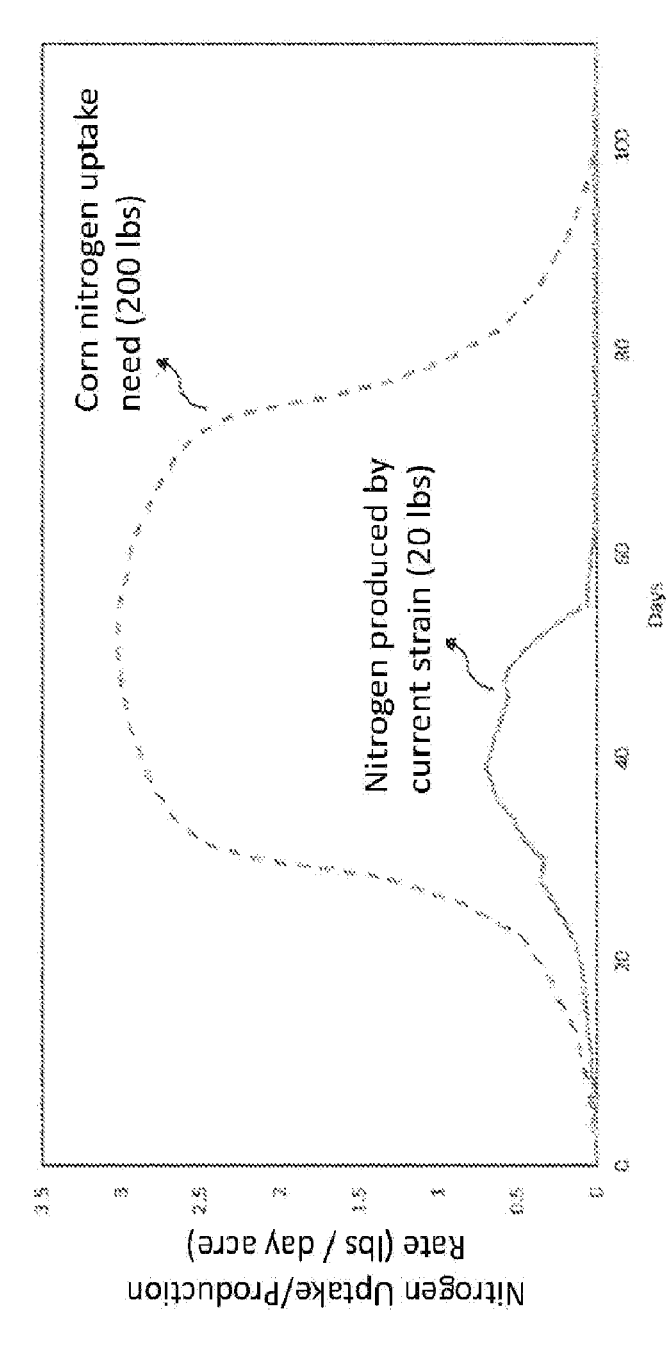
FIG. 4 depicts the nitrogen needs of a corn plant throughout the growing season. In order for a nitrogen fixing microbe to supply a corn plant with all of its nitrogen needs over a growing season, and thus completely replace synthetic fertilizer, then the microbes (in the aggregate) need to produce about 200 pounds of nitrogen per acre. The figure also illustrates that strain 201712002 (i.e. the remodeled *Klebsiella variicola*) supplies about 20 pounds of nitrogen per acre.

Example 2—Guided Microbial Remodeling (GMR) Campaign Utilizing Genetic Features The overall goal of the GMR campaigns is to develop microbes that are capable of supplying all of the nitrogen needs of a corn plant throughout the entirety of a growing season. In FIG. 4, it was calculated that for a nitrogen fixing microbe to supply a corn plant with all of its nitrogen needs over a growing season, the microbes (in the aggregate) should produce about 200 pounds of nitrogen per acre. FIG. 4 also illustrates that strain 201712002 (i.e., the remodeled *Klebsiella variicola*) supplies about 20 pounds of nitrogen per acre.

Figure 5A:
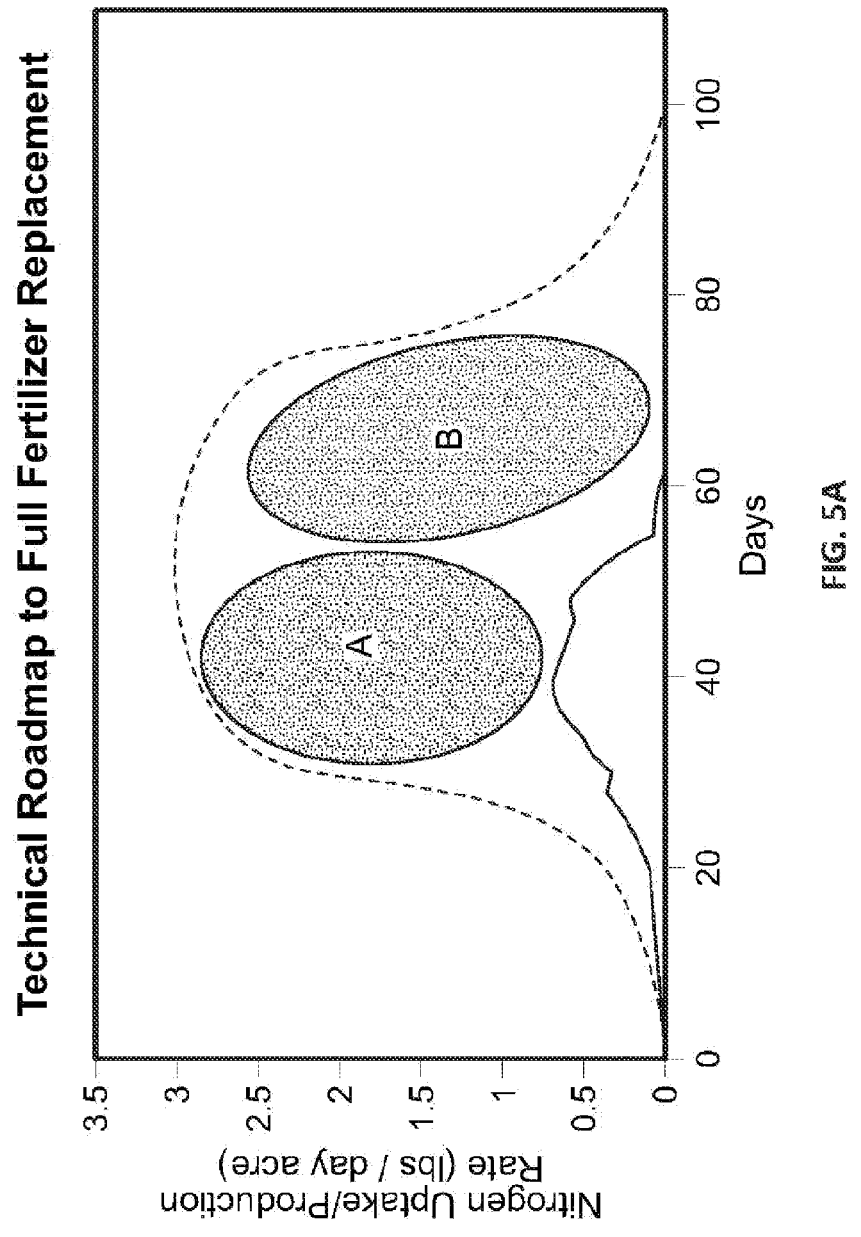
FIG. 5A provides a scenario whereby fertilizer could be replaced by the remodeled microbes of the disclosure. The large dashed line is the nitrogen required by the corn (about 200 pounds per acre). The solid line is the current nitrogen amount that can be supplied by the remodeled strain 201712002 (about 20 pounds per acre). In the "A" bubble scenario, an increase in the activity of strain 201712002 by 5 fold is expected (see FIG. 6 for GMR campaign strategy to achieve such). In the "B" scenario, a remodeled microbe with a particular colonization profile that is complementary to that of the 201712002 strain is expected to be utilized, and which will supply nitrogen to the plant at later stages of the growth cycle.
Figure 5B:
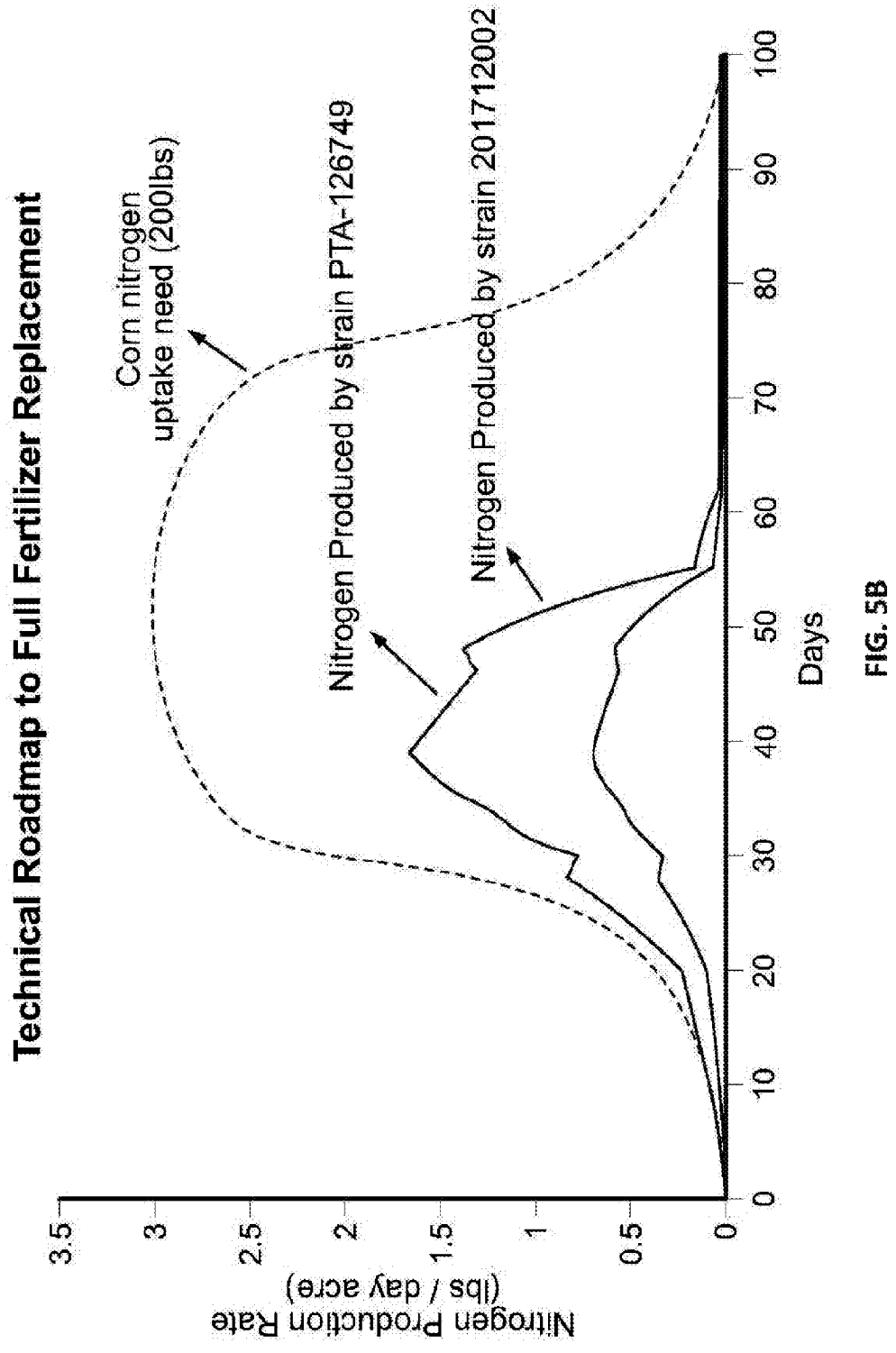
FIG. 5B shows the nitrogen production by a further remodeled strain PTA-126749 at the time of the present application relative to the nitrogen production by the strain 201712002 from the time of the provisional application. The dashed line indicates the nitrogen needs of a corn plant throughout the growing season.
Figure 6A:
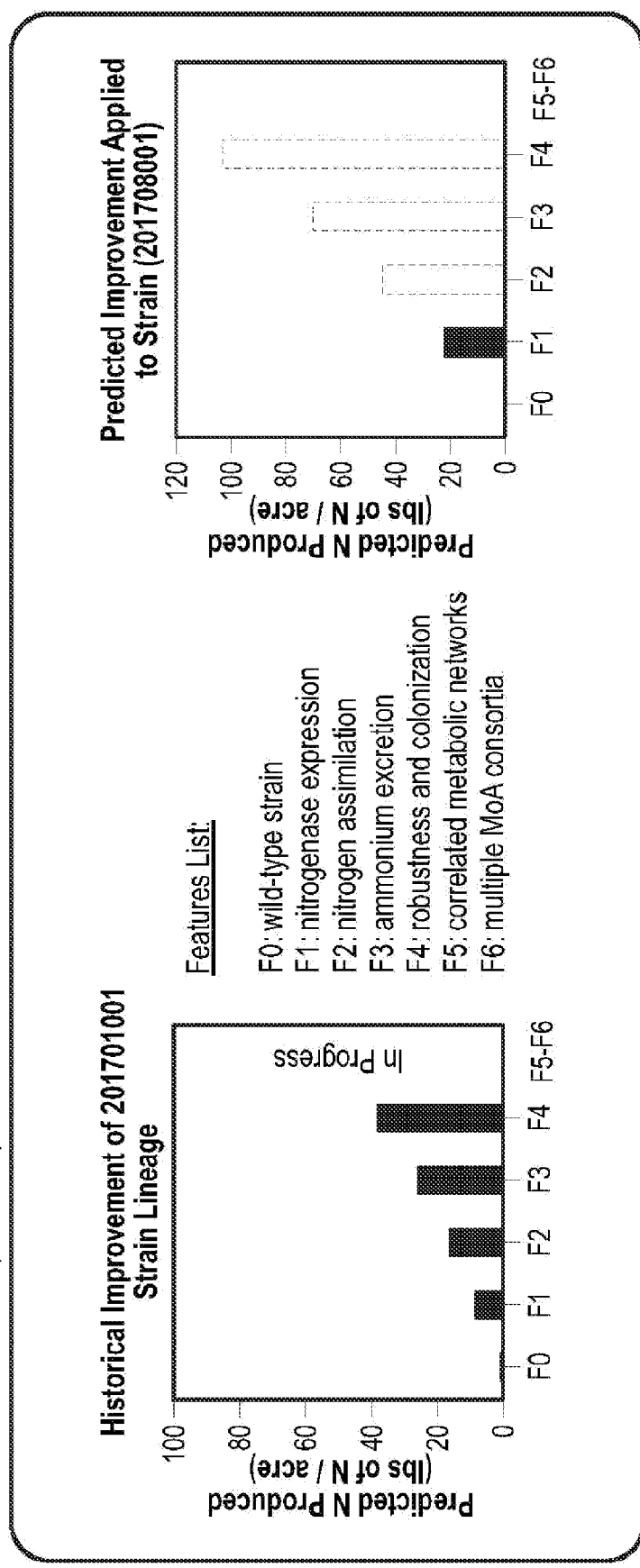
FIG. 6A illustrates genetic features (i.e. non-intergeneric genetic modifications) that were used with respect to a GMR campaign for a *Kosakonia sacchari* strain. The predicted N produced (lbs of N per acre) increased with each additional feature engineered into the microbial strain.

FIG. 5B shows the nitrogen produced by strain PTA-126749, a further remodeled strain of *Klebsiella variicola*. FIG. 5A provides a scenario whereby fertilizer could be replaced by the engineered microbes of the disclosure. The large dashed line is the nitrogen required by the corn (about 200 pounds per acre). The solid line is the current nitrogen amount that can be supplied by the remodeled 201712002 strain (about 20 pounds per acre). In the gray-shaded oval "A" scenario of FIG. 5A, it is expected that the activity of the 201712002 strain will increase by 5 fold (see FIG. 6 for GMR campaign strategy to achieve such). In the gray-shaded oval "B" scenario of FIG. 5A, the expectation of utilizing a remodeled microbe with a particular colonization profile that is complementary to that of the 201712002 strain, and which will supply nitrogen to the plant at later stages of the growth cycle. The nitrogen production activity of the 201712002 strain has been improved through the GMR campaign. Specifically, FIG. 5B shows the nitrogen production by the strain PTA-126749, which is a further remodeled strain of 201712002 obtained by employing the GMR campaign (see, e.g. International Publication No. WO 2020/014498).

Various truncations and deletions of GlnD were performed to see how they impact fixation and excretion of nitrogen. Several glnD mutations modifying the UTase, UR and ACT1/2 (glutamine-sensing) domains lead to increases in activity as measured in ARA and ammonium excretion assays. FIG. 2 demonstrates several glnD modifications which lead to increased ammonium excretion in mutnants of *K. variicola* CI137; FIG. 3 demonstrates several glnD modifications which lead to increases ammonium excretion in mutants of *K. sacchari* strain CI006. As shown in FIG. 5B, the nitrogen production activity of PTA-126749 is substantially improved compared to 201712002.

Figure 6B:
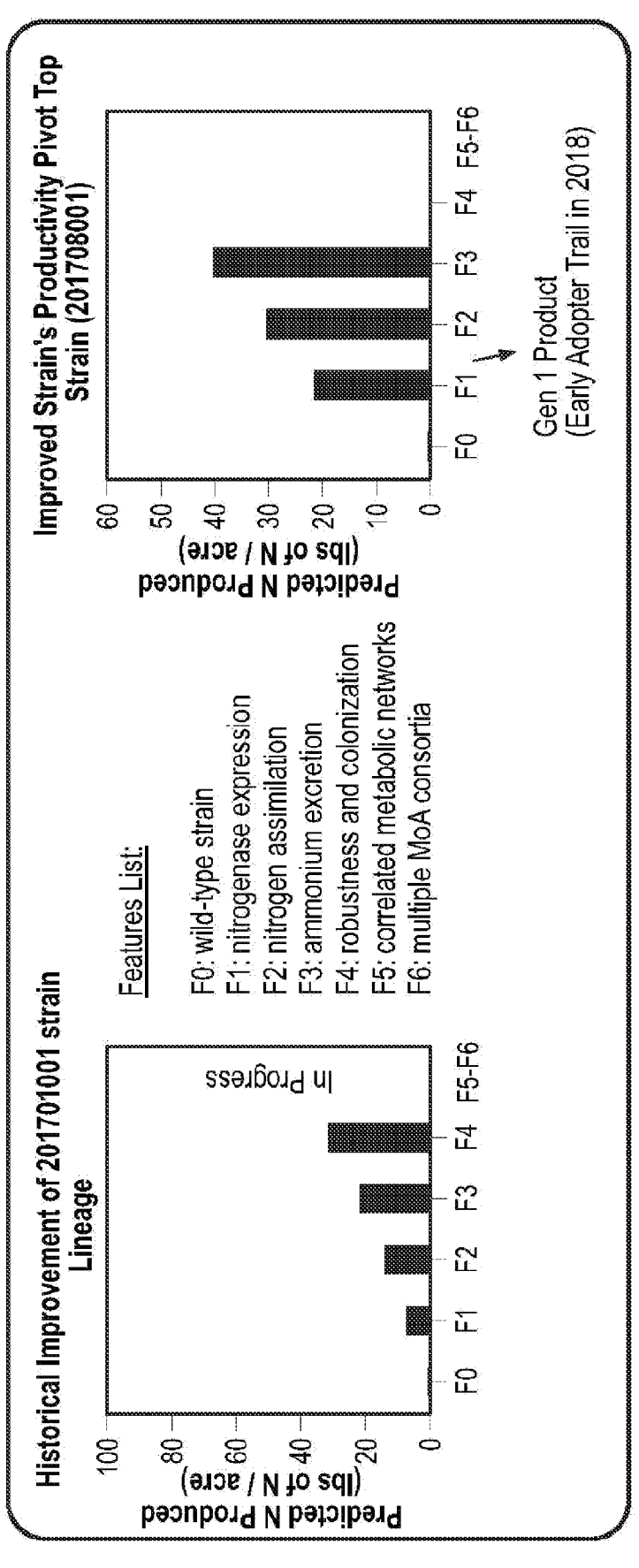
FIG. 6B illustrates genetic features (i.e. non-intergeneric genetic modifications) that were used with respect to a GMR campaign for 201701001 (*Kosakonia sacchari*). The predicted N produced (lbs of N per acre) increased with each additional feature engineered into the microbial strain.
Figure 9A:
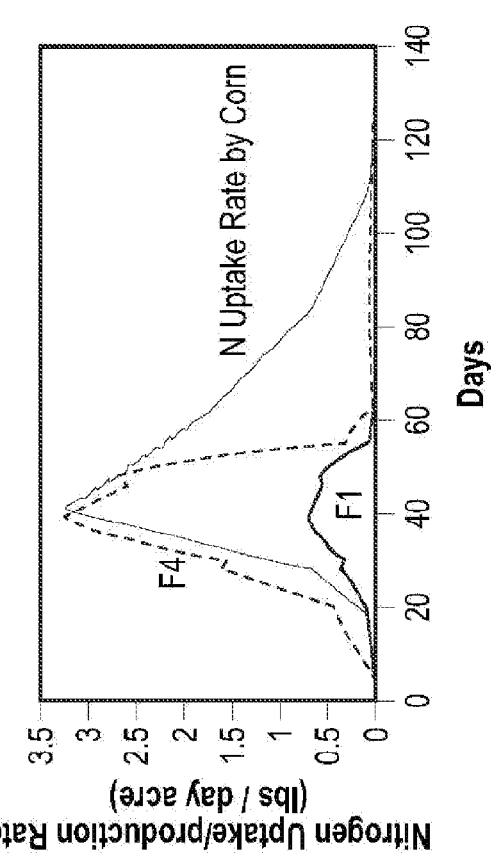
FIG. 9A depicts the same expectation as presented in FIG. 6A, and maps the expected gains in nitrogen production to the applicable feature set.
Figure 9A:
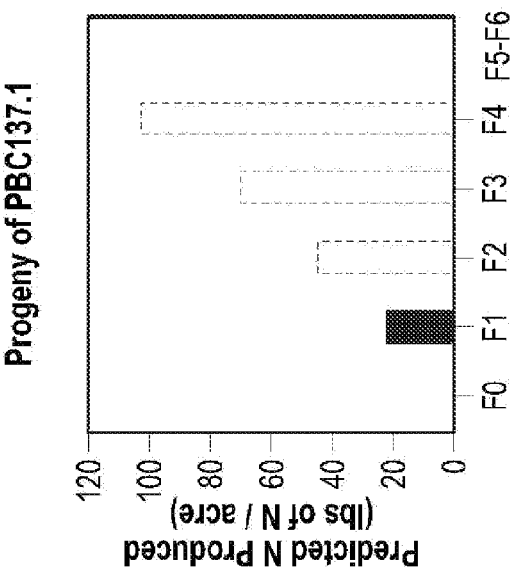
Figure 9B:
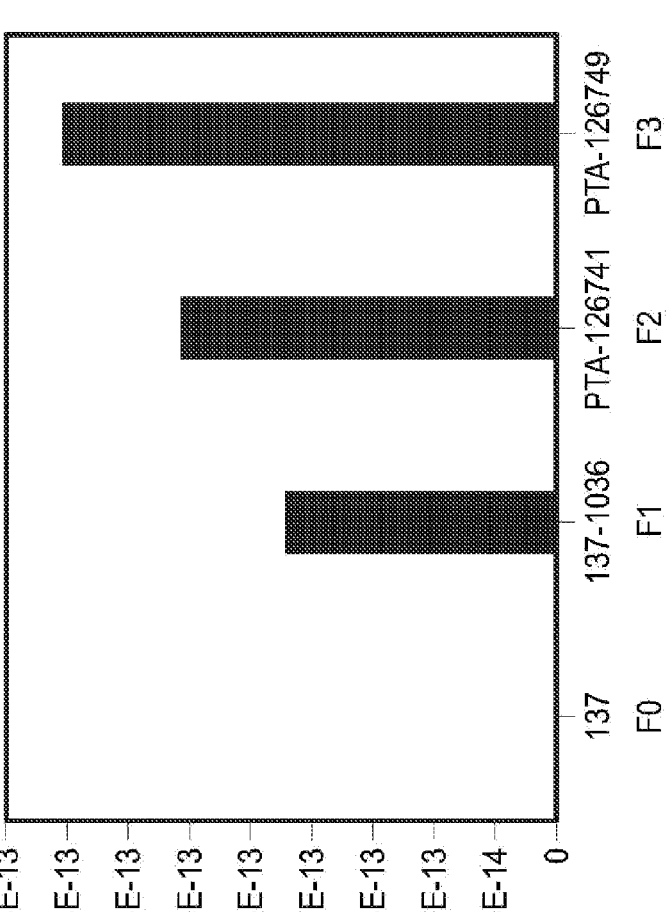
FIG. 9B depicts N produced as mmol of N/CFU per hour by the remodeled strains of *K. variicola* 201708001 once the features F1 (nitrogenase expression), F2 (nitrogen assimilation), and F3 (ammonium excretion) were incorporated.

Further, FIG. 9A depicted the same expectation, and mapped the expected gains in nitrogen production to the applicable feature set at the time the provisional application was filed. The features F2 (nitrogen assimilation) and F3 (ammonium excretion) have been engineered into the *K. variicola* 201708001 host strain. FIG. 6B, right panel, depicts the N produced by the remodeled strains upon incorporation of the features F1-F3. As can be seen from the right panel of FIG. 6B, the N produced (lbs of N per acre) increased with each additional feature engineered into the microbial strain. FIG. 9B depicts N produced as mmol of N/CFU per hour by the remodeled strains of *K. variicola*

201708001 once the features F1 (nitrogenase expression), F2 (nitrogen assimilation), and F3 (ammonium excretion) were incorporated.

Figure 7:
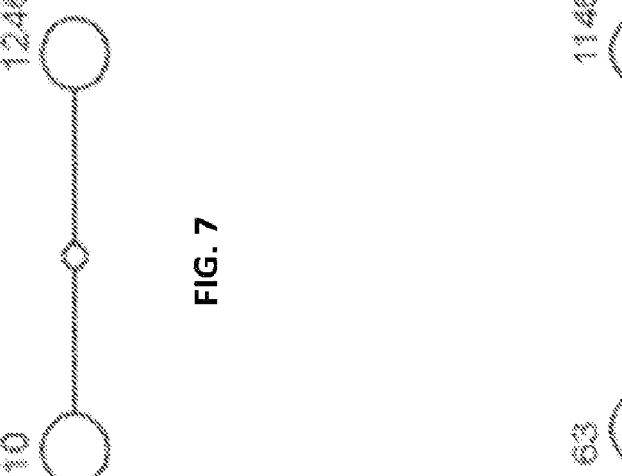
FIG. 7 depicts the lineage of modified strains containing a promoter insertion and nifL deletion mutation, analogous to those described in Table 4, that were derived from strain 910 (*Kluyvera intermedia* WT).
Figure 8:
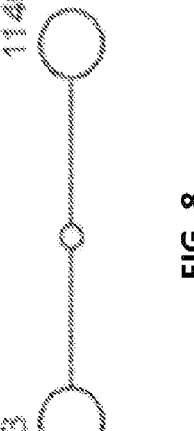
FIG. 8 depicts the lineage of modified strains containing a promoter insertion and nifL deletion mutation, analogous to those described in Table 4, that were derived from strain 63 (*Rahnella aquatilis* WT).

The mutations made to the *K. variicola* 201708001 WT strain to incorporate the features F1-F3 are summarized in Table 4 below. FIG. 7 depicts the lineage of modified strains containing a promoter insertion and nifL deletion mutation analogous to those described in Table 4 that were derived from strain 910 (*Kluyvera intermedia* WT). FIG. 8 depicts the lineage of modified strains containing a promoter insertion and nifL deletion mutation analogous to those described in table 4 that were derived from strain 63 *Rahnella aquatilis* WT).

TABLE 4

| List of isolated and derivative *K. variicola* 201708001 strains | | | |
|---|---|---|---|
| Strain ID | Genotype | Mutation | Mutation Description |
| 201708001 | WT | WT | Wild type *Klebsiella variicola* strain. |
| 201712002 | ΔnifL::PinfC | ΔnifL::PinfC | Deletion of the nifL gene from 20 bp after the ATG (start) to 87 bp before the TGA (stop) of the gene. A 500 bp fragment of the region upstream of the infC gene containing the promoter of the infC gene was inserted (PinfC) upstream of nifA, replacing the deleted portion of nifL. |
| PTA-126741 | ΔnifL::PinfC, ΔglnD_UTase_deactivation, NC_nifA_copy::Prm1.2 | ΔnifL::PinfC | Deletion of the nifL gene from 20 bp after the ATG (start) to 87 bp before the TGA (stop) of the gene. A 500 bp fragment of the region upstream of the infC gene containing the promoter of the infC gene was inserted (PinfC) upstream of nifA, replacing the deleted portion of nifL. |
| | | ΔglnD_UTase_Deactivation | Deactivation of the uridylyltransferase (UT) domain of the bifunctional uridylyltransferase/uridylyl-removing enzyme, glnD, by mutating amino acid residues 90 and 91 from GG to LD as well as residue 104 from D to A |
| | | NC-nifA_copy::Prm1.2 | Insertion of a copy of the nifA gene into a noncoding region of 137. This copy is being driven by a 400 bp promoter (Prm1.2) derived from a region upstream of the cspE gene. |
| PTA-126749 | ΔnifL::Prml.2, ΔglnE$_{AR}$-KO2, NtrC D54A | ΔnifL::Prml.2 | Deletion of the nifL gene from 20 bp after the ATG (start) to 87 bp before the TGA (stop) of the gene. A 400 bp fragment from the region upstream of the cspE gene containing the promoter of the cspE gene was inserted (Prm1.2) upstream of nifA, replacing the deleted portion of nifL. |
| | | ΔglnEAR-KO2 | Deletion of 1647 bp after the start codon of the glnE gene. |
| | | NtrC D54A | Deactivation of the phosphorylation site of the DNA-binding transcriptional regulator NrtC by swapping the 54$^{th}$ amino acid from aspartate to alanine (D to A). Disables the ability of NtrC to be phosphorylated. |

Example 3—Strains PTA-126740, PTA-126749, PTA-126741, and PTA-126743 Fix Nitrogen in the Presence of Nitrogen and Excrete Ammonium in Aerobic and Hypoxic Conditions To determine the ability of strains PTA-126740, PTA-126749, PTA-126741, and PTA-126743 to fix nitrogen in the Initial culture biomass was compared to ending biomass by measuring optical density at 590 nm. Cells were then separated by centrifugation, and supernatant from the reactor broth was assayed for free ammonia using the Megazyme Ammonia Assay kit (P/N K-AMIAR) normalized to biomass at each timepoint. See, also Example 2 of International patent publication WO2020/006246.

TABLE 5

| Strains and genotypes used in ARA and ammonium excretion studies. | | |
| --- | --- | --- |
| Lineage | Strain | Genotype |
| K. variicola 201708001 | 201708001 | WT |
| K. variicola 201708001 | 201712001 | glnE __KO2 |
| K. variicola 201708001 | 201712002 | ΔnifL::PinfC |
| K. variicola 201708001 | 137-2084 | glnE __KO2, ΔnifL::Prm1.2 |
| K. variicola 201708001 | PTA-126740 | ΔnifL::PinfC, glnD-AUTase |
| K. variicola 201708001 | PTA-126749 | glnE __KO2, ΔnifL::Prm1.2, NtrC__D54A |
| K. variicola 201708001 | PTA-126741 | ΔnifL::PinfC, glnD::UTase-deactivation, nifA copy |
| K. sacchari 201701001 | 201701001 | WT |
| K. sacchari 201701001 | 6-397 | ΔnifL::Prm5 |
| K. sacchari 201701001 | 6-411 | ΔglnE::KO1 |
| K. sacchari 201701001 | 6-412 | ΔnifL::Prm5, ΔglnE::KO1 |
| K. sacchari 201701001 | PTA-126743 | ΔnifL::Prm5, ΔglnE::KO1, ΔglnD | presence of exogenous nitrogen and excrete bioavailable nitrogen into the environment, acetylene reduction assays (ARAs) and ammonium excretion assays were performed. Control strains contained either single edits or subsets of the edits that are present in strains PTA-126740, PTA-126749, PTA-126741, and PTA-126743.

To measure nitrogenase activity, the ARAs were performed as follows. Strains were propagated from a single colony in SOB broth (RPI Research Products International, Mount Prospect, IL, Product No. S25040-1000) at 30° C. with shaking at 200 RPM for 24 hours and then subcultured 1:25 into growth medium and grown aerobically for 24 hours (30° C., 200 RPM). One (1) ml of the culture then was added to 4 ml of minimal media (per liter, 5 g $Na_2HPO_4$, 0.1 g $CaCL_2$-$2H_2O$, 3 g $KH_2PO_4$, 0.25 g $MgSO_4$ $7H_2O$, 1 g NaCl, 2.9 mg $FeCl_3$, 0.25 mg $Na_2MoO_4$ $2H_2O$, and 20 g sucrose) supplemented with 0 to 10 mM glutamine in air-tight Hungate tubes and grown anaerobically for 4 hours (30° C., 200 RPM). 1000 of headspace gas was removed then replaced by an equal volume of acetylene by injection, and incubation continued for 1 hr. Subsequently, 2 ml of headspace gas was removed via gas tight syringe for quantification of ethylene production using an Agilent 6850 gas chromatograph equipped with a flame ionization detector (FID). See, also Example 2 of International patent publication WO2020006246.

Excretion of fixed nitrogen in the form of ammonia was measured using batch fermentation in anaerobic bioreactors. Strains were propagated from single colony in 1 ml/well of SOB in a 96 well deep well plate. The plate was incubated at 30° C. with shaking at 200 RPM for 24 hours and then diluted 1:25 into a fresh plate containing 1 ml/well of minimal growth medium supplemented with nitrogen to form the seed culture. Seed cultures were incubated for 24 hours (30° C., 200 RPM) and then diluted 1:10 into a fresh plate containing minimal medium. The plate was transferred to an anaerobic chamber with a gas mixture of >98.5% nitrogen, 1.2-1.5% hydrogen and <30 ppM oxygen and incubated at 1350 RPM, room temperature for 66-70 hrs.

Figure 10A:
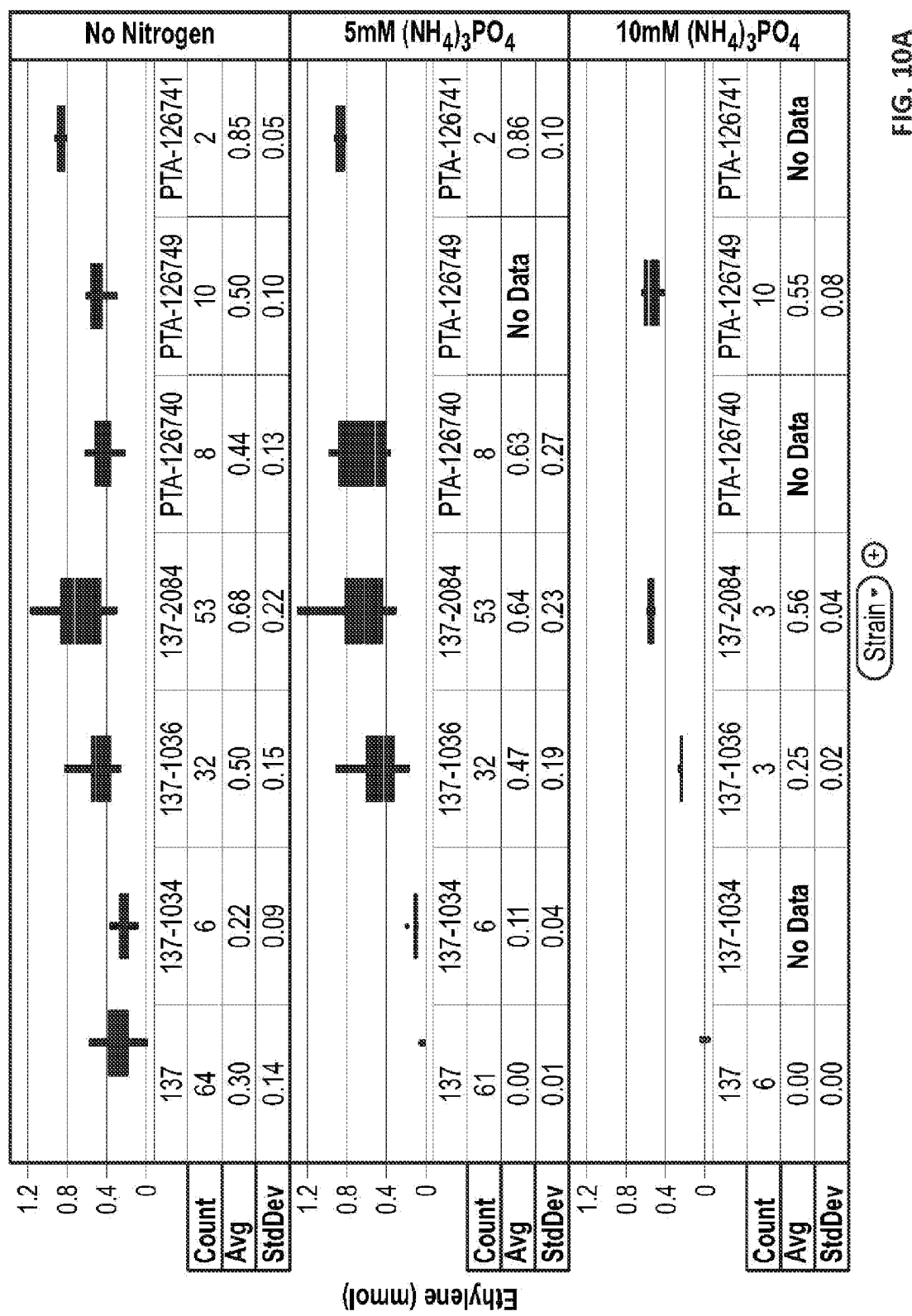
Figure 11A:
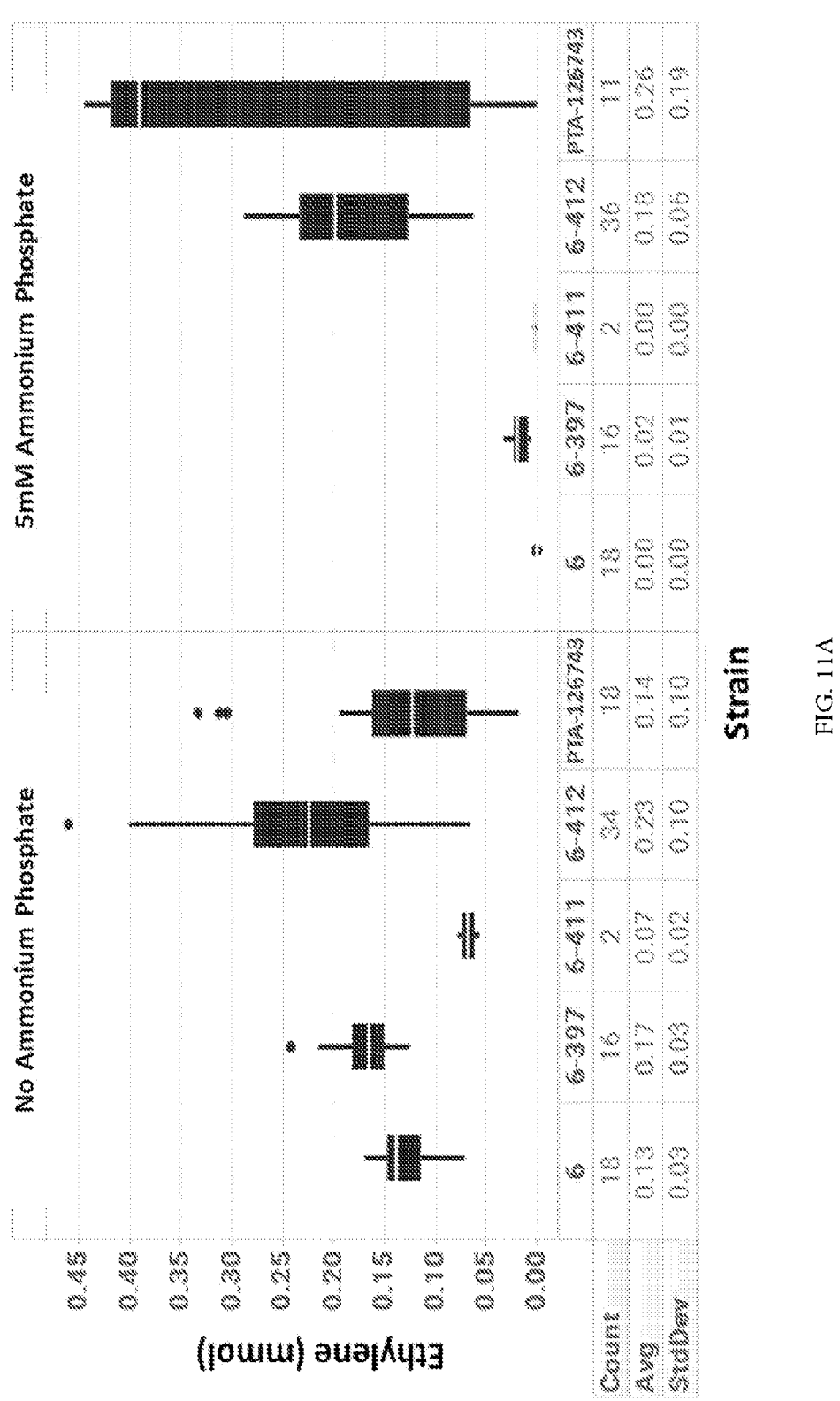
FIGS. 11A and 11B show the compiled results of several ARAs with *K. sacchari* 201701001 strains at 0 mM and 5 mM ammonium phosphate, expressed both as titer of ethylene produced (mmol) (FIG. 11A) and rate of ethylene produced per cell and hour (mmol/CFU·hr) (FIG. 11B).
Figure 11B:
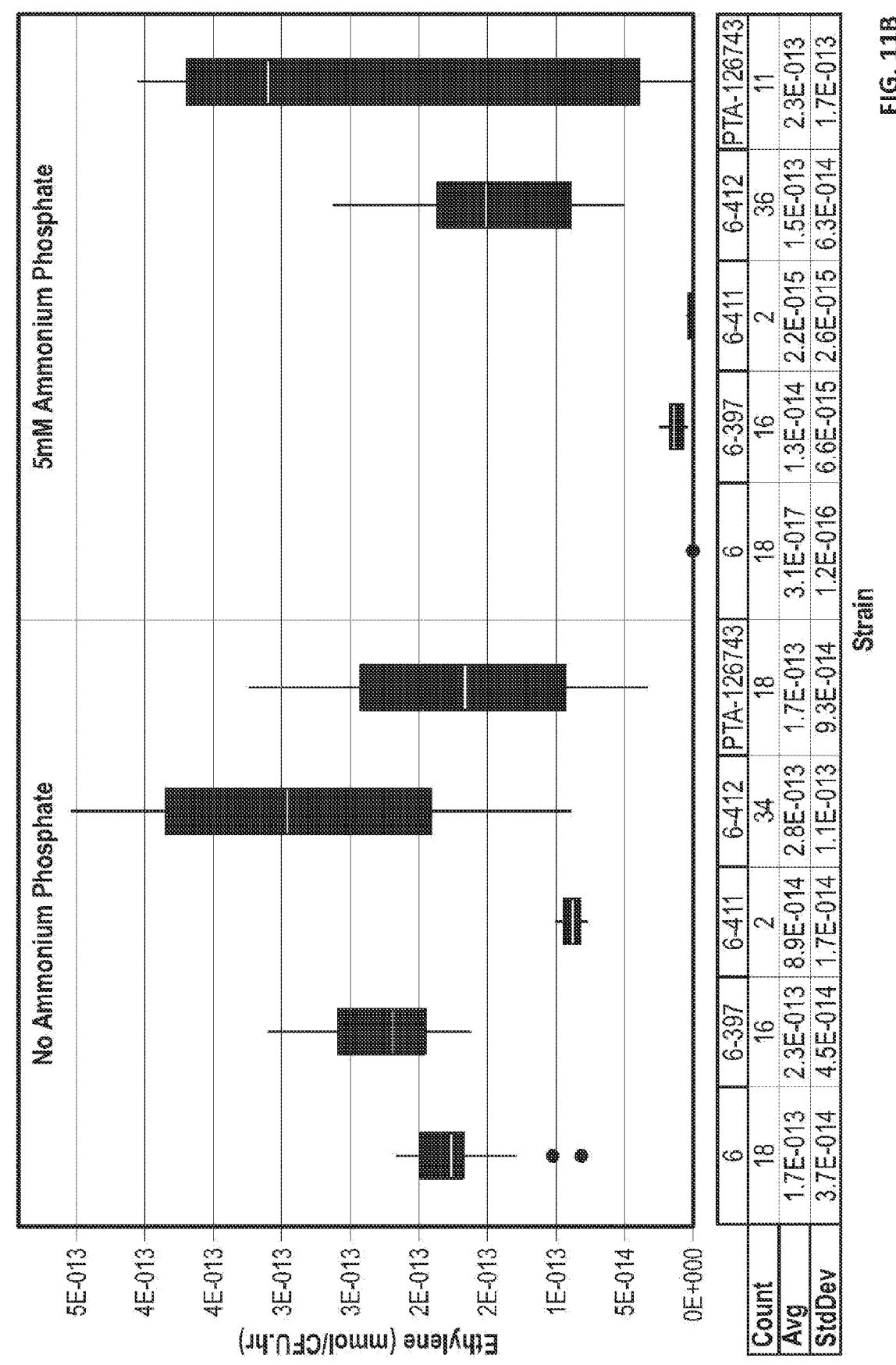

Strains PTA-126740, PTA-126749, and PTA-126741 all showed significantly increased nitrogenase activity compared to WT at both 5 mM and 10 mM ammonium phosphate. PTA-126740 and PTA-126741 both showed improved ethylene titer and acetylene reduction rate compared to parent strain 201712002 at 5 mM ammonium phosphate (FIGS. 10A,B). PTA-126749 showed improved acetylene reduction rate compared to parent strain 137-2084 at 10 mM ammonium phosphate (FIG. 10B). At 5 mM ammonium phosphate, PTA-126743 showed variable but high nitrogenase activity when compared to 201701001 WT, which shows no detectable acetylene reduction (FIG. 11A). PTA-126743 also reduced acetylene to a higher titer of ethylene and at a higher rate than the single mutant strains 6-397 and 6-411 at 5 mM ammonium phosphate (FIG. 11A, 11B). These results show that these strains are capable of fixing nitrogen in the presence of nitrogen, and that the gene edits in the strains played a significant part in this phenotype.

Figure 12A:
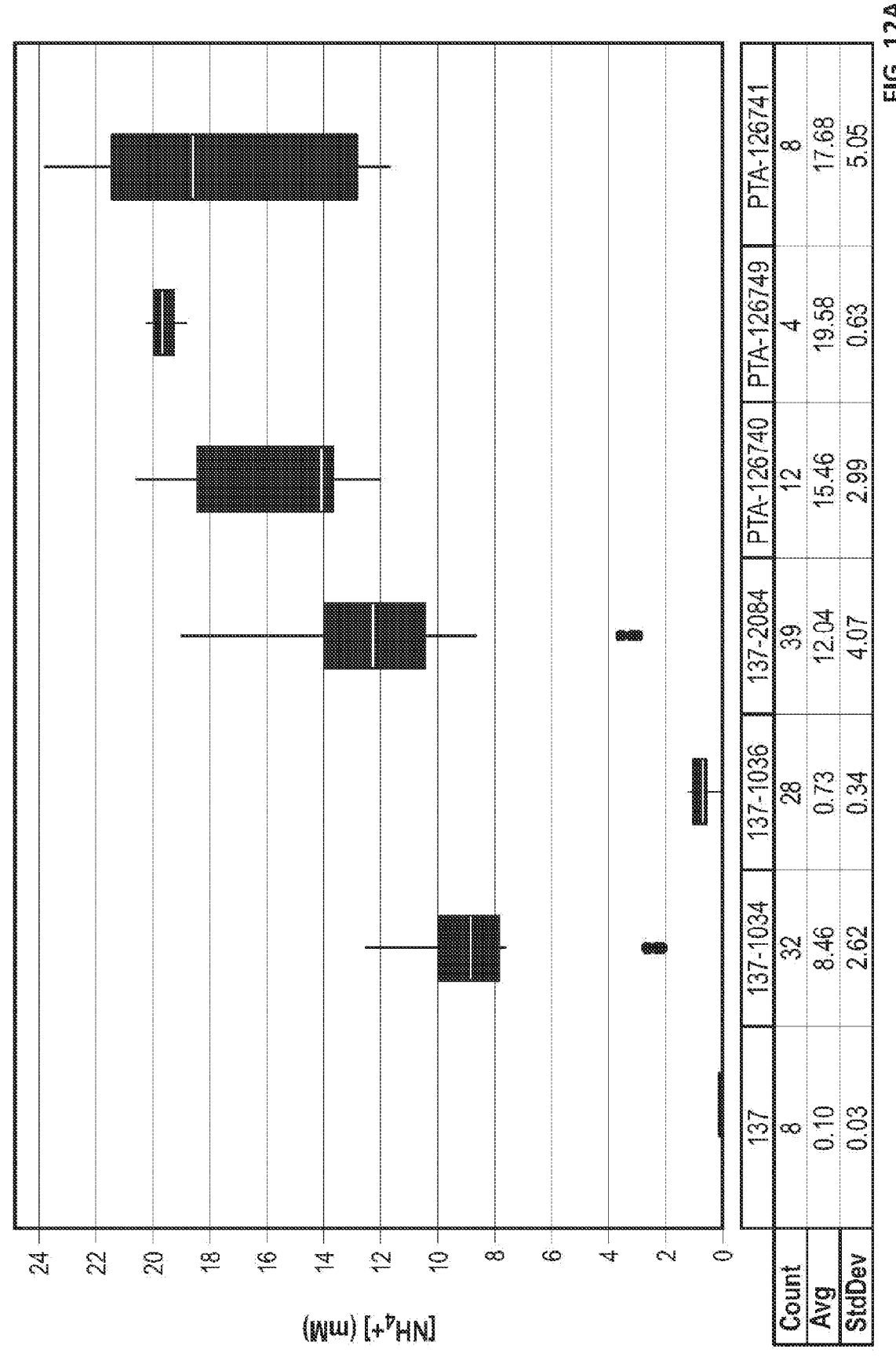
FIGS. 12A and 12B show the compiled results of several anaerobic ammonium excretion assays with *K. variicola* 137 strains, expressed as both ammonium titer ($[NH_4^+]$ mM) (FIG. 12A) and rate of ammonium excretion ($NH_4^+$ excreted, mM/OD hr) (FIG. 12B).
Figure 12B:
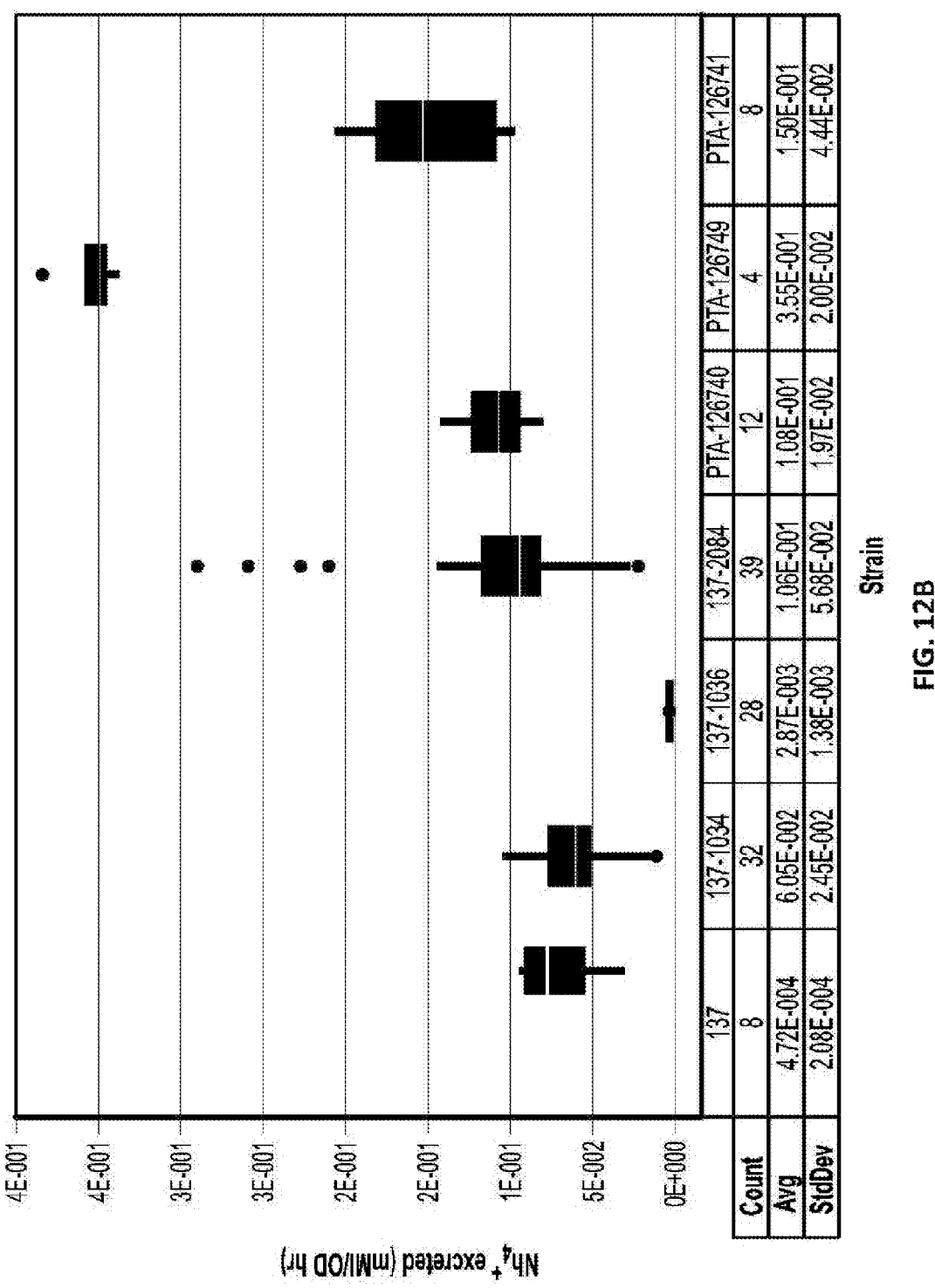
Figure 13A:
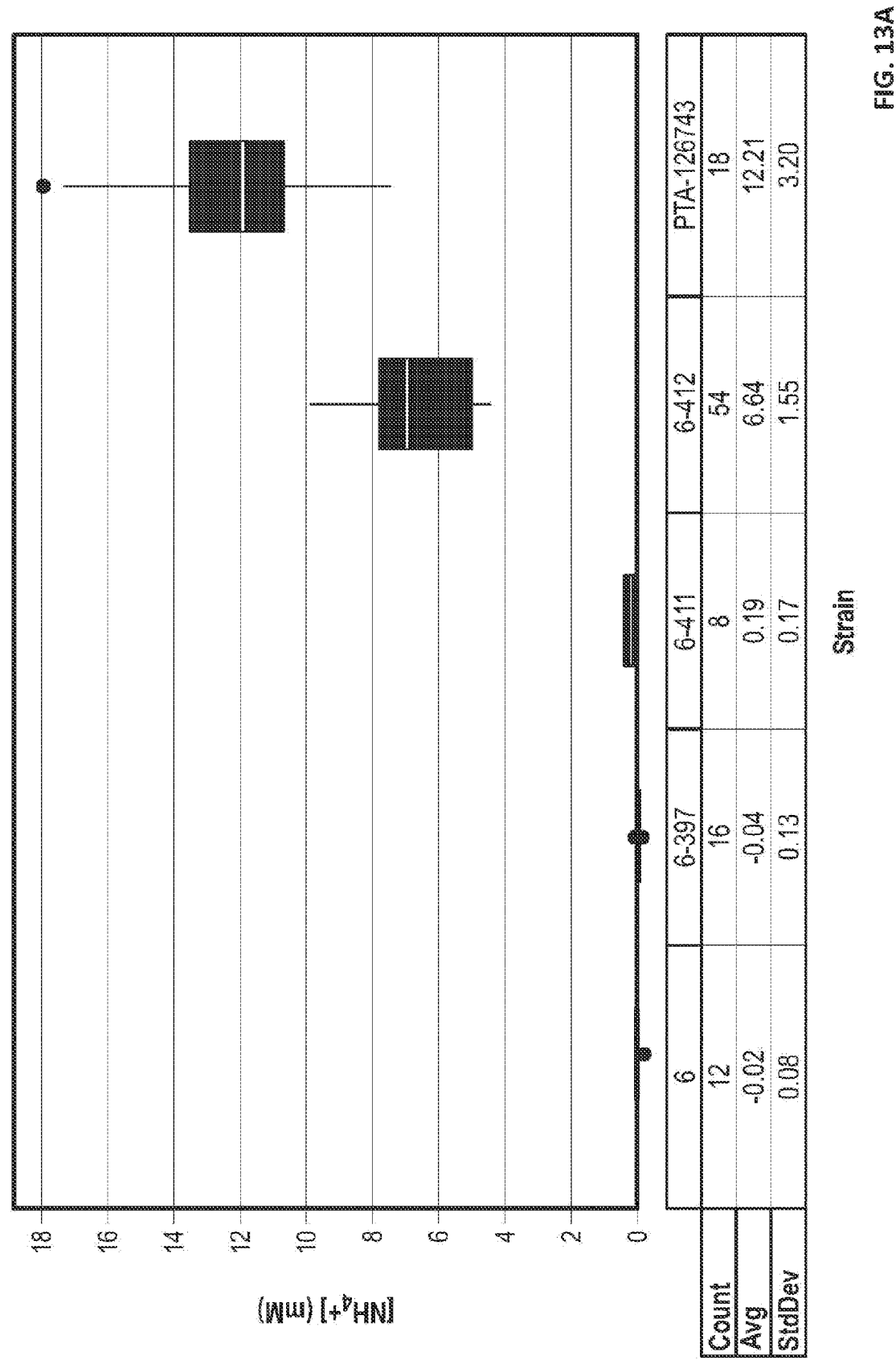
FIGS. 13A and 13B show the compiled results of several anaerobic ammonium excretion assays with PTA-126743 and other *K. sacchari* strains, expressed as both ammonium titer ($[NH_4^+]$ mM) (FIG. 13A) and rate of ammonium excretion ($NH_4^+$ excreted, mM/OD hr) (FIG. 13B).
Figure 13B:
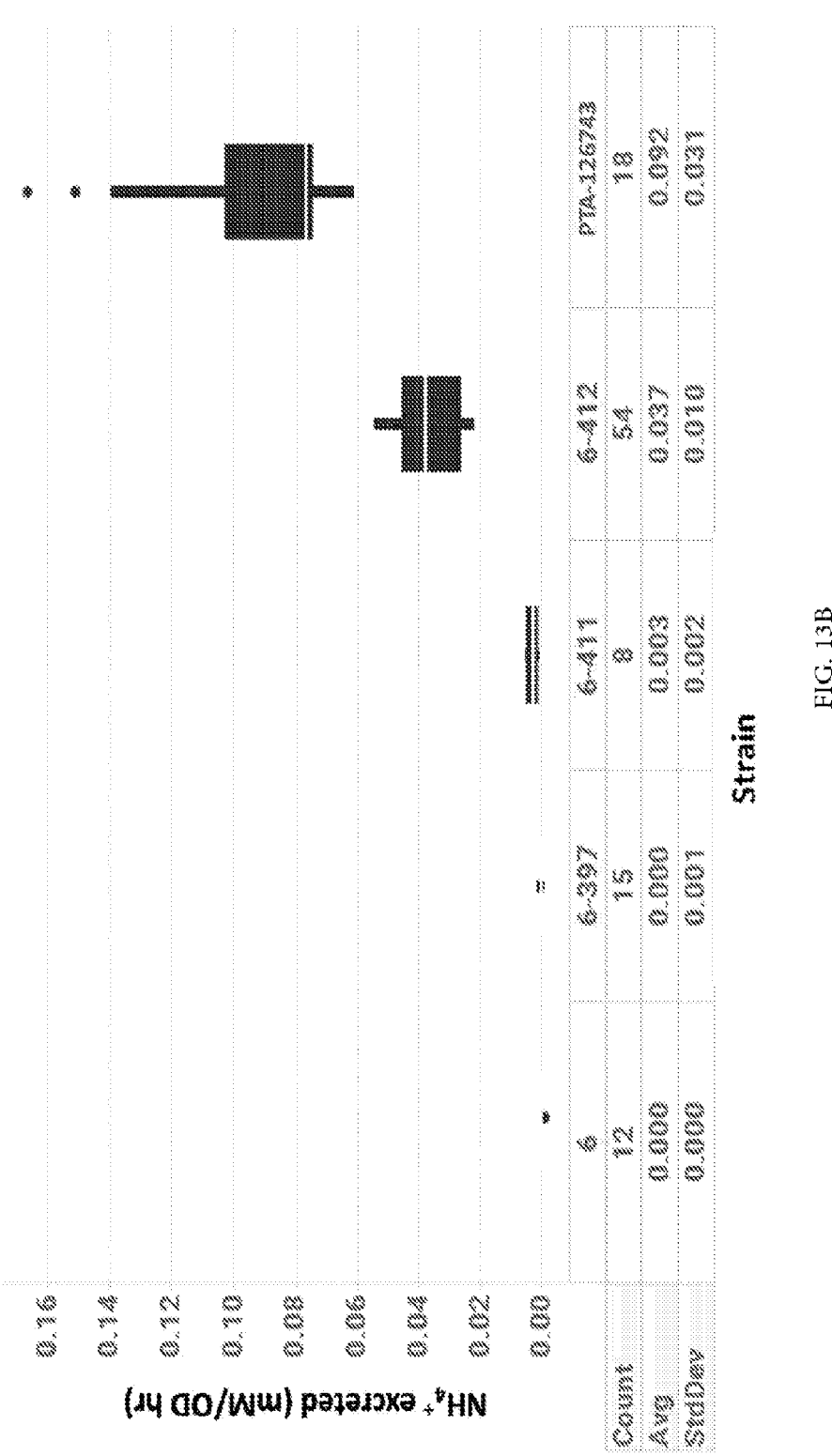

Ammonium excretion in anaerobic conditions was measured in each strain. PTA-126740, PTA-126749 and PTA-126741 all excrete ammonium to higher titers than all parent strains tested (FIG. 12A) and excrete ammonium at a rate higher than the single mutant parents 201712001 and 201712002 (FIG. 12B). PTA-126743 excretes ammonium both to a higher titer of ethylene and at a higher rate than all parent strains tested (FIG. 13A, 13B). These results show that the disclosed strains are able to excrete newly-fixed nitrogen into their environment.

Figure 14A:
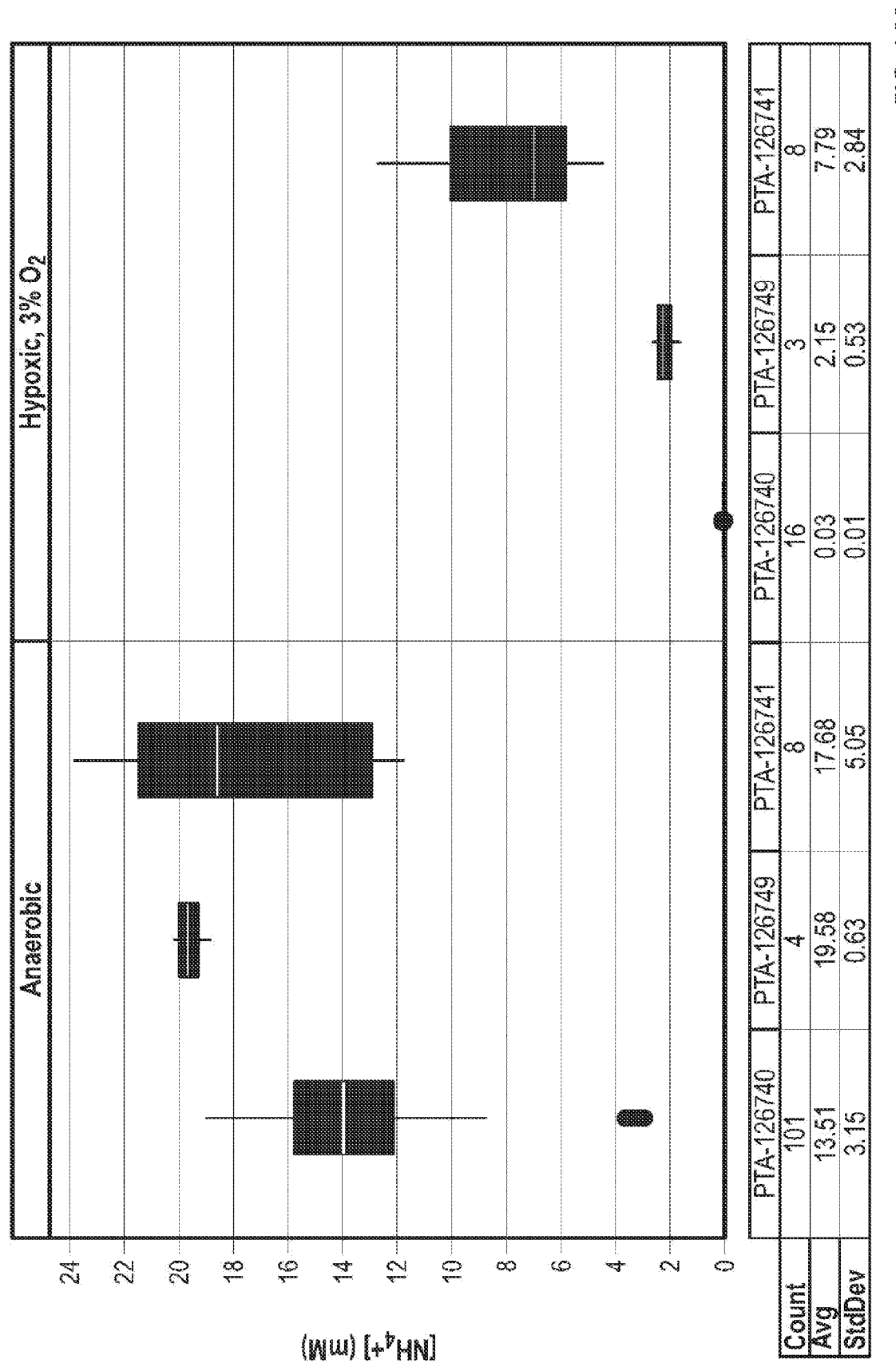
FIGS. 14A and 14B show ammonium excretion ($[NH_4^+]$ mM) by Kv137 lineage strains at 0% (anaerobic) and 3% oxygen (hypoxic). Single mutant strains NCMA 201712001 and NCMA 201712002 were not tested in hypoxic conditions.
Figure 14B:
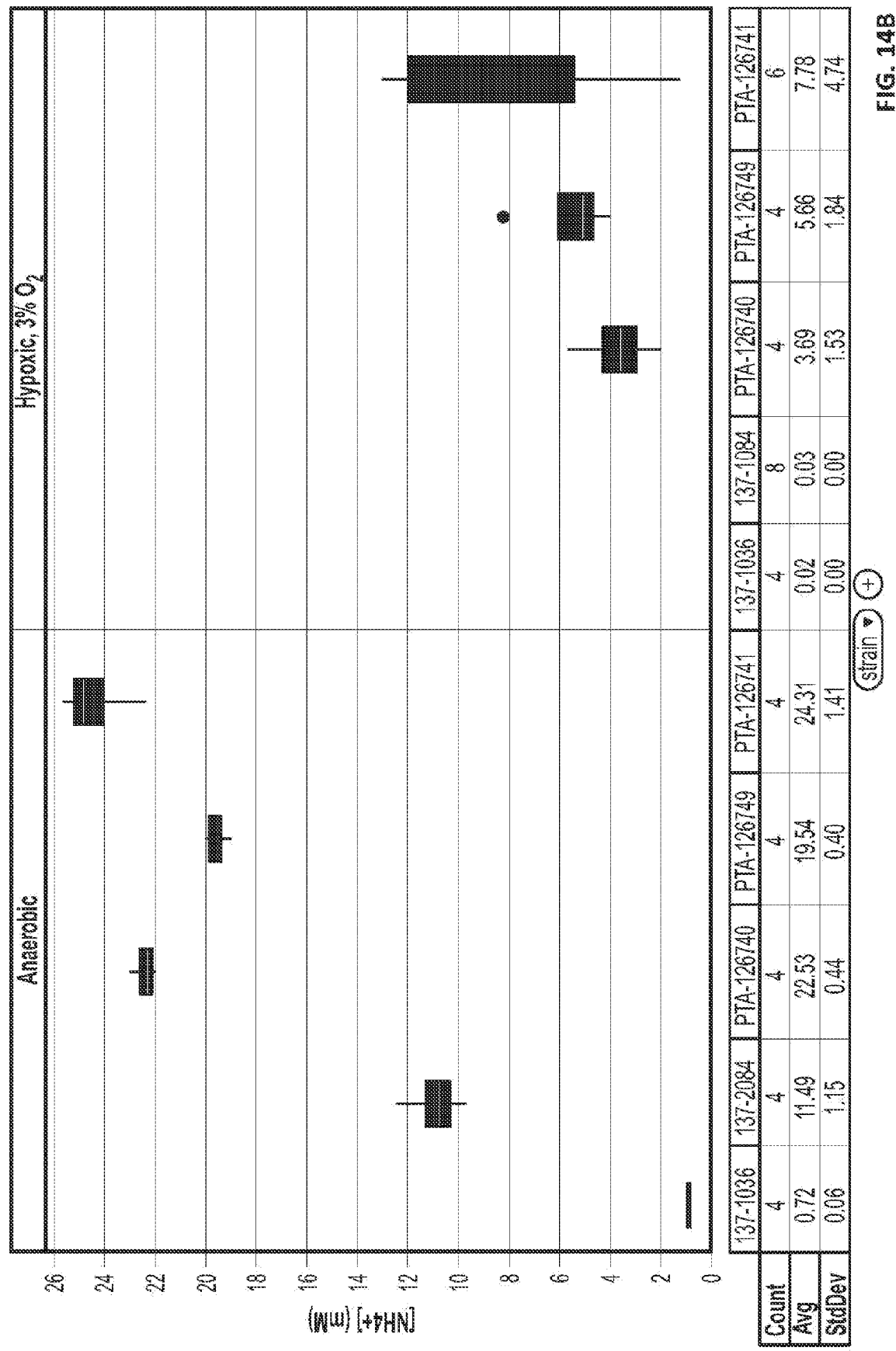

To assess the robustness of these strains in different oxygen conditions, the strains were tested for ammonium excretion as described above, except that instead of being run in an anaerobic chamber, the assay was carried out in a hypoxic chamber at varying oxygen concentrations. FIG. 14A represents an experiment where the seed culture was supplemented with 10 mM glutamine; FIG. 14B represents an experiment where the seed was supplemented with 10 mM ammonium phosphate. All K. variicola strains (PTA-126740, PTA-126749, and PTA-126741) excreted ammonium to significant detectable titers in 3% oxygen. PTA-126749 excreted significantly more ammonium than parent strain 137-2084 at 3% oxygen in both experiments (FIG.

Figure 15:
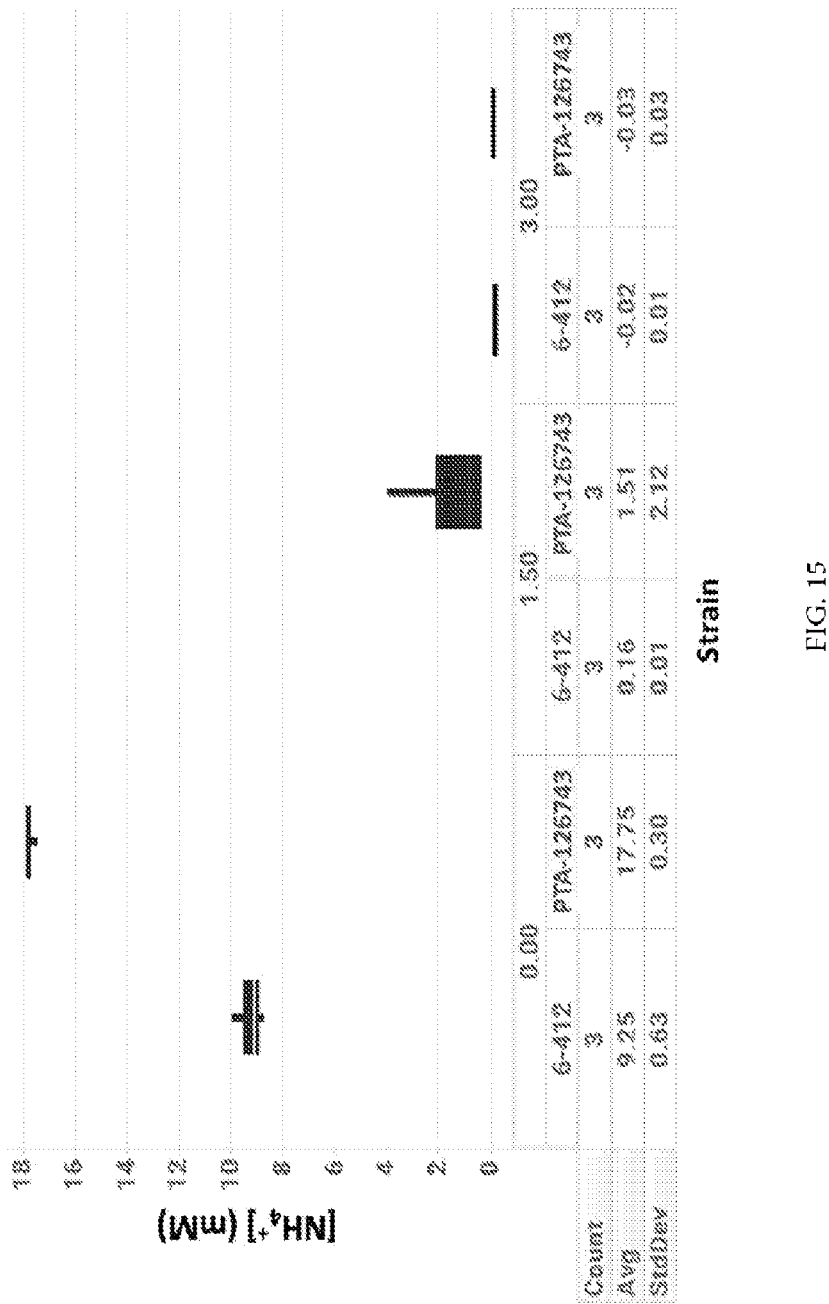
FIG. 15 shows ammonium excretion ($[NH_4^+]$ mM) by mutant *K. sacchari* 6 strains at 0%, 1.5%, and 3% oxygen.
Figure 16A:
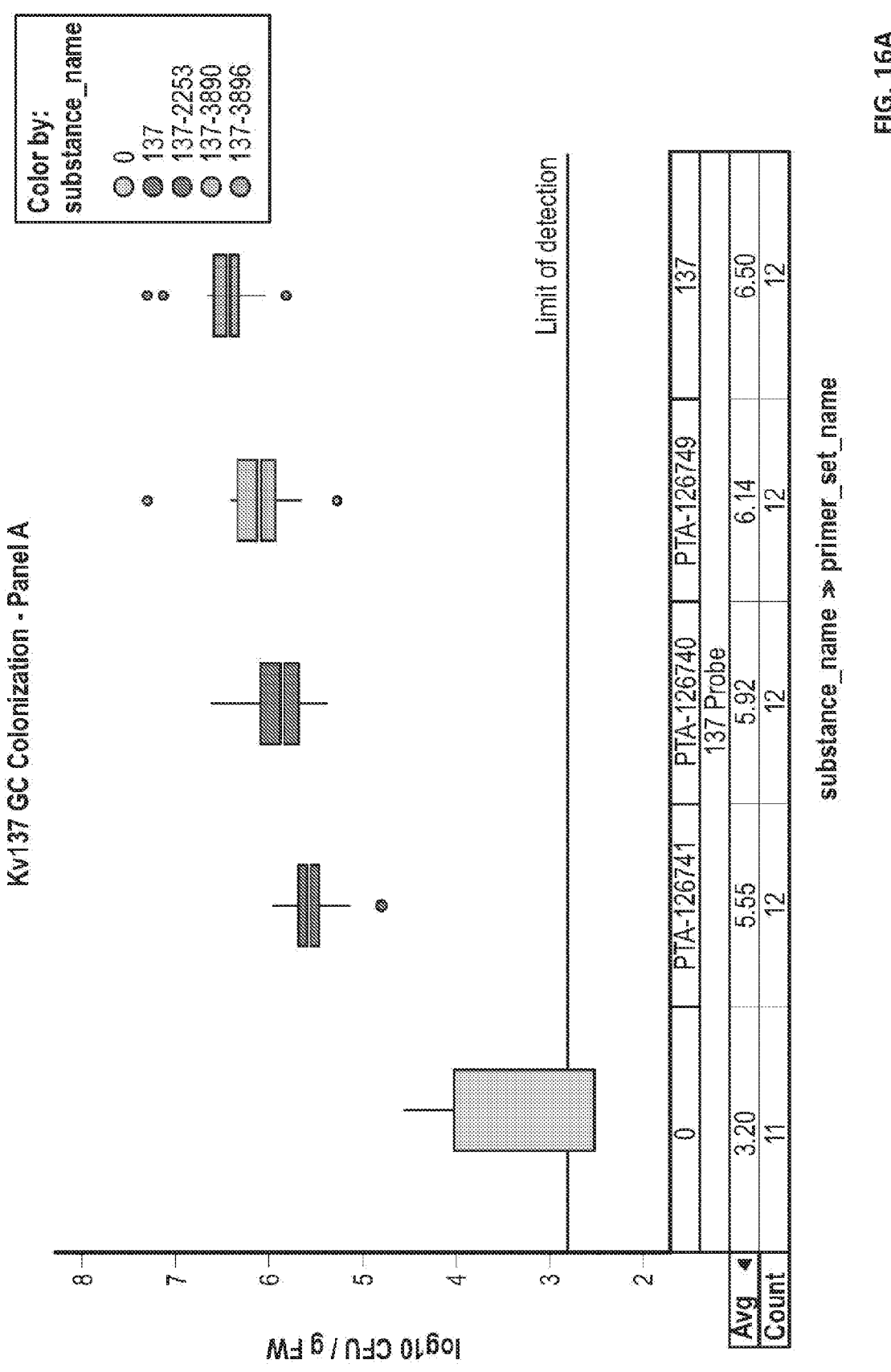
FIGS. 16A-16D represent independent growth chamber colonization experiments of *K. variicola* 137 and its deriva-
Figure 16B:
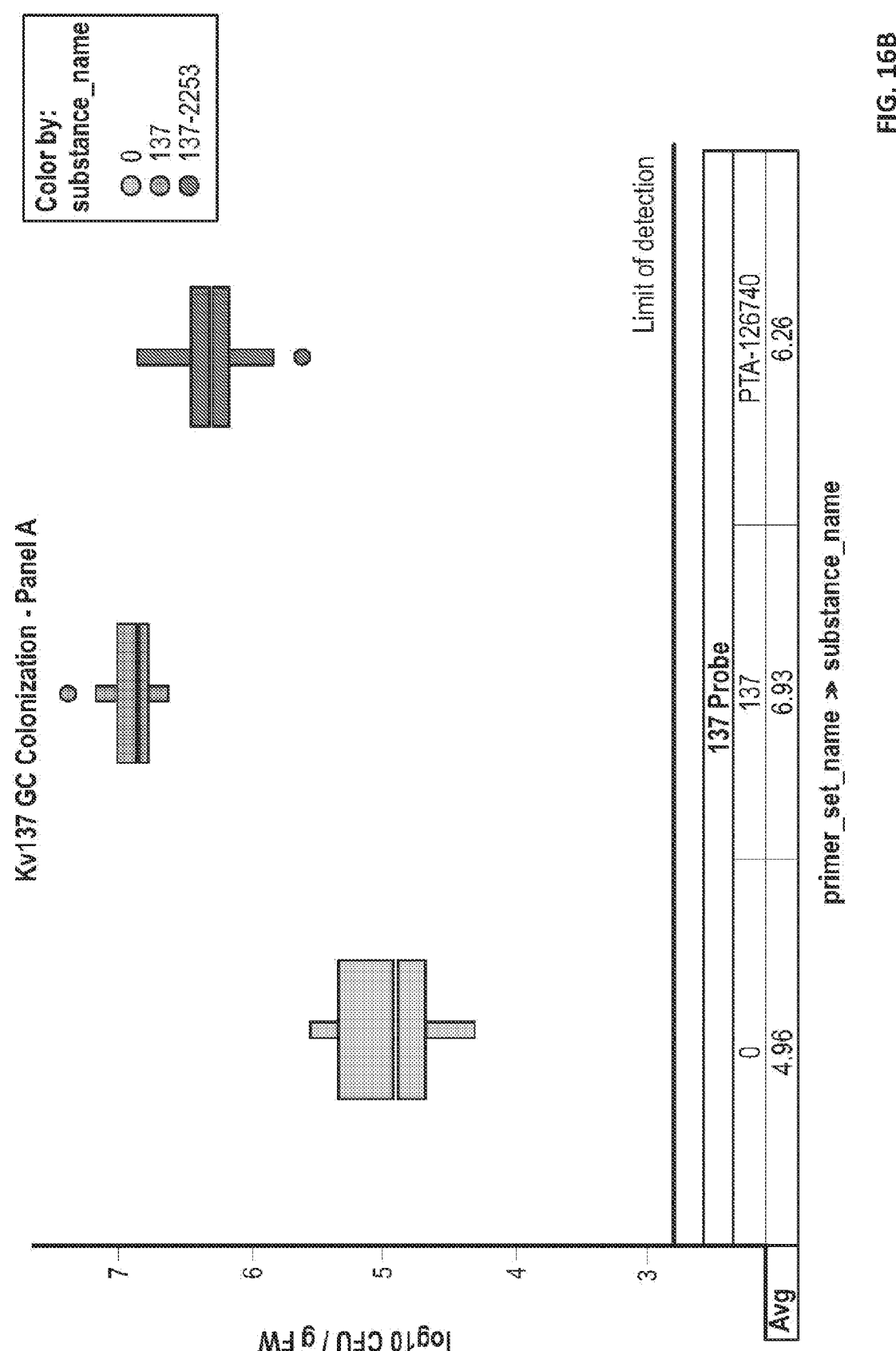
Figure 16C:
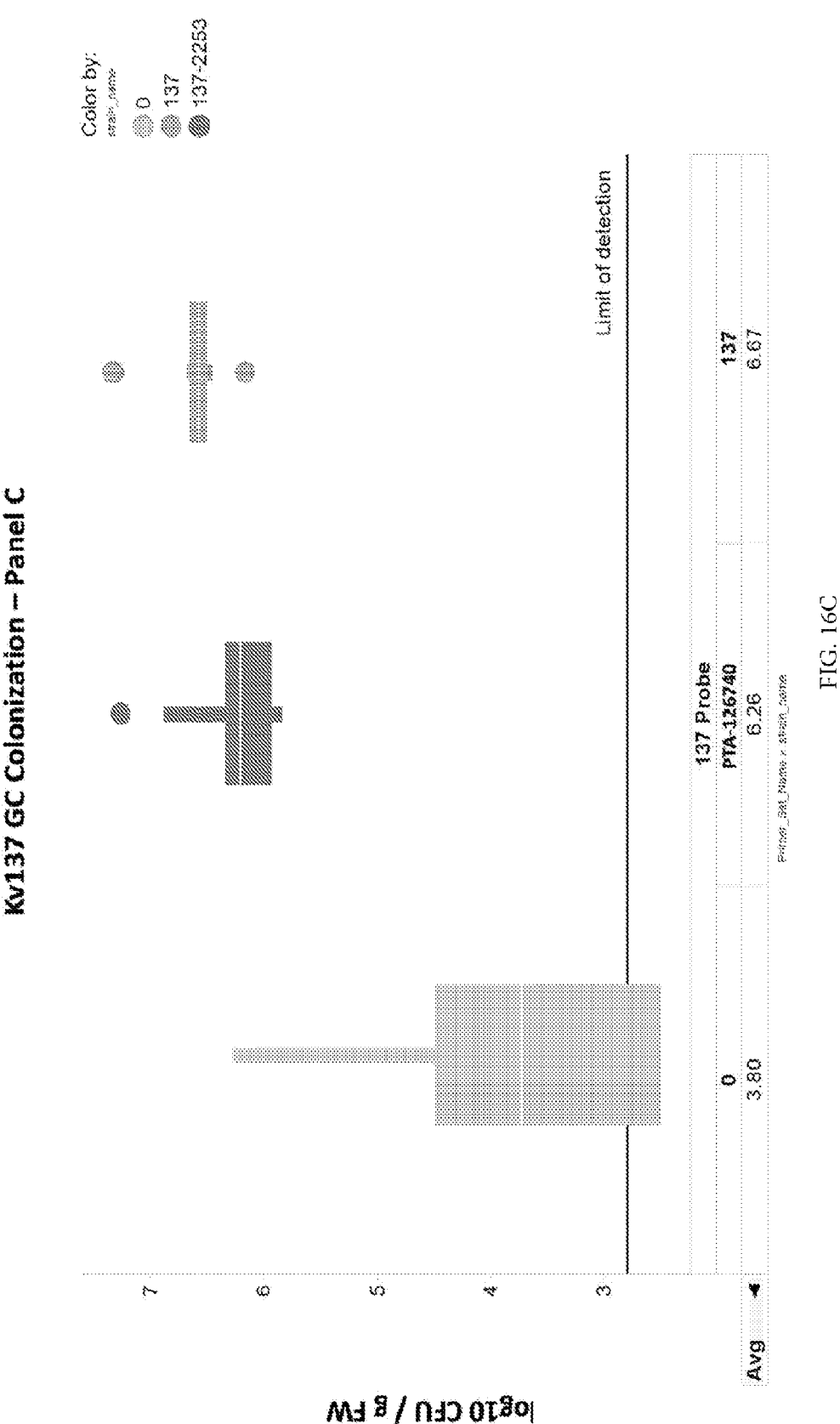
Figure 16D:
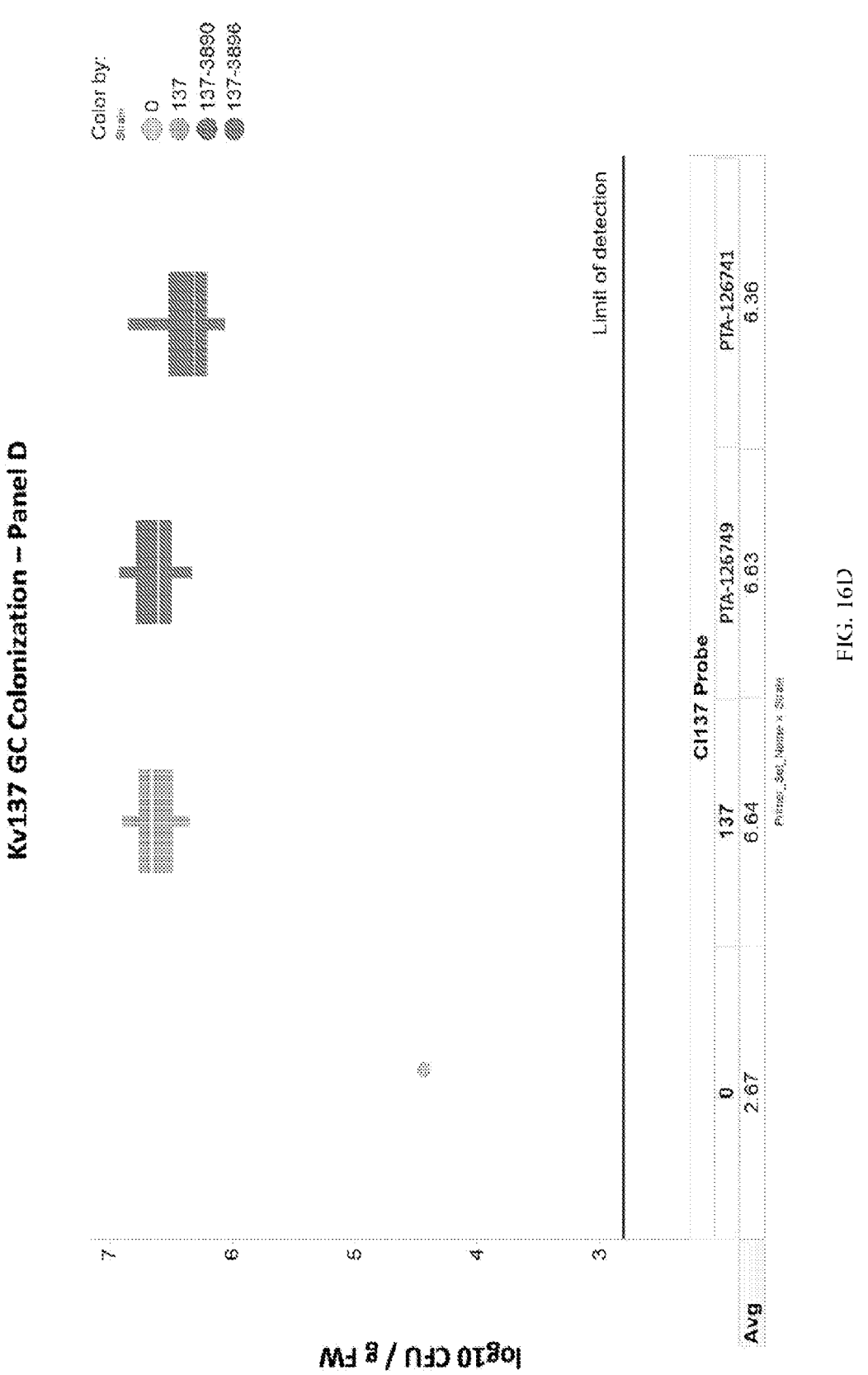

14A, 14B). PTA-126740 excreted significantly more ammonium than its parent strain 201712002 at 3% oxygen in the experiment in which it was tested (FIG. 14B). PTA-126741 exhibited the highest average ammonium excretion at 3% oxygen of all strains in both experiments (FIG. 14A, 14B). Similar assays were carried out with PTA-126743 and parent strain 6-412 (FIG. 15). At 1.5% oxygen, PTA-126743 excreted measurable amounts of ammonium, 10× more than the parent strain 6-412. Neither strain excreted detectable ammonium at 3% oxygen. These results suggest that these strains are able to fix nitrogen in a range of oxygen concentrations.

Example 4—Kv137 Strains Exhibit Robust Colonization of Corn Roots in Growth Chamber Studies

*K. variicola* strains were tested in a number of growth chamber colonization studies. Corn seed was planted in autoclaved soil and inoculated with 1×10$^9$ CFU/seed at the time of planting; untreated control (UTC, sometimes denoted as "0" in graphs) plants were mock-inoculated with a sterile PBS solution. Plants were maintained in a growth chamber using fluorescent lamps and a 16-hour day length with a 26° C. day temperature and 22° C. night temperature. After three weeks, roots were harvested, shaken free of sand, washed, and prepared for qPCR measurement of colonization. The root samples were homogenized using QIAGEN Tissuelyzer and the DNA was exracted using QIAMP DNA Mini Kit (Qiagen). qPCR was performed using a Strategene Mx3005P RT-PCR on the DNA extracts, using a qPCR primer/probe set targeting a sequence in the 201708001 strain which is also present in the edited strains. See also, Example 5 of international patent publication WO2019/084342 for the sample analysis by qPCR. As shown in FIGS. 16A-D, *K. variicola* 201708001 and its derivatives were able to robustly colonize the roots of corn. The gene-edited strains overall show a slight decrease in colonization compared to WT, ranging from a 10× decrease in PTA-126741 in FIG. 16A, to nearly identical colonization levels in PTA-126749 in FIG. 16D. While there is some assay to assay variability in colonization levels, all of the strains consistently exhibited colonization levels over 10$^5$ CFU/g root fresh weight (FW) and typically over 10$^6$ CFU/g root FW.

Example 5—*K. sacchari* PTA-126743 Exhibits Robust Colonization and Nitrogenase Gene Transcription in Growth Chamber Conditions

*K. sacchari* PTA-126743 was tested alongside parent strain 6-412 and the nifH knockout mutant version of 6-412 (ΔnifH) for colonization in a similar growth chamber assay as the one described in Example 2. Plants were fertilized twice per week with a modified Hoagland's fertilizer solution containing 2 mM KNO$_3$. At two weeks after planting, roots were harvested, shaken free of sand, washed, and prepared for qPCR measurement of colonization, as described above. The WT *K. sacchari* 201701001 strain was analyzed using a qPCR primer-probe set that targets a sequence within the WT strain (black bars in FIG. 17A); the edited strains were analyzed using a qPCR primer-probe set that targets a unique sequence combination in the ΔnifL:: Prm mutation (hatched bars in FIG. 17A). From the same experiment, root samples were analyzed via nanostring as described in international patent publication WO2020/006246 (Example 2, Methods, In Planta Transcriptomics), to determine the level of nifA and nifH gene transcripts in these strain in the rhizosphere of a fertilized corn plant (FIG. 17B).

Figure 17B:
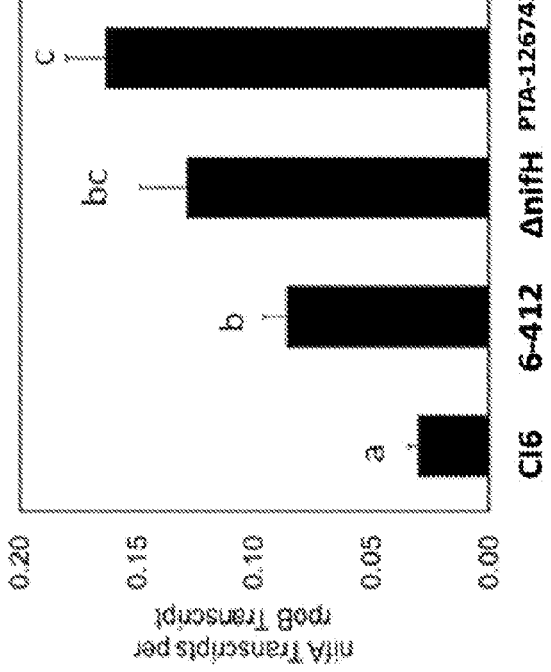

All *K. sacchari* strains exhibited high colonization of corn roots at levels over 10$^6$ CFU/g root FW in growth chamber conditions, with the edited strains showing a slight decrease in colonization (FIG. 17A). Nanostring analysis showed that all edited strains showed an elevated level of nifA transcript in the corn rhizosphere compared to WT (FIG. 17B, left panel), as well as elevated nifH transcription in PTA-126743 (FIG. 17B, right panel). Within each panel of FIG. 17, letters indicate groups for which p<0.05 according to a two-tailed, two-sample unequal variance t-test.

Example 6—Strains PTA-126740, PTA-126749, PTA-126741, and PTA-126743 Lead to an Increase in Corn Shoot Biomass when Applied to Corn Roots Two greenhouse experiments were performed to determine the impact of remodeled strains on corn growth. Plant growth assays were performed under standard greenhouse conditions with a 15-hour day length and temperature set points of 25° C. during daylight hours and 22° C. during night hours. Seeds were planted in standard potting mix combined 1:1 with calcined clay by pressing (2) 2-inch holes near the center of each pot with a planting tool. One seed was then dropped into each prepared hole and inoculated with either cells or a mock solution. For the *K. variicola* 137 experiment, seeds were inoculated either with 20 mL 5×10$^9$ CFU/mL culture or 20 mL of sterilized spent media. For the PTA-126743 experiment, seeds were inoculated with either 1 mL 5×10$^9$ CFU/mL culture or 1 mL of sterile PBS. Seedlings were given water only for the first week, then thinned to a single plant per pot by selecting the most vigorous seedling and removing the remaining plant at approximately 7 days after planting. At one-week post planting, fertigation began on all plants using a modified Hoagland's solution containing either 2 mM (FIG. 18) or 8 mM (FIG. 19) of total nitrogen. Fertigation typically occurred twice per week, and additional water was given to all plants as needed throughout the duration of the experiment. For the *K. variicola* experiments (PTA-126740, PTA-126741, and PTA-126749), plants were re-inoculated at 14 and 28 days after planting with either 20 mL 5×10$^9$ CFU/mL culture or 20 mL of sterilized spent media. Plants were harvested 5 weeks after planting, at approximately the V8 growth stage, by cutting the shoot at the soil level and bagging the shoot tissue for drying. Dry weight (weight in grams of whole plant shoot after complete drying to a stable weight) was measured approximately 14 days after plant harvest. Total plant nitrogen was also measured by grinding the entire dried biomass to a relatively fine powder and mixing for consistency, then analyzing a subset of this tissue for percent nitrogen using a modified Dumas method. As shown in FIGS. 18A and 18B, corn plants treated with Kv137 edited strains exhibited greater biomass compared to plants without a microbial treatment. As shown in FIGS. 19A and 19B, corn plants treated with PTA-126743 exhibited greater biomass compared to plants without a microbial treatment (p<0.05 according to a paired t-test).

Example 7—PTA-126740 Colonizes Corn Roots and Leads to an Increase in Corn Yield in Field Trials PTA-126740 was tested in a field trial at twenty locations across the Corn Belt. The objective of the trial was to evaluate the efficacy of PTA-126740 on corn growth and yield in commercial field settings. It was designed as a replicated strip trial with five treatments, including one untreated check (UTC), and three repetitions. The plots were 8 rows wide and 200 feet long and laid out as shown in FIG. 20.

Uniform fields that were low in residual nitrogen and that would be highly responsive to any added nitrogen were used. Well-adapted corn hybrids for the area were used. The overall fertilizer rate was determined for each individual location by a pre-plant soil sample from that location. After identifying the overall rate, the overall rate of nitrogen was cut by 25 pounds per acre from the recommended rate for that location. Pest control and irrigation, if available, was applied as needed following best management practices for the area. Root samples were collected as described below to measure colonization during the season, as well as yield data at harvest.

Individual plots were assessed for quality by an agronomist, and plots with severe quality issues that would have an outside impact on the data—for example but not limited to stand damage, insect or other pest pressure, flooding or planter error—were identified as low-quality. As a result, the analysis was performed twice, once with all the data and once upon removal of the lowest quality (or failed) plots. A linear mixed effect model was used for analysis. The spatial variation within locations was accounted for with a random effect term for the replicate blocks. Likewise, a random effect was used to account for among location variance. Table 6 includes results for the analyses performed without and with removal of plots that failed agronomy QC, respectively labeled as "Without plot QC" and "With plot QC." Estimated marginal means were used to predict the yield for the UTC and *Klebsiella variicola* PTA-126740 while controlling for other terms in the linear model. The confidence bounds in the table are those for the 95% confidence interval. P values shown reflect the comparison of PTA-126740 to the UTC within each analysis. *K. variicola* PTA-126740 showed a modest positive trend in yield as compared to the UTC (Table 6). The positive trend estimated for *K. variicola* PTA-126740 is robust to the removal of the failed plots.

described above in Example 2 (see also international patent publication WO2019084342) with primers targeting either the wild-type strain genome or the mutated region, as needed to show treated plant colonization was distinguishable from background noise detected in untreated plants.

Across the four locations tested for colonization, the average colonization of PTA-126740 was detectable above the background untreated control (UTC) (FIG. 21). The average within location ranged from around $10^4$ CFU/g FW to $10^6$ CFU/g FW.

Example 8—Complementarity and Compatibility of PTA-126740 and PTA-126743

The effects of PTA-126743 and PTA-126740 may be complementary to one another because of their ability to grow and fix nitrogen optimally at different concentrations of oxygen. This is evidenced in the hypoxic ARA excretion data, where PTA-126743 shows little ammonium excretion at 1.5% oxygen and no excretion at 3% oxygen (FIG. 17), while PTA-126740 still excretes ammonium to ~4 mM in 3% oxygen (FIG. 14B).

To investigate growth of the *K. variicola* 201708001 and *K. sacchari* 201701001 strains at different levels of oxygen, a microbioreactor experiment was carried out as described in FIGS. 22A-22C. The results are shown in FIGS. 23A-23C. Each line represents the average of three replicate cultures of the indicated strain or uninoculated control. The results show that while *K. variicola* 201708001 grows to a lower final biomass at 0.5% oxygen compared to 1.5% or 3% oxygen, *K. sacchari* 201701001 grows to the same final biomass at all three concentrations. This suggests that *K. sacchari* 201701001 may complement a decrease in growth and nitrogen fixation by *K. variicola* 201708001 at oxygen concentrations of 0.5% or lower.

Example 9—Systems for Plant Growth and Measurement of Nitrogen Incorporation

The maize hybrid DKC 66-40 was grown under standard greenhouse growth conditions with a 15-hour day length and temperature set points of 25° C. during daylight hours and

TABLE 6

Yield results from replicated strip trial analysis of PTA-126740.

| Analysis | Treatment | Predicted yield (bu/acre) | 95% confidence interval (bu/acre) | standard error (bu/acre) | p value |
|---|---|---|---|---|---|
| Without plot QC | UTC | 169.8 | ±18.8 | 9.6 | 0.11 |
| | PTA-126740 | 173.1 | ±18.8 | 2.1 | |
| With plot QC | UTC | 176.6 | ±16.2 | 8.3 | 0.16 |
| | PTA-126740 | 179 | ±16.2 | 1.7 | |

Colonization Sampling Methods

A subset of four locations were tested for colonization. Between V4-V6, roots were dug from the outer rows of each replicate plot of treated and untreated plants, shaken to dislodge loose soil, and packed on ice for overnight shipment to the lab for processing. On arrival, root balls were washed free of clinging soil and a 1-2 inch segment of seminal and first nodal roots was cut from the region below the seed. This root sample was chopped into small pieces and a 0.05 g subsample was further processed to extract genomic DNA. Colonization was assessed using qPCR as 22° C. during night hours. Seeds were planted in standard potting mix combined 1:1 with calcined clay by pressing (2) 2-inch holes near the center of each pot with a planting tool. One seed was then dropped into each prepared hole and inoculated with sterile PBS (UTC controls) or a bacterial suspension of the strain PTA-126749, a microbe with an increased potential to fix nitrogen in planta, using cells diluted to a prescribed optical density. Seedlings were given water only for the first week, then thinned to a single plant per pot by selecting the most vigorous seedling and removing the remaining plant at approximately 7 days after planting. At one-week post planting, fertigation began on all plants using a modified Hoagland's solution containing 2 mM of total nitrogen. Fertigation typically occurred twice per week, and additional water was given to all plants as needed.

At 3 weeks post-planting, plants were moved to chamber. After closing and sealing the chamber, 20 L of gas were removed from the chamber and replaced with the same volume of 98% atom $^{15}N$ gas (obtained from Sigma-Aldrich, St. Louis, MO), such that the internal atmosphere of chamber 102 was raised to approximately 0.5 atom % $^{15}N$. Growth conditions in the chamber were controlled such that plants experienced a constant humidity of approximately 60%, supplemental light from metal halide lamps for 15 hours per day, and day and night temperatures as described above. Oxygen and carbon dioxide levels were monitored and adjusted as necessary to pre-determined set values. Irrigation with the same 2 mM modified Hoagland's solution was performed two times per week without opening chamber to the external environment.

Plants were harvested after two weeks in the chamber and approximately five weeks after planting (e.g., at the V8 growth stage). Plants were sectioned into four distinct portions: root tissue, newly emerged whorl tissue, top-collared leaf tissue, and all remaining vegetative tissue (other vegetative tissue). Dry weight (weight in grams of whole plant after complete drying to a stable weight) was measured approximately 14 days after plant harvest for each tissue portion. Samples were then ground to a fine powder and isotopic analysis was performed at the UC Davis Stable Isotope Facility (Davis, CA, USA). For each sample, percent nitrogen and percent $^{15}N$ were determined.

For whorl tissue top-collared leaf tissue, other vegetative tissue, and root tissue derived from inoculated plants, nitrogen incorporation—as measured by the change in $^{15}N$ abundance in the tissues—was higher than for corresponding tissues of non-inoculated plants.

A biologically pure culture of *Klebsiella variicola* was deposited on Apr. 2, 2020, with the American Type Culture Collection (ATCC; an International Depositary Authority), Manassas, VA, USA, and assigned ATTC Patent Deposit Designation number PTA-126749. This deposit was made under the provisions of the Budapest Treaty on the International Recognition of the Deposit of Microorganisms for the Purpose of Patent Procedure and the Regulations (Budapest Treaty).

Example 10—Combinations of PTA-126743 and PTA-126740 Under Field Conditions

Two different protocols were used to test combinations of PTA-126743 and PTA-126740 under field conditions. In the 20-ZEAMX-US403 mini-strip protocol, the combination of PTA-126743/PTA-126740 was compared with an untreated control (UTC), and with both PTA-126743 and PTA-126740 as separate single entries. The 20-ZEAMX-US403 protocol consisted of replicated plots of 8 corn rows by 100 feet at 25 locations through the Midwest corn growing seasons. Four of these locations failed a quality control and were not used in the analysis.

In the second protocol, the 20-ZEAMX-US501 on-farm protocol, the PTA-126743/PTA-126740 combination was compared with untreated control (UTC) and with PTA-126740 as a single separate entry. This protocol consisted of 20 unreplicated locations at real working farms. Plot size was variable.

Each plot in both protocol was sampled for whole plant nitrogen and nitrogen percent at the reproductive growth stage of corn, referred to as VT. From each plot, three entire plants were harvested and shipped to a tissue laboratory for processing. At the lab, the plants were dry and weighed. The nitrogen content subsample of the dried material was measured. This provided a measurement at each plot of both the nitrogen content per plant, N(g), as well as the nitrogen percent for each plot, N %. To determine the effect of each strain on N(g) and N %, a Bayesian hierarchical model was fit to the data using the R package BRMS. In this model effects were fit for replicates and locations, allowing a calibrated comparison between the sites.

The PTA-126743/PTA-126740 combination was significant at the $p<0.05$ in both protocols for N(g) per plant. The PTA-126743/PTA-126740 combination was significant at $p<0.01$ in the mini-strip protocol and $p<0.10$ in the on-farm protocol. While PTA-126743 & PTA-126740 showed $p>0.10$ in both measures at both protocols, they both produced a positive response in N % and N(g). FIG. 25A depicts the nitrogen percent at VT and FIG. 25B depicts the whole plant nitrogen at VT as an effect.

The Bayesian model used produced a posterior distribution, allowing comparison of the combination strain with each of the entries. These comparisons are in Table 7 and range between an 80.2% and a 99.6% that the combination strain is better than the individual strain, depending on the protocol and the measurement.

TABLE 7

| | | | |
|---|---|---|---|
| | | Trial Design Summary | |
| Measurement | Comparison Strain | Protocol | Probability Combo Better than Single |
| N(g) at VT | PTA-126743 | 20-ZEAMX-US403 | 80.2% |
| N(g) at VT | PTA-126740 | 20-ZEAMX-US403 | 92.0% |
| N(g) at VT | PTA-126740 | 20-ZEAMX-US501 | 97.4% |
| N % at VT | PTA-126743 | 20-ZEAMX-US403 | 88.3% |
| N % at VT | PTA-126740 | 20-ZEAMX-US403 | 99.6% |
| N % at VT | PTA-126740 | 20-ZEAMX-US501 | 91.4% |

Example 11—Systems for Plant Growth and Measurement of Nitrogen Incorporation Multiple trials were used to evaluate the combination of PTA-126740 and PTA-126743. There were three main trial designs with each contributing some, but not all, of the data. These included the trials 20-ZEAMX-US403 (403) and 20-ZEAMX-US503 (503). The other design included the trials US-ZEAMX-US501 (501) and 20-ZEAMX-US502). Each of these protocols is described below.
20-ZEAMX-US403

The 403 trials were conducted with 30 contracted research organizations which are commonly referred to as CROs or cooperators. The CROs were given a detailed protocol for the trial, and were responsible for all management activities of the trial from planting to harvest including collecting all data. The individual trial locations were selected based on geographical location so that the major corn growing regions of the United States were represented.

The 403 trials consisted of nine treatments replicated four to six times. The number of planted repetitions was based on the overall trial footprint and the available land at the research site. The trial design was a large plot Randomized Complete block design (RCB). This is the standard trial design for testing different treatments in agricultural field research. Each plot was 8 rows wide and 60-100 feet long, which varied based on the field layout. The larger plot size allows for better comparison to field scale production and allows for more tissue sampling without compromising the integrity of the plot.

Only the yield and tissue nutrient analysis was used in performance analysis.

20-ZEAMX-US503

The 503 trials were placed with 23 different growers across the Corn Belt. The grower was usually assisted by a company agronomist at planting to help ensure the treatments were applied correctly. Further, the agronomist assisted at harvest to collect harvest data and information.

The design was a field length strip usually around 2 acres per treatment. The treatments were not replicated in the field. There were two treatment sets each with the same biological treatments and controls. The two sets differed by the amount of nitrogen fertilizer applied. The data were collected by the area agronomist and grouped together and analyzed.

20-ZEAMX-US501 and 20-ZEAMX-US502

The design for these trials were large block trials with two different treatments planted in 20-acre blocks and a designated non-treated control area. Within each 20-acre microbial treated block was to be a strip with a reduced nitrogen rate of 50 pounds of nitrogen per acre. The overall design of the two trials were the same, differing only with the treatments in each trial.

TABLE 8

| | | | |
|---|---|---|---|
| | Trial Design Summary | | |
| | 403 | 501, 502 | 503 |
| Also called | Large Plot or Small Strip | Strip | On-Farm Strip |
| QC | Most consistent results with clearest signal | Data cleaning performed | Major VT tissue sample mix up at Waypoint lab |
| Implementer | Contract Research Organizations | Growers (real field conditions) | Growers (real field conditions) |
| Application | in-furrow | in-furrow | in-furrow |
| Size estimate | med | largest | large |
| per plot | ~0.08 acres | Variable, ~15 acres | Variable, 2-5 acres |
| Replication | 4-6 | none | none |
| Treatments | 9: 6 products at −50 lbs N, +3 NTC | 5: NTC + (2 products * 2 fertilizer rates) | 12: (5 products + NTC) * (2 fertilizer rates) |
| Fertilizer rates | All strains at (100% N −50 lbs), positive control has 100% N | Strains at both (100% N) and (100% −50 lb N) | Strains at both (100% N) and (100% −50 lb N) |

Data Analysis

Data from the corn trials were analyzed using various methods. The analyses were compared and each strain was ranked by performance (Table 9). Yield and tissue analyses were compared on win rate, effect size, and by Bayesian ranking. Ranking numbers were assigned based on overall differences. If two strains performed similarly even if one was slightly higher, they were assigned the same number.

The single strains as well as the combination were compared to each other and patterns were identified. The combination of PTA-126740 and PTA-126743 outperformed the individual microbes in more categories. The combination was more consistent and showed a clear pattern of improvement in most categories over the single strains. On average, of the tested treatments, the strain combination only underperformed the +50 lbs N treatment in plant yield, but outperformed even that treatment in measured plant nitrogen.

TABLE 9

| Trait | Protocols | Analysis | +50 lbs N | NCMA 201712002 | PTA-126740 + PTA-126743 | PTA-126740 | PTA-126749 | PTA-126743 |
|---|---|---|---|---|---|---|---|---|
| yield (403, 501, 502, 503) | all | Win Rate | 1 | 3 | 2 | 4 | 3 | 4 |
| | all | Effect Size | 1 | 3 | 2 | 2 | 4 | 4 |
| yield 403 | 403 | Win Rate | 1 | 3 | 4 | 4 | 2 | 3 |
| | 403 | Effect Size | 1 | 2 | 2 | 4 | 3 | 3 |

TABLE 9-continued

| | | | | | PTA-126740 + | | | |
|---|---|---|---|---|---|---|---|---|
| Trait | Protocols | Analysis | +50 lbs N | NCMA 201712002 | PTA-126743 | PTA-126740 | PTA-126749 | PTA-126743 |
| yield 403 | 403 | Bayesian ranking | 1 | 2 | 2 | 4 | 3 | 4 |
| yield 503 | 503 | Win Rate | 1 | 3 | 1 | 2 | 3 | NA |
| weigh wagon | 503 | Effect Size | 1 | 3 | 2 | 2 | 3 | NA |
| yield 503 | 503 | Bayesian ranking | 1 | 2 | 2 | 2 | 3 | NA |
| | Avg Rank Yield | | 1.0 | 2.6 | 2.1 | 3.0 | 3.0 | 3.6 |
| plant lb N/ acre, VT | all | Effect Size | 1 | 4 | 2 | 4 | 4 | 4 |
| | all | Win Rate | 1 | 3 | 2 | 5 | 4 | 5 |
| plant lb N/ acre-VT | all | Bayesian ranking | 1 | 3 | 1 | 3 | 4 | 2 |
| plant lb N/ acre | 403 | Bayesian ranking | 1 | 3 | 1 | 3 | 3 | 2 |
| leaf N dry weight | 503 | Win Rate | 6 | 2 | 1 | 4 | 5 | NA |
| leaf lb N/ acre | 503 | Win Rate | 1 | 1 | 2 | 1 | 4 | NA |
| | 503 | Effect Size | 2 | 1 | 2 | 1 | 3 | NA |
| | Avg Rank Nitrogen | | 1.9 | 2.4 | 1.6 | 3.0 | 3.9 | 3.3 |

Other Crops:

Field trials also were conducted on grain *sorghum* and spring wheat in the United States. The trials were managed by contract research organizations. The primary objective of these trials was to determine the performance of NCMA 201712002, PTA-126740, and PTA-126743 in reduced nitrogen environments. Both trials were established as a large plot randomized complete block design. The spring wheat had five treatments and the *sorghum* had four. Both were replicated four times. Only the single strains were tested with other crops.

Trial quality was assessed by the field trial manager with input from the CRO and other Pivot Bio agronomists who visited the sites. One site from the spring wheat and three from the *sorghum* did not meet quality standards and were removed from analysis. As with the corn strain selection, yield and tissue analysis was used to compare the microbes for advancement. Unlike the corn trials, there were no whole plant samples collected for the spring wheat trial while there were for the *sorghum*. Only the flag leaves from wheat were collected and analyzed. The level of analysis for both data sets was not as in depth as it was for the corn trials.

Data were analyzed using the statistical software JMP. Like the corn data the results for spring wheat and grain *sorghum* were compared across treatments and ranked by highest to lowest. A means comparison test (Student's t) was run for all data sets and showed no significance at the a=0.1 level.

Wheat:

Average treatment yields for psring wheat across all sites was relatively flat. No clear indication of a yield advantage was observed from any treatment including the 100% check. It is thought that based on the weather and overall growing conditions, nitrogen was not a limiting factor for yield. This seems to be confirmed with the Leaf % N data. There were no major differences in % N indicating that nitrogen was not limiting.

*Sorghum:*

*Sorghum* showed a similar yield increase as the strip trials. However, there was more variability across sites. Compared to the reduced N check, NCMA 201712002 and PTA-126740 had similar win rates but the yields were higher for NCMA 201712002 (Table 10). Whole plant dry weight was also numerically higher for NCMA 201712002 while the 100% N check had the lowest average (Table 11). This again can be attributed to nitrogen not being a limiting factor in these fields. Selection was based on the yield data being consistent across two years of field trials.

TABLE 10

Yield data for sorghum

| | 20-SORVU-US401 - Yield (bu/acre) | | | |
|---|---|---|---|---|
| Trial ID | NCMA 201712002 Mean | Check 100% Mean | Check –25 lb Mean | PTA-126740 Mean |
| 20-SORVU-US401-KS02-SWRC | 146.70 | 126.63 | 136.00 | 136.40 |
| 20-SORVU-US401-NE01-MIRE | 140.45 | 146.68 | 142.70 | 146.53 |
| 20-SORVU-US401-TX01-AGGI | 119.65 | 122.85 | 117.33 | 124.23 |
| 20-SORVU-US401-TX02-GRPL | 110.73 | 112.48 | 110.15 | 106.80 |
| 20-SORVU-US401-TX03-GRPL | 113.75 | 119.53 | 112.60 | 112.98 |
| 20-SORVU-US401-TX04-HOAS | 86.93 | 77.05 | 70.08 | 54.70 |
| 20-SORVU-US401-TX05-RARI | 66.65 | 68.75 | 67.40 | 68.20 |
| Mean | 112.12 | 110.56 | 108.04 | 107.12 |

US 12,643,837 B2

113

TABLE 11

Plant Dry Weight for sorghum

| Trial ID | NCMA 201712002 Mean | Check −25 lb Mean | PTA- 126740 Mean | Check 100% Mean |
|---|---|---|---|---|
| 20-SORVU-US401-KS02-SWRC | 342.25 | 285.43 | 287.40 | 289.10 |
| 20-SORVU-US401-NE01-MIRE | 85.83 | 103.23 | 91.85 | 84.53 |
| 20-SORVU-US401-TX01-AGGI | 186.08 | 172.50 | 173.03 | 169.00 |
| 20-SORVU-US401-TX02-GRPL | 80.75 | 80.73 | 63.73 | 78.90 |
| 20-SORVU-US401-TX03-GRPL | 214.85 | 224.98 | 185.63 | 172.28 |
| 20-SORVU-US401-TX04-HOAS | 224.18 | 183.68 | 179.05 | 218.13 |
| 20-SORVU-US401-TX05-RARI | 284.65 | 347.20 | 309.38 | 262.95 |
| Mean | 202.65 | 199.68 | 184.29 | 182.13 |

Example 12—Yield Stability is Improved with Combinations of PTA-126743 and PTA-126740

In 15 locations of non-replicated on-farm trials, the effect of a combination of strains (PTA-126740+PTA-126743) was compared with that of 50 pounds per acre of added nitrogen fertilizer and with untreated control. The plots were variable in size but were always greater than 0.5 acre. Yield was collected using combines, allowing the collection of at least 700 data points per plot (median=9923). To measure the variability of yield, the non-parametric interquartile range (IQR) metric was used as this statistic represents variability in a way that is robust to outliers. A bayesian mixed effect model was fit for IQR with fertilization rate and microbial treatments as fixed effects and each location as a random effect. To control for the variation in mean yield between sites and the variable size of plots, mean yield and log of number of yield data points were used in the model as fixed effects. The probability that the strain combination has lower yield variability by the IQR metric than both a reduced nitrogen control (Check) and adding 50 lb Nitrogen fertilizer per acre (Check+50 lb N) was 91%. The strain combination's yield variability was 15.4% lower than that of an additional 50 lbs of nitrogen fertilizer and 13.9% lower than that in the reduced nitrogen control. These differences are represented in the associated figure which shows conditional mean posterior values for each treatment type (x axis) and their associated frequency (posterior density) in a 4000-iteration monte-carlo sample.

Example 13—Combinations of PTA-126743 and PTA-126740 Increase Plant Fresh Weight in Rice, Soy, and Wheat Plants treated with a combined bacterial suspension of PTA-126740 and PTA-126743 were compared to a control with no inoculated cells in three greenhouse growth experiments. Additionally, soybean plants were treated with USDA-110 *Bradyrhizobiom japonicum* (NRRL No. B-4361, USDA-ARS) as a positive control for biological nitrogen fixation. All plants were grown under nitrogen limiting conditions except a positive control (+ Nitrogen Check) to test for nitrogen response under these assay conditions.

All plant growth assays were performed under standard greenhouse conditions with a 15-hour day length and temperature set points of 25° C. during daylight hours and 22° C. during night hours. Seeds were planted in standard potting mix combined 1:1 with calcined clay by pressing approximately 2-inch holes near the center of each pot with a planting tool. Seeds of either *Oryza sativa* (rice), *Triticum aestivum* (wheat), or *Glycine max* (soybean) were then dropped into each prepared hole and inoculated with sterile PBS (Untreated Check and + Nitrogen Check), an equal volume of bacterial suspension using cells diluted to a set optical density, or the same volume of cells after being devitalized by autoclaving (Heat killed cells). All pots from the + Nitrogen Check (alternatively labeled Untreated+ Nitrogen control group) were also amended with a slow-release nitrogen fertilizer to serve as a positive check for plant response to nitrogen. The nitrogen in the positive nitrogen check provides between 25% and 50% of the plants total nitrogen need, depending on plant species.

The seedlings were given water only for the first week, then thinned to a single plant per pot (maize and soybean) or three plants per pot (rice and wheat) by selecting the most vigorous seedling(s) and removing the remaining plant(s) at approximately 7 days after planting. At one-week post planting, fertigation began on all plants using a complete fertilizer solution containing approximately 4 mM of total nitrogen. Fertigation typically occurred twice per week, and additional water was given to all plants as needed throughout the duration of the experiment.

At 35 days after planting, all plants were harvested. Fresh weight (weight in grams of all vegetative tissues) was measured immediately at the time of harvest, and dry weight (weight in grams of all vegetative tissues after complete drying to a stable weight) was measured approximately 14 days after plant harvest.

Statistically analysis performed using JMP 14 software, and comparison made using a Tukey HSD test with a level of significance of 0.05. For all variables with the same letter, the difference between the means is not statistically significant.

The combination of microbes increased plant fresh weight in each of three species tested, *Glycine max* (soybean), *Triticum aestivum* (wheat), and *Oryza sativa* (rice) by 13%, 20%, and 11%, respectively. Significant (p<0.05) increases in plant fresh weights were observed for both soybean and wheat as compared to Untreated Check plants (see FIGS. 27A and 27B), and soybean plants treated with USDA-110 were not significantly different that those treated with PTA-126740 and PTA-126743. Non-significant (p=0.26) increases in plant fresh weight were observed for rice plants as compared to Untreated Check (FIG. 27C). All+ Nitrogen Check entries were significantly different than the Untreated Check in the same experiment (p<0.0001).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of increasing the amount of atmospheric derived nitrogen in a plant, the method comprising contacting the plant, a part of the plant, or soil into which the plant is planted with a plurality of genetically engineered *Klebsiella variicola* bacteria comprising one or more genetic modifications in a gene regulating nitrogen fixation or assimilation and a plurality of genetically engineered *Kosakonia sacchari* bacteria comprising one or more genetic modifications in a gene regulating nitrogen fixation or assimilation, wherein:

the one or more genetic modifications in the plurality of genetically engineered *Klebsiella variicola* bacteria comprise a deletion of all or a portion of the coding sequence of the nifL gene and a deletion of a portion of the coding sequence of the glnD gene, and the one or more genetic modifications in the plurality of genetically engineered *Kosakonia sacchari* bacteria comprise a deletion of all or a portion of the coding sequence of the nif gene, a deletion of all of the coding sequence of the glnD gene, and a deletion of a portion of the coding sequence of the glnE gene.

2. The method of claim 1, wherein all or a portion of the nifL coding sequence is replaced by a promoter.

3. The method of claim 2, wherein the promoter is a non-intergeneric promoter.

4. The method of claim 1, wherein the plurality of genetically engineered *Klebsiella variicola* bacteria are represented by bacteria deposited as ATCC Accession No. PTA-126740.

5. The method of claim 1, wherein the plurality of genetically engineered *Kosakonia sacchari* bacteria are represented by bacteria deposited as ATCC Accession No. PTA-126743.

6. The method of claim 1, wherein at least one of the plurality of genetically engineered *Klebsiella variicola* bacteria and the plurality of genetically engineered *Kosakonia sacchari* bacteria are non-intergeneric.

7. A composition comprising a genetically engineered *Klebsiella variicola* bacterium and a genetically engineered *Kosakonia sacchari* bacterium, wherein the genetically engineered *Klebsiella variicola* bacterium and the genetically engineered *Kosakonia sacchari* bacterium each comprise one or more genetic modifications in a gene regulating nitrogen fixation or assimilation, wherein:

the one or more genetic modifications in the genetically engineered *Klebsiella variicola* bacterium comprise a deletion of all or a portion of the coding sequence of the nifL gene and a deletion of a portion of the coding sequence of the glnD gene, and the one or more genetic modifications in the genetically engineered *Kosakonia sacchari* bacterium comprise a deletion of all or a portion of the coding sequence of the nifL gene, a deletion of all of the coding sequence of the glnD gene, and a deletion of a portion of the coding sequence of the glnE gene.

8. The composition of claim 7, wherein at least one of the one or more genetic modifications results in expression of nifA in nitrogen replete conditions in the genetically engineered *Klebsiella variicola* bacterium, in the genetically engineered *Kosakonia sacchari* bacterium, or both of the genetically engineered bacteria.

9. The composition of claim 7, wherein all or a portion of the nifL coding sequence is replaced by a promoter.

10. The composition of claim 9, wherein the promoter is a non-intergeneric promoter.

11. The composition of claim 7, wherein at least one of the genetically engineered *Klebsiella variicola* bacterium and the genetically engineered *Kosakonia sacchari* bacterium are non-intergeneric.

12. The composition of claim 7, wherein the genetically engineered *Klebsiella variicola* bacterium is represented by a bacterium deposited as ATCC Accession No. PTA-126740.

13. The composition of claim 7, wherein the genetically engineered *Kosakonia sacchari* bacterium is represented by a bacterium deposited as ATCC Accession No. PTA-126743.

14. A microbial composition comprising a *Kosakonia sacchari* bacterium represented by a bacterium deposited as ATCC Accession No. PTA-126743, and a *Klebsiella variicola* bacterium represented by a bacterium deposited as ATCC Accession No. PTA-126740.

* * * * *